US012428483B2

(12) United States Patent
Gao et al.

(10) Patent No.: US 12,428,483 B2
(45) Date of Patent: Sep. 30, 2025

(54) BISPECIFIC TETRAVALENT ANTIBODIES AND METHODS OF MAKING AND USING THEREOF

(71) Applicant: Systimmune, Inc., Redmond, WA (US)

(72) Inventors: Zeren Gao, Bellevue, WA (US); Phil Tan, Bellevue, WA (US); Brian R. Kovacevich, Bellevue, WA (US); Blair R. Renshaw, Bellevue, WA (US); Jeffrey B. Adamo, Bellevue, WA (US); Nge Sze Amanda Mak, Bellevue, WA (US); Shi Zhuo, Chengdu (CN); Lan Chen, Chengdu (CN); Yi Zhu, Chengdu (CN)

(73) Assignee: SystImmune, Inc., Redmond, WA (US)

( * ) Notice: Subject to any disclaimer, the term of this patent is extended or adjusted under 35 U.S.C. 154(b) by 1150 days.

(21) Appl. No.: 17/143,204

(22) Filed: Jan. 7, 2021

(65) Prior Publication Data

US 2021/0277128 A1 Sep. 9, 2021

Related U.S. Application Data

(63) Continuation of application No. 15/119,694, filed as application No. PCT/US2015/066951 on Dec. 19, 2015, now Pat. No. 10,919,977.

(60) Provisional application No. 62/095,348, filed on Dec. 22, 2014.

(51) Int. Cl.

| | |
|---|---|
| ***C07K 16/28*** | (2006.01) |
| ***A61K 31/337*** | (2006.01) |
| ***A61K 33/243*** | (2019.01) |
| ***A61K 45/06*** | (2006.01) |
| ***A61K 47/68*** | (2017.01) |
| ***A61P 35/00*** | (2006.01) |
| ***C07K 14/705*** | (2006.01) |
| ***C07K 16/32*** | (2006.01) |
| *A61K 39/00* | (2006.01) |

(52) U.S. Cl.

CPC ........ *C07K 16/2863* (2013.01); *A61K 31/337* (2013.01); *A61K 33/243* (2019.01); *A61K 45/06* (2013.01); *A61K 47/6843* (2017.08); *A61P 35/00* (2018.01); *C07K 14/70521* (2013.01); *C07K 14/70532* (2013.01); *C07K 14/70578* (2013.01); *C07K 16/32* (2013.01); *A61K 2039/505* (2013.01)

(58) Field of Classification Search

CPC .......... C07K 16/2863; C07K 14/70521; C07K 14/70532; C07K 14/70578; C07K 16/32; C07K 2317/732; C07K 2317/90; C07K 14/71; C07K 2317/31; A61K 31/337; A61K 33/243; A61K 45/06; A61K 47/6843; A61K 2039/505; A61P 35/00

See application file for complete search history.

(56) References Cited

U.S. PATENT DOCUMENTS

| | | | | |
|---|---|---|---|---|
| 5,641,870 | A | 6/1997 | Rinderknecht et al. | |
| 7,332,585 | B2 | 2/2008 | Adams et al. | |
| 10,919,977 | B2 | 2/2021 | Gao et al. | |
| 2003/0153735 | A1 | 8/2003 | Breece et al. | |
| 2010/0256338 | A1 | 10/2010 | Brinkmann et al. | |
| 2012/0134993 | A1 | 5/2012 | Pan et al. | |
| 2012/0270801 | A1* | 10/2012 | Frejd | A61P 43/00 514/19.5 |
| 2014/0056895 | A1 | 2/2014 | Baurin et al. | |
| 2014/0135482 | A1 | 5/2014 | Bossenmaier et al. | |
| 2014/0170147 | A1 | 6/2014 | Shulok et al. | |
| 2014/0170148 | A1 | 6/2014 | Goeij et al. | |

FOREIGN PATENT DOCUMENTS

| | | | | |
|---|---|---|---|---|
| CN | 102250246 A | | 11/2011 | |
| CN | 102250247 A | | 11/2011 | |
| EP | 2727942 | | 5/2014 | |
| WO | WO 2007/147001 | | 12/2007 | |
| WO | WO 2008/119566 | * | 10/2008 | C07K 16/28 |
| WO | WO 2008/140493 | * | 11/2008 | A61K 39/395 |
| WO | WO 2010/095031 | * | 8/2010 | C07K 16/28 |
| WO | WO 2010/115552 | | 10/2010 | |
| WO | WO 2012/085113 | | 6/2012 | |
| WO | WO 2012/143523 | | 10/2012 | |
| WO | WO 2013/096346 | | 6/2013 | |
| WO | WO 2014/144357 | | 9/2014 | |
| WO | WO 2015/066543 | | 5/2015 | |
| WO | WO 2016/106157 | | 6/2016 | |

OTHER PUBLICATIONS

Dong et al. (mAbs, 3(3): 273-288, 2011).*
Hoet et al. (Nature Biotechnology, 23(3): 344-349, 2005).*
International Search Report and Written Opinion dated May 6, 2016 for International Patent Application No. PCT/US2015/066951 (13 pages).
Arteaga et al., 2011, "Treatment of HER2-positive breast cancer: current status and future perspectives," Nature Reviews Clinical Oncology, 9:16-32.
Badache et al., 2004, "A new therapeutic antibody masks ErbB2 to its partners," Cancer Cell, 5(4):299-301.
Ben-Kasus et al., 2009, "Persistent elimination of ErbB-2/HER2-overexpressing tumors using combinations of monoclonal antibodies: Relevance of receptor endocytosis," Proc Natl Acad Sci USA, 106(9):3294-3329.
Baselga et al., 2012, "Pertuzumab plus Trastuzumab plus Docetaxel for Metastatic Breast Cancer" N Engl J Med, 366:109-119.

(Continued)

*Primary Examiner* — Nelson B Moseley, II
(74) *Attorney, Agent, or Firm* — Jones Day

(57) ABSTRACT

A bispecific tetravalent antibody comprising an IgG having a pair of heavy chains and a pair of light chains, and two scFv components being connected to either C or N terminals of the heavy or light chains. The bispecific tetravalent antibody may have a binding specificity for two different members of EGFR family.

14 Claims, 33 Drawing Sheets

Specification includes a Sequence Listing.

(56) References Cited

OTHER PUBLICATIONS

Bode et al., 2012, "Nimotuzumab treatment of malignant gliomas," Expert Opin Biol Ther., 12(12):1649-59.
Buck, 2006, "Inactivation of Akt by the epidermal growth factor receptor inhibitor erlotinib is mediated by HER-3 in pancreatic and colorectal tumor cell lines and contributes to erlotinib sensitivity", Mol. Cancer Ther., 5:2051-2059.
Brack et al, 2014, "A Bispecific HER2-Targeting FynomAb with Superior Antitumor Activity and Novel Mode of Action", Molecular Cancer Therapeutics, US, 13(8):2030-2039.
Byrne et al., 2013, "A tale of two specificities: bispecific antibodies for therapeutic and diagnostic applications", Trends Biotechnol., 31(11):621-32.
Chen et al., 2013, "Fusion protein linkers: Property, design and functionality," Advanced Drug Delivery Reviews, 65:1357-1369.
Cohen, 2014, "Current challenges and clinical investigations of epidermal growth factor receptor (EGFR)- and ErbB family-targeted agents in the treatment of head and neck squamous cell carcinoma (HNSCC)," Cancer Treatment Reviews, 40:567-577.
Coloma et al., 1997, "Design and production of novel tetravalent bispecific antibodies," Nature Biotechnology, 163(15):159.
Dhimolea et al., 2012, "World bispecific antibody summit, Sep. 27-28, 2011, Boston, MA," MABS, 4(1):4.
Dong et al., 2011, "A stable IgG-like bispecific antibody targeting the epidermal growth factor receptor and the type I insulin-like growth factor receptor demonstrates superior anti-tumor activity," mAbs, 3(3):273-288.
Erjala et al., 2006, "Signaling via ErbB2 and ErbB3 associates with resistance and epidermal growth factor receptor (EGFR) amplification with sensitivity to EGFR inhibitor gefitinib in head and neck squamous cell carcinoma cells", Clin Cancer Res, 12(13):4103-11.
Gala et al. 2014, "Molecular pathways: HER3 targeted therapy", Clin Cancer Res., 15;20(6):1410-6.
Huang, et al., 2013, "Dual Targeting of EGFR and HER3 with MEHD7945A Overcomes Acquired Resistance to EGFR Inhibitors and Radiation", Cancer Res, 73:824-833.
Hoet et al., 2005, "Generation of high-affinity human antibodies by combining donor-derived and synthetic complementarity-determining-region diversity," Nature Biotechnology, 23(3):344-349.
Horton, 2001, "HER2 and trastuzumab in breast cancer," Cancer Control, 8(1):103-110.
Hu et al., 2015, "Four-in-one antibodies have superior cancer inhibitory activity against EGFR, HER2, HER3, and VEGF through disruption of HER/MET crosstalk", Cancer Res, 75(1):159-170.
Hu et al., 2019, "Correction: Four-in-one antibodies have superior cancer inhibitory activity against EGFR, HER2, HER3, and VEGF through disruption of HER/MET crosstalk", Cancer Res 79(13):3525.
Jackman et al., 2010, "Clinical Definition of Acquired Resistance to Epidermal Growth Factor Receptor Tyrosine Kinase Inhibitors in Non-Small-Cell Lung Cancer," J Clin Oncol, 28(2):357-60.
Jiang et al, 2012, "Advances in Targeting HER3 as an Anticancer Therapy," Chemotherapy Research and Practice, vol. 2012, Article ID 817304, 9 pages.
Kasprzyk et al., 1992, "Therapy of an Animal Model of Human Gastric Cancer Using a Combination of Anti-erbB-2 Monoclonal Antibodies," Cancer Res, 52(10):2771-2776.
King et al., 1985, "Amplification of a Novel v-erbB-Related Gene in a Human Mammary Carcinoma," Science, 229(4717):974-976.
Kontermann, 2012, "Dual targeting startegies with dispecific antibodies," Mabs, 4(2):182-197.
Li et al, 2013, "Bispecific antibody to ErbB2 overcomes trastuzumab resistance through comprehensive blockade of ErbB2 heterodimerization", Cancer Research, American Association for Cancer Research, US, 73(21):6471-6483.
Lutterbuese et al., 2010, "T cell-engaging BiTE antibodies specific for EGFR potently eliminate KRAS- and BRAF-mutated colorectal cancer cells," Proceedings of the National Academy of Sciences of the United States of America, 107(28):12605-12610.
Ma et al., 2014, "Targeting of erbB3 receptor to overcome resistance in cancer treatment", Molecular Cancer 13:105.
May et al., 2012, "Advances in bispecific biotherapeutics for the treatment of cancer", Biochemical Pharmacology, 84:1105-1112.
Mariuzza, 1987, "The structural basis of antigen-antibody recognition," Annu. Rev. Biophys. Biophys. Chem., 16:139-159.
McDonagh, et al. 2012, "Antitumor Activity of a Novel Bispecific Antibody That Targets the ErbB2/ErbB3 Oncogenic Unit and Inhibits Heregulin-Induced Activation of ErbB3", Mol Cancer Ther, 11:582-593.
O'Sullivan et al., 2014, "Pertuzumab and its accelerated approval: evolving treatment paradigms and new challenges in the management of HER2-positive breast cancer," Oncology, 28(3):186-194.
Perez et al., 2014, "EGFR-targeting therapy as an evolving concept: learning from nimotuzumab clinical development," Chin Clin Oncol, 3(1):5.
Price et al., 2014, "Panitumumab versus cetuximab in patients with chemotherapy-refractory wild-type KRAS exon 2 metastatic colorectal cancer (ASPECCT): a randomised, multicentre, open-label, non-inferiority phase 3 study," The Lancet Oncology, 15(6):569-579.
Price et al., 2012, "Current Treatment Options for Metastatic Head and Neck Cancer," Curr Treat Options Oncol., 13(1):35-46.
Robinson et al., 2008, "Targeting ErbB2 and ErbB3 with a bispecific single-chain Fv enhances targeting selectivity and induces a therapeutic effect in vitro", British Journal of Cancer, 99:1415-1425.
Safdari et al., 2014, "Recent advances in head and neck squamous cell carcinoma—a review.", Clin Biochem., 47(13-14):1195-202.
Schaefer et al., 2011, "A Two-in-One Antibody against HER3 and EGFR Has Superior Inhibitory Activity Compared with Monospecific Antibodies," Cancer Cell, 20(4):472-86.
Schanzer et al., 2011, "Development of Tetravalent, Bispecific CCR5 Antibodies with Antiviral Activity against CCR5 Monoclonal Antibody-Resistant HIV-1 Strains," Antimicrob. Agents Chemother., 55(5):2369.
Sergina et al., "Escape from HER family tyrosine kinase inhibitor therapy by the kinase inactive HER3", Nature Jan. 25, 2007; 445(7126): 437-441.
Slamon et al., 1989, "Studies of the HER-2/neu Proto-Oncogene in Human Breast and Ovarian Cancer," Science, 244(4905):707-712.
Tao et al., 2014, "Antagonism of EGFR and HER3 enhances the response to inhibitors of the PI3K-Akt pathway in triple-negative breast cancer", Sci Signal, 7(318):29.
Tom et al., 2008, "Transfection of HEK293-EBNA1 Cells in Suspension with Linear PEI for Production of Recombinant Proteins", CSH Protocols; doi:10.1101/pdb.prot4977.
Zapata et al., 1995, "Engineering linear F(ab')2 fragments for efficient production in *Escherichia coli* and enhanced antiproliferative activity," Protein Eng., 8(10):1057-1062.

* cited by examiner grey, filled histogram = isotype control grey, filled histogram = isotype control

| Antibody | IC50 (nM) |
|---|---|
| SI-1X4.2 (N3) | 4.02 |
| SI-1C5.2 (N) | 2.62 |
| SI-1C1 (3) | N/A* |

* IC50 not calculated - plateau not reached

| Antibody | IC50 (nM) |
|---|---|
| SI-1X4.2 (N3) | 2.28 |
| SI-1C5.2 (N) | 1.75 |
| SI-1C1 (3) | N/A* |

* IC50 not calculated - plateau not reached

| A431 IC50 values (nM) | | | | |
|---|---|---|---|---|
| SI-1C1 | SI-1C3 | SI-1C1 + SI-1C3 | SI-1X1 | SI-1X2 |
| N/A | 0.83 | 1.91 | 6.84 | 0.37 |

| A431 IC50 values (nM) | | | | |
|---|---|---|---|---|
| SI-1C1 | SI-1C6 | SI-1C1 + SI-1C6 | SI-1X5 | SI-1X6 |
| N/A | 0.64 | 0.84 | 1.30 | 0.68 |

| BxPC3 IC50 values (nM) | | | | |
|---|---|---|---|---|
| SI-1C1 | SI-1C3 | SI-1C1 + SI-1C3 | SI-1X1 | SI-1X2 |
| 8.48 | 0.14 | 0.13 | 0.53 | 0.07 |

| BxPC3 IC50 values (nM) | | | | |
|---|---|---|---|---|
| SI-1C1 | SI-1C6 | SI-1C1 + SI-1C6 | SI-1X5 | SI-1X6 |
| 8.48 | 0.37 | ambiguous | 0.01 | 0.03 |

| Antibody | IC50 (nM) |
|---|---|
| SI-1X4.2 (N3) | 0.54 |
| SI-1C5.2 (N) | 27.73 * |
| SI-1C1 (3) | N/A |
| SI-1X5.2 (N) + SI-1C1 (3) | 35.04 * |

* IC50 approximate - baseline not reached

| Antibody | IC50 (nM) |
|---|---|
| SI-1X4.2 (N3) | no baseline |
| SI-1C5.2 (N) | no baseline |
| SI-1C1 (3) | N/A |
| SI-1X5.2 (N) + SI-1C1 (3) | no baseline |

* IC50 approximate - baseline not reached

| Antibody | EC50 (nM) |
|---|---|
| SI-1X6.4 (C3) | 0.008 |
| SI-1C6.2 (C) | 0.009 |
| SI-1C6.2 (C) + SI-1C7 (3) | 0.011 |
| SI-1C7 (3) | N/A* |
| SI-1C4 (2in1) | 0.068 |
| SI-3C9 (control) | - |

* EC50 not calculated - plateau not reached (a)

| Antibody | EC50 (nM) |
|---|---|
| SI-1X4.2 (N3) | 1.49 |
| SI-1C5.2 (N) | N/A* |
| SI-1C5.2 (N) + SI-1C7 (3) | 2.16 |
| SI-1C7 (3) | N/A* |
| SI-1C4 (2in1) | 0.068 |
| SI-3C9 (control) | - |

*EC50 not calculated - plateau not reached (b)

| Antibody | EC50 (nM) |
|---|---|
| SI-1X6.4 (C3) | 0.016 |
| SI-1C6.2 (C) | 0.014 |
| SI-1C6.2 (C) + SI-1C7 (3) | 0.039 |
| SI-1C7 (3) | N/A* |
| SI-1C4 (2in1) | 0.589 |
| SI-3C9 (control) | - |

* EC50 not calculated - plateau not reached (a)

| Antibody | EC50 (nM) |
|---|---|
| SI-1X4.2 (N3) | 2.62 |
| SI-1C5.2 (N) | 1.63 |
| SI-1C5.2 (N) + SI-1C7 (3) | 1.87 |
| SI-1C7 (3) | N/A* |
| SI-1C4 (2in1) | 0.589 |
| SI-3C9 (control) | - |

*EC50 not calculated - plateau not reached (b)

| | Day 0 | Day 3 (37°C) | Day 7 (37°C) | Day 7 (55°C) |
|---|---|---|---|---|
| EC50 | 5.897e-010 | 7.021e-010 | 7.552e-010 | 6.522e-009 |

(a)

| | Day 0 | Day 3 (37°C) | Day 7 (37°C) | Day 7 (55°C) |
|---|---|---|---|---|
| EC50 | 4.293e-010 | 5.089e-010 | 4.667e-010 | 4.248e-009 |

(b)

| | Day 0 | Day 3 (37°C) | Day 7 (37°C) | Day 7 (55°C) |
|---|---|---|---|---|
| EC50 | 2.182e-010 | 2.651e-010 | 2.266e-010 | 1.322e-009 |

(c)

| | Day 0 | Day 3 (37°C) | Day 7 (37°C) | Day 7 (55°C) |
|---|---|---|---|---|
| EC50 | ~ 2.093e-010 | 2.300e-010 | 2.373e-010 | 4.112e-009 |

(d)

BISPECIFIC TETRAVALENT ANTIBODIES AND METHODS OF MAKING AND USING THEREOF

CROSS REFERENCE TO RELATED PATENT APPLICATIONS

This application is continuation of U.S. patent application Ser. No. 15/119,694, filed Aug. 17, 2016, now U.S. Pat. No. 10,919,977, which is a U.S. National Stage PCT/US15/66951, filed Dec. 19, 2015, which claims the benefit of U.S. Provisional Application No. 62/095,348, filed Dec. 22, 2014, the disclosure of each of which is incorporated by reference herein in its entirety.

SEQUENCE LISTING

This application incorporates by reference in its entirety the Computer Readable Form (CRF) of a Substitute Sequence Listing in ASCII text format submitted via Patent Center. The Substitute Sequence Listing text file submitted via Patent Center is entitled "14247-823-999_SUB_SEQ-_LISTING.txt," was created on Sep. 22, 2024, and is 430,494 bytes in size.

TECHNICAL FIELD

The present disclosure generally relates to the technical field of antibody therapeutic agents, and more particularly relates to bispecific tetravalent antibodies against two different members of EGFR family.

BACKGROUND

Overexpression and/or deregulation of members of the ErbB/HER receptor family such as EGFR, HER2, HER3, HER4 have been shown to play an important role in tumorigenesis in cancers. Mutation and amplification of EGFR or HER2 produce aberrant growth signal which activates downstream signaling pathway contributing to tumorigenesis. Therapeutic antibodies and small-molecule inhibitors directed against EGFR and HER2 have been approved for use in the treatment of cancer (Arteaga et al., *Nature Reviews Clinical Oncology* 9 16-32, January 2012). Monoclonal antibodies against members of EGFR family such as EGFR and HER2, have demonstrated good clinical responses in colon cancer (Price et al., The Lancet Oncology 15(6), Pages 569-579, May 2014), squamous cell carcinoma of head and neck (Cohen, *Cancer Treatment Reviews* 40 (2014) 567-577), breast and gastric cancers (Arteaga et al., *Nature Reviews Clinical Oncology* 9 16-32, January 2012). Several therapeutic anti-EGFR antibodies, including cetuximab, panitumumab and nimotuzumab are approved therapeutics for several cancers including metastatic colorectal cancer, head and neck squamous cell carcinoma and glioma (Price and *Cohen, Curr Treat Options Oncol.* 2012 March; 13(1): 35-46; Bode et al., Expert Opin Biol Ther. 2012 December; 12(12):1649-59). Unfortunately, many tumors that initially respond to these therapeutic agents eventually progress due to an acquired resistance to the agents (Jackman et al. *J Clin Oncol* 2010; 28:357-60). Therefore, there exists a need for better cancer therapeutics.

SUMMARY

The disclosure provides bispecific tetravalent antibodies. The bispecific tetravalent antibodies may include an immunoglobulin G (IgG) moiety with two heavy chains and two light chains, and two scFv moieties being covalently connected to either C or N terminals of the heavy or light chains. The IgG moiety may have a binding specificity to a first member of EGFR family. The scFv moiety may have a binding specificity to a second member of the EGFR family. The IgG moiety and two scFv moieties are covalently connected to be functional as a bispecific tetravalent antibody. The objectives and advantages of the disclosure will become apparent from the following detailed description of preferred embodiments thereof in connection with the accompanying drawings.

BRIEF DESCRIPTION OF THE DRAWINGS

Preferred embodiments according to the present disclosure will now be described with reference to the FIGS, in which like reference numerals denote like elements.

DETAILED DESCRIPTION

Figure 1:
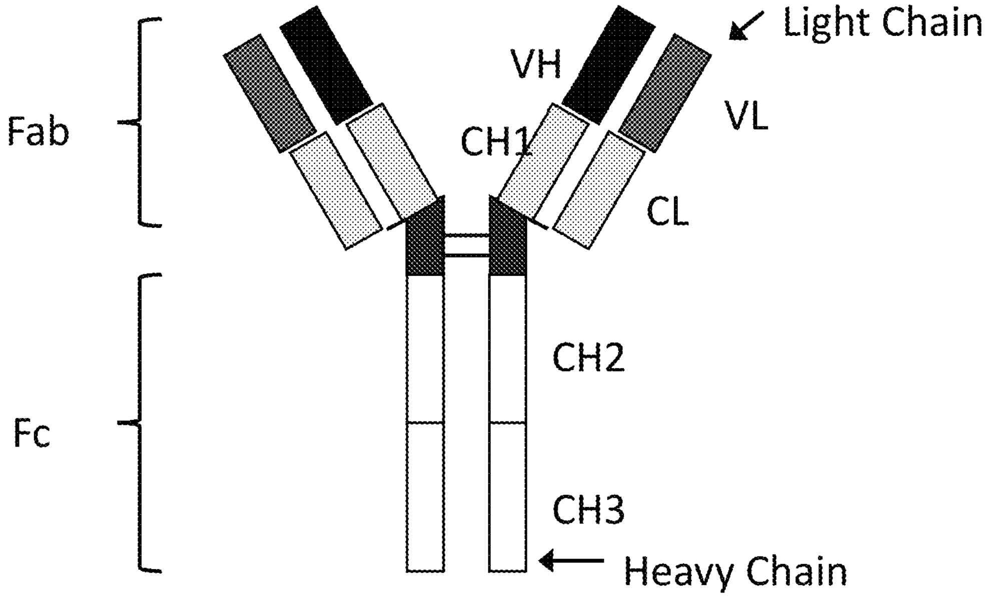
FIG. 1 is a diagram showing the domain structures of an example bivalent monospecific immunoglobulin G (IgG) antibody.

The present disclosure This disclosure provides bispecific tetravalent antibodies with superior therapeutic properties or efficacies over the currently known anti-EGFR antibodies. In one embodiment, the antibodies target two members of EGFR family including, without limitation, EFFR and HER3. The bispecific tetravalent antibodies may inhibit both EGFR and HER3 mediated signaling simultaneously therefore overcome resistance in EGFR inhibitor or monoclonal antibody treatment.

It must be noted that as used herein and in the appended claims, the singular forms "a", "and", and "the" in Throughout this specification and claims, the word "comprise," or variations such as "comprises" or "comprising," will be understood to imply the inclusion of a stated integer or group of integers but not the exclusion of any other integer or group of integers include plural referents unless the context clearly dictates otherwise. "Antibody fragments" comprise a portion of an intact antibody, preferably the antigen-binding or variable region of the intact antibody.

Examples of antibody fragments include Fv, Fab, Fab', F(ab')2, Fab'-SH; diabodies; linear antibodies (see U.S. Pat. No. 5,641,870, Example 2; Zapata et al., Protein Eng. 8(10): 1057-1062 (1995)); single-chain antibody molecules (e.g. scFv). While in the present description, and throughout the specification, reference is made to antibodies and various properties of antibodies, the same disclosure also applies to functional antibody fragments, e.g. dual action Fab fragments.

In one aspect, the bispecific tetravalent antibodies may include an immunoglobulin G (IgG) moiety with two heavy chains and two light chains, and two scFv moieties being covalently connected to either C or N terminals of the heavy or light chains. The IgG moiety may have a binding specificity to a first member of EGFR family. The scFv moiety may have a binding specificity to a second member of the EGFR family. The IgG moiety may provide stability to the scFv moiety. The bispecific tetravalent antibody may block signalling for both AKT and MAPK/ERK pathways and may mediate antibody dependent cell-mediated cytotoxicity (ADCC) towards cells expressing either one or both antigens. In one embodiment, the bispecific tetravalent antibody is capable of binding both antigens simultaneously. In some embodiments, the bispecific tetravalent antibody provides stronger tumour inhibition in proliferation assays in vitro and in vivo than the mono-specific antibody parental control or combination of the mono-specific antibody parental controls.

In one embodiment, the disclosure provides a bispecific tetravalent antibody having two IgG1 heavy chains, two kappa light chains, and two single chain Fv (scFv) domains. The two IgG1 heavy chains and kappa light chains form an IgG moiety with a binding specificity to a first member of the EGFR family.

The two scFv domains have a binding specificity to a second member of the EGFR family, and each scFv domain is connected to the C-terminus of either of the IgG1 heavy chains by a connector with an amino acid sequence (gly-gly-gly-gly-ser)$_n$, also known as $(G_4S)_n$, to provide a IgG1-connector connection. n is an integral of at least 1. For example, n may be 2, 3, 4, 5, 6, 7, 8, 9, 10, or 17. Each scFv domain has a structure order of N terminus-variable heavy-linker-variable light-C terminus. The linker may have an amino acid sequence of (gly-gly-gly-gly-ser)$_m$, also known as $(G_4S)_m$. m may be an integral of at least 2 or at least 3. For example, m may be 3, 4, 5, 6, 11, or 12. In some embodiments, at least one or both of the IgG1 heavy chains are humanized or human. In some embodiments, at least one or both of the kappa light chains are humanized or human.

The EGFR family members may include EGFR, HER2, HER3, a fragment or a derivative thereof. In some embodiments, the first member of the EGFR family may be EGFR, HER2, a fragment or a derivative thereof. In some embodiments, the second member of the EGFR family may be HER3, a fragment or a derivative thereof. In one embodiment, the IgG moiety may have a binding specificity for HER3. In one embodiment, the scFv domains may have a binding specificity for EGFR. In one embodiment, the IgG moiety may have a binding specificity for HER3, and the scFv domains may have a binding specificity for EGFR. In one embodiment, the IgG moiety may have a binding specificity for EGFR. In one embodiment, the scFv domains may have a binding specificity for HER3. In one embodiment, the IgG moiety may a binding specificity for EGFR, and the scFv domains may have a binding specificity for HER3.

In some embodiments, the C terminus of one or both of the IgG1 heavy chains misses an amino acid residue. For example, the lysine reside may be deleted from the C terminus of the IgG1 chain before the connector is fused onto the C-terminus. The deletion of the lysine residue makes the IgG1-connector connection resistant to protease activity.

In some embodiments, one or both of the IgG1 heavy chains contain two mutations in the CH3 domain. For example, the two mutations may be reversion to the common residues in human CH3 domain.

In some embodiments, the IgG1 heavy chains may an amino acid sequences of or with at least 95%, 98% or 99% similarity to SEQ ID NO 7, 15, 23, 31, 39, 47, and 127. In some embodiments, the IgG1 heavy chain, connector, and scFv domain may have an amino acid sequence of or with at least 95%, 98% or 99% similarity to SEQ ID NO 56, 66, 76, 86, 98, 108, 118, and 136. In some embodiments, the kappa light chains may have an amino acid sequence of or with at least 95%, 98% or 99% similarity to SEQ ID NO 3, 11, 19, 27, 35, 43, 51, 61, 71, 81, 92, 103, 113, 123, and 131. In some embodiments, the variable light chain may an amino acid sequence of or with at least 95%, 98% or 99% similarity to SEQ ID NO 4, 12, 20, 28, 36, 44, 52, 62, 72, 82, 93, 104, 114, 124, and 132. In some embodiment, the variable heavy chain may have an amino acid sequence of or with at least 95%, 98% or 99% similarity to SEQ ID NO 8, 16, 24, 32, 40, 48, 57, 67, 77, 87, 99, 109, 119, 128, and 137.

In some embodiments, the IgG moiety has a binding specificity for HER3, and the scFv domains have a binding specificity for EGFR. In one embodiment, the IgG1 heavy chain, connector, and scFv domain have an amino acid sequence of SEQ ID NO 56, and the kappa light chain has an amino acid sequence of SEQ ID NO 51. In one embodiment, the IgG1 heavy chain, connector, and scFv domain have an amino acid sequence of SEQ ID NO 76, and the kappa light chain has an amino acid sequence of SEQ ID NO 71. In one embodiment, the IgG1 heavy chain, connector, and scFv domain have an amino acid sequence of SEQ ID NO 108, and the kappa light chain has an amino acid sequence of SEQ ID NO 103.

In some embodiments, the IgG moiety has a binding specificity for EGFR, and the scFv domains have a binding specificity for HER3. In one embodiment, the IgG1 heavy chain, connector, and scFv domain have an amino acid sequence of SEQ ID NO 66, and the kappa light chain has an amino acid sequence of SEQ ID NO 61. In one embodiment, the IgG1 heavy chain, connector, and scFv domain have an amino acid sequence of SEQ ID NO 86, and the kappa light chain has an amino acid sequence of SEQ ID NO 81. In one embodiment, the IgG1 heavy chain, connector, and scFv domain have an amino acid sequence of SEQ ID NO 98, and the kappa light chain has an amino acid sequence of SEQ ID NO 92. In one embodiment, the IgG1 heavy chain, connector, and scFv domain have an amino acid sequence of SEQ ID NO 118, and the kappa light chain has an amino acid sequence of SEQ ID NO 113. In one embodiment, the IgG1 heavy chain, connector, and scFv domain have an amino acid sequence of SEQ ID NO 136, and the kappa light chain has an amino acid sequence of SEQ ID NO 131.

The bispecific tetravalent antibodies have the activity of inhibiting cancer cell growth. In certain embodiments, an antibody of the invention has a dissociation constant (Kd) of ≤80 nM, ≤50 nM, ≤30 nM, ≤20 nM, ≤10 nM, or ≤0.1 nM for its target EGRF or HER3. The antibody may bind to both targets simultaneously. In some embodiments, the antibody binds to EGRF and HER3 with a Kd less than 50 nM. In some embodiments, the antibody binds to EGRF and/or HER3 with a Kd less than 40, 30, 25, 20, 19, 18 or 10 nM. In one embodiment, the antibody binds to EGRF with a Kd less than 30 nM and binds to HER3 with a Kd less than 30 nM. In one embodiment, the antibody binds to EGRF with a Kd less than 50 nM and binds to HER3 with a Kd less than 50 nM simultaneously.

In another aspect, the disclosure provides isolated nucleic acids encoding the bispecific tetravalent antibodies or its sub-component disclosed herein. The sub-component may be the IgG1 heavy chain, the kappa light chain, the variable light chain, or the variable heavy chain.

In a further aspect, the disclosure provides expression vectors having the isolated nucleic acids encoding the bispecific tetravalent antibody or its sub-component disclosed herein. The vectors may be expressible in a host cell. The host cell may be prokaryotic or eukaryotic.

In a further aspect, the disclosure provides host cells having the isolated nucleic acids encoding the bispecific tetravalent antibodies disclosed herein or the expression vectors including such nucleic acid sequences.

In a further aspect, the disclosure provides methods for producing bispecific tetravalent antibodies. In one embodiment, the method may include culturing the above-described host cells so that the antibody is produced.

In a further aspect, the disclosure provides immunoconjugates including the bispecific tetravalent antibodies described herein and a cytotoxic agent.

In a further aspect, the disclosure provides pharmaceutical compositions. The pharmaceutical composition may include the bispecific tetravalent antibodies or the immunoconjugates described herein and a pharmaceutically acceptable carrier. In some embodiments, the composition may further include radioisotope, radionuclide, a toxin, a therapeutic agent, a chemotherapeutic agent or a combination thereof.

In a further aspect, the disclosure provides methods of treating a subject with a cancer. In one embodiment, the method includes the step of administering to the subject an effective amount of a bispecific tetravalent antibody described herein. The cancer may include cells expressing at least two members of EGFR family including, for example, EGFR, HER2, HER3, a fragment or a derivative thereof. The cancer may be breast cancer, colorectal cancer, pancreatic cancer, head and neck cancer, melanoma, ovarian cancer, prostate cancer, and non-small lung cell cancer, glioma, esophageal cancer, nasopharyngeal cancer, anal cancer, rectal cancer, gastric cancer, bladder cancer, cervical cancer and brain cancer.

In one embodiment, the method may further include co-administering an effective amount of a therapeutic agent. The therapeutic agent may be, for example, an antibody, a chemotherapy agent, a cytotoxic agent, an enzyme, or a combination thereof. In some embodiments, the therapeutic agent may be an anti-estrogen agent, a receptor tyrosine inhibitor, or a combination thereof. In some embodiments, the therapeutic agent may be biologics. In one embodiment, the therapeutic agent may be a checkpoint inhibitor. In some embodiments, the therapeutic agent may include PD1, PDL1, CTLA4, 4-1BB, OX40, GITR, TIM3, LAG3, TIGIT, CD40, CD27, HVEM, BTLA, VISTA, B7H4, a derivative, a conjugate, or a fragment thereof. In some embodiments, the therapeutic agent may be capecitabine, cisplatin, trastuzumab, fulvestrant, tamoxifen, letrozole, exemestane, anastrozole, aminoglutethimide, testolactone, vorozole, formestane, fadrozole, letrozole, erlotinib, lafatinib, dasatinib, gefitinib, imatinib, pazopinib, lapatinib, sunitinib, nilotinib, sorafenib, nab-palitaxel, or a derivative thereof. In some embodiments, the subject in need of such treatment is a human.

In one embodiment, the disclosure provides methods for treating a subject by administering to the subject an effective amount of the bispecific tetravalent antibody to inhibit a biological activity of a HER receptor.

In one embodiment, the disclosure provides solutions having an effective concentration of the bispecific tetravalent antibody. In one embodiment, the solution is blood plasma in a subject.

A diagram of the general structure of IgG is shown in FIG. 1.

Figure 2:
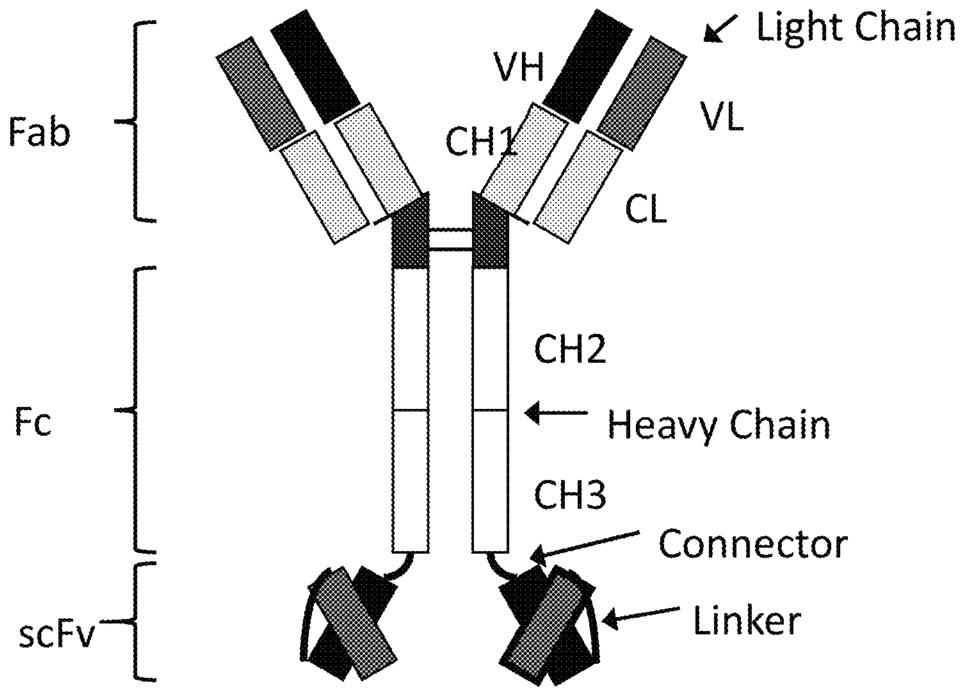
FIG. 2 is a diagram showing the domain structure of an example tetravalent bispecific antibody comprising an IgG moiety and two scFv moieties in accordance with one embodiment of the present invention.
Figure 3:
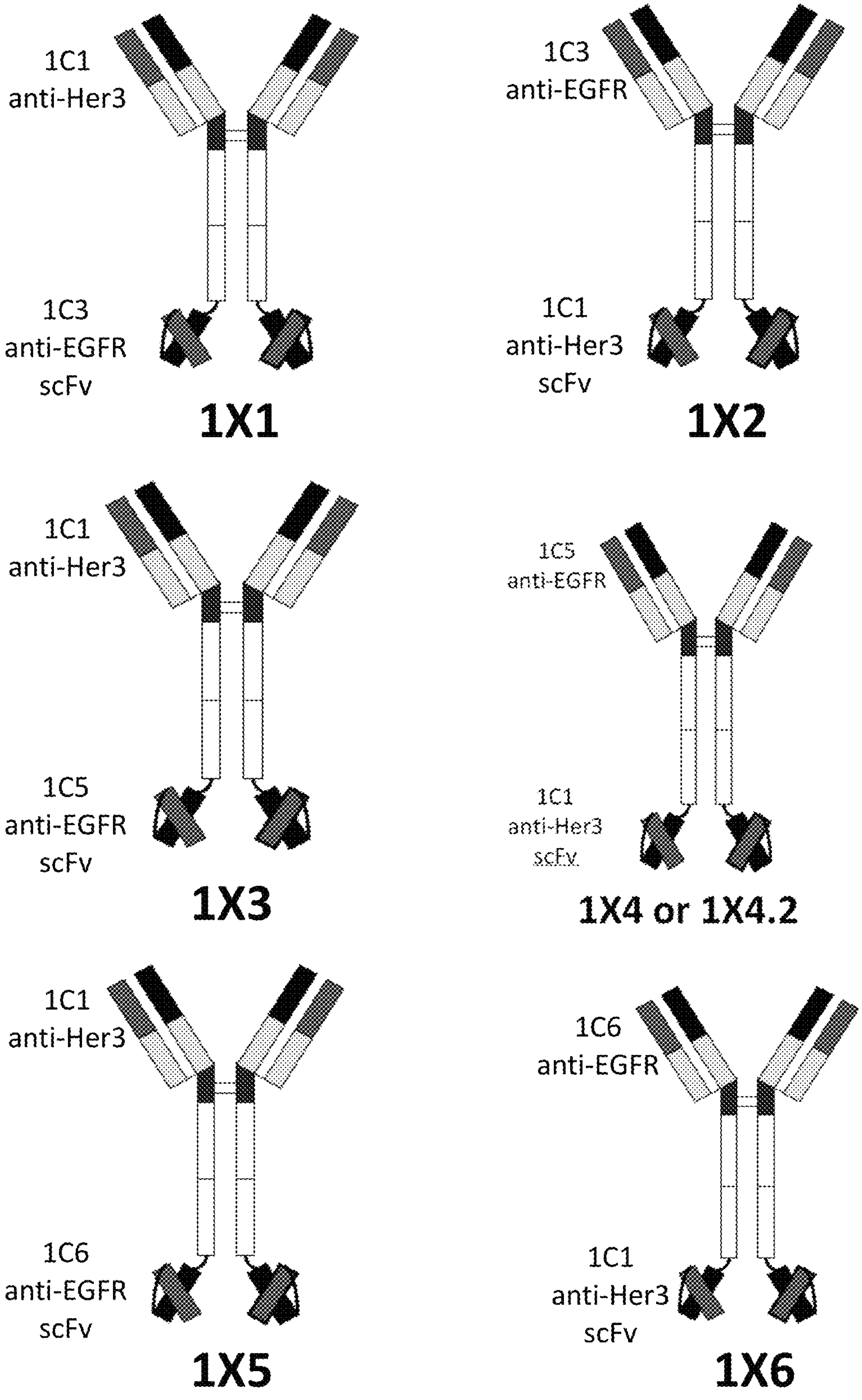
FIG. 3 shows the domain structure diagrams of example tetravalent bispecific antibodies 1×1, 1×2, 1×3, 1×4, 1×4.2, 1×5 and 1×6.

A diagram of the representative structure of the bispecific tetravalent antibodies according to some embodiments is shown in FIG. 2. In this example, the bispecific tetravalent antibody includes two human IgG1 heavy chains, two human kappa light chains, and two single chain Fv (scFv) domains. The two human IgG1 heavy chains and human kappa light chains form an IgG moiety with a binding specificity to one member of the EGFR family, and each of the two scFv domains is connected to the C-terminal residue of either of the human IgG1 heavy chains by a connector with an amino acid sequence of gly-gly-gly-gly-ser-gly-gly-gly-gly-ser ($(G_4S)_2$). Each scFv domain is in the order: N terminus-variable heavy-linker-variable light-C terminus. The linker is comprised of amino acid sequence of gly-gly-gly-gly-ser-gly-gly-gly-gly-ser-gly-gly-gly-gly-ser, also known as $(G_4S)_3$. For some embodiments of the bispecific tetravalent antibodies, the CH1, CH2, CH3, CL, Connector and Linker amino acid sequences are identical. Each bispecific tetravalent antibody has a bivalent anti-HER3 binding specificity on one end of the antibody and a bivalent anti-EGFR binding specificity on the other end. One pair of anti-HER3 variable heavy chain and variable light chain is designated as 1C1, and four pairs of anti-EGFR variable heavy chains and variable light chains are designated as 1C3, 1C5, 1C5.2, 1C6 and 1C6.4, respectively. The bispecific tetravalent antibodies are designated as 1×1, 1×2, 1×3, 1×4, 1×4.2, 1×5, 1×5.2, 1×6, and 1×6.4 In addition, a control molecule 1C4 (also designated as SI-1C4) was used in some of the studies. 1C4 is a bispecific antibody against EGFR and HER3 built on the two-in-one platform described by Schaefer et. al., 2011 (Schaefer et al., Cancer Cell. 2011 Oct. 18; 20(4):472-86). IC4 has a similar structure to a monoclonal antibody. The molecule can bind to either EGFR or HER3 on each Fab arm, but cannot engage both targets simultaneously on each Fab arm.

Variable light chain, variable heavy chain and single chain Fv (scFv) DNA fragments were generated by gene synthesis through an outside vendor. Human Gamma-1 heavy chain and human kappa light chain DNA fragments were generated by gene synthesis through an outside vendor. The fragments were assembled together by DNA ligation using restriction sites and cloned into a vector that is designed for transient expression in mammalian cells. The vector contains a strong CMV-derived promoter, and other upstream and downstream elements required for transient expression. The resulting IgG expression plasmids were verified as containing the expected DNA sequences by DNA sequencing.

Transient expression of the antibody constructs was achieved using transfection of suspension-adapted HEK293F cells with linear PEI as described elsewhere (see CSH Protocols; 2008; doi:10.1101/pdb.prot4977). Antibodies were purified from the resulting transfection supernatants using protein affinity chromatography and size exclusion chromatography if needed. Protein quality is analysed by Superdex 200 column. Protein used for all the assays have a purity of greater than 90%.

The bispecific antibody may be used for the treatment of cancer types with EGFR and HER3 co-expressions, including without limitation colon cancer, head and neck squamous cell carcinoma, lung cancer, glioma, pancreatic cancer, nasopharyngeal cancer and other cancer types.

The bispecific antibody is of tetravalent dual specificity. The example antibody may include an IgG and two scFv, which provides two different binding specificities compared to mono-specific antibody IgG. The IgG component provides stability and improved serum half-life over other bispecific antibodies that used only scFv such as BiTE technology (Lutterbuese et al., *Proceedings of the National Academy of Sciences of the United States of America* 107.28 (2010): 12605-12610. PMC. Web. 2 Dec. 2014) and others (for example, U.S. Pat. No. 7,332,585B2). It is also capable of mediating ADCC while those without Fc component cannot (for example, U.S. Pat. No. 7,332,585B2). The tetravalent dual specificity nature provides the bispecific antibody a simultaneous binding capability over some other bispecific antibodies, which may only bind one antigen at a time (Schanzer et al, *Antimicrob. Agents Chemother.* 2011, 55(5):2369; EP272942A1).

For the convenient of narration, the sequences of or related to the bispecific antibodies are summarized in TABLE 1 herein below.

TABLE 1

Summary of nucleotide and amino acid sequences of or related to the bispecific antibodies.

| | |
|---|---|
| SI-1C1 SEQUENCES | |
| SEQ ID NO 1 | SI-1C1 LIGHT CHAIN FULL-LENGTH NUCLEOTIDE SEQUENCE |
| SEQ ID NO 2 | SI-1C1 LIGHT CHAIN VARIABLE LIGHT CHAIN NUCLEOTIDE SEQUENCE |
| SEQ ID NO 3 | SI-1C1 LIGHT CHAIN FULL-LENGTH AMINO ACID SEQUENCE. HUMAN KAPPA CONSTANT DOMAIN IS UNDERLINED |
| SEQ ID NO 4 | SI-1C1 LIGHT CHAIN VARIABLE LIGHT CHAIN AMINO ACID SEQUENCE. COMPLEMENTARITY DETERMINING REGIONS ARE UNDERLINED |
| SEQ ID NO 5 | SI-1C1 HEAVY CHAIN FULL-LENGTH NUCLEOTIDE SEQUENCE |
| SEQ ID NO 6 | SI-1C1 HEAVY CHAIN VARIABLE HEAVY CHAIN NUCLEOTIDE SEQUENCE |
| SEQ ID NO 7 | SI-1C1 HEAVY CHAIN FULL-LENGTH AMINO ACID SEQUENCE. HUMAN GAMMA-1 DOMAIN IS UNDERLINED |
| SEQ ID NO 8 | SI-1C1 HEAVY CHAIN VARIABLE HEAVY CHAIN AMINO ACID SEQUENCE. COMPLEMENTARITY DETERMINING REGIONS ARE UNDERLINED |
| SI-1C3 SEQUENCES | |
| SEQ ID NO 9 | SI-1C3 LIGHT CHAIN FULL-LENGTH NUCLEOTIDE SEQUENCE |
| SEQ ID NO 10 | SI-1C3 LIGHT CHAIN VARIABLE LIGHT CHAIN NUCLEOTIDE SEQUENCE |
| SEQ ID NO 11 | SI-1C3 LIGHT CHAIN FULL-LENGTH AMINO ACID SEQUENCE. HUMAN KAPPA CONSTANT DOMAIN IS UNDERLINED |
| SEQ ID NO 12 | SI-1C3 LIGHT CHAIN VARIABLE LIGHT CHAIN AMINO ACID SEQUENCE. COMPLEMENTARITY DETERMINING REGIONS ARE UNDERLINED |
| SEQ ID NO 13 | SI-1C3 HEAVY CHAIN FULL-LENGTH NUCLEOTIDE SEQUENCE |

TABLE 1-continued

| Summary of nucleotide and amino acid sequences of or related to the bispecific antibodies. | |
|---|---|
| SEQ ID NO 14 | SI-1C3 HEAVY CHAIN VARIABLE HEAVY CHAIN NUCLEOTIDE SEQUENCE |
| SEQ ID NO 15 | SI-1C3 HEAVY CHAIN FULL-LENGTH AMINO ACID SEQUENCE. HUMAN GAMMA-1 DOMAIN IS UNDERLINED |
| SEQ ID NO 16 | SI-1C3 HEAVY CHAIN VARIABLE HEAVY CHAIN AMINO ACID SEQUENCE. COMPLEMENTARITY DETERMINING REGIONS ARE UNDERLINED |
| SI-1C4 SEQUENCES | |
| SEQ ID NO 17 | SI-1C4 LIGHT CHAIN FULL-LENGTH NUCLEOTIDE SEQUENCE |
| SEQ ID NO 18 | SI-1C4 LIGHT CHAIN VARIABLE LIGHT CHAIN NUCLEOTIDE SEQUENCE |
| SEQ ID NO 19 | SI-1C4 LIGHT CHAIN FULL-LENGTH AMINO ACID SEQUENCE. HUMAN KAPPA CONSTANT DOMAIN IS UNDERLINED |
| SEQ ID NO 20 | SI-1C4 LIGHT CHAIN VARIABLE LIGHT CHAIN AMINO ACID SEQUENCE. COMPLEMENTARITY DETERMINING REGIONS ARE UNDERLINED |
| SEQ ID NO 21 | SI-1C4 HEAVY CHAIN FULL-LENGTH NUCLEOTIDE SEQUENCE |
| SEQ ID NO 22 | SI-1C4 HEAVY CHAIN VARIABLE HEAVY CHAIN NUCLEOTIDE SEQUENCE |
| SEQ ID NO 23 | SI-1C4 HEAVY CHAIN FULL-LENGTH AMINO ACID SEQUENCE. HUMAN GAMMA-1 DOMAIN IS UNDERLINED |
| SEQ ID NO 24 | SI-1C4 HEAVY CHAIN VARIABLE HEAVY CHAIN AMINO ACID SEQUENCE. COMPLEMENTARITY DETERMINING REGIONS ARE UNDERLINED |
| SI-1C5 SEQUENCES | |
| SEQ ID NO 25 | SI-1C5 LIGHT CHAIN FULL-LENGTH NUCLEOTIDE SEQUENCE |
| SEQ ID NO 26 | SI-1C5 LIGHT CHAIN VARIABLE LIGHT CHAIN NUCLEOTIDE SEQUENCE |
| SEQ ID NO 27 | SI-1C5 LIGHT CHAIN FULL-LENGTH AMINO ACID SEQUENCE. HUMAN KAPPA CONSTANT DOMAIN IS UNDERLINED |
| SEQ ID NO 28 | SI-1C5 LIGHT CHAIN VARIABLE LIGHT CHAIN AMINO ACID SEQUENCE. COMPLEMENTARITY DETERMINING REGIONS ARE UNDERLINED |
| SEQ ID NO 29 | SI-1C5 HEAVY CHAIN FULL-LENGTH NUCLEOTIDE SEQUENCE |
| SEQ ID NO 30 | SI-1C5 HEAVY CHAIN VARIABLE HEAVY CHAIN NUCLEOTIDE SEQUENCE |
| SEQ ID NO 31 | SI-1C5 HEAVY CHAIN FULL-LENGTH AMINO ACID SEQUENCE. HUMAN GAMMA-1 DOMAIN IS UNDERLINED |
| SEQ ID NO 32 | SI-1C5 HEAVY CHAIN VARIABLE HEAVY CHAIN AMINO ACID SEQUENCE. COMPLEMENTARITY DETERMINING REGIONS ARE UNDERLINED |
| SI-1C5.2 SEQUENCES | |
| SEQ ID NO 33 | SIIC5.2 LIGHT CHAIN FULL-LENGTH NUCLEOTIDE SEQUENCE |
| SEQ ID NO 34 | SI-1C5.2 LIGHT CHAIN VARIABLE LIGHT CHAIN NUCLEOTIDE SEQUENCE |
| SEQ ID NO 35 | SI-1C5.2 LIGHT CHAIN FULL-LENGTH AMINO ACID SEQUENCE. HUMAN KAPPA CONSTANT DOMAIN IS UNDERLINED |
| SEQ ID NO 36 | SI-1C5.2 LIGHT CHAIN VARIABLE LIGHT CHAIN AMINO ACID SEQUENCE. COMPLEMENTARITY DETERMINING REGIONS ARE UNDERLINED |
| SEQ ID NO 37 | SI-1C5.2 HEAVY CHAIN FULL-LENGTH NUCLEOTIDE SEQUENCE |
| SEQ ID NO 38 | SI-1C5.2 HEAVY CHAIN VARIABLE HEAVY CHAIN NUCLEOTIDE SEQUENCE |
| SEQ ID NO 39 | SI-1C5.2 HEAVY CHAIN FULL-LENGTH AMINO ACID SEQUENCE. HUMAN GAMMA-1 DOMAIN IS UNDERLINED |
| SEQ ID NO 40 | SI-1C5.2 HEAVY CHAIN VARIABLE HEAVY CHAIN AMINO ACID SEQUENCE. COMPLEMENTARITY DETERMINING REGIONS ARE UNDERLINED |

TABLE 1-continued

| Summary of nucleotide and amino acid sequences of or related to the bispecific antibodies. | |
|---|---|
| SI-1C6 SEQUENCES | |
| SEQ ID NO 41 | SI-1C6 LIGHT CHAIN FULL-LENGTH NUCLEOTIDE SEQUENCE |
| SEQ ID NO 42 | SI-1C6 LIGHT CHAIN VARIABLE LIGHT CHAIN NUCLEOTIDE SEQUENCE |
| SEQ ID NO 43 | SI-1C6 LIGHT CHAIN FULL-LENGTH AMINO ACID SEQUENCE. HUMAN KAPPA CONSTANT DOMAIN IS UNDERLINED |
| SEQ ID NO 44 | SI-1C6 LIGHT CHAIN VARIABLE LIGHT CHAIN AMINO ACID SEQUENCE. COMPLEMENTARITY DETERMINING REGIONS ARE UNDERLINED |
| SEQ ID NO 45 | SI-1C6 HEAVY CHAIN FULL-LENGTH NUCLEOTIDE SEQUENCE |
| SEQ ID NO 46 | SI-1C6 HEAVY CHAIN VARIABLE HEAVY CHAIN NUCLEOTIDE SEQUENCE |
| SEQ ID NO 47 | SI-1C6 HEAVY CHAIN FULL-LENGTH AMINO ACID SEQUENCE. HUMAN GAMMA-1 DOMAIN IS UNDERLINED |
| SEQ ID NO 48 | SI-1C6 HEAVY CHAIN VARIABLE HEAVY CHAIN AMINO ACID SEQUENCE. COMPLEMENTARITY DETERMINING REGIONS ARE UNDERLINED |
| SI-1X1 SEQUENCES | |
| SEQ ID NO 49 | SI1X1 LIGHT CHAIN FULL-LENGTH NUCLEOTIDE SEQUENCE |
| SEQ ID NO 50 | SI-1X1 LIGHT CHAIN VARIABLE LIGHT CHAIN NUCLEOTIDE SEQUENCE |
| SEQ ID NO 51 | SI-1X1 LIGHT CHAIN FULL-LENGTH AMINO ACID SEQUENCE. HUMAN KAPPA CONSTANT DOMAIN IS UNDERLINED |
| SEQ ID NO 52 | SI-1X1 LIGHT CHAIN VARIABLE LIGHT CHAIN AMINO ACID SEQUENCE. COMPLEMENTARITY DETERMINING REGIONS ARE UNDERLINED |
| SEQ ID NO 53 | SI1X1 BISPECIFIC HEAVY CHAIN FULL-LENGTH NUCLEOTIDE SEQUENCE |
| SEQ ID NO 54 | SI-1X1 BISPECIFIC HEAVY CHAIN VARIABLE HEAVY CHAIN NUCLEOTIDE SEQUENCE |
| SEQ ID NO 55 | SI-1X1 BISPECIFIC HEAVY CHAIN SCFV NUCLEOTIDE SEQUENCE |
| SEQ ID NO 56 | SI-1X1 BISPECIFIC HEAVY CHAIN FULL-LENGTH AMINO ACID SEQUENCE. HUMAN GAMMA-1 DOMAIN IS UNDERLINED, CONNECTOR IS IN ITALICS, SCFV IS IN BOLD |
| SEQ ID NO 57 | SI-1X1 BISPECIFIC HEAVY CHAIN VARIABLE HEAVY CHAIN AMINO ACID SEQUENCE. COMPLEMENTARITY DETERMINING REGIONS ARE UNDERLINED |
| SEQ ID NO 58 | SI1X1 BISPECIFIC HEAVY CHAIN SCFV AMINO ACID SEQUENCE. ORDER: VH-LINKER-VL. COMPLEMENTARITY DETERMINING REGIONS ARE UNDERLINED. LINKER IS IN BOLD ITALICS |
| SI-1X2 SEQUENCES | |
| SEQ ID NO 59 | SI-1X2 LIGHT CHAIN FULL-LENGTH NUCLEOTIDE SEQUENCE |
| SEQ ID NO 60 | SI-1X2 LIGHT CHAIN VARIABLE LIGHT CHAIN NUCLEOTIDE SEQUENCE |
| SEQ ID NO 61 | SI-1X2 LIGHT CHAIN FULL-LENGTH AMINO ACID SEQUENCE. HUMAN KAPPA CONSTANT DOMAIN IS UNDERLINED |
| SEQ ID NO 62 | SI-1X2 LIGHT CHAIN VARIABLE LIGHT CHAIN AMINO ACID SEQUENCE. COMPLEMENTARITY DETERMINING REGIONS ARE UNDERLINED |
| SEQ ID NO 63 | SI-1X2 BISPECIFIC HEAVY CHAIN FULL-LENGTH NUCLEOTIDE SEQUENCE |
| SEQ ID NO 64 | SI-1X2 BISPECIFIC HEAVY CHAIN VARIABLE HEAVY CHAIN NUCLEOTIDE SEQUENCE |
| SEQ ID NO 65 | SI-1X2 BISPECIFIC HEAVY CHAIN SCFV NUCLEOTIDE SEQUENCE |
| SEQ ID NO 66 | SI-1X2 BISPECIFIC HEAVY CHAIN FULL-LENGTH AMINO ACID SEQUENCE. HUMAN GAMMA-1 DOMAIN IS UNDERLINED, CONNECTOR IS IN ITALICS, SCFV IS IN BOLD |

TABLE 1-continued

| Summary of nucleotide and amino acid sequences of or related to the bispecific antibodies. | |
|---|---|
| SEQ ID NO 67 | SI-1X2 BISPECIFIC HEAVY CHAIN VARIABLE HEAVY CHAIN AMINO ACID SEQUENCE. COMPLEMENTARITY DETERMINING REGIONS ARE UNDERLINED |
| SEQ ID NO 68 | SI-1X2 BISPECIFIC HEAVY CHAIN SCFV AMINO ACID SEQUENCE. ORDER: VH-LINKER-VL. COMPLEMENTARITY DETERMINING REGIONS ARE UNDERLINED. LINKER IS IN BOLD ITALICS |
| SI-1X3 SEQUENCES | |
| SEQ ID NO 69 | SI-1X3 LIGHT CHAIN FULL-LENGTH NUCLEOTIDE SEQUENCE |
| SEQ ID NO 70 | SI-1X3 LIGHT CHAIN VARIABLE LIGHT CHAIN NUCLEOTIDE SEQUENCE |
| SEQ ID NO 71 | SI-1X3 LIGHT CHAIN FULL-LENGTH AMINO ACID SEQUENCE. HUMAN KAPPA CONSTANT DOMAIN IS UNDERLINED |
| SEQ ID NO 72 | SI-1X3 LIGHT CHAIN VARIABLE LIGHT CHAIN AMINO ACID SEQUENCE. COMPLEMENTARITY DETERMINING REGIONS ARE UNDERLINED |
| SEQ ID NO 73 | SI-1X3 BISPECIFIC HEAVY CHAIN FULL-LENGTH NUCLEOTIDE SEQUENCE |
| SEQ ID NO 74 | SI-1X3 BISPECIFIC HEAVY CHAIN VARIABLE HEAVY CHAIN NUCLEOTIDE SEQUENCE |
| SEQ ID NO 75 | SI-1X3 BISPECIFIC HEAVY CHAIN SCFV NUCLEOTIDE SEQUENCE |
| SEQ ID NO 76 | SI-1X3 BISPECIFIC HEAVY CHAIN FULL-LENGTH AMINO ACID SEQUENCE. HUMAN GAMMA-1 DOMAIN IS UNDERLINED, CONNECTOR IS IN ITALICS, SCFV IS IN BOLD |
| SEQ ID NO 77 | SI-1X3 BISPECIFIC HEAVY CHAIN VARIABLE HEAVY CHAIN AMINO ACID SEQUENCE. COMPLEMENTARITY DETERMINING REGIONS ARE UNDERLINED |
| SEQ ID NO 78 | SI-1X3 BISPECIFIC HEAVY CHAIN SCFV AMINO ACID SEQUENCE. ORDER: VH-LINKER-VL. COMPLEMENTARITY DETERMINING REGIONS ARE UNDERLINED. LINKER IS IN BOLD ITALICS |
| SI-1X4 SEQUENCES | |
| SEQ ID NO 79 | SI-1X4 LIGHT CHAIN FULL-LENGTH NUCLEOTIDE SEQUENCE |
| SEQ ID NO 80 | SI-1X4 LIGHT CHAIN VARIABLE LIGHT CHAIN NUCLEOTIDE SEQUENCE |
| SEQ ID NO 81 | SI-1X4 LIGHT CHAIN FULL-LENGTH AMINO ACID SEQUENCE. HUMAN KAPPA CONSTANT DOMAIN IS UNDERLINED |
| SEQ ID NO 82 | SI-1X4 LIGHT CHAIN VARIABLE LIGHT CHAIN AMINO ACID SEQUENCE. COMPLEMENTARITY DETERMINING REGIONS ARE UNDERLINED |
| SEQ ID NO 83 | SI-1X4 BISPECIFIC HEAVY CHAIN FULL-LENGTH NUCLEOTIDE SEQUENCE |
| SEQ ID NO 84 | SI-1X4 BISPECIFIC HEAVY CHAIN VARIABLE HEAVY CHAIN NUCLEOTIDE SEQUENCE |
| SEQ ID NO 85 | SI-1X4 BISPECIFIC HEAVY CHAIN SCFV NUCLEOTIDE SEQUENCE |
| SEQ ID NO 86 | SI-1X4 BISPECIFIC HEAVY CHAIN FULL-LENGTH AMINO ACID SEQUENCE. HUMAN GAMMA-1 DOMAIN IS UNDERLINED, CONNECTOR IS IN ITALICS, SCFV IS IN BOLD |
| SEQ ID NO 87 | SI-1X4 BISPECIFIC HEAVY CHAIN VARIABLE HEAVY CHAIN AMINO ACID SEQUENCE. COMPLEMENTARITY DETERMINING REGIONS ARE UNDERLINED |
| SEQ ID NO 88 | SI-1X4 BISPECIFIC HEAVY CHAIN SCFV AMINO ACID SEQUENCE. ORDER: VH-LINKER-VL. COMPLEMENTARITY DETERMINING REGIONS ARE UNDERLINED. LINKER IS IN BOLD ITALICS |
| SI-1X4.2 SEQUENCES | |
| SEQ ID NO 89 | SI-1X4.2 LIGHT CHAIN FULL-LENGTH NUCLEOTIDE SEQUENCE |
| SEQ ID NO 90 | SI-1X4.2 LIGHT CHAIN VARIABLE LIGHT CHAIN NUCLEOTIDE SEQUENCE |

TABLE 1-continued

| Summary of nucleotide and amino acid sequences of or related to the bispecific antibodies. | |
|---|---|
| SEQ ID NO 91 | SI-1X4.2 LIGHT CHAIN VARIABLE LIGHT CHAIN NUCLEOTIDE SEQUENCE CODON OPTIMIZED FOR CHO EXPRESSION |
| SEQ ID NO 92 | SI-1X4.2 LIGHT CHAIN FULL-LENGTH AMINO ACID SEQUENCE. HUMAN KAPPA CONSTANT DOMAIN IS UNDERLINED |
| SEQ ID NO 93 | SI-1X4.2 LIGHT CHAIN VARIABLE LIGHT CHAIN AMINO ACID SEQUENCE. COMPLEMENTARITY DETERMINING REGIONS ARE UNDERLINED |
| SEQ ID NO 94 | SI-1X4.2 BISPECIFIC HEAVY CHAIN FULL-LENGTH NUCLEOTIDE SEQUENCE |
| SEQ ID NO 95 | SI-1X4.2 BISPECIFIC HEAVY CHAIN VARIABLE HEAVY CHAIN NUCLEOTIDE SEQUENCE |
| SEQ ID NO 96 | SI-1X4.2 BISPECIFIC HEAVY CHAIN VARIABLE HEAVY CHAIN NUCLEOTIDE SEQUENCE CODON OPTIMIZED FOR CHO EXPRESSION |
| SEQ ID NO 97 | SI-1X4.2 BISPECIFIC HEAVY CHAIN SCFV NUCLEOTIDE SEQUENCE |
| SEQ ID NO 98 | SI-1X4.2 BISPECIFIC HEAVY CHAIN FULL-LENGTH AMINO ACID SEQUENCE. HUMAN GAMMA-1 DOMAIN IS UNDERLINED, CONNECTOR IS IN ITALICS, SCFV IS IN BOLD |
| SEQ ID NO 99 | SI-1X4.2 BISPECIFIC HEAVY CHAIN VARIABLE HEAVY CHAIN AMINO ACID SEQUENCE. COMPLEMENTARITY DETERMINING REGIONS ARE UNDERLINED |
| SEQ ID NO 100 | SI-1X4.2 BISPECIFIC HEAVY CHAIN SCFV AMINO ACID SEQUENCE. ORDER: VH-LINKER-VL. COMPLEMENTARITY DETERMINING REGIONS ARE UNDERLINED. LINKER IS IN BOLD ITALICS |
| SI-1X5 SEQUENCES | |
| SEQ ID NO 101 | SI-1X5 LIGHT CHAIN FULL-LENGTH NUCLEOTIDE SEQUENCE |
| SEQ ID NO 102 | SI-1X5 LIGHT CHAIN VARIABLE LIGHT CHAIN NUCLEOTIDE SEQUENCE |
| SEQ ID NO 103 | SI-1X5 LIGHT CHAIN FULL-LENGTH AMINO ACID SEQUENCE. HUMAN KAPPA CONSTANT DOMAIN IS UNDERLINED |
| SEQ ID NO 104 | SI-1X5 LIGHT CHAIN VARIABLE LIGHT CHAIN AMINO ACID SEQUENCE. COMPLEMENTARITY DETERMINING REGIONS ARE UNDERLINED |
| SEQ ID NO 105 | SI-1X5 BISPECIFIC HEAVY CHAIN FULL-LENGTH NUCLEOTIDE SEQUENCE |
| SEQ ID NO 106 | SI-1X5 BISPECIFIC HEAVY CHAIN VARIABLE HEAVY CHAIN NUCLEOTIDE SEQUENCE |
| SEQ ID NO 107 | SI-1X5 BISPECIFIC HEAVY CHAIN SCFV NUCLEOTIDE SEQUENCE |
| SEQ ID NO 108 | SI-1X5 BISPECIFIC HEAVY CHAIN FULL-LENGTH AMINO ACID SEQUENCE. HUMAN GAMMA-1 DOMAIN IS UNDERLINED, CONNECTOR IS IN ITALICS, SCFV IS IN BOLD |
| SEQ ID NO 109 | SI-1X5 BISPECIFIC HEAVY CHAIN VARIABLE HEAVY CHAIN AMINO ACID SEQUENCE. COMPLEMENTARITY DETERMINING REGIONS ARE UNDERLINED |
| SEQ ID NO 110 | SI-1X5 BISPECIFIC HEAVY CHAIN SCFV AMINO ACID SEQUENCE. ORDER: VH-LINKER-VL. COMPLEMENTARITY DETERMINING REGIONS ARE UNDERLINED. LINKER IS IN BOLD ITALICS |
| SI-1X6 SEQUENCES | |
| SEQ ID NO 111 | SI-1X6 LIGHT CHAIN FULL-LENGTH NUCLEOTIDE SEQUENCE |
| SEQ ID NO 112 | SI-1X6 LIGHT CHAIN VARIABLE LIGHT CHAIN NUCLEOTIDE SEQUENCE |
| SEQ ID NO 113 | SI-1X6 LIGHT CHAIN FULL-LENGTH AMINO ACID SEQUENCE. HUMAN KAPPA CONSTANT DOMAIN IS UNDERLINED |
| SEQ ID NO 114 | SI-1X6 LIGHT CHAIN VARIABLE LIGHT CHAIN AMINO ACID SEQUENCE. COMPLEMENTARITY DETERMINING REGIONS ARE UNDERLINED |
| SEQ ID NO 115 | SI-1X6 BISPECIFIC HEAVY CHAIN FULL-LENGTH NUCLEOTIDE SEQUENCE |
| SEQ ID NO 116 | SI-1X6 BISPECIFIC HEAVY CHAIN VARIABLE HEAVY CHAIN NUCLEOTIDE SEQUENCE |

TABLE 1-continued

| Summary of nucleotide and amino acid sequences of or related to the bispecific antibodies. | |
|---|---|
| SEQ ID NO 117 | SI-1X6 BISPECIFIC HEAVY CHAIN SCFV NUCLEOTIDE SEQUENCE |
| SEQ ID NO 118 | SI-1X6 BISPECIFIC HEAVY CHAIN FULL-LENGTH AMINO ACID SEQUENCE. HUMAN GAMMA-1 DOMAIN IS UNDERLINED, CONNECTOR IS IN ITALICS, SCFV IS IN BOLD |
| SEQ ID NO 119 | SI-1X6 BISPECIFIC HEAVY CHAIN VARIABLE HEAVY CHAIN AMINO ACID SEQUENCE. COMPLEMENTARITY DETERMINING REGIONS ARE UNDERLINED |
| SEQ ID NO 120 | SI-1X6 BISPECIFIC HEAVY CHAIN SCFV AMINO ACID SEQUENCE. ORDER: VH-LINKER-VL. COMPLEMENTARITY DETERMINING REGIONS ARE UNDERLINED. LINKER IS IN BOLD ITALICS |
| SI-1C6.2 SEQUENCES | |
| SEQ ID NO 121 | SI-1C6.2 LIGHT CHAIN FULL-LENGTH NUCLEOTIDE SEQUENCE |
| SEQ ID NO 122 | SI-1C6.2 LIGHT CHAIN VARIABLE LIGHT CHAIN NUCLEOTIDE SEQUENCE |
| SEQ ID NO 123 | SI-1C6.2 LIGHT CHAIN FULL-LENGTH AMINO ACID SEQUENCE. HUMAN KAPPA CONSTANT DOMAIN IS UNDERLINED |
| SEQ ID NO 124 | SI-1C6.2 LIGHT CHAIN VARIABLE LIGHT CHAIN AMINO ACID SEQUENCE. COMPLEMENTARITY DETERMINING REGIONS ARE UNDERLINED |
| SEQ ID NO 125 | SI-1C6.2 HEAVY CHAIN FULL-LENGTH NUCLEOTIDE SEQUENCE |
| SEQ ID NO 126 | SI-1C6.2 HEAVY CHAIN VARIABLE HEAVY CHAIN NUCLEOTIDE SEQUENCE |
| SEQ ID NO 127 | SI-1C6.2 HEAVY CHAIN FULL-LENGTH AMINO ACID SEQUENCE. HUMAN GAMMA-1 DOMAIN IS UNDERLINED |
| SEQ ID NO 128 | SI-1C6.2 HEAVY CHAIN VARIABLE HEAVY CHAIN AMINO ACID SEQUENCE. COMPLEMENTARITY DETERMINING REGIONS ARE UNDERLINED |
| SI-1X6.4 SEQUENCES | |
| SEQ ID NO 129 | SI-1X6.4 LIGHT CHAIN FULL-LENGTH NUCLEOTIDE SEQUENCE |
| SEQ ID NO 130 | SI-1X6.4 LIGHT CHAIN VARIABLE LIGHT CHAIN NUCLEOTIDE SEQUENCE |
| SEQ ID NO 131 | SI-1X6.4 LIGHT CHAIN FULL-LENGTH AMINO ACID SEQUENCE. HUMAN KAPPA CONSTANT DOMAIN IS UNDERLINED |
| SEQ ID NO 132 | SI-1X6.4 LIGHT CHAIN VARIABLE LIGHT CHAIN AMINO ACID SEQUENCE. COMPLEMENTARITY DETERMINING REGIONS ARE UNDERLINED |
| SEQ ID NO 133 | SI-1X6.4 BISPECIFIC HEAVY CHAIN FULL-LENGTH NUCLEOTIDE SEQUENCE |
| SEQ ID NO 134 | SI-1X6.4 BISPECIFIC HEAVY CHAIN VARIABLE HEAVY CHAIN NUCLEOTIDE SEQUENCE |
| SEQ ID NO 135 | SI-1X6.4 BISPECIFIC HEAVY CHAIN SCFV NUCLEOTIDE SEQUENCE |
| SEQ ID NO 136 | SI-1X6.4 BISPECIFIC HEAVY CHAIN FULL-LENGTH AMINO ACID SEQUENCE. HUMAN GAMMA-1 DOMAIN IS UNDERLINED, CONNECTOR IS IN ITALICS, SCFV IS IN BOLD |
| SEQ ID NO 137 | SI-1X6.4 BISPECIFIC HEAVY CHAIN VARIABLE HEAVY CHAIN AMINO ACID SEQUENCE. COMPLEMENTARITY DETERMINING REGIONS ARE UNDERLINED |
| SEQ ID NO 138 | SI-1X6.4 BISPECIFIC HEAVY CHAIN SCFV AMINO ACID SEQUENCE. ORDER: VH-LINKER-VL. COMPLEMENTARITY DETERMINING REGIONS ARE UNDERLINED. LINKER IS IN BOLD ITALICS |

EXAMPLES

While The following examples are provided by way of illustration only and not by way of limitation. Those of skill in the art will readily recognize a variety of non-critical parameters that could be changed or modified to yield essentially the same or similar results.

Example 1: Sequence Differences Between SI-1×4 and SI-1×4.2

Figure 4:
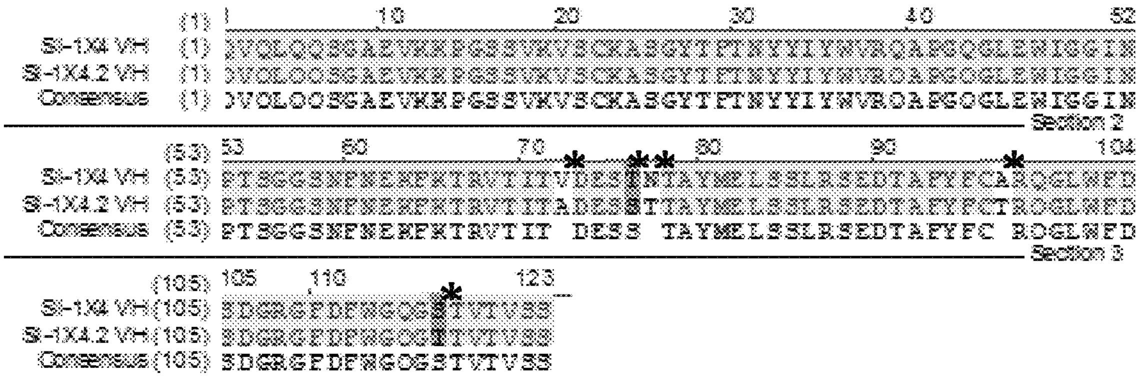
FIG. 4 shows the VH domain sequence comparison between SI-1×4 and SI-1×4.2 showing the 5 amino acid differences.

SI-1×4.2 is a modification of SI-1×4 molecule and contained 5 amino acid changes as follows: V71A, T75S, N76S, A93T and S107T using the Kabat numbering system. Some of these changes especially positions 75, 76 and 93 potentially made interaction with antigen even though these are not in the CDR loops and are essential for binding and activity. FIG. 4 shows the 5 amino acid differences between SI-1×4.2 and SI-1×4.

Figure 5:
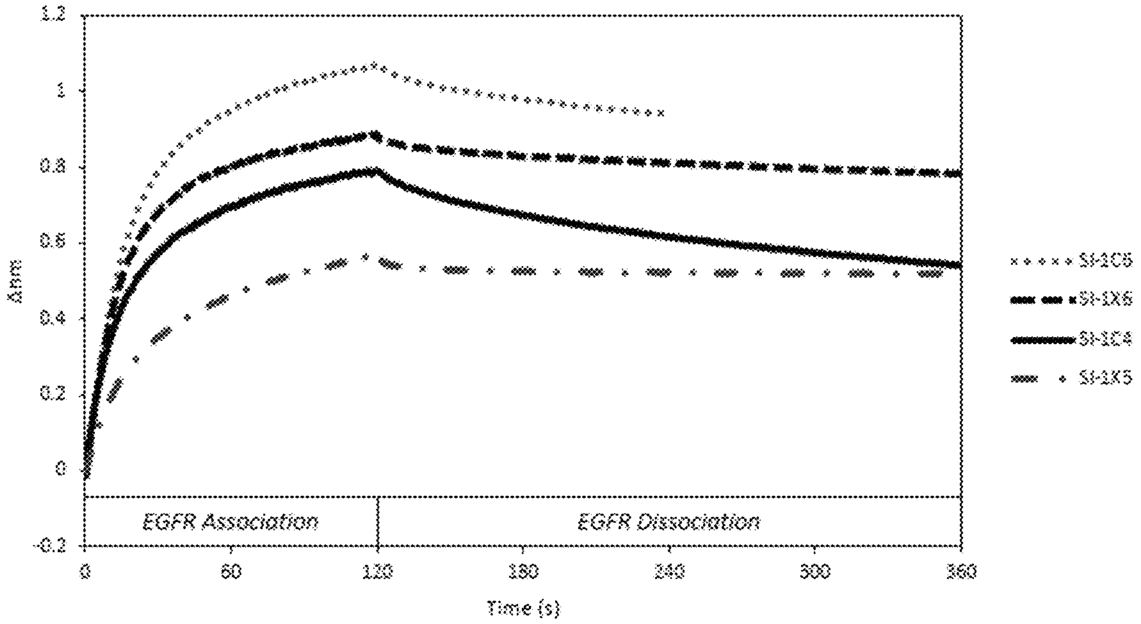
FIGS. 5 and 6 are graphs showing monomeric EGFR binding by BLI.
Figure 6:
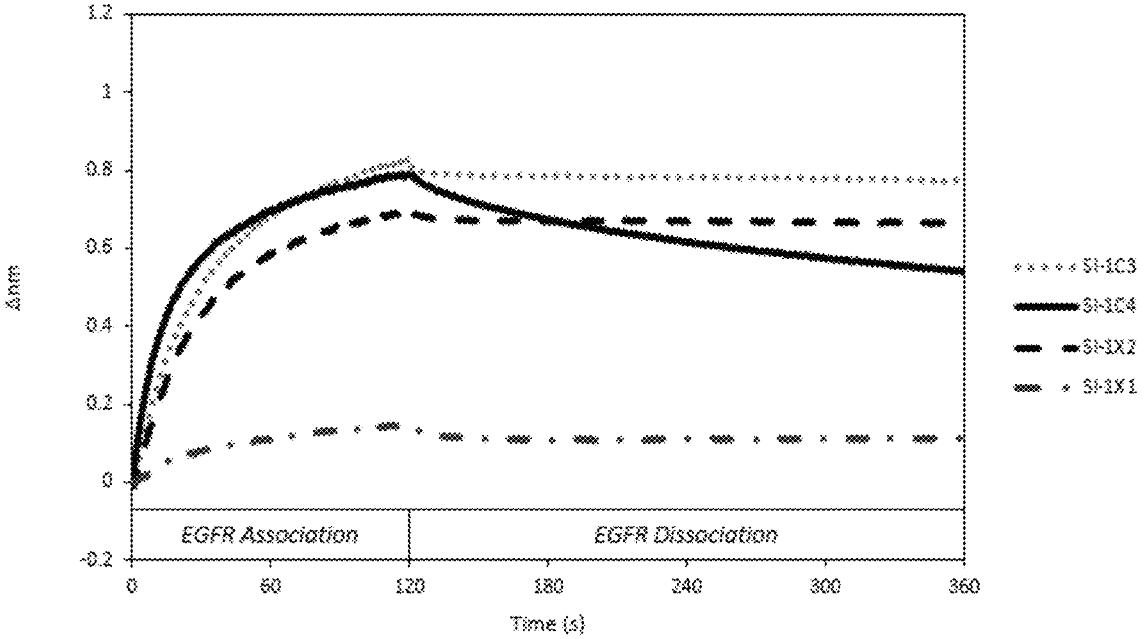
Figure 7:
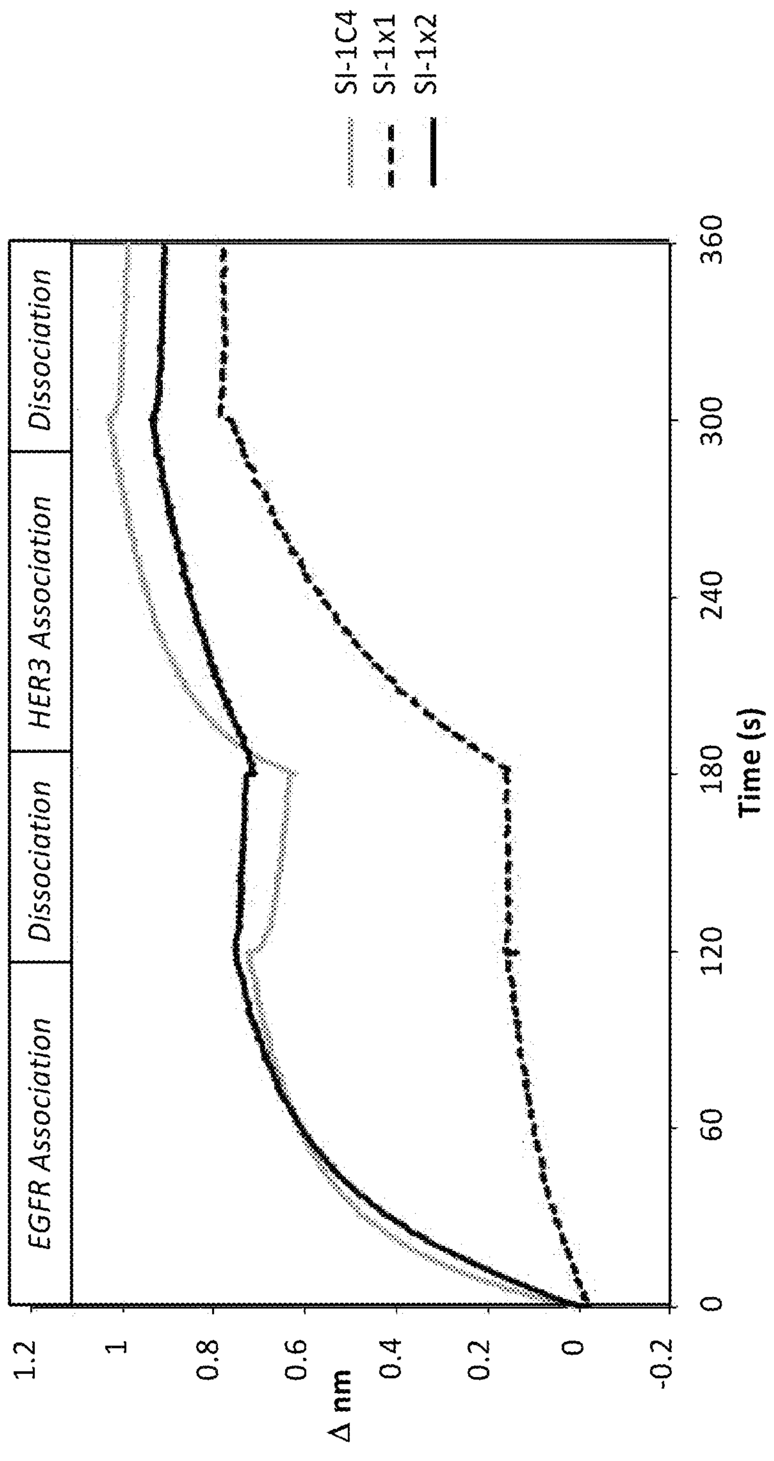
FIGS. 7, 8, and 9 are graphs showing bispecific ELI binding.
Figure 8:
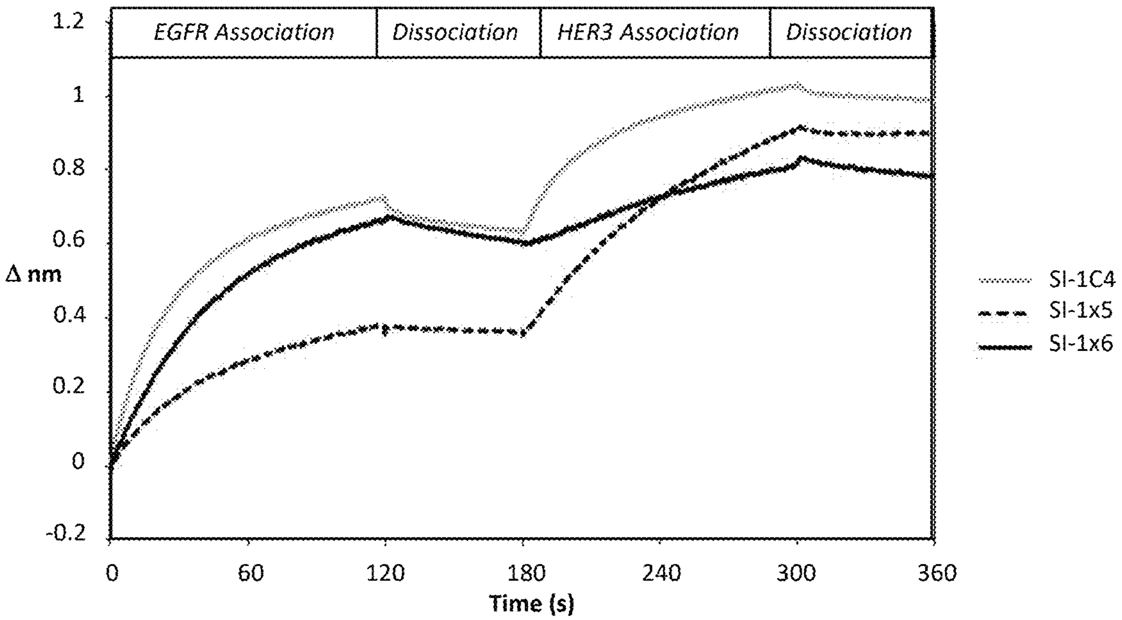

Example 2: Characterization of Antibodies Against Epidermal Growth Factor Receptor Using BLI Monomeric EGFR extracellular domain binding was measured in a biolayer interferometry (BLI) binding assay on a BLitz instrument (ForteBio, Inc.). 25 μg/mL of SI-1C3, SI-1C4, SI-1C6, SI-1×1, SI-1×2, SI-1×5, and SI-1×6 were diluted in PBS and captured on anti-hulgG Fc BLitz biosensor tips for 120 seconds. Tips were washed for 30 seconds in PBS and moved to an EGFR (ProSpec Bio, PKA-344) sample for binding at 588 nM. Binding of EGFR ECD to the tips was recorded as biolayer interferometry signals (Δnm) over an association time of 120 seconds. Tips were moved to PBS and dissociation was observed for 240 seconds (*SI-1C6 dissociation time of only 120 seconds observed). FIGS. 5 and 6 report data starting at the association step of EGFR to the antibody-loaded biosensor. Each Figure shows comparison to SI-1C4 as a benchmark antibody.

Since SI-1C3 and SI-1×2 share their EGFR binding domain displayed as a Fab, their binding profiles are similar and stronger than the scFv form displayed on SI-1×1 (FIG. 6). Each has a very slow off-rate to EGFR compared to SI-1C4 and is not affected by their on-rate. SI-1×1 may show weaker on-rate binding to EGFR, but stays bound very strongly. The same trend is observed in FIG. 5, where the Fab versions of the EGFR binding domains displayed on SI-1C6 and SI-1×6 bind at a faster rate than their representative scFv displayed on SI-1×5. Having the EGFR binding domain on the Fab side of the bispecifics antibody appears to bind with faster on-rates than the scFv versions, yet exhibit similar off-rates. SI-1×3 and SI-1×4 do not exhibit monomeric EGFR binding in this assay (data not shown) and dimeric EGFR binding is investigated in an ELISA below.

Example 3: Characterization of Antibodies Against EGFR and Her3 Using BL1

Bispecific binding to EGFR and Her3 extracellular domains was measured in a biolayer interferometry (BLI) binding assay on a BLitz instrument (ForteBio, Inc.). 200 nM of SI-1C1, SI-1C3, SI-1C4, SI-1C6, SI-1×1, SI-1×2, SI-1×3, SI-1×4, SI-1×5, and SI-1×6 were diluted in 1× Kinetics Buffer (ForteBio, Inc.) and captured on anti-hulgG Fc BLitz biosensor tips for 120 seconds. Tips were washed in KB for 30 seconds and moved to an EGFR sample (ProSpec Bio, PKA-344) for binding at 200 nM. Binding of EGFR ECD to the tips was recorded as biolayer interferometry signals (Anm) over an association time of 120 seconds. Tips were moved to KB and dissociation was observed for 60 seconds. The process was repeated with Her3 ECD sample (Sino Biological, 10201-H08H-10) at 200 nM for 120 seconds and a similar dissociation step of 60 seconds in KB. FIGS. 8-10 7-9 report data starting at the association step of EGFR to the antibody-loaded biosensor. Antibodies are able to exhibit simultaneous bispecific binding of EGFR and Her3 while being bound by the Fc to the sensor. As observed in FIG. 7 and FIG. 8, the display of the EGFR binding domain as Fab (SI-1×2, SI-1×6) has stronger on-rate binding than their scFv forms (SI-1×1, SI-1×5, respectively). Here, both EGFR and Her3 exhibit the same Fab>>scFv on-rate trend. SI-1×3 and SI-1×4 do not exhibit binding to monomeric EGFR, however each has the ability to bind Her3, as expected since each molecule uses the same αHer3 binding domain as SI-1×1, SI-1×2, SI-1×5, and SI-1×6. SI-1×3 and SI-1×4 are investigated for dimeric EGFR binding in an ELISA below.

Example 4: Dimeric EGFR ELISA Assay

Figure 9:
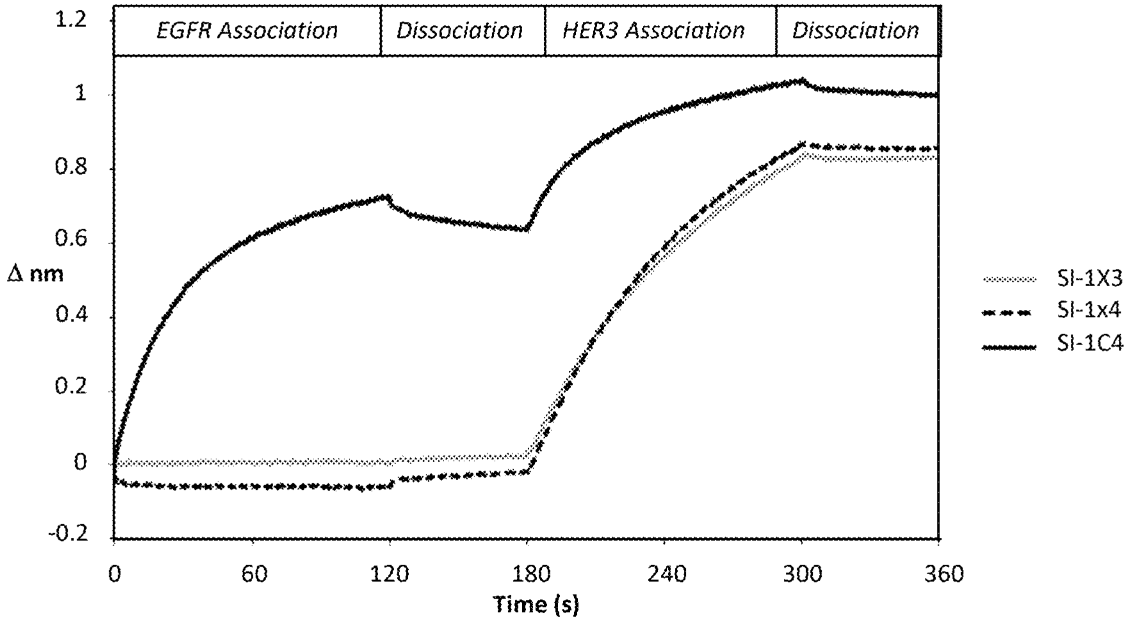

As observed earlier, SI-1×3 and SI-1×4 were unable to bind a monomeric form of EGFR in a BLI assay (FIG. 9). It has been suggested that in order for the αEGFR binding domain used in SI-1C5, SI-1×3, and SI-1×4 to bind to EGFR in vitro, bivalent binding is required (Perez et al, *Chin Clin Oncol* 2014; 3(1):5). To observe this, we utilized ELISA for antibody binding relative to other EGFR binding antibodies using a dimeric form of EGFR.

Figure 10:
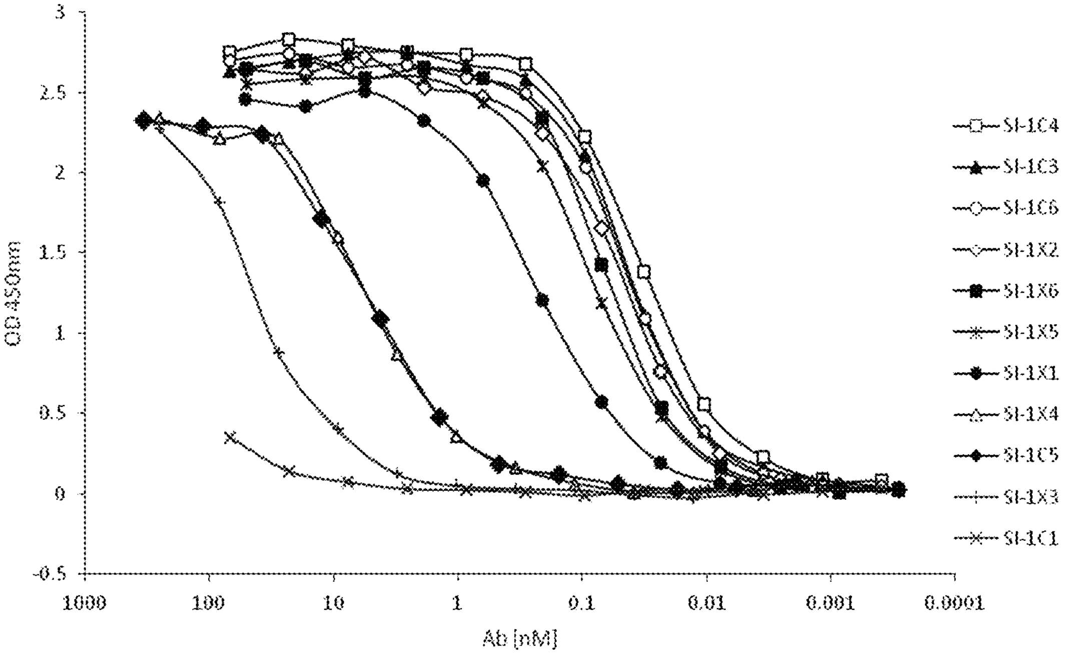
FIG. 10 is a graph showing dimeric EGFR ELISA.

ELISA was performed using dimeric EGFR ECD reagent, SI-2C1, fused to rabbit Fc created in house. EGFR was coated onto Maxisorp immunoplates (Nunc) at 3 μg/mL in PBS at 4° C. overnight. Plates were blocked in PBS with 3% BSA and 0.05% Tween20 for 2 hours at room temperature. Antibodies were captured at starting at 10ug/mL except for SI-1C5, SI-1×3, and SI-1×4 which started at 50 μg/mL for (reported in nM), all with 3× dilutions in PBST (1% BSA) for 1 hour at room temperature. Goat αhuman IgG-HRP antibody (Jackson ImmunoResearch, 109-035-098) was used for detection of the Fc portion of the antibodies at 1:2000 dilution in PBST (1% BSA) and developed in TMB (Thermo Scientific) for 5 minutes with 2M $H_2SO_4$ as a stop solution. 3 washes with PBST (1% BSA) were performed between each step. All data points were performed in triplicate and collected at 450 nm (FIG. 10). SI-1C5, SI-1×3, and SI-1×4 all bound to the dimeric EGFR ECD in this ELISA format at high concentrations as compared to the other molecules.

Example 5: Binding Kinetics of 1C5.2 and 1×4.2 using Octet

Figure 11:
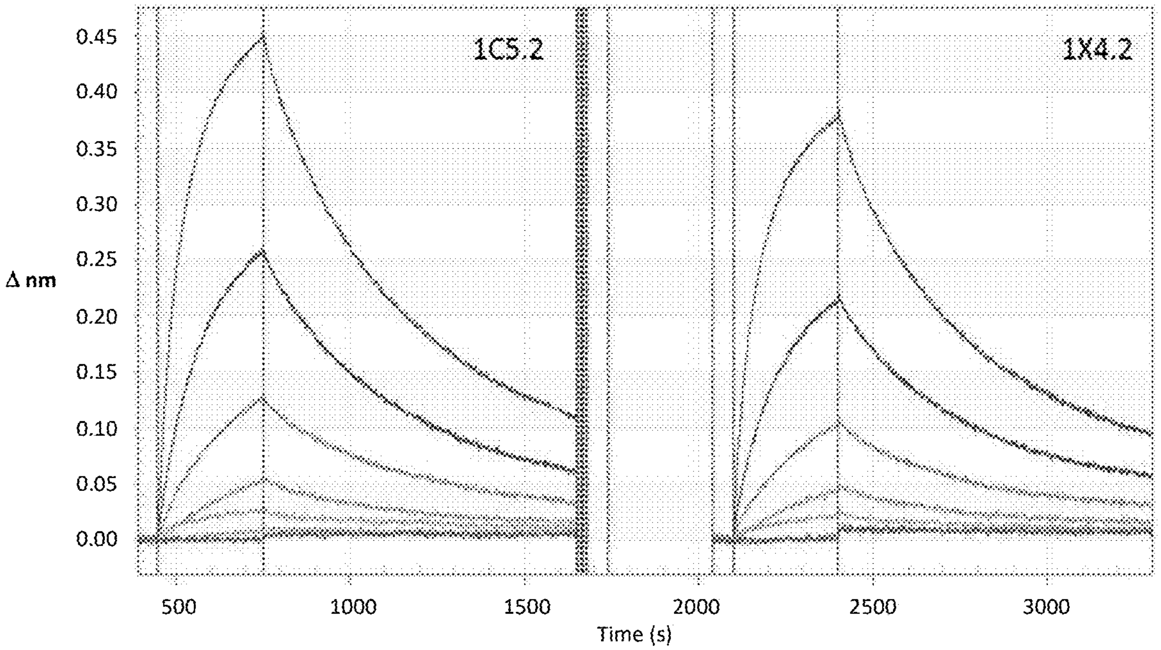
FIG. 11 shows binding kinetics of SI-1C5.2 and SI-1×4.2 with monomeric EGFR as analyzed by Octet.

Kinetics determined using ForteBio Octet Red96 instrument with anti-human Fc sensors (ForteBio, AHC #18-5060). Binding experiments performed at 30° C. with 1000 RPM mixing. EGFR protein is extracellular domain (Met 1-Ser 645) of human EGFR with a C-terminal polyhistidine tag. All samples diluted in 10× Kinetics Buffer (ForteBio #18-5032). 1C5.2, 1×6 and 1×4.2 were loaded onto 8 sensors at 10 μg/ml each for 300 seconds followed by a Baseline for 60 seconds in 10× Kinetics Buffer. Association with EGFR protein was performed for 300 seconds with each sensor in a single concentration of EGFR protein (300, 100, 33.33, 11.11, 3.705, 1.235, 0.4116 and 0 nM). Dissociation was then performed in 10× Kinetics Buffer for 900 seconds. A typical association and dissociation trace for 1C5.2 and 1×4.2 is shown in FIG. 11.

Data analysis was performed using ForteBio Data Analysis Software v9.0. Software curve-fitting was performed and the four most optimal curve fits for each 1C5.2 (TABLE 2), 1×4.2 (TABLE 3) and 1×6 (TABLE 4) were used and averaged to determine KD, k(on) and k(dis). The average KD for SI-1C5.2 and SI-1×4.2 were 19.2 nM and 18.4 nM respectively. The average KD for SI-1C6 was 3.04 nM 1C5.2 and 1×4.2 contained five amino acid changes as compared to 1C5 and 1×4 as described in example 1. These changes accounted for improved binding to EGFR ECD when compared to data generated for 1C5 and 1×4 in FIG. 10.

TABLE 2

Summary of KD, KON and KDIS for 1C5.2

| | EGFR (NM) | KD (M) | KON (1/MS) | KDIS (1/S) |
|---|---|---|---|---|
| SI-1C5.2 | 300 | 3.74E−08 | 4.61E+04 | 1.72E−03 |
| SI-1C5.2 | 100 | 2.23E−08 | 7.89E+04 | 1.76E−03 |
| SI-1C5.2 | 33.3 | 9.94E−09 | 1.60E+05 | 1.59E−03 |
| SI-1C5.2 | 11.1 | 7.08E−09 | 2.12E+05 | 1.50E−03 |
| AVERAGES | | 1.92E−08 | 1.24E+05 | 1.64E−03 |

TABLE 3

Summary of KD, KON and KDIS for 1X4.2

| | EGFR (NM) | KD (M) | KON (1/MS) | KDIS (1/S) |
|---|---|---|---|---|
| SI-1X4.2 | 300 | 3.69E−08 | 4.63E+04 | 1.71E−03 |
| SI-1X4.2 | 100 | 2.10E−08 | 7.88E+04 | 1.65E−03 |
| SI-1X4.2 | 33.3 | 9.44E−09 | 1.58E+05 | 1.49E−03 |
| SI-1X4.2 | 11.1 | 6.19E−09 | 2.18E+05 | 1.35E−03 |
| AVERAGES | | 1.84E−08 | 1.25E+05 | 1.55E−03 |

TABLE 4

Summary of KD, KON and KDIS for 1X6

| | EGFR (NM) | KD (M) | KON (1/MS) | KDIS (1/S) |
|---|---|---|---|---|
| SI-1C6 | 300 | 3.04E−09 | 4.11E+05 | 1.25E−03 |
| SI-1C6 | 100 | 3.04E−09 | 4.11E+05 | 1.25E−03 |
| SI-1C6 | 33.3 | 3.04E−09 | 4.11E+05 | 1.25E−03 |
| SI-1C6 | 11.1 | 3.04E−09 | 4.11E+05 | 1.25E−03 |
| AVERAGES | | 3.04E−09 | 4.11E+05 | 1.25E−03 |

Figure 12:
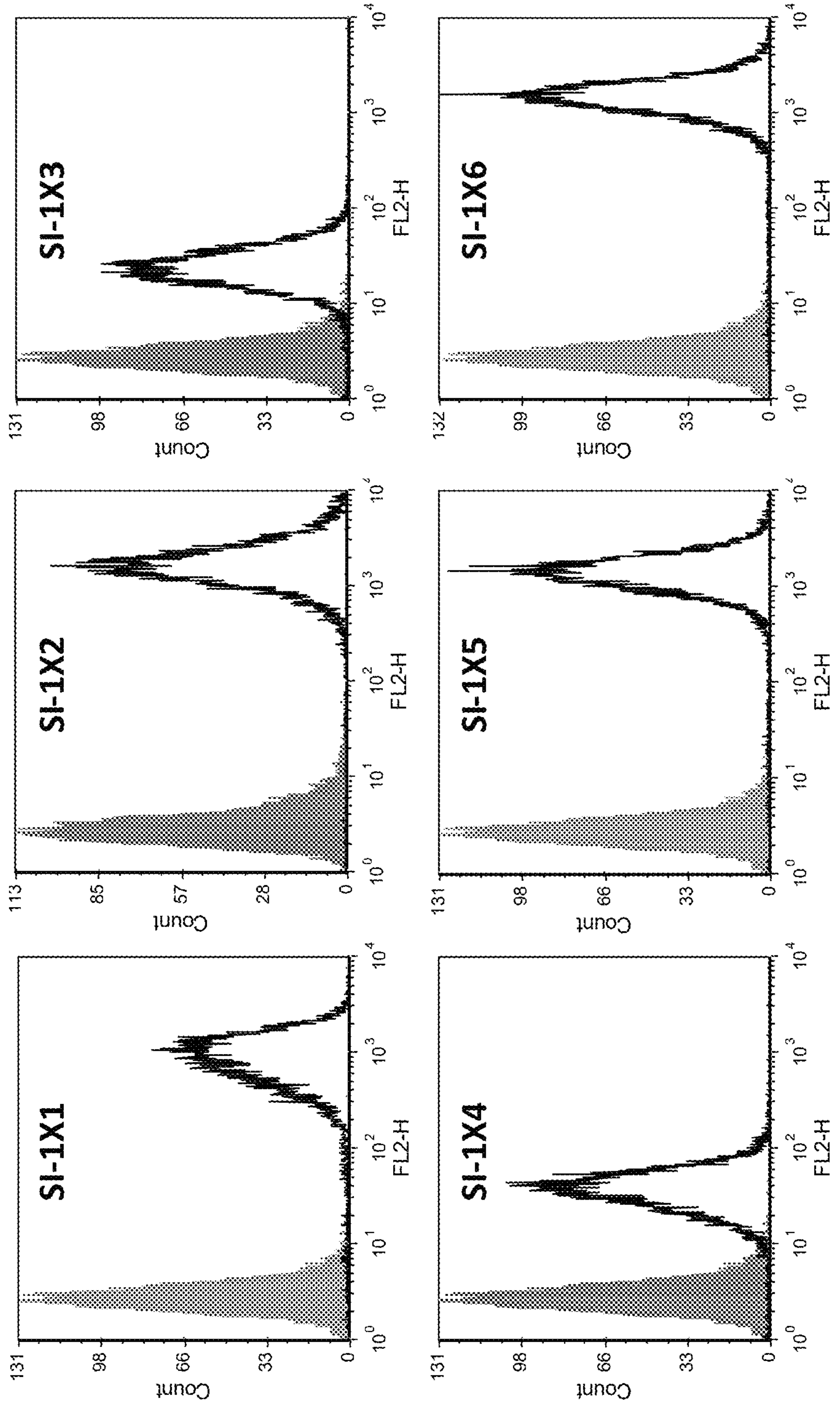
FIG. 12 shows flow cytometric analysis of SI-1× antibodies binding to A431 cells.
Figure 13:
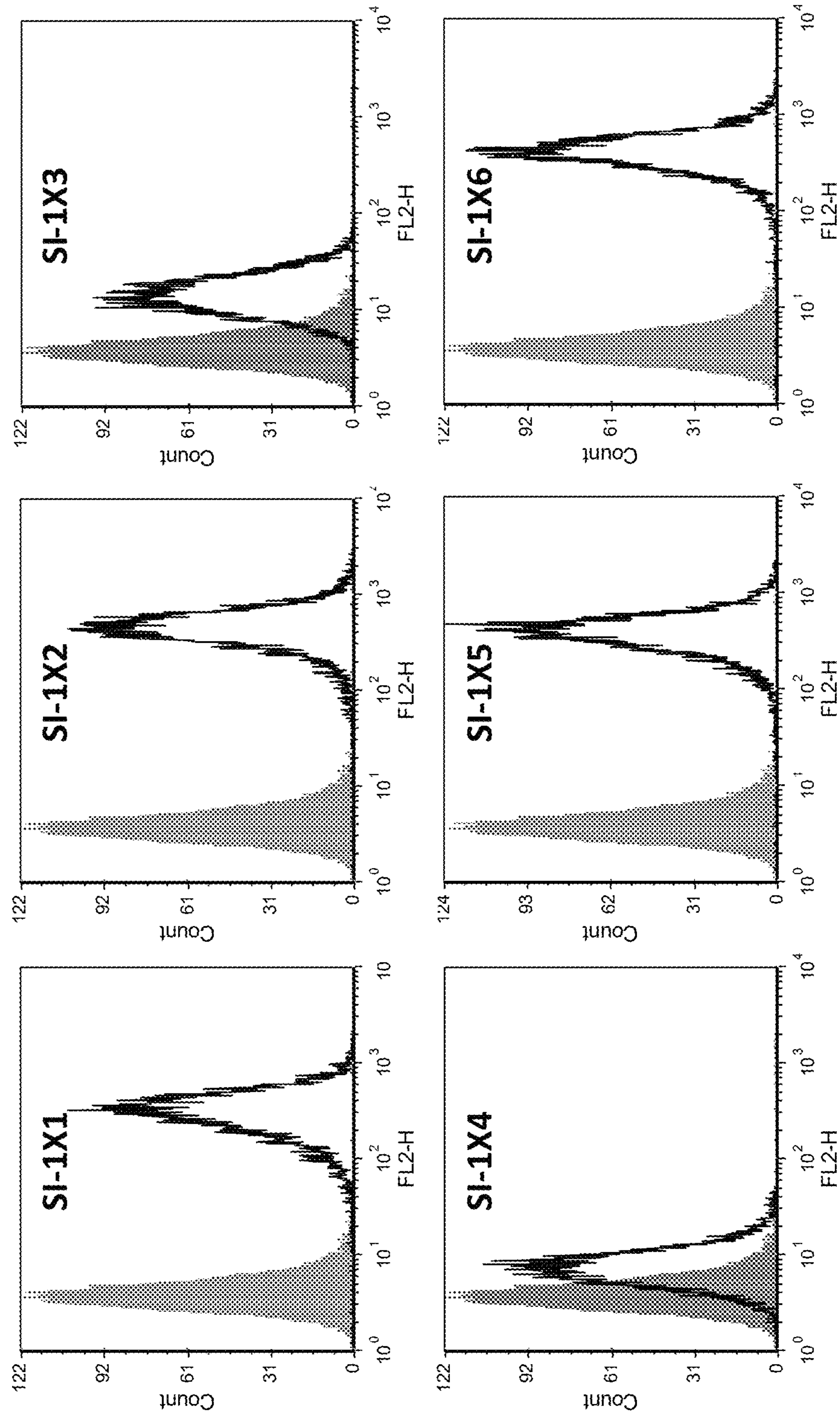
FIG. 13 shows flow cytometric analysis of SI-1× antibodies binding to B×PC3 cells.

Example 6: Binding Tests of Example Bispecific Antibodies to Tumor Cell Lines The bispecific antibodies SI-1×1, SI-1×2, SI-1×3, SI-1×4, SI-1×5, and SI-1×6, as well as an isotype control were tested for binding to the tumor cell lines, A431 (epidermoid carcinoma, ATCC CRL-1555) and B×PC3 (pancreatic adenocarcinoma, ATCC CRL-1687) by flow cytometry. Cells were grown in RPMI-1640 medium containing 10% fetal bovine serum and were harvested for analysis while in exponential growth phase. Aliquots of $5\times10^6$ cells were washed once in PBS, then resuspended in 250 μl of PBS+1% bovine serum albumin (BSA) and incubated at 4° C. for 15 minutes to block membranes from non-specific binding. 250 μl of antibody, diluted to 10 μg/ml in PBS/1% BSA, was added to each sample for a final antibody concentration of 5 μg/ml. Cells were incubated in primary antibody for 1 hour at 4° C. with mixing. Cells were then washed twice with 1 ml PBS/1% BSA and then resuspended in 500 μl of PE-conjugated mouse-anti-human IgG-Fc and incubated at 4° C. with mixing for 45 minutes. Samples were again washed twice with 1 ml PBS/1% BSA, resuspended in 300 ml PBS and analyzed using a FACScalibur flow cytometer. For each sample, 10000 events were collected in the FL-2 channel. Histograms were generated using FCS Express software and SI-1× histograms were overlaid with histograms from the isotype control staining. All six bispecific antibodies displayed histogram shifts with respect to control staining indicating cell binding. This data is displayed in FIG. 12 (A431 cell binding) and FIG. 13 (B×PC3 cell binding).

Example 7: Characterization of SI-1C5.2 and SI-1×4.2 by Cell Binding Assays

Figure 14:
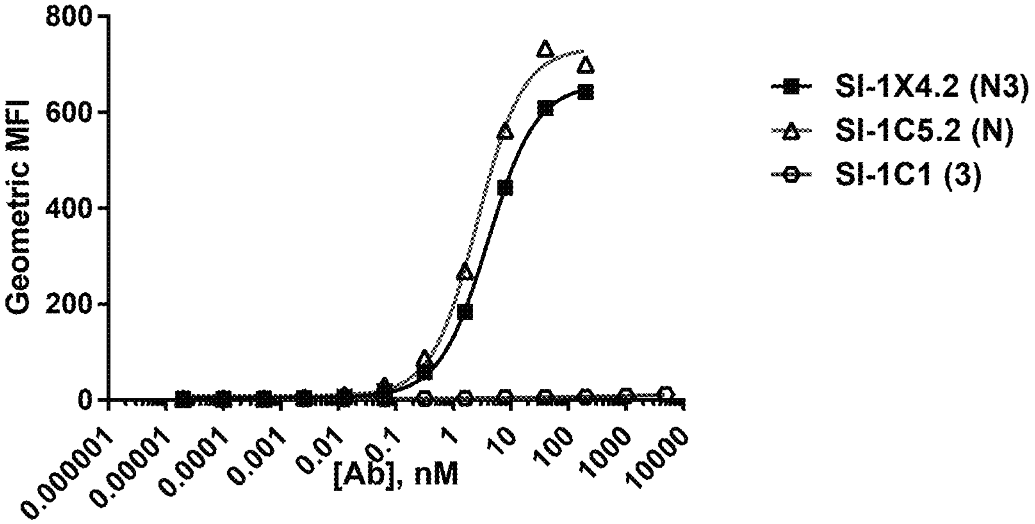
FIG. 14 shows flow cytometric analysis of SI-1×4.2 antibody binding to Fadu cells.
Figure 15:
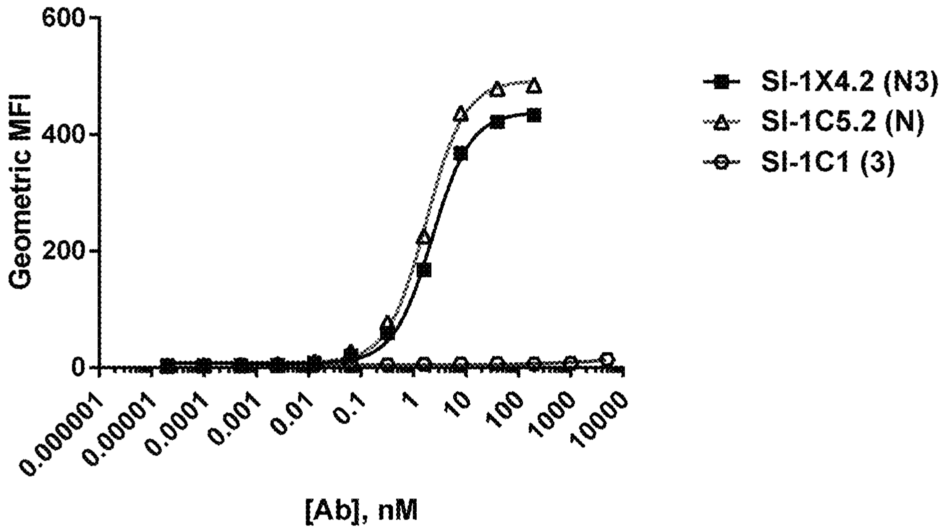
FIG. 15 shows flow cytometric analysis of SI-1×4.2 antibody binding to A431 cells.

The bispecific antibody, SI-1×4.2, monospecific antibodies, SI-1C5.2 and SI-1C1, as well as an isotype control were tested for binding to the tumor cell lines, A431 (epidermoid carcinoma, ATCC CRL-1555) (FIG. 14) and FaDu (hypopharyngeal squamous cell carcinoma, ATCC HTB-43) (FIG. 15) by flow cytometry. Cells were grown in RPMI-1640 medium containing 10% fetal bovine serum and were harvested for analysis while in exponential growth phase. Cells were washed once in PBS, then resuspended in PBS+5% fetal bovine serum albumin (FBS) at a concentration of $5\times10^6$ cells/ml and incubated at 4° C. for 15 minutes to block membranes from non-specific binding. 100 μl aliquots of cells were added to 100 μl aliquots of antibody (also diluted in PBS+5% FBS) in a 96-well plate. Samples were incubated in primary antibody for 45 minutes on ice. Cells were then washed twice with 200 μl of PBS+5% FBS and then resuspended in 100 μl of PE-conjugated mouse-anti-human IgG-Fc and incubated on ice 30 minutes. Samples were again washed twice with 200 μl of PBS+5% FBS, resuspended in 200 μl PBS and analyzed using a FACScalibur flow cytometer. For each sample, 10000 events were collected in the FL-2 channel. Histograms were analyzed using FCS Express software and the geometric mean fluorescence intensity (GMFI) was determined for each data set. EC50 binding values were determined by plotting the GMFI versus antibody concentration using Graphpad Prism software. The bispecific antibody, SI-1×4.2 displayed similar binding profile as the monospecific anti-EGFR antibody, SI-1C5.2 with similar EC50 in both cell lines. The other monospecific anti-Her3 antibody, SI-1C1 binds weakly to the two cell lines probably due to low level of expression of Her3 on the surface of the cells. 1C5.2 and 1×4.2 contained five amino acid changes as compared to 1C5 and 1×4 as described in example 1. These changes accounted for improved binding to target cells when compared to the parental molecule, 1×4.

Example 8: Anti-Proliferative Effect of SI-1× Antibodies on Tumor Cell Lines

To assess the growth inhibitory potential of anti-Her3/EGFR bispecific antibodies, the effect on proliferation of A431 cells (ATCC CRL-1555, Manassas, Va.) which are an epidermoid carcinoma tumor line was tested. The effect on proliferation of B×PC3 (ATCC CRL-1687, Manassas, Va.), a pancreatic adenocarcinoma tumor line was also tested. For each line, cells were seeded into 96-well tissue culture plates at a density of 6000 cells/well in 100 μl RPMI-1640 medium containing 1% fetal bovine serum. After 4 hours, test antibodies were added at various concentrations, ranging from 0.0015 nM to 100 nM. Cells were cultured in the presence of test antibodies for 72 hours. To each well, 20 μl of MTS reagent (Promega, Madison, WI) was added and cells were incubated at 37° C. for 2 hours. MTS is readily taken up by actively proliferating cells, reduced into formazan (which readily absorbs light at 490 nm), and then secreted into the culture medium. Following incubation, OD490 values were measured using a BioTek (Winooski, VT) ELx800 absorbance reader. OD490 values for control cells (treated with medium only) were also obtained in this manner at the time of antibody addition in order to establish baseline metabolic activity. Proliferation may be calculated by subtracting the control baseline OD490 from the 72 hour OD490. Data from antibody titrations was expressed at % of control population according to the following formula: % of control proliferation=(test proliferation/control proliferation)*100.

Figure 16:
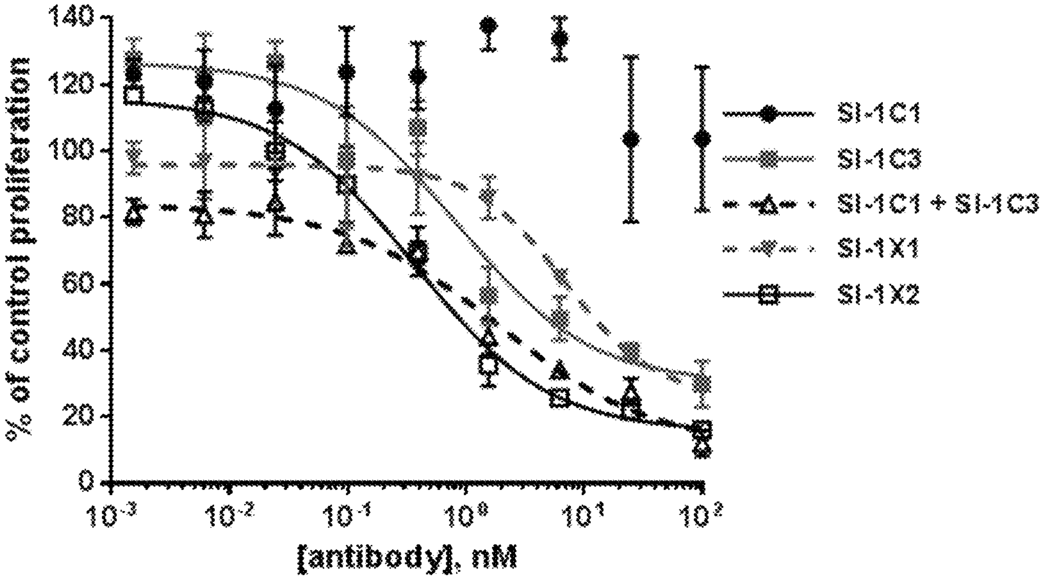
FIG. 16 shows effect of SI-1× antibodies on A431 cell proliferation.
Figure 17:
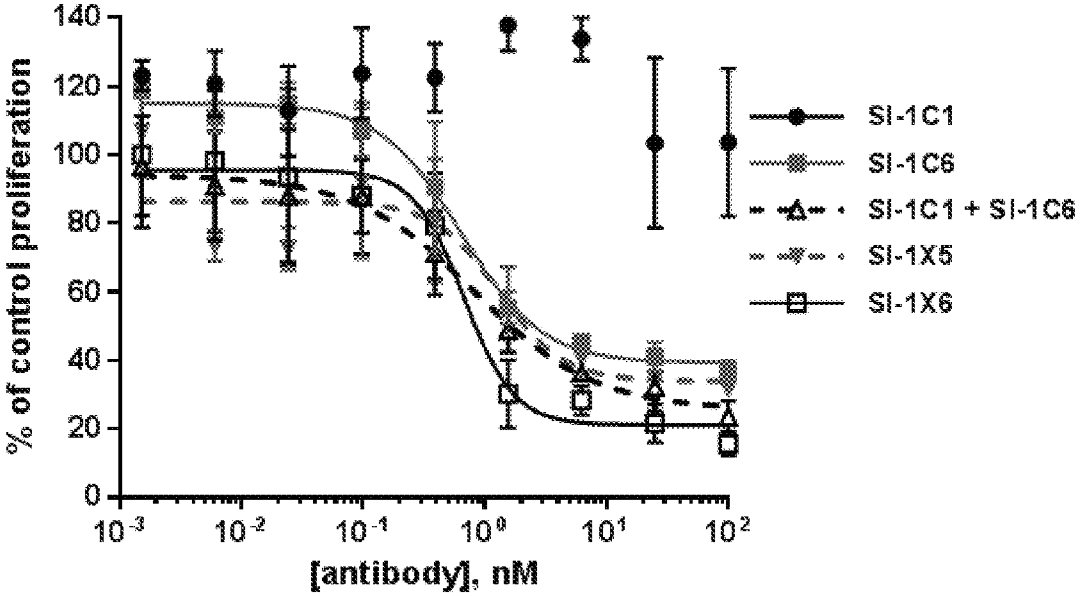
FIG. 17 shows effect of SI-1× antibodies on A431 cell proliferation.

The effects of various bispecific anti-Her3/anti-EGFR antibodies on A431 cell proliferation are shown in FIG. 16 and FIG. 17. SI-1×2 demonstrated more efficacious antiproliferative effect than the control antibodies SI-1C1 (anti-Her3), SI-1C3 (anti-EGFR), or SI-1C1 and SI-1C3 applied together. SI-1×1 exhibited antiproliferative effects, although not to the degree seen with SI-1C3 and the combination of SI-1C1 and SI-1C3. Inhibition plots as well as IC50 values are shown in FIG. 17. Similar results were observed for SI-1×5 and SI-1×6, where SI-1×6 is more potent than SI-1×5 and the control antibody SI-1C1 (anti-Her3), however it displayed similar antiproliferative potential as the control antibody SI-1C6 (anti-EGFR) and the combination of SI-1C1 and SI-1C6. This may be seen along with IC50 values in FIG. 17.

Figure 18:
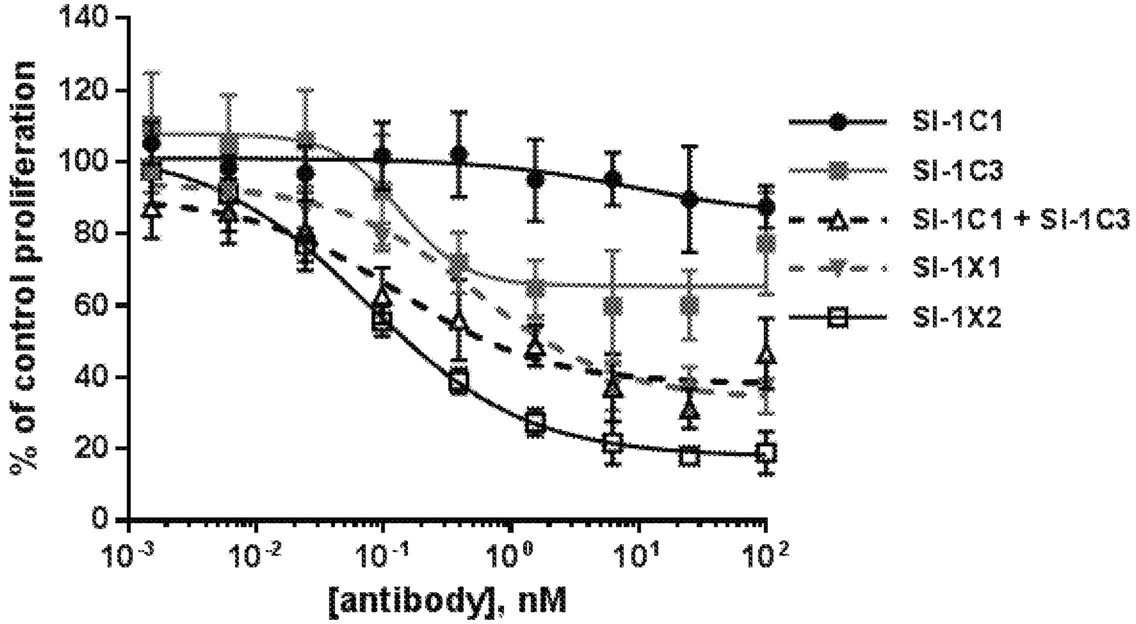
FIG. 18 shows effect of SI-1× antibodies on B×PC3 cell proliferation.
Figure 19:
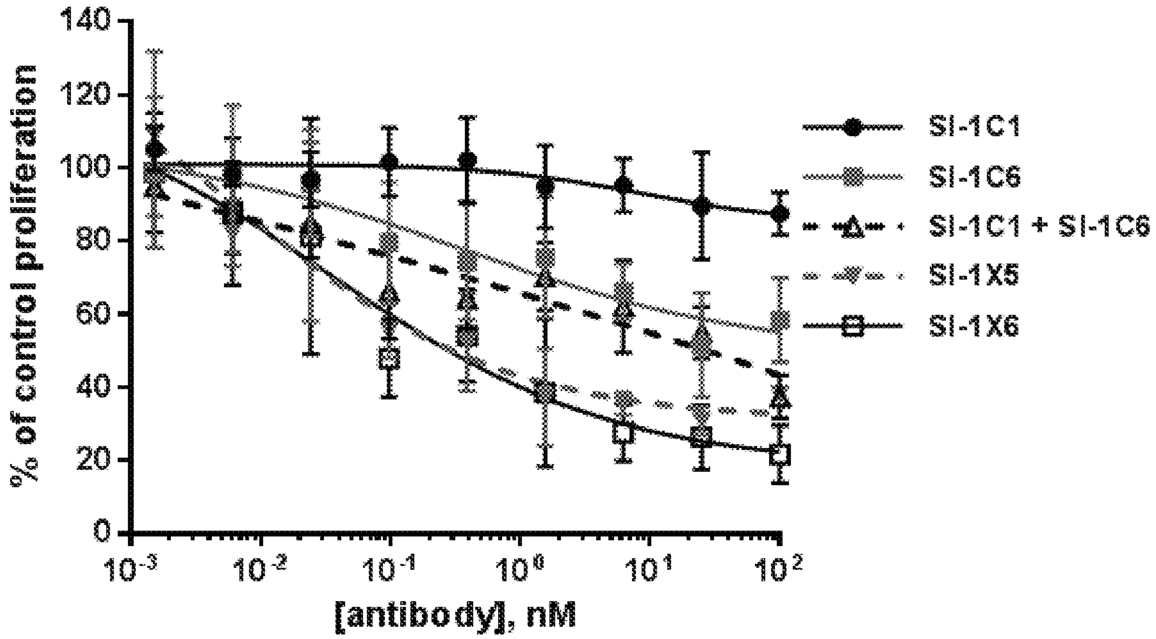
FIG. 19 shows effect of SI-1× antibodies on B×PC3 cell proliferation.

These molecules were also tested for antiproliferative effects in the BxPC3 cell line (FIG. 18 and FIG. 19). Again, SI-1×2 demonstrated more efficacious antiproliferative effect than the control antibodies SI-1C1 (anti-Her3), SI-1C3 (anti-EGFR), or SI-1C1 and SI-1C3 applied together. SI-1×1 was more efficacious than SI-1C1, but weaker than SI-1C3 and the combination of SI-1C1 and SI-1C3. Inhibition curves and IC50 values are displayed in FIG. 19. BxPC3 proliferation was more strongly inhibited by both SI-1×5 and SI-1×6 than with the control antibodies SI-1C1 (anti-Her3), SI-1C6 (anti-EGFR), or SI-1C1 and SI-1C6 in combination. This data along with IC50 values is shown in FIG. 19.

Example 9: Anti-Proliferative Effect of SI-1C5.2 and SI-1×4.2 on Tumor Cell Lines To assess the growth inhibitory potential of anti-Her3/EGFR bispecific antibodies, the effect on proliferation of FaDu (nasopharyngeal squamous cell carcinoma line, ATCC HTB-43) and A431 (epidermoid carcinoma, ATCC CRL-1555) cells were tested. Cells were seeded into 96-well tissue culture plates at a density of 6000 cells/well in 100 μl RPMI-1640 medium containing 1% fetal bovine serum. After 4 hours, test antibodies were added at various concentrations, ranging from 0.0015 nM to 100 nM. Cells were cultured in the presence of test antibodies for 72 hours. To each well, 11μl of alamar blue reagent (Thermo Scientific) was added and cells were incubated at 37° C. for 2 hours. Alamar blue is readily taken up by actively proliferating cells, reduced, and then secreted into the culture medium. The reduced form of alamar blue is strongly fluorescent. Following incubation, fluorescence was measured using a Molecular Devices (Sunnyvale, CA) FilterMax F5 multimode plate reader using an excitation wavelength of 535 nm and an emission wavelength of 595 nm. Fluorescence values for control cells (treated with medium only) were also obtained in this manner at the time of antibody addition in order to establish baseline metabolic activity. Proliferation may be calculated by subtracting the control baseline fluorescence from the 72-hour fluorescence values. Data from antibody titrations was expressed at % of control population according to the following formula: % of control proliferation=(test proliferation/control proliferation)*100.

Figure 20:
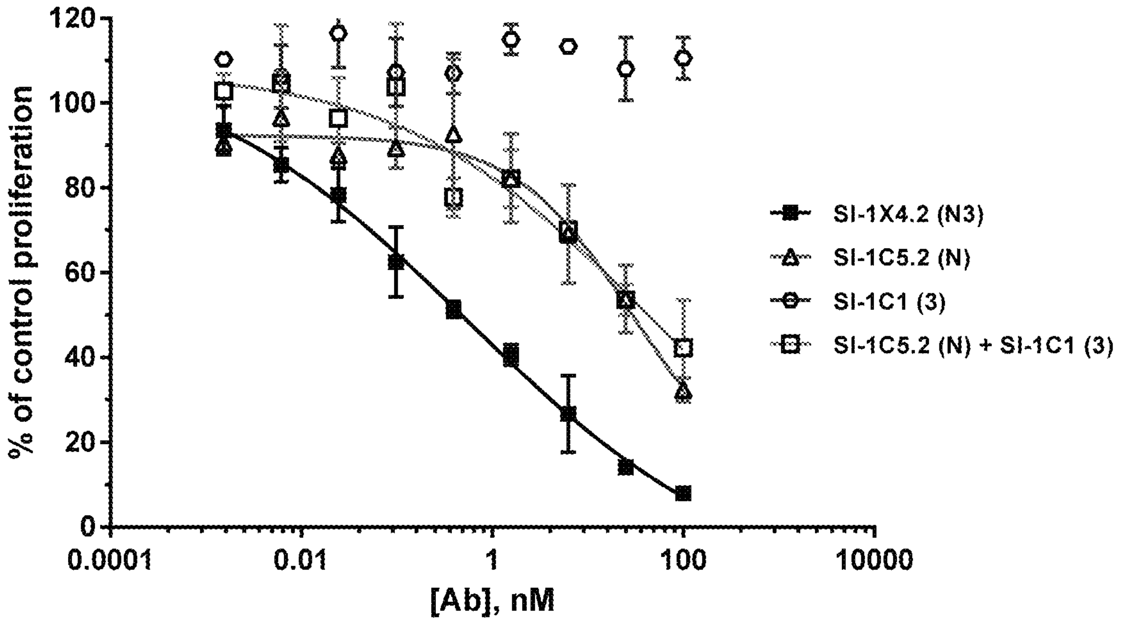
FIG. 20 shows effect of SI-1×4.2 antibodies on Fadu cell proliferation.
Figure 21:
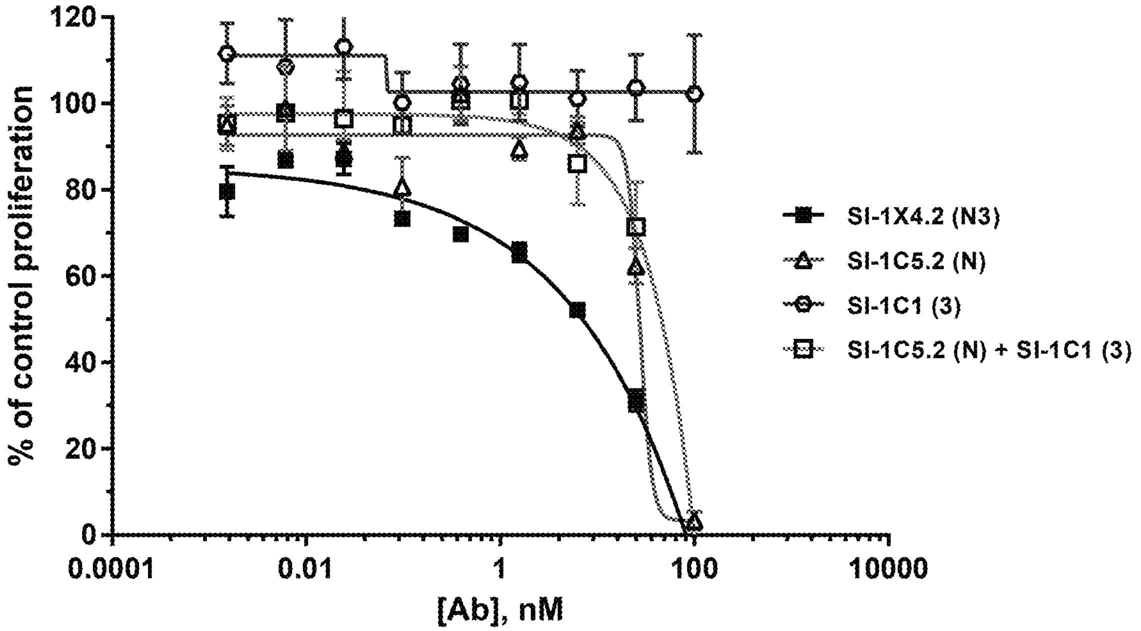
FIG. 21 shows effect of SI-1×4.2 antibodies on A431 cell proliferation.

The effects of SI-1C5.2 and SI-1×4.2 on Fadu and A431 cell proliferation are shown in FIG. 20 and FIG. 21 respectively. In both cell lines, SI-1×4.2 demonstrated improved efficacious anti-proliferative effect than the control antibodies, SI-1C5.2 (anti-EGFR Mab), SI-1C1 (anti-Her3 Mab) or SI-1C1 and SI-1C7 applied together.

Example 10: ADCC Activities of SI-1× Bispecific Antibodies

The ability of SI-1× antibodies to mediate cellular cytotoxicity against several tumor cell lines was tested. Whole blood was obtained from normal, healthy volunteers. Blood was diluted with an equal volume of phosphate buffered saline (PBS). 20 ml aliquots of diluted blood were carefully layered over 15 ml Ficol Pacque PLUS (GE Life Sciences cat #17-1440-02; Pittsburgh, PA). Tubes were centrifuged at 300 g for 40 minutes with no brake. Following centrifugation most of the plasma layer was carefully aspirated and the buffy coat (containing PBMC) was carefully removed with a pipet in the smallest possible volume. PBMCs were pooled in 50 ml tubes and PBS added to bring each tube up to 50 ml. Tubes were centrifuged at 1300RPM for 10 minutes and the supernatant was carefully aspirated. Cells were resuspended in 40 ml PBS and centrifuged again. The process was repeated for a total of 2 washes.

Following the final wash, cells were resuspended in 30 ml RPMI-1630+10% FBS and incubated overnight at 37° C., 5% $CO_2$.

Target cells tested were the head and neck squamous cell carcinoma line, FaDu (ATCC HTB-43, Manassas, VA) and the non-small cell lung adenocarcinoma cell line, NCI-H1975 (ATCC CRL-5908, Manassas, VA). Target cells were labeled with calcein as follows. Cells were grown as monolayers and were detached by incubation with accutase. Cells were washed twice in RPMI with no serum. 1 ml of cells at $4\times10^6$ cells/ml was mixed with 1 ml RPMI (no serum)+20 μM calcein AM (Sigma cat #C1359; St. Louis, MO). Cells were incubated at 37° C. for 30 minutes, with gentle mixing every 10 minutes. Following labeling, cells were washed twice with 14 ml RPMI+10% FBS+2.5 mM probenecid (assay medium). Probenecid (Sigma cat #P8761; St. Louis, MO) is an anionic transporter inhibitor and is known to reduce spontaneous release of intracellular calcein. Cells were resuspended in 20 ml assay medium and allowed to recover for 2 hours at 37° C., 5% $CO_2$. Cells were then washed once with assay medium and diluted to 200,000 cells/ml. Aliquots of 50 μl (10,000 cells) calcein-labeled cells were aliquoted to 96-well round-bottom plates. 50 μl of antibody (at 3× final concentration) was added to cells and allowed to bind for 40 minutes on ice.

PBMCs from the previous day were centrifuged at 300 g for 5 minutes, resuspended in 20 ml fresh assay medium, counted, and diluted to $6\times10^6$ cells/ml. 50 μl PBMC (300,000) were added to each well and plates incubated at 37° C., 5% $CO_2$ for 4 hours. Each antibody was titrated in triplicate via 10-fold serial dilutions, starting at 50 nM and going down to 0.00005 nM. Control wells were also set up containing labeled target cells in the absence of antibody and effector cells in order to measure maximal and spontaneous calcein release.

At the end of the 4-hour incubation, 50 µl of assay medium containing 8% IGEPAL CA-630 (Sigma cat #18896; St. Louis, MO) was added to control wells containing labeled target cells only (to measure the maximal calcein release). 50 µl of assay medium was added to all the other wells to bring the total volume to 200 µl per well. Plates were centrifuged at 2000RPM for 10 minutes and 150 µl supernatant was carefully transferred to V-bottom 96-well plates. These plates were centrifuged at 2000RPM for an additional 10 minutes and 100 ml supernatant was carefully transferred to black, clear-bottom 96-well plates. Calcein in the supernatant was quantitated by measuring the fluorescence of each sample using an excitation wavelength of 485 nM and an emission wavelength of 535 nM. The percentage of specific lysis was calculated as follows:

% specific lysis=[(test sample value−spontaneous release)/(maximal release−spontaneous release)] *100

Figure 22:
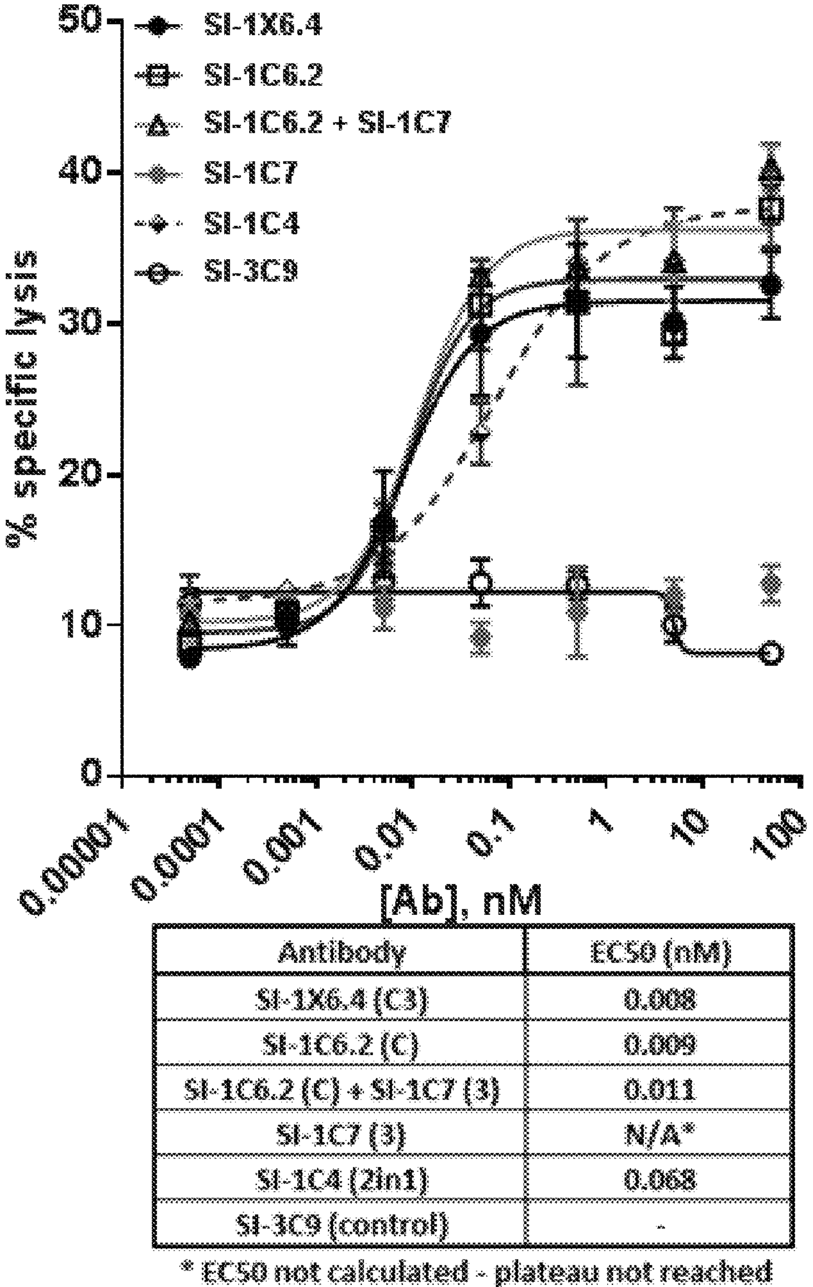
FIG. 22 shows ADCC activity of SI-1× antibodies on Fadu cell.
Figure 22:
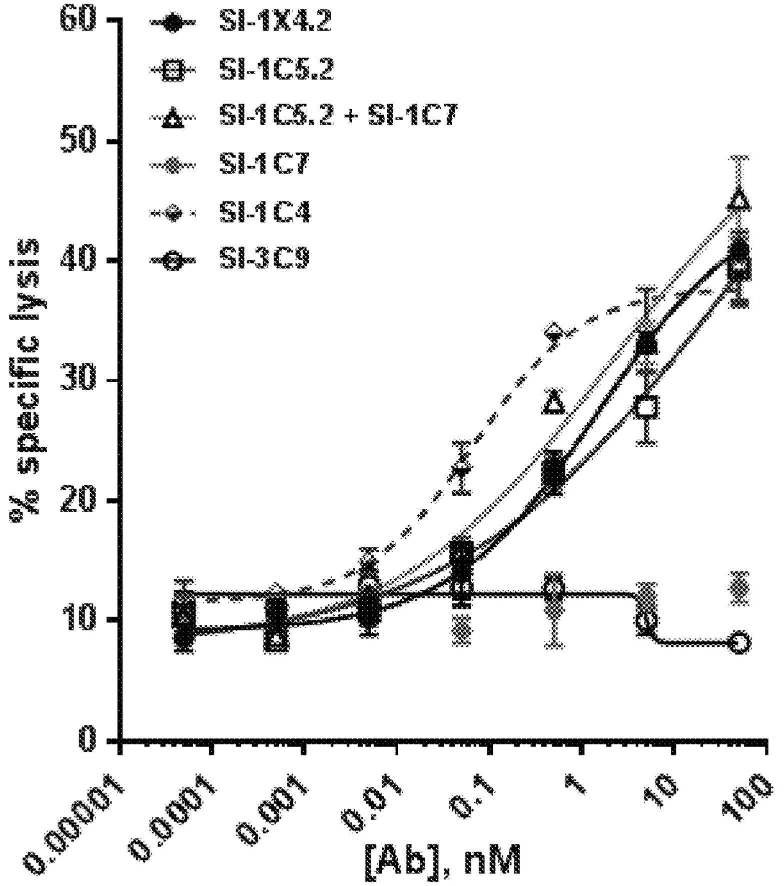
Figure 23:
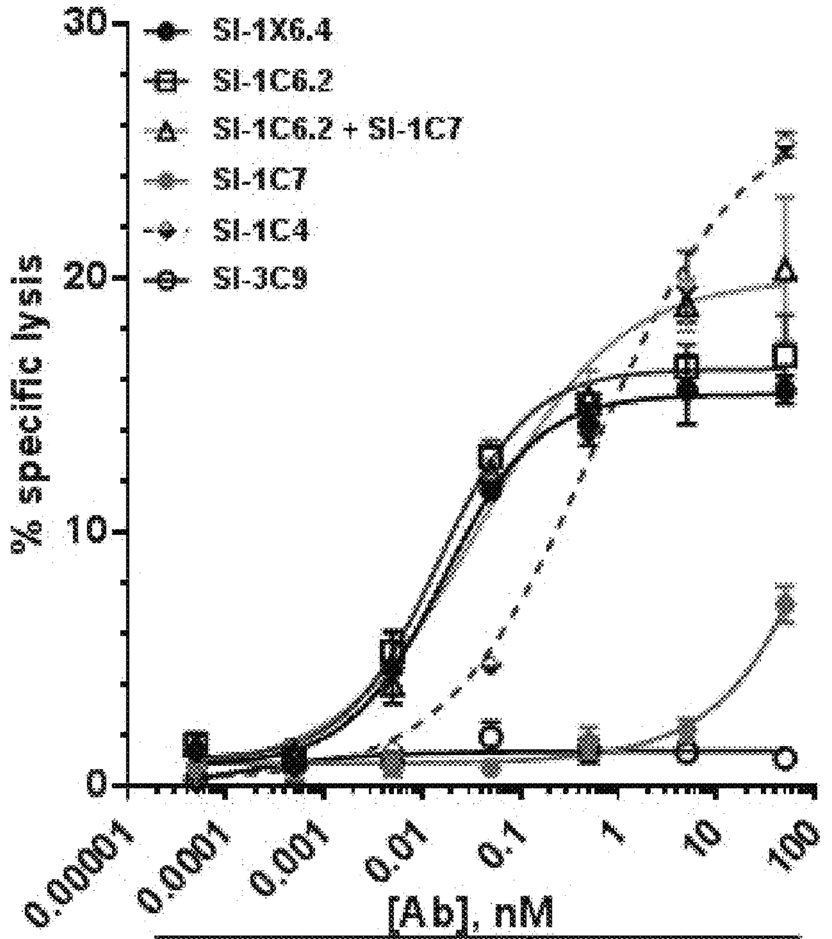
FIG. 23 shows ADCC activity of SI-1× antibodies on NCI-H1975 cells.
Figure 23:
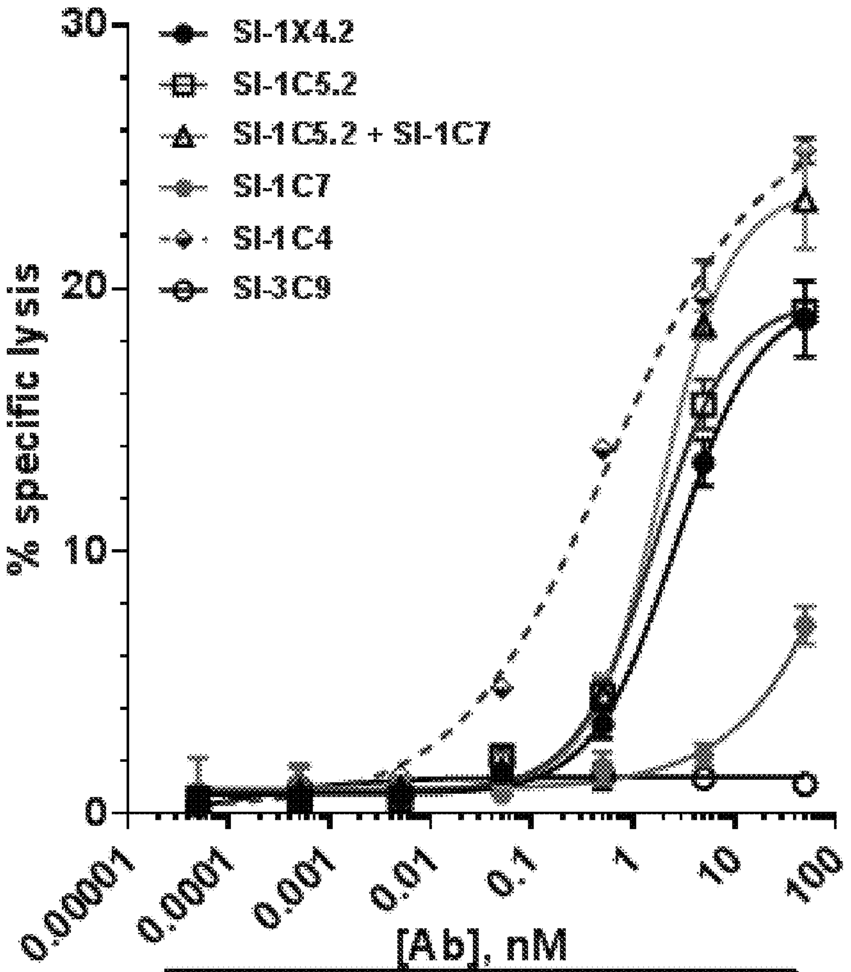

The data is shown in FIG. 22 and FIG. 23. For both cell lines, SI-1×6.4 mediated cellular cytotoxicity, but was not particularly more effective than the control antibodies, SI-1C6.2, SI-1C7, or the combination of SI-1C6.2+SI-1C7. SI-1×6.4 did mediate cytotoxicity with a lower EC50 than our benchmark antibody, SI-1C4. For both cell lines, SI-1×4.2 mediated cellular cytotoxicity at about the same degree as the control antibodies. However, it was not as effective as mediating cellular cytotoxicity as the benchmark, SI-1C4. This is likely due to the lower affinity of SI-1×4.2.

Example 11: Thermal Stability of SI-1× Bispecific Antibodies

Figure 24:
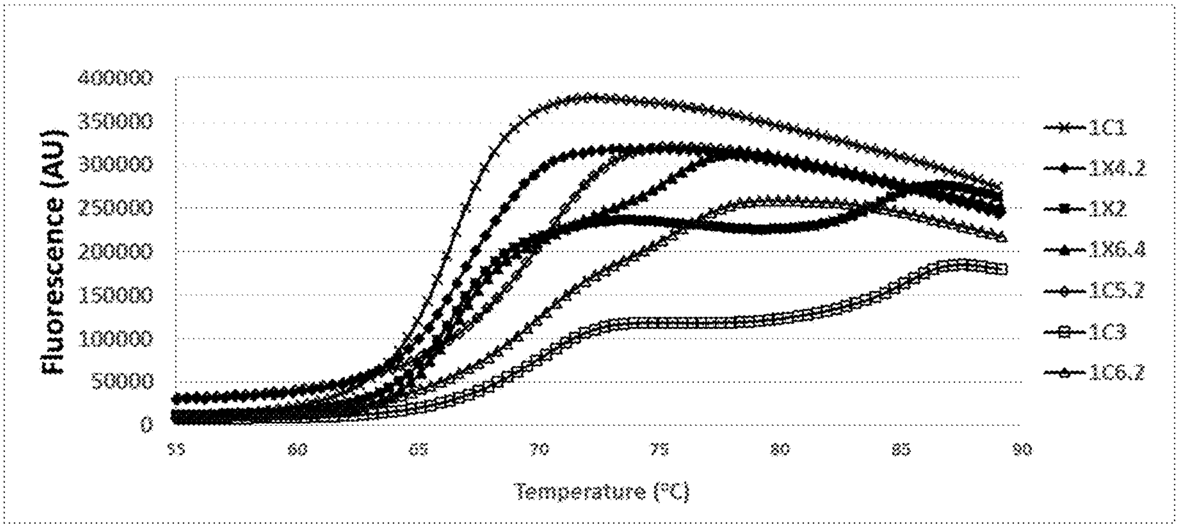
FIG. 24 shows the thermal melting of SI-1× antibodies to demonstrate their stability.

Protein Thermal Shift Study was performed for protein thermal stability analysis. Protein melt reactions were set up using Protein Thermal Shift Buffer™ and the Protein Thermal Shift Dye™ (Applied Biosystems). In brief, the 20ul reaction mixture contains 5ug protein, 5ul Protein Thermal Shift Buffer™ and 2.5µ 8× diluted Protein Thermal Shift™ Dye. For the negative control, PBS was used instead. The reaction mixture was added into MicroAmp Optical Reaction Plate and sealed with MicroAmp Optical Adhesive Film. Each sample consisted of 4 repeats. The protein melt reactions were run on Applied Biosystem Real-Time PCR System from 25-90° C. in 1% increment and then analyzed by Protein Thermal Shift Software™. FIG. 24 shows the thermal curve of SI-1×2, SI-1×4.2, SI-1×6.4, SI-1C3, SI-1C3, SI-1C6.2, SI-1C5.2 and SI-1C7. TABLE 5 shows Tm for these molecules. Tm is defined as the temperature needed to unfold 50% of the protein. The bispecific molecules, 1×2, 1×4.2 and 1×6 all have Tm around 66° C. which are comparable to all the MAbs (1C3, 1C6.2, 1C5.2) and the Fc-scFv (1C7) molecules.

TABLE 5

| Protein Name | Tm (° C.) |
|---|---|
| SI-1X2 | 66.52 |
| SI-1C3 | 70.06 |
| SI-1X4.2 | 66.94 |
| SI-1C5.2 | 70.26 |
| SI-1X6.4 | 66.50 |
| SI-1C6.2 | 70.12 |
| SI-1C7 | 66.40 |

Example 12: Serum Stability of SI-1× Bispecific Antibodies

Serum stability of the molecules SI-1C5.2, SI-1C6.2, SI-1×4.2, and SI-1×6.4 was determined by comparative binding to monomeric EGFR ECD by ELISA after incubation at 100 µg/mL in 95% human serum (Atlanta Biologics, S40110) at 37° C. for Days 0, 3, and 7 time points with an extra time point of 55° C. on Day 7 to provide a known condition where degradation occurs. ELISA plates were coated with monomeric EGFR ECD (SI-2R4) at 3 µg/mL in PBS at 4° C. overnight. Coated ELISA plates were blocked with 3% BSA PBST for 2 hours at 25° C. and then washed 3 times with PBST. SI-1C6.2 and SI-1×6.4 were diluted 1:10 with 1% BSA PBST and diluted 4× across the plate. SI-1C5.2 and SI-1×4.2 were diluted 1:2 with 1% BSA PBST and diluted 4× across the plate and incubated at 25° C. for 1 hour. 3 more washes with PBST were performed before antigen capture with 1 µg/mL Her3 ECD Rabbit IgG1 (SI-1R1) for 1 hour at 25° C. in 1% BSA PBST. 3 more washes with PBST were performed before goat anti-rabbit IgG-HRP (Bio-Rad 172-1019) secondary antibody was applied at 1:5000 dilution in 1% BSA PBST at 25° C. for 1 hour. 3 final washes with PBST before development with 100 µl Pierce 1-step Ultra TMB ELISA (Pierce, 34028) for 10 minutes with a final quench of 100 µl 2M $H_2SO_4$. Plates were read at 450 nm. ELISA data was plotted and curves created using GraphPad Prism 6.

Figure 25:
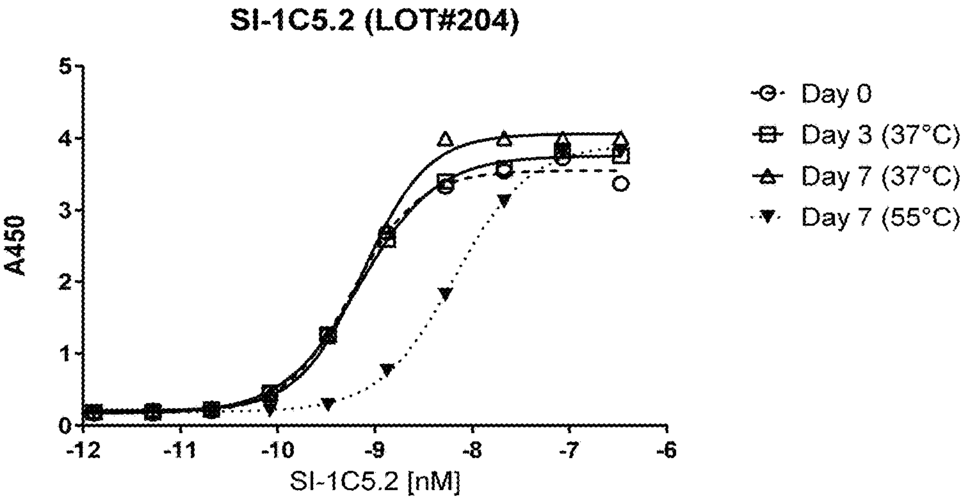
FIG. 25 shows the serum stability of SI-1× antibodies over 7 days period.
Figure 25:
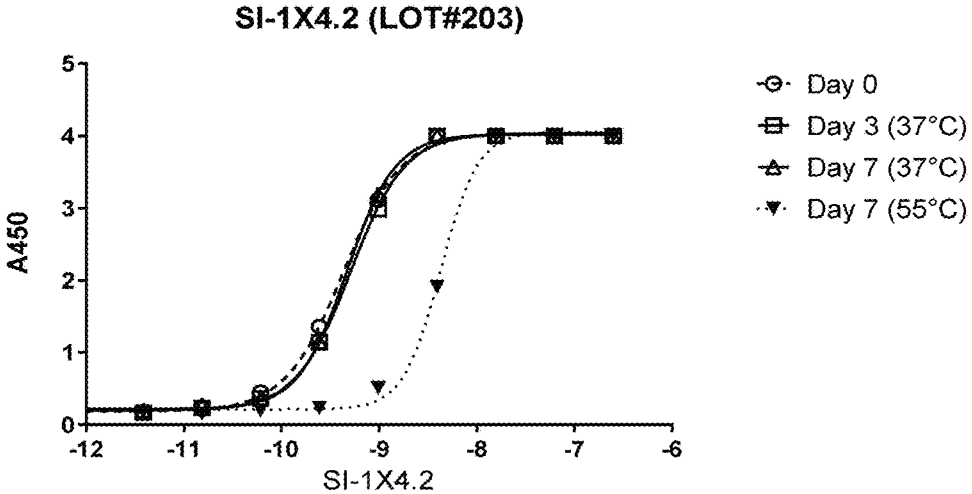
Figure 25:
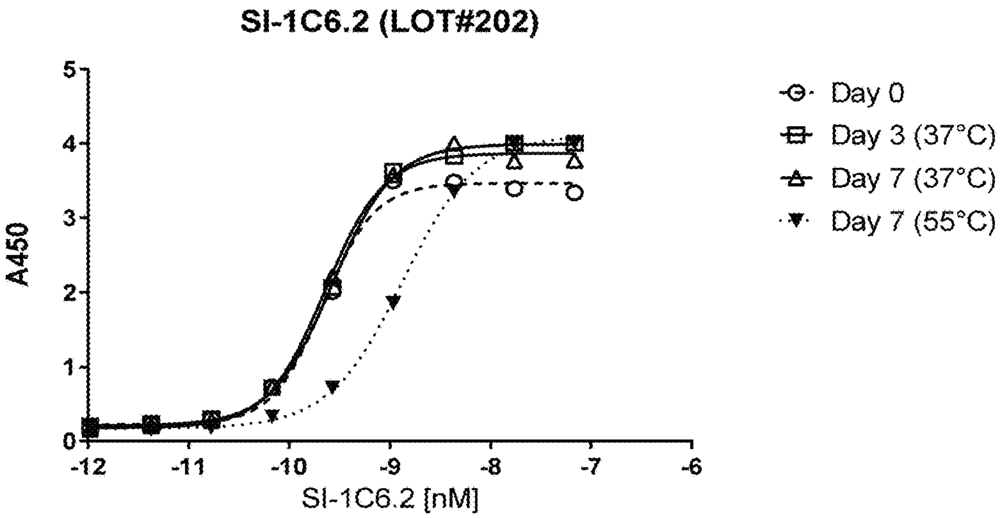
Figure 25:
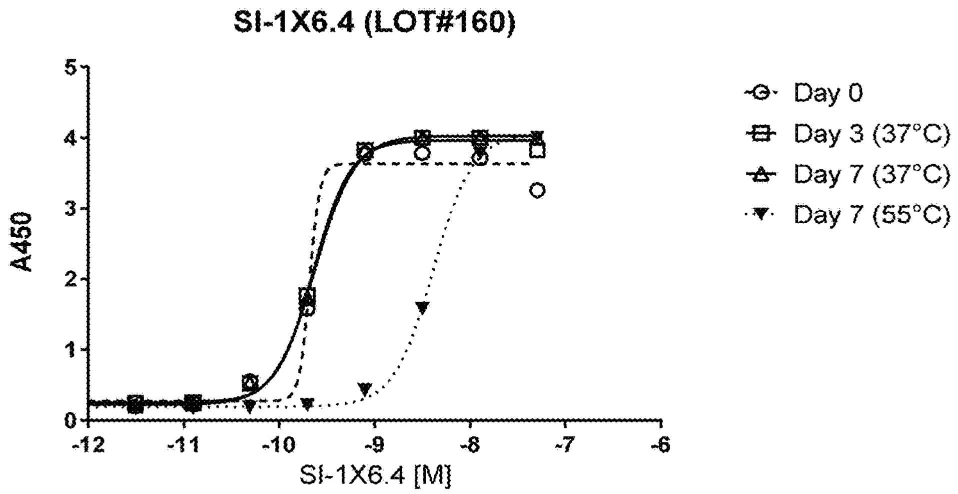

Results of the ELISA are reported by EC50 on FIG. 25 and indicate a favorable profile of minor degradation when held at 37° C. When placed in 55° C., the EC50 shifts roughly a log as the molecules are subjected to degradation conditions. EC50 values for SI-1C5.2 shift from 589.7 µM on Day 0 to 755.2 µM on Day 7 at 37° C. (A165.5 µM) with a shift to 6.522 nM on Day 7 at 55° C. (A5932.3 µM). EC50 values for SI-1C6 shift from 218.2 µM on Day 0 to 226.6 µM on Day 7 at 37° C. (A8.4 µM) with a shift to 1.322 nM on Day 7 at 55° C. (A1103 µM). EC50 values for SI-1×4.2 shift from 429.3 µM on Day 0 to 466.7 µM on Day 7 at 37° C. (A37.4 µM) with a shift to 4.248 nM on Day 7 at 55° C. (A3818.7 µM). EC50 values for SI-1×6 shift from 209.3 µM on Day 0 to 237.3 µM on Day 7 at 37° C. (A28 µM) with a shift to 4.112 nM on Day 7 at 55° C. (A3902.7 µM).

Example 13: PK Half-Life of SI-1× Molecules

To test their half-life in vivo, pharmacokinetic experiments were performed in SD rats. A single, intravenous tail vein injection of bispecific Abs (1C6 10 mg/kg, 1×6 10 mg/kg, 1×2 10 mg/kg, 1×4 32 mg/kg) were given to groups of 4 female rats randomized by body weight (190-212 g range). Blood (~150 µL) was drawn from the orbital plexus at each time point, processed for serum, and stored at −80° C. until analysis. Study durations were 28 days.

Antibody concentrations were determined using three ELISA assays. In assay 1 (EGFR ECD coated ELISA), recombinant EGFR-rabbit Fc was coated to the plate, wells were washed with PBST (phosphate buffered saline with 0.05% Tween) and blocked with 1% BSA in PBST. Serum or serum diluted standards were then added, followed by PBST washing, addition of HRP labeled rabbit-anti-human IgG (BOSTER), and additional PBST washing. TMB was then added and the plates were incubated 2.5 minutes in the dark. Color reaction was stopped by adding 2M sulfuric acid. Plate was read at 450 nm wavelength. For assay 2 (Her3 coated ELISA), serum was detected using a similar ELISA, but recombinant HER3-His was used as capture reagent. For assay 3 (Sandwich ELISA), recombinant HER3-His was coated, serum or serum diluted standard were added, followed by PBST washing, addition of EGFR-rabbit Fc in PBST, and additional PBST washing. HRP labeled goat-anti-rabbit IgG (BOSTER) was then added. PK parameters were determined with a non-compartmental model.

Figure 26:
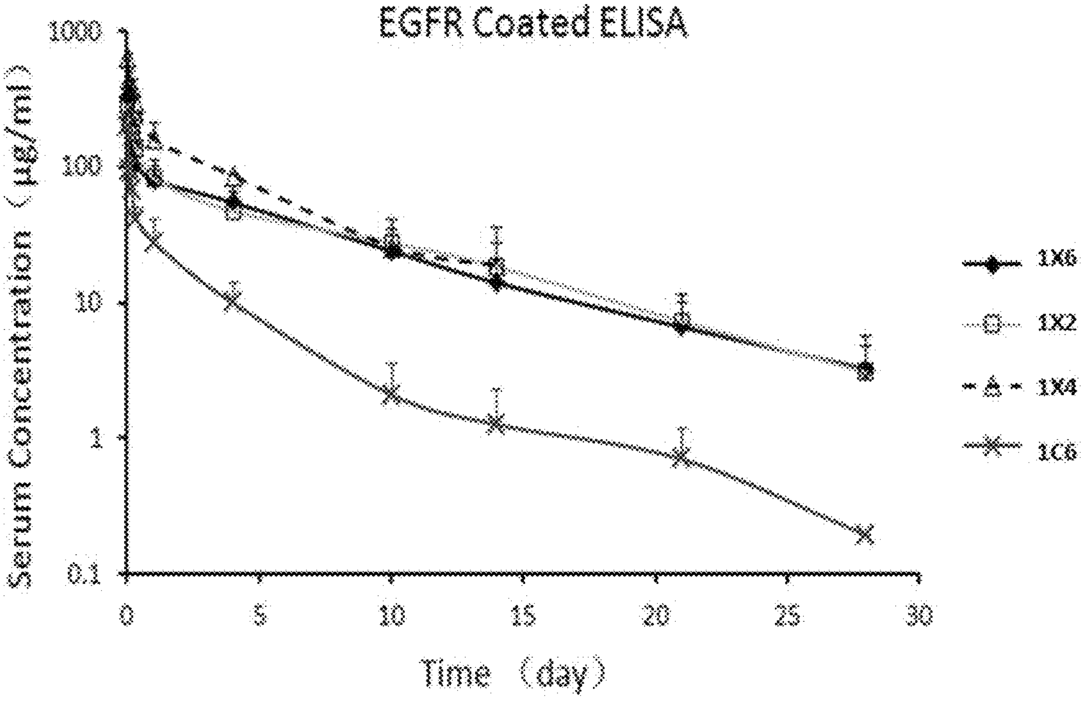
FIG. 26 is a graph showing the results of EGFR coated ELISA for the PK study in rat.
Figure 27:
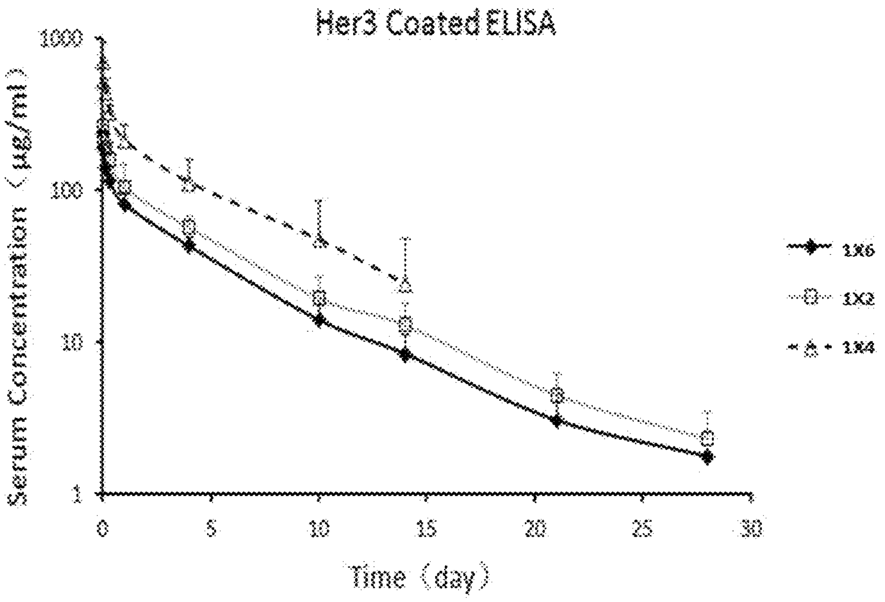
FIG. 27 is a graph showing the results of HER3 coated ELISA for the PK study in rat.
Figure 28:
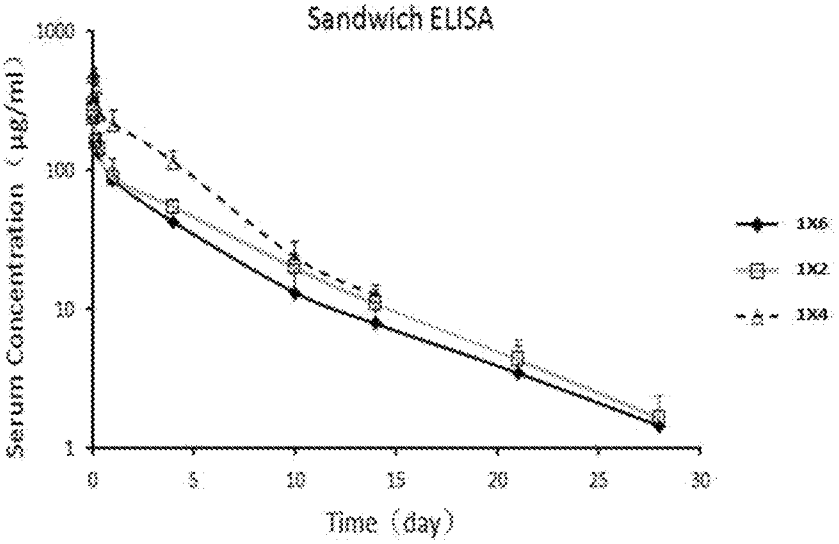
FIG. 28 is a graph showing the results of sandwich ELISA for the PK study in rat.

FIGS. 26-28 show serum concentration data for four antibodies with three different assays respectively. Fitted PK parameters from in vivo PK studies are provided in TABLE 6. PK data include half-life, which represents the beta phase that characterizes elimination of antibody from serum and Cmax, which represents the maximal observed serum concentration, AUC, which represents the area under the concentration time curve.

TABLE 6

| Assay | Sample | Half-Life (h) | Cmax (μg/ml) | AUC (μg/ml * h) |
|---|---|---|---|---|
| EGFR | SI-1X6 | 159 | 326.5 | 18250.6 |
| Coated | SI-1X2 | 130 | 280.3 | 18889.8 |
| ELISA | SI-1X4.2 | 146 | 627.8 | 31317.0 |
| | SI-1C6 | 130 | 196.4 | 3790.3 |
| Her3 | SI-1X6 | 142 | 236.7 | 14213.6 |
| Coated | SI-1X2 | 136 | 264.8 | 19012.2 |
| ELISA | SI-1X4.2 | 124 | 716.6 | 40063.4 |
| Sandwich | SI-1X6 | 136 | 301.6 | 14182.6 |
| ELISA | SI-1X2 | 123 | 297.6 | 17203.9 |
| | SI-1X4.2 | 211 | 518.9 | 34874.6 |

Example 14: Mouse Xenograft Studies

The example tested the activity of SI-1×2, SI-1×4.2 and SI-1×6 of concomitant blockade of EGFR, HER3 in preclinical models of Fadu (head and neck squamous cell carcinoma xenograft model) and compared their potency with cetuximab and cetuximab in combination with an anti-HER3 antibody.

All mouse studies were conducted through Institutional Animal care and used committee-approved animal protocols in accordance with institutional guidelines. Six-week-old female Balb/c Nude mice were purchased from Beijing Vital River Laboratories and housed in air-filtered laminar flow cabinets with a 12—hour light cycle and food and water ad libitum. The size of the animal groups was calculated to measure means difference between placebo and treatment groups of 25% with a power of 80% and a P value of 0.01. Host mice carrying xenografts were randomly and equally assigned to either control or treatment groups. Animal experiments were conducted in a controlled and non-blinded manner. For cell line-derived xenograft studies, mice were injected subcutaneously with 2×106 Fadu suspended 150 μl of culture medium per mouse.

Once tumors reached an average volume of 100-250 mm3, mice were randomized into 9 groups, with 6 mice per group. Vehicle Control, 1C6 (25 mg/kg), 1C4 (25 mg/kg), 1C6+1C1 (25 mg/kg+50 mg/kg), SI-1×2 (25 mg/kg), SI-1×6 (10 mg/kg), SI-1×6 (25 mg/kg), and SI-1×4.2 (10 mg/kg) SI-1×4 (25 mg/kg). All test articles were administered once weekly via intravenous injection. Tumors were measured by digital caliper over the entire treatment period every 3 days and the volume was determined using the following formula: ½×lenth×width2. The body weight of mice were recorded before the first dose and followed by every week during the treatment period and recovery period.

Figure 29:
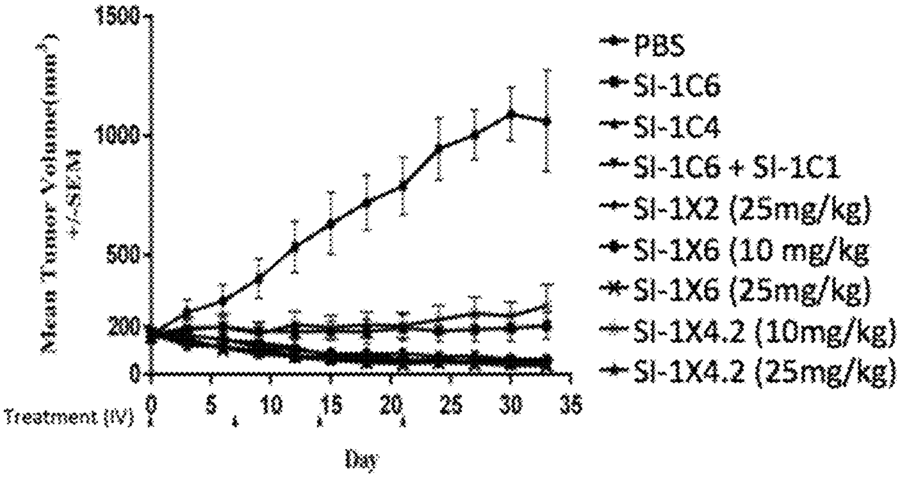
FIG. 29 is a graph showing a plot of mean tumor volume vs days in the mouse xenograft study
Figure 30:
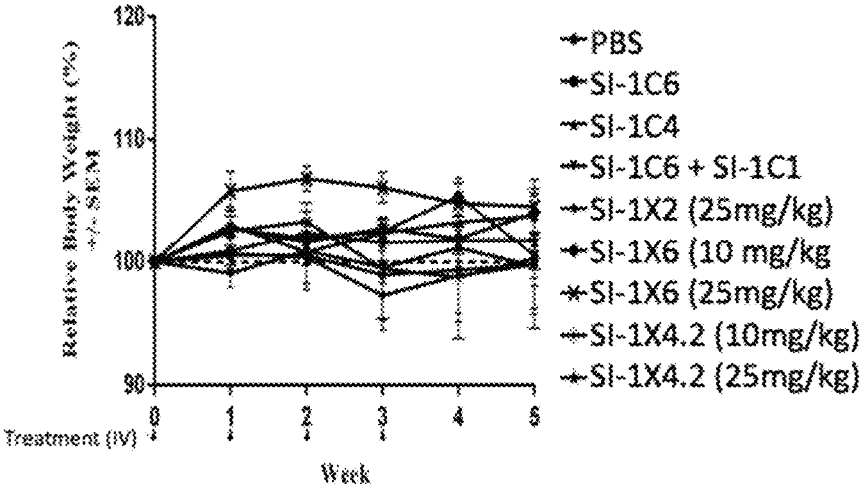
FIG. 30 is a graph showing a plot relative body weight vs weeks in the mouse xenograft study.

All the test groups of SI-1×2, SI-1×6 and SI-1×4.2 and SI-1×6 combination yielded significantly tumor growth inhibition compared to positive control of SI-1C6 excluding the low dose SI-1×4.2 10 mg/kg group (FIGS. 29-30). Moreover, no relapses were observed 2 weeks after treatment cessation excluding the low dose SI-1×4.2 10 mg/kg group.

Pharmaceutical Compositions

The term "effective amount" refers to an amount of a drug effective to achieve a desired effect, e.g., to ameliorate disease in a subject. Where the disease is a caner, the effective amount of the drug may inhibit (for example, slow to some extent, inhibit or stop) one or more of the following example characteristics including, without limitation, cancer cell growth, cancer cell proliferation, cancer cell motility, cancer cell infiltration into peripheral organs, tumor metastasis, and tumor growth. Wherein the disease is a caner, the effective amount of the drug may alternatively do one or more of the following when administered to a subject: slow or stop tumor growth, reduce tumor size (for example, volume or mass), relieve to some extent one or more of the symptoms associated with the cancer, extend progression free survival, result in an objective response (including, for example, a partial response or a complete response), and increase overall survival time. To the extent the drug may prevent growth and/or kill existing cancer cells, it is cytostatic and/or cytotoxic.

With respect to the formulation of suitable compositions for administration to a subject such as a human patient in need of treatment, the antibodies disclosed herein may be mixed or combined with pharmaceutically acceptable carriers known in the art dependent upon the chosen route of administration. There are no particular limitations to the modes of application of the antibodies disclosed herein, and the choice of suitable administration routes and suitable compositions are known in the art without undue experimentation.

Although many forms of administration are possible, an example administration form would be a solution for injection, in particular for intravenous or intra-arterial injection. Usually, a suitable pharmaceutical composition for injection may include pharmaceutically suitable carriers or excipients such as, without limitation, a buffer, a surfactant, or a stabilizer agent. Example buffers may include, without limitation, acetate, phosphate or citrate buffer. Example surfactants may include, without limitation, polysorbate. Example stabilizer may include, without limitation, human albumin.

Similarly, persons skilled in the art have the ability to determine the effective amount or concentration of the antibodies disclosed therein to effective treat a condition such as a cancer. Other parameters such as the proportions of the various components in the pharmaceutical composition, administration does and frequency may be obtained by person skilled in the art without undue experimentation. For example, a suitable solution for injection may contain, without limitation, from about 1 to about 20, from about 1 to about 10 mg antibodies per ml. The example dose may be, without limitation, from about 0.1 to about 20, from about 1 to about 5 mg/Kg body weight. The example administration frequency could be, without limitation, once per day or three times per week.

While the present disclosure has been described with reference to particular embodiments or examples, it may be understood that the embodiments are illustrative and that the disclosure scope is not so limited. Alternative embodiments of the present disclosure may become apparent to those having ordinary skill in the art to which the present disclosure pertains. Such alternate embodiments are considered to be encompassed within the scope of the present disclosure. Accordingly, the scope of the present disclosure is defined by the appended claims and is supported by the foregoing description.

SEQUENCE LISTING

<160> NUMBER OF SEQ ID NOS: 329

<210> SEQ ID NO 1
<211> LENGTH: 654
<212> TYPE: DNA
<213> ORGANISM: artificial sequence
<220> FEATURE:
<223> OTHER INFORMATION: Synthesized

<400> SEQUENCE: 1

```
cagtctgccc tgactcagcc tgcctccgtg tctgggtctc ctggacagtc gatcaccatc     60

tcctgcactg gaaccagcag tgacgttggt ggttataact ttgtctcctg gtaccaacaa    120

cacccaggca aagcccccaa actcatgatc tatgatgtca gtgatcggcc ctcaggggtg    180

tctgatcgct tctccggctc caagtctggc aacacggcct ccctgatcat ctctggcctc    240

caggctgacg acgaggctga ttattactgc agctcatatg ggagcagcag cactcatgtg    300

attttcggcg gagggaccaa gctgaccgtc ctacgtacgg tggctgcacc atctgtcttc    360

atcttcccgc catctgatga gcagttgaaa tctggaactg cctctgttgt gtgcctgctg    420

aataacttct atcccagaga ggccaaagta cagtggaagg tggataacgc cctccaatcg    480

ggtaactccc aggagagtgt cacagagcag gacagcaagg acagcaccta cagcctcagc    540

agcaccctga cgctgagcaa agcagactac gagaaacaca aagtctacgc ctgcgaagtc    600

acccatcagg gcctgagctc gcccgtcaca aagagcttca acaggggaga gtgt          654
```

<210> SEQ ID NO 2
<211> LENGTH: 333
<212> TYPE: DNA
<213> ORGANISM: artificial sequence
<220> FEATURE:
<223> OTHER INFORMATION: Synthesized

<400> SEQUENCE: 2

```
cagtctgccc tgactcagcc tgcctccgtg tctgggtctc ctggacagtc gatcaccatc     60

tcctgcactg gaaccagcag tgacgttggt ggttataact ttgtctcctg gtaccaacaa    120

cacccaggca aagcccccaa actcatgatc tatgatgtca gtgatcggcc ctcaggggtg    180

tctgatcgct tctccggctc caagtctggc aacacggcct ccctgatcat ctctggcctc    240

caggctgacg acgaggctga ttattactgc agctcatatg ggagcagcag cactcatgtg    300

attttcggcg gagggaccaa gctgaccgtc cta                                 333
```

<210> SEQ ID NO 3
<211> LENGTH: 218
<212> TYPE: PRT
<213> ORGANISM: artificial sequence
<220> FEATURE:
<223> OTHER INFORMATION: Synthesized

<400> SEQUENCE: 3

```
Gln Ser Ala Leu Thr Gln Pro Ala Ser Val Ser Gly Ser Pro Gly Gln
1               5                   10                  15
```

-continued

```
Ser Ile Thr Ile Ser Cys Thr Gly Thr Ser Ser Asp Val Gly Gly Tyr
            20                  25                  30

Asn Phe Val Ser Trp Tyr Gln Gln His Pro Gly Lys Ala Pro Lys Leu
        35                  40                  45

Met Ile Tyr Asp Val Ser Asp Arg Pro Ser Gly Val Ser Asp Arg Phe
    50                  55                  60

Ser Gly Ser Lys Ser Gly Asn Thr Ala Ser Leu Ile Ile Ser Gly Leu
65                  70                  75                  80

Gln Ala Asp Asp Glu Ala Asp Tyr Tyr Cys Ser Ser Tyr Gly Ser Ser
                85                  90                  95

Ser Thr His Val Ile Phe Gly Gly Gly Thr Lys Leu Thr Val Leu Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215


<210> SEQ ID NO 4
<211> LENGTH: 110
<212> TYPE: PRT
<213> ORGANISM: artificial sequence
<220> FEATURE:
<223> OTHER INFORMATION: Synthesized

<400> SEQUENCE: 4

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
            20                  25                  30

Asn Phe Val Ser Trp Tyr Gln Gln His Pro Gly Lys Ala Pro Lys Leu
        35                  40                  45

Met Ile Tyr Asp Val Ser Asp Arg Pro Ser Gly Val Ser Asp Arg Phe
    50                  55                  60

Ser Gly Ser Lys Ser Gly Asn Thr Ala Ser Leu Ile Ile Ser Gly Leu
65                  70                  75                  80

Gln Ala Asp Asp Glu Ala Asp Tyr Tyr Cys Ser Ser Tyr Gly Ser Ser
                85                  90                  95

Ser Thr His Val Ile Phe Gly Gly Gly Thr Lys Leu Thr Val
            100                 105                 110


<210> SEQ ID NO 5
<211> LENGTH: 1344
<212> TYPE: DNA
<213> ORGANISM: artificial sequence
<220> FEATURE:
<223> OTHER INFORMATION: Synthesized

<400> SEQUENCE: 5
```

```
caggtgcagc tgcaggagtc gggggggaggc ctggtcaagc ctggagggtc cctgagactc     60
tcctgtgcag cctctggatt cacctttagt agttattgga tgagctgggt ccgccaggct    120
ccagggaagg ggctggagtg ggtggccaac ataaaccgcg atggaagtgc gagttactat    180
gtggactctg tgaagggccg attcaccatc tccagagacg acgccaagaa ctcactgtat    240
ctgcaaatga acagcctgag agctgaggac acggctgtgt attactgtgc gagagatcgt    300
ggggtgggct acttcgatct ctggggccgt ggcaccctgg tcaccgtctc gagcgctagc    360
accaagggcc catcggtctt ccccctggca ccctcctcca agagcacctc tgggggcaca    420
gcggccctgg gctgcctggt caaggactac ttccccgaac cggtgacggt gtcgtggaac    480
tcaggcgccc tgaccagcgg cgtgcacacc ttcccggctg tcctacagtc ctcaggactc    540
tactccctca gcagcgtggt gaccgtgccc tccagcagct tgggcaccca gacctacatc    600
tgcaacgtga atcacaagcc cagcaacacc aaggtggaca agagagttga gcccaaatct    660
tgtgacaaaa ctcacacatg cccaccgtgc ccagcacctg aactcctggg gggaccgtca    720
gtcttcctct tccccccaaa acccaaggac accctcatga tctcccggac ccctgaggtc    780
acatgcgtgg tggtggacgt gagccacgaa gaccctgagg tcaagttcaa ctggtacgtg    840
gacggcgtgg aggtgcataa tgccaagaca aagccgcggg aggagcagta caacagcacg    900
taccgtgtgg tcagcgtcct caccgtcctg caccaggact ggctgaatgg caaggagtac    960
aagtgcaagg tctccaacaa agccctccca gcccccatcg agaaaaccat ctccaaagcc   1020
aaagggcagc cccgagaacc acaggtgtac accctgcccc catcccggga ggagatgacc   1080
aagaaccagg tcagcctgac ctgcctggtc aaaggcttct atcccagcga catcgccgtg   1140
gagtgggaga gcaatgggca gccggagaac aactacaaga ccacgcctcc cgtgctggac   1200
tccgacggct ccttcttcct ctatagcaag ctcaccgtgg acaagagcag gtggcagcag   1260
gggaacgtct tctcatgctc cgtgatgcat gaggctctgc acaaccacta cacgcagaag   1320
agcctctccc tgtctccggg taaa                                          1344
```

<210> SEQ ID NO 6
<211> LENGTH: 354
<212> TYPE: DNA
<213> ORGANISM: artificial sequence
<220> FEATURE:
<223> OTHER INFORMATION: Synthesized

<400> SEQUENCE: 6

```
caggtgcagc tgcaggagtc gggggggaggc ctggtcaagc ctggagggtc cctgagactc     60
tcctgtgcag cctctggatt cacctttagt agttattgga tgagctgggt ccgccaggct    120
ccagggaagg ggctggagtg ggtggccaac ataaaccgcg atggaagtgc gagttactat    180
gtggactctg tgaagggccg attcaccatc tccagagacg acgccaagaa ctcactgtat    240
ctgcaaatga acagcctgag agctgaggac acggctgtgt attactgtgc gagagatcgt    300
ggggtgggct acttcgatct ctggggccgt ggcaccctgg tcaccgtctc gagc          354
```

<210> SEQ ID NO 7
<211> LENGTH: 448
<212> TYPE: PRT
<213> ORGANISM: artificial sequence
<220> FEATURE:
<223> OTHER INFORMATION: Synthesized

<400> SEQUENCE: 7

-continued

```
Gln Val Gln Leu Gln Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Trp Met Ser Trp Val Arg Gln Ala Pro Gly Lys Gly Leu Glu Trp Val
        35                  40                  45

Ala Asn Ile Asn Arg Asp Gly Ser Ala Ser Tyr Tyr Val Asp Ser Val
    50                  55                  60

Lys Gly Arg Phe Thr Ile Ser Arg Asp Asp Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Arg Gly Val Gly Tyr Phe Asp Leu Trp Gly Arg Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Arg Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Glu Glu Met Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
```

```
            420                 425                 430

Leu His Asn His Tyr Thr Gln Lys Ser Leu Ser Leu Ser Pro Gly Lys
        435                 440                 445


<210> SEQ ID NO 8
<211> LENGTH: 118
<212> TYPE: PRT
<213> ORGANISM: artificial sequence
<220> FEATURE:
<223> OTHER INFORMATION: Synthesized

<400> SEQUENCE: 8

Gln Val Gln Leu Gln Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Trp Met Ser Trp Val Arg Gln Ala Pro Gly Lys Gly Leu Glu Trp Val
        35                  40                  45

Ala Asn Ile Asn Arg Asp Gly Ser Ala Ser Tyr Tyr Val Asp Ser Val
    50                  55                  60

Lys Gly Arg Phe Thr Ile Ser Arg Asp Asp Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Arg Gly Val Gly Tyr Phe Asp Leu Trp Gly Arg Gly Thr
            100                 105                 110

Leu Val Thr Val Ser Ser
        115


<210> SEQ ID NO 9
<211> LENGTH: 642
<212> TYPE: PRT
<213> ORGANISM: artificial sequence
<220> FEATURE:
<223> OTHER INFORMATION: Synthesized

<400> SEQUENCE: 9

Gly Ala Cys Ala Thr Cys Cys Ala Gly Ala Thr Gly Ala Cys Cys Cys
1               5                   10                  15

Ala Gly Thr Cys Thr Cys Cys Ala Thr Cys Cys Thr Cys Cys Cys Thr
            20                  25                  30

Gly Thr Cys Thr Gly Cys Ala Thr Cys Thr Gly Thr Ala Gly Gly Ala
        35                  40                  45

Gly Ala Cys Ala Gly Ala Gly Thr Cys Ala Cys Cys Ala Thr Cys Ala
    50                  55                  60

Cys Thr Thr Gly Cys Cys Ala Gly Gly Cys Gly Ala Gly Thr Cys Ala
65                  70                  75                  80

Gly Gly Ala Cys Ala Thr Cys Ala Gly Cys Ala Ala Cys Thr Ala Thr
                85                  90                  95

Thr Thr Ala Ala Ala Thr Thr Gly Gly Thr Ala Thr Cys Ala Gly Cys
            100                 105                 110

Ala Gly Ala Ala Ala Cys Cys Ala Gly Gly Gly Ala Ala Ala Gly Cys
        115                 120                 125

Cys Cys Cys Thr Ala Ala Ala Cys Thr Cys Cys Thr Gly Ala Thr Cys
    130                 135                 140

Thr Ala Cys Gly Ala Thr Gly Cys Ala Thr Cys Cys Ala Ala Thr Thr
145                 150                 155                 160
```

-continued

```
Thr Gly Gly Ala Ala Ala Cys Ala Gly Gly Gly Gly Thr Cys Cys Cys
                165                 170                 175

Ala Thr Cys Ala Ala Gly Gly Thr Thr Cys Ala Gly Thr Gly Gly Ala
            180                 185                 190

Ala Gly Thr Gly Gly Ala Thr Cys Thr Gly Gly Gly Ala Cys Ala Gly
        195                 200                 205

Ala Thr Thr Thr Thr Ala Cys Thr Thr Thr Cys Ala Cys Cys Ala Thr
    210                 215                 220

Cys Ala Gly Cys Ala Gly Cys Cys Thr Gly Cys Ala Gly Cys Cys Thr
225                 230                 235                 240

Gly Ala Ala Gly Ala Thr Ala Thr Thr Gly Cys Ala Ala Cys Ala Thr
                245                 250                 255

Ala Thr Thr Thr Cys Thr Gly Thr Cys Ala Ala Cys Ala Cys Thr Thr
            260                 265                 270

Thr Gly Ala Thr Cys Ala Thr Cys Thr Cys Cys Cys Gly Cys Thr Cys
        275                 280                 285

Gly Cys Thr Thr Thr Cys Gly Gly Cys Gly Gly Ala Gly Gly Gly Ala
    290                 295                 300

Cys Cys Ala Ala Gly Gly Thr Gly Gly Ala Ala Ala Thr Thr Ala Ala
305                 310                 315                 320

Ala Cys Gly Thr Ala Cys Gly Gly Thr Gly Gly Cys Thr Gly Cys Ala
                325                 330                 335

Cys Cys Ala Thr Cys Thr Gly Thr Cys Thr Thr Cys Ala Thr Cys Thr
            340                 345                 350

Thr Cys Cys Cys Gly Cys Cys Ala Thr Cys Thr Gly Ala Thr Gly Ala
        355                 360                 365

Gly Cys Ala Gly Thr Thr Gly Ala Ala Ala Thr Cys Thr Gly Gly Ala
    370                 375                 380

Ala Cys Thr Gly Cys Cys Thr Cys Thr Gly Thr Thr Gly Thr Gly Thr
385                 390                 395                 400

Gly Cys Cys Thr Gly Cys Thr Gly Ala Ala Thr Ala Ala Cys Thr Thr
                405                 410                 415

Cys Thr Ala Thr Cys Cys Cys Ala Gly Ala Gly Ala Gly Gly Cys Cys
            420                 425                 430

Ala Ala Ala Gly Thr Ala Cys Ala Gly Thr Gly Gly Ala Ala Gly Gly
        435                 440                 445

Thr Gly Gly Ala Thr Ala Ala Cys Gly Cys Cys Cys Thr Cys Cys Ala
    450                 455                 460

Ala Thr Cys Gly Gly Gly Thr Ala Ala Cys Thr Cys Cys Cys Ala Gly
465                 470                 475                 480

Gly Ala Gly Ala Gly Thr Gly Thr Cys Ala Cys Ala Gly Ala Gly Cys
                485                 490                 495

Ala Gly Gly Ala Cys Ala Gly Cys Ala Ala Gly Gly Ala Cys Ala Gly
            500                 505                 510

Cys Ala Cys Cys Thr Ala Cys Ala Gly Cys Cys Thr Cys Ala Gly Cys
        515                 520                 525

Ala Gly Cys Ala Cys Cys Cys Thr Gly Ala Cys Gly Cys Thr Gly Ala
    530                 535                 540

Gly Cys Ala Ala Ala Gly Cys Ala Gly Ala Cys Thr Ala Cys Gly Ala
545                 550                 555                 560

Gly Ala Ala Ala Cys Ala Cys Ala Ala Ala Gly Thr Cys Thr Ala Cys
                565                 570                 575

Gly Cys Cys Thr Gly Cys Gly Ala Ala Gly Thr Cys Ala Cys Cys Cys
```

-continued

```
            580                 585                 590

Ala Thr Cys Ala Gly Gly Gly Cys Cys Thr Gly Ala Gly Cys Thr Cys
        595                 600                 605

Gly Cys Cys Cys Gly Thr Cys Ala Cys Ala Ala Ala Gly Ala Gly Cys
    610                 615                 620

Thr Thr Cys Ala Ala Cys Ala Gly Gly Gly Gly Ala Gly Ala Gly Thr
625                 630                 635                 640

Gly Thr


<210> SEQ ID NO 10
<211> LENGTH: 321
<212> TYPE: DNA
<213> ORGANISM: artificial sequence
<220> FEATURE:
<223> OTHER INFORMATION: Synthesized

<400> SEQUENCE: 10

gacatccaga tgacccagtc tccatcctcc ctgtctgcat ctgtaggaga cagagtcacc      60

atcacttgcc aggcgagtca ggacatcagc aactatttaa attggtatca gcagaaacca     120

gggaaagccc ctaaactcct gatctacgat gcatccaatt tggaaacagg ggtcccatca     180

aggttcagtg gaagtggatc tgggacagat tttactttca ccatcagcag cctgcagcct     240

gaagatattg caacatattt ctgtcaacac tttgatcatc tcccgctcgc tttcggcgga     300

gggaccaagg tggaaattaa a                                               321


<210> SEQ ID NO 11
<211> LENGTH: 214
<212> TYPE: PRT
<213> ORGANISM: artificial sequence
<220> FEATURE:
<223> OTHER INFORMATION: Synthesized

<400> SEQUENCE: 11

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Asp Ala Ser Asn Leu Glu Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Phe Cys Gln His Phe Asp His Leu Pro Leu
                85                  90                  95

Ala Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
```

-continued

```
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 12
<211> LENGTH: 107
<212> TYPE: PRT
<213> ORGANISM: artificial sequence
<220> FEATURE:
<223> OTHER INFORMATION: Synthesized

<400> SEQUENCE: 12

```
Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Asp Ala Ser Asn Leu Glu Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Phe Cys Gln His Phe Asp His Leu Pro Leu
                85                  90                  95

Ala Phe Gly Gly Gly Thr Lys Val Glu Ile Lys
            100                 105
```

<210> SEQ ID NO 13
<211> LENGTH: 1347
<212> TYPE: DNA
<213> ORGANISM: artificial sequence
<220> FEATURE:
<223> OTHER INFORMATION: Synthesized

<400> SEQUENCE: 13

```
caggtgcagc tgcaggagtc gggcccagga ctggtgaagc cttcggagac cctgtccctc     60

acctgcactg tctctggtgg ctccgtcagc agtggtgatt actactggac ctggatccgg    120

cagtccccag ggaagggact ggagtggatt ggacacatct attacagtgg gaacaccaat    180

tataacccct ccctcaagag ccgactcacc atatcaattg acacgtccaa gactcagttc    240

tccctgaagc tgagttctgt gaccgctgcg gacacggcca tttattactg tgtgcgagat    300

cgagtgactg gtgcttttga tatctggggc caagggacaa tggtcaccgt ctcgagcgct    360

agcaccaagg gcccatcggt cttcccccctg gcaccctcct ccaagagcac ctctgggggc    420

acagcggccc tgggctgcct ggtcaaggac tacttccccg aaccggtgac ggtgtcgtgg    480

aactcaggcg ccctgaccag cggcgtgcac accttcccgg ctgtcctaca gtcctcagga    540

ctctactccc tcagcagcgt ggtgaccgtg ccctccagca gcttgggcac ccagacctac    600

atctgcaacg tgaatcacaa gcccagcaac accaaggtgg acaagagagt tgagcccaaa    660

tcttgtgaca aaactcacac atgcccaccg tgcccagcac ctgaactcct ggggggaccg    720

tcagtcttcc tcttcccccc aaaacccaag gacaccctca tgatctcccg gacccctgag    780

gtcacatgcg tggtggtgga cgtgagccac gaagaccctg aggtcaagtt caactggtac    840

gtggacggcg tggaggtgca taatgccaag acaaagccgc gggaggagca gtacaacagc    900
```

-continued

```
acgtaccgtg tggtcagcgt cctcaccgtc ctgcaccagg actggctgaa tggcaaggag    960

tacaagtgca aggtctccaa caaagccctc ccagccccca tcgagaaaac catctccaaa   1020

gccaaagggc agccccgaga accacaggtg tacaccctgc ccccatcccg ggaggagatg   1080

accaagaacc aggtcagcct gacctgcctg gtcaaaggct tctatcccag cgacatcgcc   1140

gtggagtggg agagcaatgg gcagccggag aacaactaca agaccacgcc tcccgtgctg   1200

gactccgacg gctccttctt cctctatagc aagctcaccg tggacaagag caggtggcag   1260

caggggaacg tcttctcatg ctccgtgatg catgaggctc tgcacaacca ctacacgcag   1320

aagagcctct ccctgtctcc gggtaaa                                       1347
```

<210> SEQ ID NO 14
<211> LENGTH: 357
<212> TYPE: DNA
<213> ORGANISM: artificial sequence
<220> FEATURE:
<223> OTHER INFORMATION: Synthesized

<400> SEQUENCE: 14

```
caggtgcagc tgcaggagtc gggcccagga ctggtgaagc cttcggagac cctgtccctc     60

acctgcactg tctctggtgg ctccgtcagc agtggtgatt actactggac ctggatccgg    120

cagtccccag ggaagggact ggagtggatt ggacacatct attacagtgg gaacaccaat    180

tataacccct ccctcaagag ccgactcacc atatcaattg acacgtccaa gactcagttc    240

tccctgaagc tgagttctgt gaccgctgcg gacacggcca tttattactg tgtgcgagat    300

cgagtgactg gtgcttttga tatctggggc caagggacaa tggtcaccgt ctcgagc       357
```

<210> SEQ ID NO 15
<211> LENGTH: 449
<212> TYPE: PRT
<213> ORGANISM: artificial sequence
<220> FEATURE:
<223> OTHER INFORMATION: Synthesized

<400> SEQUENCE: 15

```
Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Val Ser Ser Gly
            20                  25                  30

Asp Tyr Tyr Trp Thr Trp Ile Arg Gln Ser Pro Gly Lys Gly Leu Glu
        35                  40                  45

Trp Ile Gly His Ile Tyr Tyr Ser Gly Asn Thr Asn Tyr Asn Pro Ser
    50                  55                  60

Leu Lys Ser Arg Leu Thr Ile Ser Ile Asp Thr Ser Lys Thr Gln Phe
65                  70                  75                  80

Ser Leu Lys Leu Ser Ser Val Thr Ala Ala Asp Thr Ala Ile Tyr Tyr
                85                  90                  95

Cys Val Arg Asp Arg Val Thr Gly Ala Phe Asp Ile Trp Gly Gln Gly
            100                 105                 110

Thr Met Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
```

```
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Arg Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys


<210> SEQ ID NO 16
<211> LENGTH: 119
<212> TYPE: PRT
<213> ORGANISM: artificial sequence
<220> FEATURE:
<223> OTHER INFORMATION: Synthesized

<400> SEQUENCE: 16

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Val Ser Ser Gly
            20                  25                  30

Asp Tyr Tyr Trp Thr Trp Ile Arg Gln Ser Pro Gly Lys Gly Leu Glu
        35                  40                  45

Trp Ile Gly His Ile Tyr Tyr Ser Gly Asn Thr Asn Tyr Asn Pro Ser
    50                  55                  60

Leu Lys Ser Arg Leu Thr Ile Ser Ile Asp Thr Ser Lys Thr Gln Phe
65                  70                  75                  80
```

Ser Leu Lys Leu Ser Ser Val Thr Ala Ala Asp Thr Ala Ile Tyr Tyr
85 90 95

Cys Val Arg Asp Arg Val Thr Gly Ala Phe Asp Ile Trp Gly Gln Gly
100 105 110

Thr Met Val Thr Val Ser Ser
115

<210> SEQ ID NO 17
<211> LENGTH: 642
<212> TYPE: DNA
<213> ORGANISM: artificial sequence
<220> FEATURE:
<223> OTHER INFORMATION: Synthesized

<400> SEQUENCE: 17
gatatccaga tgacccagtc cccgagctcc ctgtccgcct ctgtgggcga tagggtcacc 60
atcacctgcc gtgccagtca gaatattgct actgatgtag cctggtatca acagaaacca 120
ggaaaagctc cgaagcttct gatttactcg gcatccttcc tctactctgg agtcccttct 180
cgcttctctg gtagcggttc cgggacggat ttcactctga ccatcagcag tctgcagccg 240
gaagacttcg caacttatta ctgtcagcaa agtgagccgg agccgtacac gttcggacag 300
ggtaccaagg tggagatcaa acgtacggtg gctgcaccat ctgtcttcat cttcccgcca 360
tctgatgagc agttgaaatc tggaactgcc tctgttgtgt gcctgctgaa taacttctat 420
cccagagagg ccaaagtaca gtggaaggtg gataacgccc tccaatcggg taactcccag 480
gagagtgtca cagagcagga cagcaaggac agcacctaca gcctcagcag caccctgacg 540
ctgagcaaag cagactacga gaaacacaaa gtctacgcct gcgaagtcac ccatcagggc 600
ctgagctcgc ccgtcacaaa gagcttcaac aggggagagt gt 642

<210> SEQ ID NO 18
<211> LENGTH: 321
<212> TYPE: DNA
<213> ORGANISM: artificial sequence
<220> FEATURE:
<223> OTHER INFORMATION: Synthesized

<400> SEQUENCE: 18
gatatccaga tgacccagtc cccgagctcc ctgtccgcct ctgtgggcga tagggtcacc 60
atcacctgcc gtgccagtca gaatattgct actgatgtag cctggtatca acagaaacca 120
ggaaaagctc cgaagcttct gatttactcg gcatccttcc tctactctgg agtcccttct 180
cgcttctctg gtagcggttc cgggacggat ttcactctga ccatcagcag tctgcagccg 240
gaagacttcg caacttatta ctgtcagcaa agtgagccgg agccgtacac gttcggacag 300
ggtaccaagg tggagatcaa a 321

<210> SEQ ID NO 19
<211> LENGTH: 214
<212> TYPE: PRT
<213> ORGANISM: artificial sequence
<220> FEATURE:
<223> OTHER INFORMATION: Synthesized

<400> SEQUENCE: 19

Asp Ile Gln Met Thr Gln Ser Pro Ser Ser Leu Ser Ala Ser Val Gly
1 5 10 15

Asp Arg Val Thr Ile Thr Cys Arg Ala Ser Gln Asn Ile Ala Thr Asp
20 25 30

-continued

```
Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Glu Pro Glu Pro Tyr
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210


<210> SEQ ID NO 20
<211> LENGTH: 107
<212> TYPE: PRT
<213> ORGANISM: artificial sequence
<220> FEATURE:
<223> OTHER INFORMATION: Synthesized

<400> SEQUENCE: 20

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asn Ile Ala Thr Asp
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Glu Pro Glu Pro Tyr
                85                  90                  95

Thr Phe Gly Gln Gly Thr Lys Val Glu Ile Lys
            100                 105


<210> SEQ ID NO 21
<211> LENGTH: 1353
<212> TYPE: DNA
<213> ORGANISM: artificial sequence
<220> FEATURE:
<223> OTHER INFORMATION: Synthesized

<400> SEQUENCE: 21

gaggtgcagc tggtcgagtc tggcggcgga ctggtgcagc ccggtggctc tctgcgactg      60
```

```
tcttgtgccg cctctggctt caccctcagt ggcgattgga tccactgggt gcgacaggct    120

cccggaaagg gcctggagtg ggtgggtgag atctctgctg ccggtggcta caccgattac    180

gccgactctg tgaagggccg attcaccatc tctgccgaca cctctaagaa caccgcctac    240

ctgcagatga actctctgcg agccgaggac accgctgtgt actactgtgc acgagaaagt    300

agagtttcct tcgaagccgc catggactac tggggccagg gcaccctggt gaccgtgtcc    360

tctgctagca ccaagggccc atcggtcttc cccctggcac cctcctccaa gagcacctct    420

gggggcacag cggccctggg ctgcctggtc aaggactact tccccgaacc ggtgacggtg    480

tcgtggaact caggcgccct gaccagcggc gtgcacacct tcccggctgt cctacagtcc    540

tcaggactct actccctcag cagcgtggtg accgtgccct ccagcagctt gggcacccag    600

acctacatct gcaacgtgaa tcacaagccc agcaacacca aggtggacaa gagagttgag    660

cccaaatctt gtgacaaaac tcacacatgc ccaccgtgcc cagcacctga actcctgggg    720

ggaccgtcag tcttcctctt ccccccaaaa cccaaggaca ccctcatgat ctcccggacc    780

cctgaggtca catgcgtggt ggtggacgtg agccacgaag accctgaggt caagttcaac    840

tggtacgtgg acggcgtgga ggtgcataat gccaagacaa agccgcggga ggagcagtac    900

aacagcacgt accgtgtggt cagcgtcctc accgtcctgc accaggactg gctgaatggc    960

aaggagtaca agtgcaaggt ctccaacaaa gccctcccag cccccatcga gaaaaccatc   1020

tccaaagcca aagggcagcc ccgagaacca caggtgtaca ccctgccccc atcccgggag   1080

gagatgacca agaaccaggt cagcctgacc tgcctggtca aaggcttcta tcccagcgac   1140

atcgccgtgg agtgggagag caatgggcag ccggagaaca actacaagac cacgcctccc   1200

gtgctggact ccgacggctc cttcttcctc tatagcaagc tcaccgtgga caagagcagg   1260

tggcagcagg ggaacgtctt ctcatgctcc gtgatgcatg aggctctgca caaccactac   1320

acgcagaaga gcctctccct gtctccgggt aaa                                1353
```

```
<210> SEQ ID NO 22
<211> LENGTH: 363
<212> TYPE: PRT
<213> ORGANISM: artificial sequence
<220> FEATURE:
<223> OTHER INFORMATION: Synthesized

<400> SEQUENCE: 22

Gly Ala Gly Gly Thr Gly Cys Ala Gly Cys Thr Gly Gly Thr Cys Gly
1               5                   10                  15

Ala Gly Thr Cys Thr Gly Gly Cys Gly Gly Cys Gly Gly Ala Cys Thr
            20                  25                  30

Gly Gly Thr Gly Cys Ala Gly Cys Cys Cys Gly Gly Thr Gly Gly Cys
        35                  40                  45

Thr Cys Thr Cys Thr Gly Cys Gly Ala Cys Thr Gly Thr Cys Thr Thr
    50                  55                  60

Gly Thr Gly Cys Cys Gly Cys Cys Thr Cys Thr Gly Gly Cys Thr Thr
65                  70                  75                  80

Cys Ala Cys Cys Cys Thr Cys Ala Gly Thr Gly Gly Cys Gly Ala Thr
                85                  90                  95

Thr Gly Gly Ala Thr Cys Cys Ala Cys Thr Gly Gly Gly Thr Gly Cys
            100                 105                 110

Gly Ala Cys Ala Gly Gly Cys Thr Cys Cys Cys Gly Gly Ala Ala Ala
        115                 120                 125
```

Gly Gly Gly Cys Cys Thr Gly Gly Ala Gly Thr Gly Gly Gly Thr Gly
    130                 135                 140

Gly Gly Thr Gly Ala Gly Ala Thr Cys Thr Cys Thr Gly Cys Thr Gly
145                 150                 155                 160

Cys Cys Gly Gly Thr Gly Gly Cys Thr Ala Cys Ala Cys Cys Gly Ala
                165                 170                 175

Thr Thr Ala Cys Gly Cys Cys Gly Ala Cys Thr Cys Thr Gly Thr Gly
            180                 185                 190

Ala Ala Gly Gly Gly Cys Cys Gly Ala Thr Thr Cys Ala Cys Cys Ala
        195                 200                 205

Thr Cys Thr Cys Thr Gly Cys Cys Gly Ala Cys Ala Cys Cys Thr Cys
    210                 215                 220

Thr Ala Ala Gly Ala Ala Cys Ala Cys Cys Gly Cys Cys Thr Ala Cys
225                 230                 235                 240

Cys Thr Gly Cys Ala Gly Ala Thr Gly Ala Ala Cys Thr Cys Thr Cys
                245                 250                 255

Thr Gly Cys Gly Ala Gly Cys Cys Gly Ala Gly Gly Ala Cys Ala Cys
            260                 265                 270

Cys Gly Cys Thr Gly Thr Gly Thr Ala Cys Thr Ala Cys Thr Gly Thr
        275                 280                 285

Gly Cys Ala Cys Gly Ala Gly Ala Ala Ala Gly Thr Ala Gly Ala Gly
    290                 295                 300

Thr Thr Thr Cys Cys Thr Thr Cys Gly Ala Ala Gly Cys Cys Gly Cys
305                 310                 315                 320

Cys Ala Thr Gly Gly Ala Cys Thr Ala Cys Thr Gly Gly Gly Gly Cys
                325                 330                 335

Cys Ala Gly Gly Gly Cys Ala Cys Cys Cys Thr Gly Gly Thr Gly Ala
            340                 345                 350

Cys Cys Gly Thr Gly Thr Cys Cys Thr Cys Thr
        355                 360

<210> SEQ ID NO 23
<211> LENGTH: 451
<212> TYPE: PRT
<213> ORGANISM: artificial sequence
<220> FEATURE:
<223> OTHER INFORMATION: Synthesized

<400> SEQUENCE: 23

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Leu Ser Gly Asp
            20                  25                  30

Trp Ile His Trp Val Arg Gln Ala Pro Gly Lys Gly Leu Glu Trp Val
        35                  40                  45

Gly Glu Ile Ser Ala Ala Gly Gly Tyr Thr Asp Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Glu Ser Arg Val Ser Phe Glu Ala Ala Met Asp Tyr Trp Gly
            100                 105                 110

Gln Gly Thr Leu Val Thr Val Ser Ser Ala Ser Thr Lys Gly Pro Ser
        115                 120                 125

-continued

```
Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Arg Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Glu Glu Met Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys
    450
```

<210> SEQ ID NO 24
<211> LENGTH: 121
<212> TYPE: PRT
<213> ORGANISM: artificial sequence
<220> FEATURE:
<223> OTHER INFORMATION: Synthesized

<400> SEQUENCE: 24

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Leu Ser Gly Asp
            20                  25                  30
```

-continued

```
Trp Ile His Trp Val Arg Gln Ala Pro Gly Lys Gly Leu Glu Trp Val
        35                  40                  45

Gly Glu Ile Ser Ala Ala Gly Gly Tyr Thr Asp Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Glu Ser Arg Val Ser Phe Glu Ala Ala Met Asp Tyr Trp Gly
            100                 105                 110

Gln Gly Thr Leu Val Thr Val Ser Ser
        115                 120
```

```
<210> SEQ ID NO 25
<211> LENGTH: 657
<212> TYPE: DNA
<213> ORGANISM: artificial sequence
<220> FEATURE:
<223> OTHER INFORMATION: Synthesized

<400> SEQUENCE: 25

gatattcaaa tgactcaatc tccttcttct ctttctgctt ctgttggtga tcgtgttact     60

attacttgtc gttcttctca aaatattgtt cattctaatg gtaatactta tcttgattgg    120

tatcaacaaa ctcctggtaa agctcctaaa cttcttattt ataaagtttc taatcgtttt    180

tctggtgttc cttctcgttt ttctggttct ggttctggta ctgattttac ttttactatt    240

tcttctcttc aacctgaaga tattgctact tattattgtt ttcaatattc tcatgttcct    300

tggacttttg gtcaaggtac taaacttcaa attactcgta cggtggctgc accatctgtc    360

ttcatcttcc cgccatctga tgagcagttg aaatctggaa ctgcctctgt tgtgtgcctg    420

ctgaataact tctatcccag agaggccaaa gtacagtgga aggtggataa cgccctccaa    480

tcgggtaact cccaggagag tgtcacagag caggacagca aggacagcac ctacagcctc    540

agcagcaccc tgacgctgag caaagcagac tacgagaaac acaaagtcta cgcctgcgaa    600

gtcacccatc agggcctgag ctcgcccgtc acaaagagct tcaacagggg agagtgt       657


<210> SEQ ID NO 26
<211> LENGTH: 336
<212> TYPE: DNA
<213> ORGANISM: artificial sequence
<220> FEATURE:
<223> OTHER INFORMATION: Synthesized

<400> SEQUENCE: 26

gatattcaaa tgactcaatc tccttcttct ctttctgctt ctgttggtga tcgtgttact     60

attacttgtc gttcttctca aaatattgtt cattctaatg gtaatactta tcttgattgg    120

tatcaacaaa ctcctggtaa agctcctaaa cttcttattt ataaagtttc taatcgtttt    180

tctggtgttc cttctcgttt ttctggttct ggttctggta ctgattttac ttttactatt    240

tcttctcttc aacctgaaga tattgctact tattattgtt ttcaatattc tcatgttcct    300

tggacttttg gtcaaggtac taaacttcaa attact                              336


<210> SEQ ID NO 27
<211> LENGTH: 219
<212> TYPE: PRT
<213> ORGANISM: artificial sequence
<220> FEATURE:
<223> OTHER INFORMATION: Synthesized
```

<400> SEQUENCE: 27

Asp Ile Gln Met Thr Gln Ser Pro Ser Ser Leu Ser Ala Ser Val Gly
1 5 10 15

Asp Arg Val Thr Ile Thr Cys Arg Ser Ser Gln Asn Ile Val His Ser
20 25 30

Asn Gly Asn Thr Tyr Leu Asp Trp Tyr Gln Gln Thr Pro Gly Lys Ala
35 40 45

Pro Lys Leu Leu Ile Tyr Lys Val Ser Asn Arg Phe Ser Gly Val Pro
50 55 60

Ser Arg Phe Ser Gly Ser Gly Ser Gly Thr Asp Phe Thr Phe Thr Ile
65 70 75 80

Ser Ser Leu Gln Pro Glu Asp Ile Ala Thr Tyr Tyr Cys Phe Gln Tyr
85 90 95

Ser His Val Pro Trp Thr Phe Gly Gln Gly Thr Lys Leu Gln Ile Thr
100 105 110

Arg Thr Val Ala Ala Pro Ser Val Phe Ile Phe Pro Pro Ser Asp Glu
115 120 125

Gln Leu Lys Ser Gly Thr Ala Ser Val Val Cys Leu Leu Asn Asn Phe
130 135 140

Tyr Pro Arg Glu Ala Lys Val Gln Trp Lys Val Asp Asn Ala Leu Gln
145 150 155 160

Ser Gly Asn Ser Gln Glu Ser Val Thr Glu Gln Asp Ser Lys Asp Ser
165 170 175

Thr Tyr Ser Leu Ser Ser Thr Leu Thr Leu Ser Lys Ala Asp Tyr Glu
180 185 190

Lys His Lys Val Tyr Ala Cys Glu Val Thr His Gln Gly Leu Ser Ser
195 200 205

Pro Val Thr Lys Ser Phe Asn Arg Gly Glu Cys
210 215

<210> SEQ ID NO 28
<211> LENGTH: 112
<212> TYPE: PRT
<213> ORGANISM: artificial sequence
<220> FEATURE:
<223> OTHER INFORMATION: Synthesized

<400> SEQUENCE: 28

Asp Ile Gln Met Thr Gln Ser Pro Ser Ser Leu Ser Ala Ser Val Gly
1 5 10 15

Asp Arg Val Thr Ile Thr Cys Arg Ser Ser Gln Asn Ile Val His Ser
20 25 30

Asn Gly Asn Thr Tyr Leu Asp Trp Tyr Gln Gln Thr Pro Gly Lys Ala
35 40 45

Pro Lys Leu Leu Ile Tyr Lys Val Ser Asn Arg Phe Ser Gly Val Pro
50 55 60

Ser Arg Phe Ser Gly Ser Gly Ser Gly Thr Asp Phe Thr Phe Thr Ile
65 70 75 80

Ser Ser Leu Gln Pro Glu Asp Ile Ala Thr Tyr Tyr Cys Phe Gln Tyr
85 90 95

Ser His Val Pro Trp Thr Phe Gly Gln Gly Thr Lys Leu Gln Ile Thr
100 105 110

<210> SEQ ID NO 29
<211> LENGTH: 1359

<212> TYPE: DNA
<213> ORGANISM: artificial sequence
<220> FEATURE:
<223> OTHER INFORMATION: Synthesized

<400> SEQUENCE: 29
caagttcaac ttcaacaatc tggtgctgaa gttaaaaaac ctggttcttc tgttaaagtt 60
tcttgtaaag cctctggtta tacttttact aattattata tttattgggt tcgtcaagct 120
cctggtcaag gtcttgaatg gattggtggt attaatccta cttctggtgg ttctaatttt 180
aatgaaaaat ttaaaactcg tgttactatt actgttgatg aatctacgaa cactgcttat 240
atggaacttt cttctcttcg ttctgaagat actgcttttt atttttgtgc gcgtcaaggt 300
ctttggtttg attctgatgg tcgtggtttt gatttttggg gtcaaggttc cactgttact 360
gtctcgagcg ctagcaccaa gggcccatcg gtcttccccc tggcaccctc ctccaagagc 420
acctctgggg gcacagcggc cctgggctgc ctggtcaagg actacttccc cgaaccggtg 480
acggtgtcgt ggaactcagg cgccctgacc agcggcgtgc acaccttccc ggctgtccta 540
cagtcctcag gactctactc cctcagcagc gtggtgaccg tgccctccag cagcttgggc 600
acccagacct acatctgcaa cgtgaatcac aagcccagca acaccaaggt ggacaagaga 660
gttgagccca aatcttgtga caaaactcac acatgcccac cgtgcccagc acctgaactc 720
ctggggggac cgtcagtctt cctcttcccc ccaaaaccca aggacaccct catgatctcc 780
cggacccctg aggtcacatg cgtggtggtg gacgtgagcc acgaagaccc tgaggtcaag 840
ttcaactggt acgtggacgg cgtggaggtg cataatgcca agacaaagcc gcgggaggag 900
cagtacaaca gcacgtaccg tgtggtcagc gtcctcaccg tcctgcacca ggactggctg 960
aatggcaagg agtacaagtg caaggtctcc aacaaagccc tcccagcccc catcgagaaa 1020
accatctcca aagccaaagg gcagccccga gaaccacagg tgtacaccct gcccccatcc 1080
cgggaggaga tgaccaagaa ccaggtcagc ctgacctgcc tggtcaaagg cttctatccc 1140
agcgacatcg ccgtggagtg ggagagcaat gggcagccgg agaacaacta caagaccacg 1200
cctcccgtgc tggactccga cggctccttc ttcctctata gcaagctcac cgtggacaag 1260
agcaggtggc agcaggggaa cgtcttctca tgctccgtga tgcatgaggc tctgcacaac 1320
cactacacgc agaagagcct ctccctgtct ccgggtaaa 1359

<210> SEQ ID NO 30
<211> LENGTH: 369
<212> TYPE: DNA
<213> ORGANISM: artificial sequence
<220> FEATURE:
<223> OTHER INFORMATION: Synthesized

<400> SEQUENCE: 30
caagttcaac ttcaacaatc tggtgctgaa gttaaaaaac ctggttcttc tgttaaagtt 60
tcttgtaaag cctctggtta tacttttact aattattata tttattgggt tcgtcaagct 120
cctggtcaag gtcttgaatg gattggtggt attaatccta cttctggtgg ttctaatttt 180
aatgaaaaat ttaaaactcg tgttactatt actgttgatg aatctacgaa cactgcttat 240
atggaacttt cttctcttcg ttctgaagat actgcttttt atttttgtgc gcgtcaaggt 300
ctttggtttg attctgatgg tcgtggtttt gatttttggg gtcaaggttc cactgttact 360
gtctcgagc 369

<210> SEQ ID NO 31

```
<211> LENGTH: 453
<212> TYPE: PRT
<213> ORGANISM: artificial sequence
<220> FEATURE:
<223> OTHER INFORMATION: Synthesized

<400> SEQUENCE: 31

Gln Val Gln Leu Gln Gln Ser Gly Ala Glu Val Lys Lys Pro Gly Ser
1               5                   10                  15

Ser Val Lys Val Ser Cys Lys Ala Ser Gly Tyr Thr Phe Thr Asn Tyr
            20                  25                  30

Tyr Ile Tyr Trp Val Arg Gln Ala Pro Gly Gln Gly Leu Glu Trp Ile
        35                  40                  45

Gly Gly Ile Asn Pro Thr Ser Gly Gly Ser Asn Phe Asn Glu Lys Phe
    50                  55                  60

Lys Thr Arg Val Thr Ile Thr Val Asp Glu Ser Thr Asn Thr Ala Tyr
65                  70                  75                  80

Met Glu Leu Ser Ser Leu Arg Ser Glu Asp Thr Ala Phe Tyr Phe Cys
                85                  90                  95

Ala Arg Gln Gly Leu Trp Phe Asp Ser Asp Gly Arg Gly Phe Asp Phe
            100                 105                 110

Trp Gly Gln Gly Ser Thr Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Arg Val Glu Pro Lys
    210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Asn Ser
    290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
            340                 345                 350

Gln Val Tyr Thr Leu Pro Pro Ser Arg Glu Glu Met Thr Lys Asn Gln
        355                 360                 365

Val Ser Leu Thr Cys Leu Val Lys Gly Phe Tyr Pro Ser Asp Ile Ala
    370                 375                 380
```

Val Glu Trp Glu Ser Asn Gly Gln Pro Glu Asn Asn Tyr Lys Thr Thr
385 390 395 400

Pro Pro Val Leu Asp Ser Asp Gly Ser Phe Phe Leu Tyr Ser Lys Leu
405 410 415

Thr Val Asp Lys Ser Arg Trp Gln Gln Gly Asn Val Phe Ser Cys Ser
420 425 430

Val Met His Glu Ala Leu His Asn His Tyr Thr Gln Lys Ser Leu Ser
435 440 445

Leu Ser Pro Gly Lys
450

<210> SEQ ID NO 32
<211> LENGTH: 123
<212> TYPE: PRT
<213> ORGANISM: artificial sequence
<220> FEATURE:
<223> OTHER INFORMATION: Synthesized

<400> SEQUENCE: 32

Gln Val Gln Leu Gln Gln Ser Gly Ala Glu Val Lys Lys Pro Gly Ser
1 5 10 15

Ser Val Lys Val Ser Cys Lys Ala Ser Gly Tyr Thr Phe Thr Asn Tyr
20 25 30

Tyr Ile Tyr Trp Val Arg Gln Ala Pro Gly Gln Gly Leu Glu Trp Ile
35 40 45

Gly Gly Ile Asn Pro Thr Ser Gly Gly Ser Asn Phe Asn Glu Lys Phe
50 55 60

Lys Thr Arg Val Thr Ile Thr Val Asp Glu Ser Thr Asn Thr Ala Tyr
65 70 75 80

Met Glu Leu Ser Ser Leu Arg Ser Glu Asp Thr Ala Phe Tyr Phe Cys
85 90 95

Ala Arg Gln Gly Leu Trp Phe Asp Ser Asp Gly Arg Gly Phe Asp Phe
100 105 110

Trp Gly Gln Gly Ser Thr Val Thr Val Ser Ser
115 120

<210> SEQ ID NO 33
<211> LENGTH: 657
<212> TYPE: DNA
<213> ORGANISM: artificial sequence
<220> FEATURE:
<223> OTHER INFORMATION: Synthesized

<400> SEQUENCE: 33
gatattcaaa tgactcaatc tccttcttct ctttctgctt ctgttggtga tcgtgttact 60
attacttgtc gttcttctca aaatattgtt cattctaatg gtaatactta tcttgattgg 120
tatcaacaaa ctcctggtaa agctcctaaa cttcttattt ataaagtttc taatcgtttt 180
tctggtgttc cttctcgttt ttctggttct ggttctggta ctgattttac ttttactatt 240
tcttctcttc aacctgaaga tattgctact tattattgtt ttcaatattc tcatgttcct 300
tggacttttg gtcaaggtac taaacttcaa attactcgta cggtggctgc accatctgtc 360
ttcatcttcc cgccatctga tgagcagttg aaatctggaa ctgcctctgt tgtgtgcctg 420
ctgaataact tctatcccag agaggccaaa gtacagtgga aggtggataa cgccctccaa 480
tcgggtaact cccaggagag tgtcacagag caggacagca aggacagcac ctacagcctc 540
agcagcaccc tgacgctgag caaagcagac tacgagaaac acaaagtcta cgcctgcgaa 600
gtcacccatc agggcctgag ctcgcccgtc acaaagagct tcaacagggg agagtgt 657

<210> SEQ ID NO 34
<211> LENGTH: 336
<212> TYPE: DNA
<213> ORGANISM: artificial sequence
<220> FEATURE:
<223> OTHER INFORMATION: Synthesized

<400> SEQUENCE: 34
gatattcaaa tgactcaatc tccttcttct ctttctgctt ctgttggtga tcgtgttact 60
attacttgtc gttcttctca aaatattgtt cattctaatg gtaatactta tcttgattgg 120
tatcaacaaa ctcctggtaa agctcctaaa cttcttattt ataaagtttc taatcgtttt 180
tctggtgttc cttctcgttt ttctggttct ggttctggta ctgattttac ttttactatt 240
tcttctcttc aacctgaaga tattgctact tattattgtt ttcaatattc tcatgttcct 300
tggacttttg gtcaaggtac taaacttcaa attact 336

<210> SEQ ID NO 35
<211> LENGTH: 218
<212> TYPE: PRT
<213> ORGANISM: artificial sequence
<220> FEATURE:
<223> OTHER INFORMATION: Synthesized

<400> SEQUENCE: 35

Gln Ser Ala Leu Thr Gln Pro Ala Ser Val Ser Gly Ser Pro Gly Gln
1 5 10 15

Ser Ile Thr Ile Ser Cys Thr Gly Thr Ser Ser Asp Val Gly Gly Tyr
20 25 30

Asn Phe Val Ser Trp Tyr Gln Gln His Pro Gly Lys Ala Pro Lys Leu
35 40 45

Met Ile Tyr Asp Val Ser Asp Arg Pro Ser Gly Val Ser Asp Arg Phe
50 55 60

Ser Gly Ser Lys Ser Gly Asn Thr Ala Ser Leu Ile Ile Ser Gly Leu
65 70 75 80

Gln Ala Asp Asp Glu Ala Asp Tyr Tyr Cys Ser Ser Tyr Gly Ser Ser
85 90 95

Ser Thr His Val Ile Phe Gly Gly Gly Thr Lys Leu Thr Val Leu Arg
100 105 110

Thr Val Ala Ala Pro Ser Val Phe Ile Phe Pro Pro Ser Asp Glu Gln
115 120 125

Leu Lys Ser Gly Thr Ala Ser Val Val Cys Leu Leu Asn Asn Phe Tyr
130 135 140

Pro Arg Glu Ala Lys Val Gln Trp Lys Val Asp Asn Ala Leu Gln Ser
145 150 155 160

Gly Asn Ser Gln Glu Ser Val Thr Glu Gln Asp Ser Lys Asp Ser Thr
165 170 175

Tyr Ser Leu Ser Ser Thr Leu Thr Leu Ser Lys Ala Asp Tyr Glu Lys
180 185 190

His Lys Val Tyr Ala Cys Glu Val Thr His Gln Gly Leu Ser Ser Pro
195 200 205

Val Thr Lys Ser Phe Asn Arg Gly Glu Cys
210 215

<210> SEQ ID NO 36

<211> LENGTH: 111
<212> TYPE: PRT
<213> ORGANISM: artificial sequence
<220> FEATURE:
<223> OTHER INFORMATION: Synthesized

<400> SEQUENCE: 36

```
Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
            20                  25                  30

Asn Phe Val Ser Trp Tyr Gln Gln His Pro Gly Lys Ala Pro Lys Leu
        35                  40                  45

Met Ile Tyr Asp Val Ser Asp Arg Pro Ser Gly Val Ser Asp Arg Phe
    50                  55                  60

Ser Gly Ser Lys Ser Gly Asn Thr Ala Ser Leu Ile Ile Ser Gly Leu
65                  70                  75                  80

Gln Ala Asp Asp Glu Ala Asp Tyr Tyr Cys Ser Ser Tyr Gly Ser Ser
                85                  90                  95

Ser Thr His Val Ile Phe Gly Gly Gly Thr Lys Leu Thr Val Leu
            100                 105                 110
```

<210> SEQ ID NO 37
<211> LENGTH: 1356
<212> TYPE: DNA
<213> ORGANISM: artificial sequence
<220> FEATURE:
<223> OTHER INFORMATION: Synthesized

<400> SEQUENCE: 37

```
caggtgcagc tgcagcagag cggcgccgag gtgaagaagc ccggcagcag cgtgaaggtg     60

agctgcaagg ccagcggcta caccttcacc aactactaca tctactgggt gcggcaggcc    120

cccggccagg gcctggagtg gatcggcggc atcaacccca ccagcggcgg cagcaacttc    180

aacgagaagt tcaagacccg ggtgaccatc accgccgacg agagcagcac caccgcctac    240

atggagctga gcagcctgcg gagcgaggac accgccttct acttctgcac ccggcagggc    300

ctgtggttcg acagcgacgg ccggggcttc gacttctggg gccagggcac caccgtgacc    360

gtgagcagcg ctagcaccaa gggcccatcg gtcttccccc tggcaccctc ctccaagagc    420

acctctgggg gcacagcggc cctgggctgc ctggtcaagg actacttccc cgaaccggtg    480

acggtgtcgt ggaactcagg cgccctgacc agcggcgtgc acaccttccc ggctgtccta    540

cagtcctcag gactctactc cctcagcagc gtggtgaccg tgccctccag cagcttgggc    600

acccagacct acatctgcaa cgtgaatcac aagcccagca acaccaaggt ggacaagaga    660

gttgagccca aatcttgtga caaaactcac acatgcccac cgtgcccagc acctgaactc    720

ctggggggac cgtcagtctt cctcttcccc ccaaaaccca aggacaccct catgatctcc    780

cggacccctg aggtcacatg cgtggtggtg gacgtgagcc acgaagaccc tgaggtcaag    840

ttcaactggt acgtggacgg cgtggaggtg cataatgcca agacaaagcc gcgggaggag    900

cagtacaaca gcacgtaccg tgtggtcagc gtcctcaccg tcctgcacca ggactggctg    960

aatggcaagg agtacaagtg caaggtctcc aacaaagccc tcccagcccc catcgagaaa   1020

accatctcca aagccaaagg gcagccccga gaaccacagg tgtacaccct gcccccatcc   1080

cgggatgagc tgaccaagaa ccaggtcagc ctgacctgcc tggtcaaagg cttctatccc   1140

agcgacatcg ccgtggagtg ggagagcaat gggcagccgg agaacaacta caagaccacg   1200
```

-continued

```
cctcccgtgc tggactccga cggctccttc ttcctctata gcaagctcac cgtggacaag   1260

agcaggtggc agcaggggaa cgtcttctca tgctccgtga tgcatgaggc tctgcacaac   1320

cactacacgc agaagagcct ctccctgtct ccgggt                             1356


<210> SEQ ID NO 38
<211> LENGTH: 369
<212> TYPE: DNA
<213> ORGANISM: artificial sequence
<220> FEATURE:
<223> OTHER INFORMATION: Synthesized

<400> SEQUENCE: 38

caggtgcagc tgcagcagag cggcgccgag gtgaagaagc ccggcagcag cgtgaaggtg     60

agctgcaagg ccagcggcta caccttcacc aactactaca tctactgggt gcggcaggcc    120

cccggccagg gcctggagtg gatcggcggc atcaacccca ccagcggcgg cagcaacttc    180

aacgagaagt tcaagacccg ggtgaccatc accgccgacg agagcagcac caccgcctac    240

atggagctga gcagcctgcg gagcgaggac accgccttct acttctgcac ccggcagggc    300

ctgtggttcg acagcgacgg ccggggcttc gacttctggg gccagggcac caccgtgacc    360

gtgagcagc                                                            369


<210> SEQ ID NO 39
<211> LENGTH: 452
<212> TYPE: PRT
<213> ORGANISM: artificial sequence
<220> FEATURE:
<223> OTHER INFORMATION: Synthesized

<400> SEQUENCE: 39

Gln Val Gln Leu Gln Gln Ser Gly Ala Glu Val Lys Lys Pro Gly Ser
1               5                   10                  15

Ser Val Lys Val Ser Cys Lys Ala Ser Gly Tyr Thr Phe Thr Asn Tyr
            20                  25                  30

Tyr Ile Tyr Trp Val Arg Gln Ala Pro Gly Gln Gly Leu Glu Trp Ile
        35                  40                  45

Gly Gly Ile Asn Pro Thr Ser Gly Gly Ser Asn Phe Asn Glu Lys Phe
    50                  55                  60

Lys Thr Arg Val Thr Ile Thr Ala Asp Glu Ser Ser Thr Thr Ala Tyr
65                  70                  75                  80

Met Glu Leu Ser Ser Leu Arg Ser Glu Asp Thr Ala Phe Tyr Phe Cys
                85                  90                  95

Thr Arg Gln Gly Leu Trp Phe Asp Ser Asp Gly Arg Gly Phe Asp Phe
            100                 105                 110

Trp Gly Gln Gly Thr Thr Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205
```

```
Asn His Lys Pro Ser Asn Thr Lys Val Asp Lys Arg Val Glu Pro Lys
    210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Asn Ser
    290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
            340                 345                 350

Gln Val Tyr Thr Leu Pro Pro Ser Arg Asp Glu Leu Thr Lys Asn Gln
        355                 360                 365

Val Ser Leu Thr Cys Leu Val Lys Gly Phe Tyr Pro Ser Asp Ile Ala
    370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
            420                 425                 430

Val Met His Glu Ala Leu His Asn His Tyr Thr Gln Lys Ser Leu Ser
        435                 440                 445

Leu Ser Pro Gly
    450


<210> SEQ ID NO 40
<211> LENGTH: 123
<212> TYPE: PRT
<213> ORGANISM: artificial sequence
<220> FEATURE:
<223> OTHER INFORMATION: Synthesized

<400> SEQUENCE: 40

Gln Val Gln Leu Gln Gln Ser Gly Ala Glu Val Lys Lys Pro Gly Ser
1               5                   10                  15

Ser Val Lys Val Ser Cys Lys Ala Ser Gly Tyr Thr Phe Thr Asn Tyr
            20                  25                  30

Tyr Ile Tyr Trp Val Arg Gln Ala Pro Gly Gln Gly Leu Glu Trp Ile
        35                  40                  45

Gly Gly Ile Asn Pro Thr Ser Gly Gly Ser Asn Phe Asn Glu Lys Phe
    50                  55                  60

Lys Thr Arg Val Thr Ile Thr Ala Asp Glu Ser Ser Thr Thr Ala Tyr
65                  70                  75                  80

Met Glu Leu Ser Ser Leu Arg Ser Glu Asp Thr Ala Phe Tyr Phe Cys
                85                  90                  95

Thr Arg Gln Gly Leu Trp Phe Asp Ser Asp Gly Arg Gly Phe Asp Phe
            100                 105                 110
```

-continued

```
Trp Gly Gln Gly Thr Thr Val Thr Val Ser Ser
        115                 120


<210> SEQ ID NO 41
<211> LENGTH: 642
<212> TYPE: DNA
<213> ORGANISM: artificial sequence
<220> FEATURE:
<223> OTHER INFORMATION: Synthesized

<400> SEQUENCE: 41

gacatcttgc tgactcagtc tccagtcatc ctgtctgtga gtccaggaga aagagtcagt      60

ttctcctgca gggccagtca gagtattggc acaaacatac actggtatca gcaaagaaca     120

aatggttctc caaggcttct cataaagtat gcttctgagt ctatctctgg gattccttcc     180

aggtttagtg gcagtggatc agggacagat tttactctta gcatcaacag tgtggagtct     240

gaagatattg cagattatta ctgtcaacaa aataataact ggccaaccac gttcggtgct     300

gggaccaagc tggagctgaa acgtacggtg gctgcaccat ctgtcttcat cttcccgcca     360

tctgatgagc agttgaaatc tggaactgcc tctgttgtgt gcctgctgaa taacttctat     420

cccagagagg ccaaagtaca gtggaaggtg gataacgccc tccaatcggg taactcccag     480

gagagtgtca cagagcagga cagcaaggac agcacctaca gcctcagcag caccctgacg     540

ctgagcaaag cagactacga gaaacacaaa gtctacgcct gcgaagtcac ccatcagggc     600

ctgagctcgc ccgtcacaaa gagcttcaac aggggagagt gt                        642


<210> SEQ ID NO 42
<211> LENGTH: 321
<212> TYPE: DNA
<213> ORGANISM: artificial sequence
<220> FEATURE:
<223> OTHER INFORMATION: Synthesized

<400> SEQUENCE: 42

gacatcttgc tgactcagtc tccagtcatc ctgtctgtga gtccaggaga aagagtcagt      60

ttctcctgca gggccagtca gagtattggc acaaacatac actggtatca gcaaagaaca     120

aatggttctc caaggcttct cataaagtat gcttctgagt ctatctctgg gattccttcc     180

aggtttagtg gcagtggatc agggacagat tttactctta gcatcaacag tgtggagtct     240

gaagatattg cagattatta ctgtcaacaa aataataact ggccaaccac gttcggtgct     300

gggaccaagc tggagctgaa a                                               321


<210> SEQ ID NO 43
<211> LENGTH: 214
<212> TYPE: PRT
<213> ORGANISM: artificial sequence
<220> FEATURE:
<223> OTHER INFORMATION: Synthesized

<400> SEQUENCE: 43

Asp Ile Leu Leu Thr Gln Ser Pro Val Ile Leu Ser Val Ser Pro Gly
1               5                   10                  15

Glu Arg Val Ser Phe Ser Cys Arg Ala Ser Gln Ser Ile Gly Thr Asn
            20                  25                  30

Ile His Trp Tyr Gln Gln Arg Thr Asn Gly Ser Pro Arg Leu Leu Ile
        35                  40                  45

Lys Tyr Ala Ser Glu Ser Ile Ser Gly Ile Pro Ser Arg Phe Ser Gly
    50                  55                  60
```

```
Ser Gly Ser Gly Thr Asp Phe Thr Leu Ser Ile Asn Ser Val Glu Ser
65                  70                  75                  80

Glu Asp Ile Ala Asp Tyr Tyr Cys Gln Gln Asn Asn Asn Trp Pro Thr
                85                  90                  95

Thr Phe Gly Ala Gly Thr Lys Leu Glu Leu Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210


<210> SEQ ID NO 44
<211> LENGTH: 107
<212> TYPE: PRT
<213> ORGANISM: artificial sequence
<220> FEATURE:
<223> OTHER INFORMATION: Synthesized

<400> SEQUENCE: 44

Asp Ile Leu Leu Thr Gln Ser Pro Val Ile Leu Ser Val Ser Pro Gly
1               5                   10                  15

Glu Arg Val Ser Phe Ser Cys Arg Ala Ser Gln Ser Ile Gly Thr Asn
            20                  25                  30

Ile His Trp Tyr Gln Gln Arg Thr Asn Gly Ser Pro Arg Leu Leu Ile
        35                  40                  45

Lys Tyr Ala Ser Glu Ser Ile Ser Gly Ile Pro Ser Arg Phe Ser Gly
    50                  55                  60

Ser Gly Ser Gly Thr Asp Phe Thr Leu Ser Ile Asn Ser Val Glu Ser
65                  70                  75                  80

Glu Asp Ile Ala Asp Tyr Tyr Cys Gln Gln Asn Asn Asn Trp Pro Thr
                85                  90                  95

Thr Phe Gly Ala Gly Thr Lys Leu Glu Leu Lys
            100                 105


<210> SEQ ID NO 45
<211> LENGTH: 1347
<212> TYPE: DNA
<213> ORGANISM: artificial sequence
<220> FEATURE:
<223> OTHER INFORMATION: Synthesized

<400> SEQUENCE: 45

caggtgcagc tgaagcagtc aggacctggc ctagtgcagc cctcacagag cctgtccatc      60

acctgcacag tctctggttt ctcattaact aactatggtg tacactgggt tcgccagtct     120

ccaggaaagg gtctggagtg gctgggagtg atatggagtg gtggaaacac agactataat     180

acacctttca catccagact gagcatcaac aaggacaatt ccaagagcca agttttcttt     240
```

-continued

```
aaaatgaaca gtctgcaatc taatgacaca gccatatatt actgtgccag agccctcacc    300

tactatgatt acgagtttgc ttactggggc caagggactc tggtcactgt ctctagcgct    360

agcaccaagg gcccatcggt cttcccccctg gcaccctcct ccaagagcac ctctgggggc    420

acagcggccc tgggctgcct ggtcaaggac tacttccccg aaccggtgac ggtgtcgtgg    480

aactcaggcg ccctgaccag cggcgtgcac accttcccgg ctgtcctaca gtcctcagga    540

ctctactccc tcagcagcgt ggtgaccgtg ccctccagca gcttgggcac ccagacctac    600

atctgcaacg tgaatcacaa gcccagcaac accaaggtgg acaagagagt tgagcccaaa    660

tcttgtgaca aaactcacac atgcccaccg tgcccagcac ctgaactcct ggggggaccg    720

tcagtcttcc tcttcccccc aaaacccaag gacaccctca tgatctcccg gacccctgag    780

gtcacatgcg tggtggtgga cgtgagccac gaagaccctg aggtcaagtt caactggtac    840

gtggacggcg tggaggtgca taatgccaag acaaagccgc gggaggagca gtacaacagc    900

acgtaccgtg tggtcagcgt cctcaccgtc ctgcaccagg actggctgaa tggcaaggag    960

tacaagtgca aggtctccaa caaagccctc ccagccccca tcgagaaaac catctccaaa   1020

gccaaagggc agccccgaga accacaggtg tacaccctgc ccccatcccg ggaggagatg   1080

accaagaacc aggtcagcct gacctgcctg gtcaaaggct tctatcccag cgacatcgcc   1140

gtggagtggg agagcaatgg gcagccggag aacaactaca agaccacgcc tcccgtgctg   1200

gactccgacg gctccttctt cctctatagc aagctcaccg tggacaagag caggtggcag   1260

caggggaacg tcttctcatg ctccgtgatg catgaggctc tgcacaacca ctacacgcag   1320

aagagcctct ccctgtctcc gggtaaa                                       1347
```

<210> SEQ ID NO 46
<211> LENGTH: 357
<212> TYPE: DNA
<213> ORGANISM: artificial sequence
<220> FEATURE:
<223> OTHER INFORMATION: Synthesized

<400> SEQUENCE: 46

```
caggtgcagc tgaagcagtc aggacctggc ctagtgcagc cctcacagag cctgtccatc     60

acctgcacag tctctggttt ctcattaact aactatggtg tacactgggt tcgccagtct    120

ccaggaaagg gtctggagtg gctgggagtg atatggagtg gtggaaacac agactataat    180

acacctttca catccagact gagcatcaac aaggacaatt ccaagagcca agttttcttt    240

aaaatgaaca gtctgcaatc taatgacaca gccatatatt actgtgccag agccctcacc    300

tactatgatt acgagtttgc ttactggggc caagggactc tggtcactgt ctctagc       357
```

<210> SEQ ID NO 47
<211> LENGTH: 449
<212> TYPE: PRT
<213> ORGANISM: artificial sequence
<220> FEATURE:
<223> OTHER INFORMATION: Synthesized

<400> SEQUENCE: 47

```
Gln Val Gln Leu Lys Gln Ser Gly Pro Gly Leu Val Gln Pro Ser Gln
1               5                   10                  15

Ser Leu Ser Ile Thr Cys Thr Val Ser Gly Phe Ser Leu Thr Asn Tyr
            20                  25                  30

Gly Val His Trp Val Arg Gln Ser Pro Gly Lys Gly Leu Glu Trp Leu
        35                  40                  45
```

-continued

```
Gly Val Ile Trp Ser Gly Gly Asn Thr Asp Tyr Asn Thr Pro Phe Thr
    50                  55                  60

Ser Arg Leu Ser Ile Asn Lys Asp Asn Ser Lys Ser Gln Val Phe Phe
65                  70                  75                  80

Lys Met Asn Ser Leu Gln Ser Asn Asp Thr Ala Ile Tyr Tyr Cys Ala
                85                  90                  95

Arg Ala Leu Thr Tyr Tyr Asp Tyr Glu Phe Ala Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Arg Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys
```

<210> SEQ ID NO 48

-continued

<211> LENGTH: 119
<212> TYPE: PRT
<213> ORGANISM: artificial sequence
<220> FEATURE:
<223> OTHER INFORMATION: Synthesized

<400> SEQUENCE: 48

```
Gln Val Gln Leu Lys Gln Ser Gly Pro Gly Leu Val Gln Pro Ser Gln
1               5                   10                  15

Ser Leu Ser Ile Thr Cys Thr Val Ser Gly Phe Ser Leu Thr Asn Tyr
            20                  25                  30

Gly Val His Trp Val Arg Gln Ser Pro Gly Lys Gly Leu Glu Trp Leu
        35                  40                  45

Gly Val Ile Trp Ser Gly Gly Asn Thr Asp Tyr Asn Thr Pro Phe Thr
    50                  55                  60

Ser Arg Leu Ser Ile Asn Lys Asp Asn Ser Lys Ser Gln Val Phe Phe
65                  70                  75                  80

Lys Met Asn Ser Leu Gln Ser Asn Asp Thr Ala Ile Tyr Tyr Cys Ala
                85                  90                  95

Arg Ala Leu Thr Tyr Tyr Asp Tyr Glu Phe Ala Tyr Trp Gly Gln Gly
            100                 105                 110

Thr Leu Val Thr Val Ser Ser
        115
```

<210> SEQ ID NO 49
<211> LENGTH: 654
<212> TYPE: DNA
<213> ORGANISM: artificial sequence
<220> FEATURE:
<223> OTHER INFORMATION: Synthesized

<400> SEQUENCE: 49

```
cagtctgccc tgactcagcc tgcctccgtg tctgggtctc ctggacagtc gatcaccatc     60

tcctgcactg gaaccagcag tgacgttggt ggttataact ttgtctcctg gtaccaacaa    120

cacccaggca aagcccccaa actcatgatc tatgatgtca gtgatcggcc ctcaggggtg    180

tctgatcgct tctccggctc caagtctggc aacacggcct ccctgatcat ctctggcctc    240

caggctgacg acgaggctga ttattactgc agctcatatg ggagcagcag cactcatgtg    300

attttcggcg gagggaccaa gctgaccgtc ctacgtacgg tggctgcacc atctgtcttc    360

atcttcccgc catctgatga gcagttgaaa tctggaactg cctctgttgt gtgcctgctg    420

aataacttct atcccagaga ggccaaagta cagtggaagg tggataacgc cctccaatcg    480

ggtaactccc aggagagtgt cacagagcag gacagcaagg acagcaccta cagcctcagc    540

agcaccctga cgctgagcaa agcagactac gagaaacaca aagtctacgc ctgcgaagtc    600

acccatcagg gcctgagctc gcccgtcaca aagagcttca acaggggaga gtgt          654
```

<210> SEQ ID NO 50
<211> LENGTH: 333
<212> TYPE: DNA
<213> ORGANISM: artificial sequence
<220> FEATURE:
<223> OTHER INFORMATION: Synthesized

<400> SEQUENCE: 50

```
cagtctgccc tgactcagcc tgcctccgtg tctgggtctc ctggacagtc gatcaccatc     60

tcctgcactg gaaccagcag tgacgttggt ggttataact ttgtctcctg gtaccaacaa    120

cacccaggca aagcccccaa actcatgatc tatgatgtca gtgatcggcc ctcaggggtg    180
```

```
tctgatcgct tctccggctc caagtctggc aacacggcct ccctgatcat ctctggcctc    240

caggctgacg acgaggctga ttattactgc agctcatatg ggagcagcag cactcatgtg    300

attttcggcg gagggaccaa gctgaccgtc cta                                 333


<210> SEQ ID NO 51
<211> LENGTH: 218
<212> TYPE: PRT
<213> ORGANISM: artificial sequence
<220> FEATURE:
<223> OTHER INFORMATION: Synthesized

<400> SEQUENCE: 51

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
            20                  25                  30

Asn Phe Val Ser Trp Tyr Gln Gln His Pro Gly Lys Ala Pro Lys Leu
        35                  40                  45

Met Ile Tyr Asp Val Ser Asp Arg Pro Ser Gly Val Ser Asp Arg Phe
    50                  55                  60

Ser Gly Ser Lys Ser Gly Asn Thr Ala Ser Leu Ile Ile Ser Gly Leu
65                  70                  75                  80

Gln Ala Asp Asp Glu Ala Asp Tyr Tyr Cys Ser Ser Tyr Gly Ser Ser
                85                  90                  95

Ser Thr His Val Ile Phe Gly Gly Gly Thr Lys Leu Thr Val Leu Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215


<210> SEQ ID NO 52
<211> LENGTH: 111
<212> TYPE: PRT
<213> ORGANISM: artificial sequence
<220> FEATURE:
<223> OTHER INFORMATION: Synthesized

<400> SEQUENCE: 52

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
            20                  25                  30

Asn Phe Val Ser Trp Tyr Gln Gln His Pro Gly Lys Ala Pro Lys Leu
        35                  40                  45

Met Ile Tyr Asp Val Ser Asp Arg Pro Ser Gly Val Ser Asp Arg Phe
```

-continued

```
    50                  55                  60

Ser Gly Ser Lys Ser Gly Asn Thr Ala Ser Leu Ile Ile Ser Gly Leu
65                  70                  75                  80

Gln Ala Asp Asp Glu Ala Asp Tyr Tyr Cys Ser Ser Tyr Gly Ser Ser
                85                  90                  95

Ser Thr His Val Ile Phe Gly Gly Gly Thr Lys Leu Thr Val Leu
            100                 105                 110


<210> SEQ ID NO 53
<211> LENGTH: 2100
<212> TYPE: DNA
<213> ORGANISM: artificial sequence
<220> FEATURE:
<223> OTHER INFORMATION: Synthesized

<400> SEQUENCE: 53

caggtgcagc tgcaggagtc gggggaggc ctggtcaagc ctggagggtc cctgagactc     60

tcctgtgcag cctctggatt cacctttagt agttattgga tgagctgggt ccgccaggct    120

ccagggaagg ggctggagtg ggtggccaac ataaaccgcg atggaagtgc gagttactat    180

gtggactctg tgaagggccg attcaccatc tccagagacg acgccaagaa ctcactgtat    240

ctgcaaatga acagcctgag agctgaggac acggctgtgt attactgtgc gagagatcgt    300

ggggtgggct acttcgatct ctggggccgt ggcaccctgg tcaccgtctc gagcgctagc    360

accaagggcc catcggtctt ccccctggca ccctcctcca agagcacctc tgggggcaca    420

gcggccctgg gctgcctggt caaggactac ttccccgaac cggtgacggt gtcgtggaac    480

tcaggcgccc tgaccagcgg cgtgcacacc ttcccggctg tcctacagtc ctcaggactc    540

tactccctca gcagcgtggt gaccgtgccc tccagcagct tgggcaccca gacctacatc    600

tgcaacgtga atcacaagcc cagcaacacc aaggtggaca agagagttga gcccaaatct    660

tgtgacaaaa ctcacacatg cccaccgtgc ccagcacctg aactcctggg gggaccgtca    720

gtcttcctct tcccccaaa acccaaggac accctcatga tctcccggac ccctgaggtc     780

acatgcgtgg tggtggacgt gagccacgaa gaccctgagg tcaagttcaa ctggtacgtg    840

gacggcgtgg aggtgcataa tgccaagaca aagccgcggg aggagcagta caacagcacg    900

taccgtgtgg tcagcgtcct caccgtcctg caccaggact ggctgaatgg caaggagtac    960

aagtgcaagg tctccaacaa agccctccca gcccccatcg agaaaaccat ctccaaagcc   1020

aaagggcagc cccgagaacc acaggtgtac accctgcccc catcccggga ggagatgacc   1080

aagaaccagg tcagcctgac ctgcctggtc aaaggcttct atcccagcga catcgccgtg   1140

gagtgggaga gcaatgggca gccggagaac aactacaaga ccacgcctcc cgtgctggac   1200

tccgacggct ccttcttcct ctatagcaag ctcaccgtgg acaagagcag gtggcagcag   1260

gggaacgtct tctcatgctc cgtgatgcat gaggctctgc acaaccacta cacgcagaag   1320

agcctctccc tgtctccggg taaaggcggt ggaggatccg gcggtggtgg atcacaggtg   1380

cagctgcagg agtcgggccc aggactggtg aagccttcgg agaccctgtc cctcacctgc   1440

actgtctctg gtggctccgt cagcagtggt gattactact ggacctggat acggcagtcc   1500

ccagggaagg gactggagtg gattggacac atctattaca gtgggaacac caattataac   1560

ccctccctca agagccgact caccatatca attgacacgt ccaagactca gttctccctg   1620

aagctgagtt ctgtgaccgc tgcggacacg gccatttatt actgtgtgcg agatcgagtg   1680

actggtgctt ttgatatctg gggccaaggg acaatggtca ccgtctcgag cggtggaggc   1740
```

-continued

```
ggttcaggcg gaggtggttc cggcggtggc ggctccgaca tccagatgac ccagtctcca   1800

tcctccctgt ctgcatctgt aggagacaga gtcaccatca cttgccaggc gagtcaggac   1860

atcagcaact atttaaattg gtatcagcag aaaccaggga aagcccctaa actcctgatc   1920

tacgatgcat ccaatttgga aacaggggtc ccatcaaggt tcagtggaag tggatctggg   1980

acagatttta ctttcaccat cagcagcctg cagcctgaag atattgcaac atatttctgt   2040

caacactttg atcatctccc gctcgctttc ggcggaggga ccaaggtgga aattaaacgt   2100
```

```
<210> SEQ ID NO 54
<211> LENGTH: 354
<212> TYPE: DNA
<213> ORGANISM: artificial sequence
<220> FEATURE:
<223> OTHER INFORMATION: Synthesized

<400> SEQUENCE: 54

caggtgcagc tgcaggagtc ggggggaggc ctggtcaagc ctggagggtc cctgagactc     60

tcctgtgcag cctctggatt cacctttagt agttattgga tgagctgggt ccgccaggct    120

ccagggaagg ggctggagtg ggtggccaac ataaaccgcg atggaagtgc gagttactat    180

gtggactctg tgaagggccg attcaccatc tccagagacg acgccaagaa ctcactgtat    240

ctgcaaatga acagcctgag agctgaggac acggctgtgt attactgtgc gagagatcgt    300

ggggtgggct acttcgatct ctggggccgt ggcaccctgg tcaccgtctc gagc          354
```

```
<210> SEQ ID NO 55
<211> LENGTH: 726
<212> TYPE: DNA
<213> ORGANISM: artificial sequence
<220> FEATURE:
<223> OTHER INFORMATION: Synthesized

<400> SEQUENCE: 55

caggtgcagc tgcaggagtc gggcccagga ctggtgaagc cttcggagac cctgtccctc     60

acctgcactg tctctggtgg ctccgtcagc agtggtgatt actactggac ctggatacgg    120

cagtccccag ggaagggact ggagtggatt ggacacatct attacagtgg gaacaccaat    180

tataacccct ccctcaagag ccgactcacc atatcaattg acacgtccaa gactcagttc    240

tccctgaagc tgagttctgt gaccgctgcg gacacggcca tttattactg tgtgcgagat    300

cgagtgactg gtgcttttga tatctggggc caagggacaa tggtcaccgt ctcgagcggt    360

ggaggcggtt caggcggagg tggttccggc ggtggcggct ccgacatcca gatgacccag    420

tctccatcct ccctgtctgc atctgtagga gacagagtca ccatcacttg ccaggcgagt    480

caggacatca gcaactattt aaattggtat cagcagaaac cagggaaagc ccctaaactc    540

ctgatctacg atgcatccaa tttggaaaca ggggtcccat caaggttcag tggaagtgga    600

tctgggacag attttacttt caccatcagc agcctgcagc ctgaagatat tgcaacatat    660

ttctgtcaac actttgatca tctcccgctc gctttcggcg gagggaccaa ggtggaaatt    720

aaacgt                                                               726
```

```
<210> SEQ ID NO 56
<211> LENGTH: 700
<212> TYPE: PRT
<213> ORGANISM: artificial sequence
<220> FEATURE:
<223> OTHER INFORMATION: Synthesized

<400> SEQUENCE: 56
```

-continued

```
Gln Val Gln Leu Gln Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Trp Met Ser Trp Val Arg Gln Ala Pro Gly Lys Gly Leu Glu Trp Val
        35                  40                  45

Ala Asn Ile Asn Arg Asp Gly Ser Ala Ser Tyr Tyr Val Asp Ser Val
    50                  55                  60

Lys Gly Arg Phe Thr Ile Ser Arg Asp Asp Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Arg Gly Val Gly Tyr Phe Asp Leu Trp Gly Arg Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Arg Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Glu Glu Met Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415
```

-continued

```
Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
        435                 440                 445

Gly Gly Gly Gly Ser Gly Gly Gly Gly Ser Gln Val Gln Leu Gln Glu
    450                 455                 460

Ser Gly Pro Gly Leu Val Lys Pro Ser Glu Thr Leu Ser Leu Thr Cys
465                 470                 475                 480

Thr Val Ser Gly Gly Ser Val Ser Ser Gly Asp Tyr Tyr Trp Thr Trp
                485                 490                 495

Ile Arg Gln Ser Pro Gly Lys Gly Leu Glu Trp Ile Gly His Ile Tyr
            500                 505                 510

Tyr Ser Gly Asn Thr Asn Tyr Asn Pro Ser Leu Lys Ser Arg Leu Thr
        515                 520                 525

Ile Ser Ile Asp Thr Ser Lys Thr Gln Phe Ser Leu Lys Leu Ser Ser
    530                 535                 540

Val Thr Ala Ala Asp Thr Ala Ile Tyr Tyr Cys Val Arg Asp Arg Val
545                 550                 555                 560

Thr Gly Ala Phe Asp Ile Trp Gly Gln Gly Thr Met Val Thr Val Ser
                565                 570                 575

Ser Gly Gly Gly Gly Ser Gly Gly Gly Gly Ser Gly Gly Gly Gly Ser
            580                 585                 590

Asp Ile Gln Met Thr Gln Ser Pro Ser Ser Leu Ser Ala Ser Val Gly
        595                 600                 605

Asp Arg Val Thr Ile Thr Cys Gln Ala Ser Gln Asp Ile Ser Asn Tyr
    610                 615                 620

Leu Asn Trp Tyr Gln Gln Lys Pro Gly Lys Ala Pro Lys Leu Leu Ile
625                 630                 635                 640

Tyr Asp Ala Ser Asn Leu Glu Thr Gly Val Pro Ser Arg Phe Ser Gly
                645                 650                 655

Ser Gly Ser Gly Thr Asp Phe Thr Phe Thr Ile Ser Ser Leu Gln Pro
            660                 665                 670

Glu Asp Ile Ala Thr Tyr Phe Cys Gln His Phe Asp His Leu Pro Leu
        675                 680                 685

Ala Phe Gly Gly Gly Thr Lys Val Glu Ile Lys Arg
    690                 695                 700
```

<210> SEQ ID NO 57
<211> LENGTH: 118
<212> TYPE: PRT
<213> ORGANISM: artificial sequence
<220> FEATURE:
<223> OTHER INFORMATION: Synthesized

<400> SEQUENCE: 57

```
Gln Val Gln Leu Gln Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Trp Met Ser Trp Val Arg Gln Ala Pro Gly Lys Gly Leu Glu Trp Val
        35                  40                  45

Ala Asn Ile Asn Arg Asp Gly Ser Ala Ser Tyr Tyr Val Asp Ser Val
    50                  55                  60

Lys Gly Arg Phe Thr Ile Ser Arg Asp Asp Ala Lys Asn Ser Leu Tyr
65                  70                  75                  80
```

```
Leu Gln Met Asn Ser Leu Arg Ala Glu Asp Thr Ala Val Tyr Tyr Cys
                85                  90                  95

Ala Arg Asp Arg Gly Val Gly Tyr Phe Asp Leu Trp Gly Arg Gly Thr
            100                 105                 110

Leu Val Thr Val Ser Ser
        115
```

<210> SEQ ID NO 58
<211> LENGTH: 242
<212> TYPE: PRT
<213> ORGANISM: artificial sequence
<220> FEATURE:
<223> OTHER INFORMATION: Synthesized

<400> SEQUENCE: 58

```
Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Val Ser Ser Gly
            20                  25                  30

Asp Tyr Tyr Trp Thr Trp Ile Arg Gln Ser Pro Gly Lys Gly Leu Glu
        35                  40                  45

Trp Ile Gly His Ile Tyr Tyr Ser Gly Asn Thr Asn Tyr Asn Pro Ser
    50                  55                  60

Leu Lys Ser Arg Leu Thr Ile Ser Ile Asp Thr Ser Lys Thr Gln Phe
65                  70                  75                  80

Ser Leu Lys Leu Ser Ser Val Thr Ala Ala Asp Thr Ala Ile Tyr Tyr
                85                  90                  95

Cys Val Arg Asp Arg Val Thr Gly Ala Phe Asp Ile Trp Gly Gln Gly
            100                 105                 110

Thr Met Val Thr Val Ser Ser Gly Gly Gly Gly Ser Gly Gly Gly Gly
        115                 120                 125

Ser Gly Gly Gly Gly Ser Asp Ile Gln Met Thr Gln Ser Pro Ser Ser
    130                 135                 140

Leu Ser Ala Ser Val Gly Asp Arg Val Thr Ile Thr Cys Gln Ala Ser
145                 150                 155                 160

Gln Asp Ile Ser Asn Tyr Leu Asn Trp Tyr Gln Gln Lys Pro Gly Lys
                165                 170                 175

Ala Pro Lys Leu Leu Ile Tyr Asp Ala Ser Asn Leu Glu Thr Gly Val
            180                 185                 190

Pro Ser Arg Phe Ser Gly Ser Gly Ser Gly Thr Asp Phe Thr Phe Thr
        195                 200                 205

Ile Ser Ser Leu Gln Pro Glu Asp Ile Ala Thr Tyr Phe Cys Gln His
    210                 215                 220

Phe Asp His Leu Pro Leu Ala Phe Gly Gly Gly Thr Lys Val Glu Ile
225                 230                 235                 240

Lys Arg
```

<210> SEQ ID NO 59
<211> LENGTH: 642
<212> TYPE: DNA
<213> ORGANISM: artificial sequence
<220> FEATURE:
<223> OTHER INFORMATION: Synthesized

<400> SEQUENCE: 59

```
gacatccaga tgacccagtc tccatcctcc ctgtctgcat ctgtaggaga cagagtcacc      60

atcacttgcc aggcgagtca ggacatcagc aactatttaa attggtatca gcagaaacca     120
```

```
gggaaagccc ctaaactcct gatctacgat gcatccaatt tggaaacagg ggtcccatca    180

aggttcagtg gaagtggatc tgggacagat tttactttca ccatcagcag cctgcagcct    240

gaagatattg caacatattt ctgtcaacac tttgatcatc tcccgctcgc tttcggcgga    300

gggaccaagg tggaaattaa acgtacggtg gctgcaccat ctgtcttcat cttcccgcca    360

tctgatgagc agttgaaatc tggaactgcc tctgttgtgt gcctgctgaa taacttctat    420

cccagagagg ccaaagtaca gtggaaggtg gataacgccc tccaatcggg taactcccag    480

gagagtgtca cagagcagga cagcaaggac agcacctaca gcctcagcag caccctgacg    540

ctgagcaaag cagactacga gaaacacaaa gtctacgcct gcgaagtcac ccatcagggc    600

ctgagctcgc ccgtcacaaa gagcttcaac aggggagagt gt                       642
```

<210> SEQ ID NO 60
<211> LENGTH: 321
<212> TYPE: DNA
<213> ORGANISM: artificial sequence
<220> FEATURE:
<223> OTHER INFORMATION: Synthesized

<400> SEQUENCE: 60

```
gacatccaga tgacccagtc tccatcctcc ctgtctgcat ctgtaggaga cagagtcacc     60

atcacttgcc aggcgagtca ggacatcagc aactatttaa attggtatca gcagaaacca    120

gggaaagccc ctaaactcct gatctacgat gcatccaatt tggaaacagg ggtcccatca    180

aggttcagtg gaagtggatc tgggacagat tttactttca ccatcagcag cctgcagcct    240

gaagatattg caacatattt ctgtcaacac tttgatcatc tcccgctcgc tttcggcgga    300

gggaccaagg tggaaattaa a                                              321
```

<210> SEQ ID NO 61
<211> LENGTH: 214
<212> TYPE: PRT
<213> ORGANISM: artificial sequence
<220> FEATURE:
<223> OTHER INFORMATION: Synthesized

<400> SEQUENCE: 61

```
Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Asp Ala Ser Asn Leu Glu Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Phe Cys Gln His Phe Asp His Leu Pro Leu
                85                  90                  95

Ala Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
```

```
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210


<210> SEQ ID NO 62
<211> LENGTH: 107
<212> TYPE: PRT
<213> ORGANISM: artificial sequence
<220> FEATURE:
<223> OTHER INFORMATION: Synthesized

<400> SEQUENCE: 62

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Asp Ala Ser Asn Leu Glu Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Phe Cys Gln His Phe Asp His Leu Pro Leu
                85                  90                  95

Ala Phe Gly Gly Gly Thr Lys Val Glu Ile Lys
            100                 105


<210> SEQ ID NO 63
<211> LENGTH: 2109
<212> TYPE: DNA
<213> ORGANISM: artificial sequence
<220> FEATURE:
<223> OTHER INFORMATION: Synthesized

<400> SEQUENCE: 63

caggtgcagc tgcaggagtc gggcccagga ctggtgaagc cttcggagac cctgtccctc      60

acctgcactg tctctggtgg ctccgtcagc agtggtgatt actactggac ctggatccgg     120

cagtccccag ggaagggact ggagtggatt ggacacatct attacagtgg gaacaccaat     180

tataacccct ccctcaagag ccgactcacc atatcaattg acacgtccaa gactcagttc     240

tccctgaagc tgagttctgt gaccgctgcg gacacggcca tttattactg tgtgcgagat     300

cgagtgactg gtgcttttga tatctggggc caagggacaa tggtcaccgt ctcgagcgct     360

agcaccaagg gcccatcggt cttccccctg gcaccctcct ccaagagcac ctctgggggc     420

acagcggccc tgggctgcct ggtcaaggac tacttccccg aaccggtgac ggtgtcgtgg     480

aactcaggcg ccctgaccag cggcgtgcac accttcccgg ctgtcctaca gtcctcagga     540

ctctactccc tcagcagcgt ggtgaccgtg ccctccagca gcttgggcac ccagacctac     600

atctgcaacg tgaatcacaa gcccagcaac accaaggtgg acaagagagt tgagcccaaa     660

tcttgtgaca aaactcacac atgcccaccg tgcccagcac ctgaactcct ggggggaccg     720
```

-continued tcagtcttcc tcttcccccc aaaacccaag gacaccctca tgatctcccg gacccctgag 780
gtcacatgcg tggtggtgga cgtgagccac gaagaccctg aggtcaagtt caactggtac 840
gtggacggcg tggaggtgca taatgccaag acaaagccgc gggaggagca gtacaacagc 900
acgtaccgtg tggtcagcgt cctcaccgtc ctgcaccagg actggctgaa tggcaaggag 960
tacaagtgca aggtctccaa caaagccctc ccagccccca tcgagaaaac catctccaaa 1020
gccaaagggc agccccgaga accacaggtg tacaccctgc ccccatcccg ggaggagatg 1080
accaagaacc aggtcagcct gacctgcctg gtcaaaggct tctatcccag cgacatcgcc 1140
gtggagtggg agagcaatgg gcagccggag aacaactaca agaccacgcc tcccgtgctg 1200
gactccgacg gctccttctt cctctatagc aagctcaccg tggacaagag caggtggcag 1260
caggggaacg tcttctcatg ctccgtgatg catgaggctc tgcacaacca ctacacgcag 1320
aagagcctct ccctgtctcc gggtaaaggc ggtggaggat ccggcggtgg tggatcacag 1380
gtgcagctgc aggagtcggg gggaggcctg gtcaagcctg gagggtccct gagactctcc 1440
tgtgcagcct ctggattcac ctttagtagt tattggatga gctgggtccg ccaggctcca 1500
gggaaggggc tggagtgggt ggccaacata aaccgcgatg gaagtgcgag ttactatgtg 1560
gactctgtga agggccgatt caccatctcc agagacgacg ccaagaactc actgtatctg 1620
caaatgaaca gcctgagagc tgaggacacg gctgtgtatt actgtgcgag agatcgtggg 1680
gtgggctact tcgatctctg ggccgtggc accctggtca ccgtctcgag cggtggaggc 1740
ggttcaggcg gaggtggttc cggcggtggc ggctcccagt ctgccctgac tcagcctgcc 1800
tccgtgtctg ggtctcctgg acagtcgatc accatctcct gcactggaac cagcagtgac 1860
gttggtggtt ataactttgt ctcctggtac caacaacacc caggcaaagc ccccaaactc 1920
atgatctatg atgtcagtga tcggccctca ggggtgtctg atcgcttctc cggctccaag 1980
tctggcaaca cggcctccct gatcatctct ggcctccagg ctgacgacga ggctgattat 2040
tactgcagct catatgggag cagcagcact catgtgattt tcggcggagg gaccaaggtg 2100
accgtccta 2109

<210> SEQ ID NO 64
<211> LENGTH: 357
<212> TYPE: DNA
<213> ORGANISM: artificial sequence
<220> FEATURE:
<223> OTHER INFORMATION: Synthesized

<400> SEQUENCE: 64
caggtgcagc tgcaggagtc gggcccagga ctggtgaagc cttcggagac cctgtccctc 60
acctgcactg tctctggtgg ctccgtcagc agtggtgatt actactggac ctggatccgg 120
cagtccccag ggaagggact ggagtggatt ggacacatct attacagtgg gaacaccaat 180
tataacccct ccctcaagag ccgactcacc atatcaattg acacgtccaa gactcagttc 240
tccctgaagc tgagttctgt gaccgctgcg gacacggcca tttattactg tgtgcgagat 300
cgagtgactg gtgcttttga tatctggggc caagggacaa tggtcaccgt ctcgagc 357

<210> SEQ ID NO 65
<211> LENGTH: 732
<212> TYPE: DNA
<213> ORGANISM: artificial sequence
<220> FEATURE:
<223> OTHER INFORMATION: Synthesized

<400> SEQUENCE: 65

-continued

```
caggtgcagc tgcaggagtc ggggggaggc ctggtcaagc ctggagggtc cctgagactc     60

tcctgtgcag cctctggatt cacctttagt agttattgga tgagctgggt ccgccaggct    120

ccagggaagg ggctggagtg ggtggccaac ataaaccgcg atggaagtgc gagttactat    180

gtggactctg tgaagggccg attcaccatc tccagagacg acgccaagaa ctcactgtat    240

ctgcaaatga acagcctgag agctgaggac acggctgtgt attactgtgc gagagatcgt    300

ggggtgggct acttcgatct ctggggccgt ggcaccctgg tcaccgtctc gagcggtgga    360

ggcggttcag gcggaggtgg ttccggcggt ggcggctccc agtctgccct gactcagcct    420

gcctccgtgt ctgggtctcc tggacagtcg atcaccatct cctgcactgg aaccagcagt    480

gacgttggtg gttataactt tgtctcctgg taccaacaac acccaggcaa agcccccaaa    540

ctcatgatct atgatgtcag tgatcggccc tcaggggtgt ctgatcgctt ctccggctcc    600

aagtctggca acacggcctc cctgatcatc tctggcctcc aggctgacga cgaggctgat    660

tattactgca gctcatatgg gagcagcagc actcatgtga ttttcggcgg agggaccaag    720

gtgaccgtcc ta                                                        732
```

<210> SEQ ID NO 66
<211> LENGTH: 703
<212> TYPE: PRT
<213> ORGANISM: artificial sequence
<220> FEATURE:
<223> OTHER INFORMATION: Synthesized

<400> SEQUENCE: 66

```
Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Val Ser Ser Gly
            20                  25                  30

Asp Tyr Tyr Trp Thr Trp Ile Arg Gln Ser Pro Gly Lys Gly Leu Glu
        35                  40                  45

Trp Ile Gly His Ile Tyr Tyr Ser Gly Asn Thr Asn Tyr Asn Pro Ser
    50                  55                  60

Leu Lys Ser Arg Leu Thr Ile Ser Ile Asp Thr Ser Lys Thr Gln Phe
65                  70                  75                  80

Ser Leu Lys Leu Ser Ser Val Thr Ala Ala Asp Thr Ala Ile Tyr Tyr
                85                  90                  95

Cys Val Arg Asp Arg Val Thr Gly Ala Phe Asp Ile Trp Gly Gln Gly
            100                 105                 110

Thr Met Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Arg Val Glu Pro Lys Ser Cys Asp Lys
    210                 215                 220
```

-continued

```
Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys Gly Gly Gly Gly Ser Gly Gly Gly Gly Ser Gln Val Gln Leu Gln
    450                 455                 460

Glu Ser Gly Gly Gly Leu Val Lys Pro Gly Gly Ser Leu Arg Leu Ser
465                 470                 475                 480

Cys Ala Ala Ser Gly Phe Thr Phe Ser Ser Tyr Trp Met Ser Trp Val
                485                 490                 495

Arg Gln Ala Pro Gly Lys Gly Leu Glu Trp Val Ala Asn Ile Asn Arg
            500                 505                 510

Asp Gly Ser Ala Ser Tyr Tyr Val Asp Ser Val Lys Gly Arg Phe Thr
        515                 520                 525

Ile Ser Arg Asp Asp Ala Lys Asn Ser Leu Tyr Leu Gln Met Asn Ser
    530                 535                 540

Leu Arg Ala Glu Asp Thr Ala Val Tyr Tyr Cys Ala Arg Asp Arg Gly
545                 550                 555                 560

Val Gly Tyr Phe Asp Leu Trp Gly Arg Gly Thr Leu Val Thr Val Ser
                565                 570                 575

Ser Gly Gly Gly Gly Ser Gly Gly Gly Gly Ser Gly Gly Gly Gly Ser
            580                 585                 590

Gln Ser Ala Leu Thr Gln Pro Ala Ser Val Ser Gly Ser Pro Gly Gln
        595                 600                 605

Ser Ile Thr Ile Ser Cys Thr Gly Thr Ser Ser Asp Val Gly Gly Tyr
    610                 615                 620

Asn Phe Val Ser Trp Tyr Gln Gln His Pro Gly Lys Ala Pro Lys Leu
625                 630                 635                 640

Met Ile Tyr Asp Val Ser Asp Arg Pro Ser Gly Val Ser Asp Arg Phe
```

```
            645                 650                 655

Ser Gly Ser Lys Ser Gly Asn Thr Ala Ser Leu Ile Ile Ser Gly Leu
        660                 665                 670

Gln Ala Asp Asp Glu Ala Asp Tyr Tyr Cys Ser Ser Tyr Gly Ser Ser
    675                 680                 685

Ser Thr His Val Ile Phe Gly Gly Gly Thr Lys Val Thr Val Leu
690                 695                 700


<210> SEQ ID NO 67
<211> LENGTH: 119
<212> TYPE: PRT
<213> ORGANISM: artificial sequence
<220> FEATURE:
<223> OTHER INFORMATION: Synthesized

<400> SEQUENCE: 67

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Val Ser Ser Gly
            20                  25                  30

Asp Tyr Tyr Trp Thr Trp Ile Arg Gln Ser Pro Gly Lys Gly Leu Glu
        35                  40                  45

Trp Ile Gly His Ile Tyr Tyr Ser Gly Asn Thr Asn Tyr Asn Pro Ser
    50                  55                  60

Leu Lys Ser Arg Leu Thr Ile Ser Ile Asp Thr Ser Lys Thr Gln Phe
65                  70                  75                  80

Ser Leu Lys Leu Ser Ser Val Thr Ala Ala Asp Thr Ala Ile Tyr Tyr
                85                  90                  95

Cys Val Arg Asp Arg Val Thr Gly Ala Phe Asp Ile Trp Gly Gln Gly
            100                 105                 110

Thr Met Val Thr Val Ser Ser
        115


<210> SEQ ID NO 68
<211> LENGTH: 243
<212> TYPE: PRT
<213> ORGANISM: artificial sequence
<220> FEATURE:
<223> OTHER INFORMATION: Synthesized

<400> SEQUENCE: 68

Gln Val Gln Leu Gln Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Trp Met Ser Trp Val Arg Gln Ala Pro Gly Lys Gly Leu Glu Trp Val
        35                  40                  45

Ala Asn Ile Asn Arg Asp Gly Ser Ala Ser Tyr Tyr Val Asp Ser Val
    50                  55                  60

Lys Gly Arg Phe Thr Ile Ser Arg Asp Asp Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Arg Gly Val Gly Tyr Phe Asp Leu Trp Gly Arg Gly Thr
            100                 105                 110

Leu Val Thr Val Ser Ser Gly Gly Gly Gly Ser Gly Gly Gly Gly Ser
        115                 120                 125
```

```
Gly Gly Gly Gly Ser Gln Ser Ala Leu Thr Gln Pro Ala Ser Val Ser
    130                 135                 140

Gly Ser Pro Gly Gln Ser Ile Thr Ile Ser Cys Thr Gly Thr Ser Ser
145                 150                 155                 160

Asp Val Gly Gly Tyr Asn Phe Val Ser Trp Tyr Gln Gln His Pro Gly
                165                 170                 175

Lys Ala Pro Lys Leu Met Ile Tyr Asp Val Ser Asp Arg Pro Ser Gly
            180                 185                 190

Val Ser Asp Arg Phe Ser Gly Ser Lys Ser Gly Asn Thr Ala Ser Leu
        195                 200                 205

Ile Ile Ser Gly Leu Gln Ala Asp Asp Glu Ala Asp Tyr Tyr Cys Ser
    210                 215                 220

Ser Tyr Gly Ser Ser Ser Thr His Val Ile Phe Gly Gly Gly Thr Lys
225                 230                 235                 240

Val Thr Val
```

<210> SEQ ID NO 69
<211> LENGTH: 654
<212> TYPE: DNA
<213> ORGANISM: artificial sequence
<220> FEATURE:
<223> OTHER INFORMATION: Synthesized

<400> SEQUENCE: 69

```
cagtctgccc tgactcagcc tgcctccgtg tctgggtctc ctggacagtc gatcaccatc     60

tcctgcactg gaaccagcag tgacgttggt ggttataact ttgtctcctg gtaccaacaa    120

cacccaggca aagcccccaa actcatgatc tatgatgtca gtgatcggcc ctcaggggtg    180

tctgatcgct tctccggctc caagtctggc aacacggcct ccctgatcat ctctggcctc    240

caggctgacg acgaggctga ttattactgc agctcatatg ggagcagcag cactcatgtg    300

attttcggcg gagggaccaa gctgaccgtc ctacgtacgg tggctgcacc atctgtcttc    360

atcttcccgc catctgatga gcagttgaaa tctggaactg cctctgttgt gtgcctgctg    420

aataacttct atcccagaga ggccaaagta cagtggaagg tggataacgc cctccaatcg    480

ggtaactccc aggagagtgt cacagagcag gacagcaagg acagcaccta cagcctcagc    540

agcaccctga cgctgagcaa agcagactac gagaaacaca aagtctacgc ctgcgaagtc    600

acccatcagg gcctgagctc gcccgtcaca aagagcttca acaggggaga gtgt          654
```

<210> SEQ ID NO 70
<211> LENGTH: 333
<212> TYPE: DNA
<213> ORGANISM: artificial sequence
<220> FEATURE:
<223> OTHER INFORMATION: Synthesized

<400> SEQUENCE: 70

```
cagtctgccc tgactcagcc tgcctccgtg tctgggtctc ctggacagtc gatcaccatc     60

tcctgcactg gaaccagcag tgacgttggt ggttataact ttgtctcctg gtaccaacaa    120

cacccaggca aagcccccaa actcatgatc tatgatgtca gtgatcggcc ctcaggggtg    180

tctgatcgct tctccggctc caagtctggc aacacggcct ccctgatcat ctctggcctc    240

caggctgacg acgaggctga ttattactgc agctcatatg ggagcagcag cactcatgtg    300

attttcggcg gagggaccaa gctgaccgtc cta                                 333
```

<210> SEQ ID NO 71

<211> LENGTH: 218
<212> TYPE: PRT
<213> ORGANISM: artificial sequence
<220> FEATURE:
<223> OTHER INFORMATION: Synthesized

<400> SEQUENCE: 71

Gln Ser Ala Leu Thr Gln Pro Ala Ser Val Ser Gly Ser Pro Gly Gln
1 5 10 15

Ser Ile Thr Ile Ser Cys Thr Gly Thr Ser Ser Asp Val Gly Gly Tyr
20 25 30

Asn Phe Val Ser Trp Tyr Gln Gln His Pro Gly Lys Ala Pro Lys Leu
35 40 45

Met Ile Tyr Asp Val Ser Asp Arg Pro Ser Gly Val Ser Asp Arg Phe
50 55 60

Ser Gly Ser Lys Ser Gly Asn Thr Ala Ser Leu Ile Ile Ser Gly Leu
65 70 75 80

Gln Ala Asp Asp Glu Ala Asp Tyr Tyr Cys Ser Ser Tyr Gly Ser Ser
85 90 95

Ser Thr His Val Ile Phe Gly Gly Gly Thr Lys Leu Thr Val Leu Arg
100 105 110

Thr Val Ala Ala Pro Ser Val Phe Ile Phe Pro Pro Ser Asp Glu Gln
115 120 125

Leu Lys Ser Gly Thr Ala Ser Val Val Cys Leu Leu Asn Asn Phe Tyr
130 135 140

Pro Arg Glu Ala Lys Val Gln Trp Lys Val Asp Asn Ala Leu Gln Ser
145 150 155 160

Gly Asn Ser Gln Glu Ser Val Thr Glu Gln Asp Ser Lys Asp Ser Thr
165 170 175

Tyr Ser Leu Ser Ser Thr Leu Thr Leu Ser Lys Ala Asp Tyr Glu Lys
180 185 190

His Lys Val Tyr Ala Cys Glu Val Thr His Gln Gly Leu Ser Ser Pro
195 200 205

Val Thr Lys Ser Phe Asn Arg Gly Glu Cys
210 215

<210> SEQ ID NO 72
<211> LENGTH: 111
<212> TYPE: PRT
<213> ORGANISM: artificial sequence
<220> FEATURE:
<223> OTHER INFORMATION: Synthesized

<400> SEQUENCE: 72

Gln Ser Ala Leu Thr Gln Pro Ala Ser Val Ser Gly Ser Pro Gly Gln
1 5 10 15

Ser Ile Thr Ile Ser Cys Thr Gly Thr Ser Ser Asp Val Gly Gly Tyr
20 25 30

Asn Phe Val Ser Trp Tyr Gln Gln His Pro Gly Lys Ala Pro Lys Leu
35 40 45

Met Ile Tyr Asp Val Ser Asp Arg Pro Ser Gly Val Ser Asp Arg Phe
50 55 60

Ser Gly Ser Lys Ser Gly Asn Thr Ala Ser Leu Ile Ile Ser Gly Leu
65 70 75 80

Gln Ala Asp Asp Glu Ala Asp Tyr Tyr Cys Ser Ser Tyr Gly Ser Ser
85 90 95

Ser Thr His Val Ile Phe Gly Gly Gly Thr Lys Leu Thr Val Leu

-continued 100 105 110

<210> SEQ ID NO 73
<211> LENGTH: 2127
<212> TYPE: DNA
<213> ORGANISM: artificial sequence
<220> FEATURE:
<223> OTHER INFORMATION: Synthesized

<400> SEQUENCE: 73
caggtgcagc tgcaggagtc gggggaggc ctggtcaagc ctggagggtc cctgagactc 60
tcctgtgcag cctctggatt cacctttagt agttattgga tgagctgggt ccgccaggct 120
ccagggaagg ggctggagtg ggtggccaac ataaaccgcg atggaagtgc gagttactat 180
gtggactctg tgaagggccg attcaccatc tccagagacg acgccaagaa ctcactgtat 240
ctgcaaatga acagcctgag agctgaggac acggctgtgt attactgtgc gagagatcgt 300
ggggtgggct acttcgatct ctggggccgt ggcaccctgg tcaccgtctc gagcgctagc 360
accaagggcc catcggtctt ccccctggca ccctcctcca agagcacctc tgggggcaca 420
gcggccctgg gctgcctggt caaggactac ttccccgaac cggtgacggt gtcgtggaac 480
tcaggcgccc tgaccagcgg cgtgcacacc ttcccggctg tcctacagtc ctcaggactc 540
tactccctca gcagcgtggt gaccgtgccc tccagcagct tgggcaccca gacctacatc 600
tgcaacgtga atcacaagcc cagcaacacc aaggtggaca agagagttga gcccaaatct 660
tgtgacaaaa ctcacacatg cccaccgtgc ccagcacctg aactcctggg gggaccgtca 720
gtcttcctct tccccccaaa acccaaggac accctcatga tctcccggac ccctgaggtc 780
acatgcgtgg tggtggacgt gagccacgaa gaccctgagg tcaagttcaa ctggtacgtg 840
gacggcgtgg aggtgcataa tgccaagaca aagccgcggg aggagcagta caacagcacg 900
taccgtgtgg tcagcgtcct caccgtcctg caccaggact ggctgaatgg caaggagtac 960
aagtgcaagg tctccaacaa agccctccca gcccccatcg agaaaaccat ctccaaagcc 1020
aaagggcagc cccgagaacc acaggtgtac accctgcccc catcccggga ggagatgacc 1080
aagaaccagg tcagcctgac ctgcctggtc aaaggcttct atcccagcga catcgccgtg 1140
gagtgggaga gcaatgggca gccggagaac aactacaaga ccacgcctcc cgtgctggac 1200
tccgacggct ccttcttcct ctatagcaag ctcaccgtgg acaagagcag gtggcagcag 1260
gggaacgtct tctcatgctc cgtgatgcat gaggctctgc acaaccacta cacgcagaag 1320
agcctctccc tgtctccggg taaaggcggt ggaggatccg gcggtggtgg atcacaagtt 1380
caacttcaac aatctggtgc tgaagttaaa aaacctggtt cttctgttaa agtttcttgt 1440
aaagcctctg gttatacttt tactaattat tatatttatt gggttcgtca agctcctggt 1500
caaggtcttg aatggattgg tggtattaat cctacttctg gtggttctaa ttttaatgaa 1560
aaatttaaaa ctcgtgttac tattactgtt gatgaatcta cgaacactgc ttatatggaa 1620
ctttcttctc ttcgttctga agatactgct ttttattttt gtgcgcgtca aggtctttgg 1680
tttgattctg atggtcgtgg ttttgatttt tggggtcaag gttccactgt tactgtctcg 1740
agcggtggag gcggttcagg cggaggtggt tccggcggtg gcggctccga tattcaaatg 1800
actcaatctc cttcttctct ttctgcttct gttggtgatc gtgttactat tacttgtcgt 1860
tcttctcaaa atattgttca ttctaatggt aatacttatc ttgattggta tcaacaaact 1920
cctggtaaag ctcctaaact tcttatttat aaagtttcta atcgtttttc tggtgttcct 1980
tctcgttttt ctggttctgg ttctggtact gattttactt ttactatttc ttctcttcaa 2040
cctgaagata ttgctactta ttattgtttt caatattctc atgttccttg gacttttggt 2100
caaggtacta aacttcaaat tactcgt 2127

<210> SEQ ID NO 74
<211> LENGTH: 354
<212> TYPE: DNA
<213> ORGANISM: artificial sequence
<220> FEATURE:
<223> OTHER INFORMATION: Synthesized

<400> SEQUENCE: 74
caggtgcagc tgcaggagtc gggggaggc ctggtcaagc ctggagggtc cctgagactc 60
tcctgtgcag cctctggatt cacctttagt agttattgga tgagctgggt ccgccaggct 120
ccagggaagg ggctggagtg ggtggccaac ataaaccgcg atggaagtgc gagttactat 180
gtggactctg tgaagggccg attcaccatc tccagagacg acgccaagaa ctcactgtat 240
ctgcaaatga acagcctgag agctgaggac acggctgtgt attactgtgc gagagatcgt 300
ggggtgggct acttcgatct ctggggccgt ggcaccctgg tcaccgtctc gagc 354

<210> SEQ ID NO 75
<211> LENGTH: 753
<212> TYPE: DNA
<213> ORGANISM: artificial sequence
<220> FEATURE:
<223> OTHER INFORMATION: Synthesized

<400> SEQUENCE: 75
caagttcaac ttcaacaatc tggtgctgaa gttaaaaaac ctggttcttc tgttaaagtt 60
tcttgtaaag cctctggtta tacttttact aattattata tttattgggt tcgtcaagct 120
cctggtcaag gtcttgaatg gattggtggt attaatccta cttctggtgg ttctaatttt 180
aatgaaaaat ttaaaactcg tgttactatt actgttgatg aatctacgaa cactgcttat 240
atggaacttt cttctcttcg ttctgaagat actgcttttt atttttgtgc gcgtcaaggt 300
ctttggtttg attctgatgg tcgtggtttt gatttttggg gtcaaggttc cactgttact 360
gtctcgagcg gtggaggcgg ttcaggcgga ggtggttccg gcggtggcgg ctccgatatt 420
caaatgactc aatctccttc ttctctttct gcttctgttg gtgatcgtgt tactattact 480
tgtcgttctt ctcaaaatat tgttcattct aatggtaata cttatcttga ttggtatcaa 540
caaactcctg gtaaagctcc taaacttctt atttataaag tttctaatcg tttttctggt 600
gttccttctc gtttttctgg ttctggttct ggtactgatt ttacttttac tatttcttct 660
cttcaacctg aagatattgc tacttattat tgttttcaat attctcatgt tccttggact 720
tttggtcaag gtactaaact tcaaattact cgt 753

<210> SEQ ID NO 76
<211> LENGTH: 709
<212> TYPE: PRT
<213> ORGANISM: artificial sequence
<220> FEATURE:
<223> OTHER INFORMATION: Synthesized

<400> SEQUENCE: 76

Gln Val Gln Leu Gln Glu Ser Gly Gly Gly Leu Val Lys Pro Gly Gly
1 5 10 15

Ser Leu Arg Leu Ser Cys Ala Ala Ser Gly Phe Thr Phe Ser Ser Tyr
20 25 30

-continued

```
Trp Met Ser Trp Val Arg Gln Ala Pro Gly Lys Gly Leu Glu Trp Val
        35                  40                  45

Ala Asn Ile Asn Arg Asp Gly Ser Ala Ser Tyr Tyr Val Asp Ser Val
    50                  55                  60

Lys Gly Arg Phe Thr Ile Ser Arg Asp Asp Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Arg Gly Val Gly Tyr Phe Asp Leu Trp Gly Arg Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Arg Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Glu Glu Met Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
        435                 440                 445

Gly Gly Gly Gly Ser Gly Gly Gly Gly Ser Gln Val Gln Leu Gln Gln
```

-continued

```
    450                 455                 460

Ser Gly Ala Glu Val Lys Lys Pro Gly Ser Ser Val Lys Val Ser Cys
465                 470                 475                 480

Lys Ala Ser Gly Tyr Thr Phe Thr Asn Tyr Tyr Ile Tyr Trp Val Arg
                485                 490                 495

Gln Ala Pro Gly Gln Gly Leu Glu Trp Ile Gly Gly Ile Asn Pro Thr
            500                 505                 510

Ser Gly Gly Ser Asn Phe Asn Glu Lys Phe Lys Thr Arg Val Thr Ile
        515                 520                 525

Thr Val Asp Glu Ser Thr Asn Thr Ala Tyr Met Glu Leu Ser Ser Leu
    530                 535                 540

Arg Ser Glu Asp Thr Ala Phe Tyr Phe Cys Ala Arg Gln Gly Leu Trp
545                 550                 555                 560

Phe Asp Ser Asp Gly Arg Gly Phe Asp Phe Trp Gly Gln Gly Ser Thr
                565                 570                 575

Val Thr Val Ser Ser Gly Gly Gly Gly Ser Gly Gly Gly Gly Ser Gly
            580                 585                 590

Gly Gly Gly Ser Asp Ile Gln Met Thr Gln Ser Pro Ser Ser Leu Ser
        595                 600                 605

Ala Ser Val Gly Asp Arg Val Thr Ile Thr Cys Arg Ser Ser Gln Asn
    610                 615                 620

Ile Val His Ser Asn Gly Asn Thr Tyr Leu Asp Trp Tyr Gln Gln Thr
625                 630                 635                 640

Pro Gly Lys Ala Pro Lys Leu Leu Ile Tyr Lys Val Ser Asn Arg Phe
                645                 650                 655

Ser Gly Val Pro Ser Arg Phe Ser Gly Ser Gly Ser Gly Thr Asp Phe
            660                 665                 670

Thr Phe Thr Ile Ser Ser Leu Gln Pro Glu Asp Ile Ala Thr Tyr Tyr
        675                 680                 685

Cys Phe Gln Tyr Ser His Val Pro Trp Thr Phe Gly Gln Gly Thr Lys
    690                 695                 700

Leu Gln Ile Thr Arg
705


<210> SEQ ID NO 77
<211> LENGTH: 118
<212> TYPE: PRT
<213> ORGANISM: artificial sequence
<220> FEATURE:
<223> OTHER INFORMATION: Synthesized

<400> SEQUENCE: 77

Gln Val Gln Leu Gln Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Trp Met Ser Trp Val Arg Gln Ala Pro Gly Lys Gly Leu Glu Trp Val
        35                  40                  45

Ala Asn Ile Asn Arg Asp Gly Ser Ala Ser Tyr Tyr Val Asp Ser Val
    50                  55                  60

Lys Gly Arg Phe Thr Ile Ser Arg Asp Asp Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Arg Gly Val Gly Tyr Phe Asp Leu Trp Gly Arg Gly Thr
```

```
            100                 105                 110

Leu Val Thr Val Ser Ser
        115


<210> SEQ ID NO 78
<211> LENGTH: 251
<212> TYPE: PRT
<213> ORGANISM: artificial sequence
<220> FEATURE:
<223> OTHER INFORMATION: Synthesized

<400> SEQUENCE: 78

Gln Val Gln Leu Gln Gln Ser Gly Ala Glu Val Lys Lys Pro Gly Ser
1               5                   10                  15

Ser Val Lys Val Ser Cys Lys Ala Ser Gly Tyr Thr Phe Thr Asn Tyr
            20                  25                  30

Tyr Ile Tyr Trp Val Arg Gln Ala Pro Gly Gln Gly Leu Glu Trp Ile
        35                  40                  45

Gly Gly Ile Asn Pro Thr Ser Gly Gly Ser Asn Phe Asn Glu Lys Phe
    50                  55                  60

Lys Thr Arg Val Thr Ile Thr Val Asp Glu Ser Thr Asn Thr Ala Tyr
65                  70                  75                  80

Met Glu Leu Ser Ser Leu Arg Ser Glu Asp Thr Ala Phe Tyr Phe Cys
                85                  90                  95

Ala Arg Gln Gly Leu Trp Phe Asp Ser Asp Gly Arg Gly Phe Asp Phe
            100                 105                 110

Trp Gly Gln Gly Ser Thr Val Thr Val Ser Ser Gly Gly Gly Gly Ser
        115                 120                 125

Gly Gly Gly Gly Ser Gly Gly Gly Gly Ser Asp Ile Gln Met Thr Gln
    130                 135                 140

Ser Pro Ser Ser Leu Ser Ala Ser Val Gly Asp Arg Val Thr Ile Thr
145                 150                 155                 160

Cys Arg Ser Ser Gln Asn Ile Val His Ser Asn Gly Asn Thr Tyr Leu
                165                 170                 175

Asp Trp Tyr Gln Gln Thr Pro Gly Lys Ala Pro Lys Leu Leu Ile Tyr
            180                 185                 190

Lys Val Ser Asn Arg Phe Ser Gly Val Pro Ser Arg Phe Ser Gly Ser
        195                 200                 205

Gly Ser Gly Thr Asp Phe Thr Phe Thr Ile Ser Ser Leu Gln Pro Glu
    210                 215                 220

Asp Ile Ala Thr Tyr Tyr Cys Phe Gln Tyr Ser His Val Pro Trp Thr
225                 230                 235                 240

Phe Gly Gln Gly Thr Lys Leu Gln Ile Thr Arg
                245                 250


<210> SEQ ID NO 79
<211> LENGTH: 657
<212> TYPE: DNA
<213> ORGANISM: artificial sequence
<220> FEATURE:
<223> OTHER INFORMATION: Synthesized

<400> SEQUENCE: 79

gatattcaaa tgactcaatc tccttcttct ctttctgctt ctgttggtga tcgtgttact      60

attacttgtc gttcttctca aaatattgtt cattctaatg gtaatactta tcttgattgg     120

tatcaacaaa ctcctggtaa agctcctaaa cttcttattt ataaagtttc taatcgtttt     180
```

```
tctggtgttc cttctcgttt ttctggttct ggttctggta ctgattttac ttttactatt    240

tcttctcttc aacctgaaga tattgctact tattattgtt ttcaatattc tcatgttcct    300

tggacttttg gtcaaggtac taaacttcaa attactcgta cggtggctgc accatctgtc    360

ttcatcttcc cgccatctga tgagcagttg aaatctggaa ctgcctctgt tgtgtgcctg    420

ctgaataact tctatcccag agaggccaaa gtacagtgga aggtggataa cgccctccaa    480

tcgggtaact cccaggagag tgtcacagag caggacagca aggacagcac ctacagcctc    540

agcagcaccc tgacgctgag caaagcagac tacgagaaac acaaagtcta cgcctgcgaa    600

gtcacccatc agggcctgag ctcgcccgtc acaaagagct tcaacagggg agagtgt       657


<210> SEQ ID NO 80
<211> LENGTH: 336
<212> TYPE: DNA
<213> ORGANISM: artificial sequence
<220> FEATURE:
<223> OTHER INFORMATION: Synthesized

<400> SEQUENCE: 80

gatattcaaa tgactcaatc tccttcttct ctttctgctt ctgttggtga tcgtgttact     60

attacttgtc gttcttctca aaatattgtt cattctaatg gtaatactta tcttgattgg    120

tatcaacaaa ctcctggtaa agctcctaaa cttcttattt ataaagtttc taatcgtttt    180

tctggtgttc cttctcgttt ttctggttct ggttctggta ctgattttac ttttactatt    240

tcttctcttc aacctgaaga tattgctact tattattgtt ttcaatattc tcatgttcct    300

tggacttttg gtcaaggtac taaacttcaa attact                              336


<210> SEQ ID NO 81
<211> LENGTH: 219
<212> TYPE: PRT
<213> ORGANISM: artificial sequence
<220> FEATURE:
<223> OTHER INFORMATION: Synthesized

<400> SEQUENCE: 81

Asp Ile Gln Met Thr Gln Ser Pro Ser Ser Leu Ser Ala Ser Val Gly
1               5                   10                  15

Asp Arg Val Thr Ile Thr Cys Arg Ser Ser Gln Asn Ile Val His Ser
            20                  25                  30

Asn Gly Asn Thr Tyr Leu Asp Trp Tyr Gln Gln Thr Pro Gly Lys Ala
        35                  40                  45

Pro Lys Leu Leu Ile Tyr Lys Val Ser Asn Arg Phe Ser Gly Val Pro
    50                  55                  60

Ser Arg Phe Ser Gly Ser Gly Ser Gly Thr Asp Phe Thr Phe Thr Ile
65                  70                  75                  80

Ser Ser Leu Gln Pro Glu Asp Ile Ala Thr Tyr Tyr Cys Phe Gln Tyr
                85                  90                  95

Ser His Val Pro Trp Thr Phe Gly Gln Gly Thr Lys Leu Gln Ile Thr
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
```

-continued

```
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215
```

<210> SEQ ID NO 82
<211> LENGTH: 112
<212> TYPE: PRT
<213> ORGANISM: artificial sequence
<220> FEATURE:
<223> OTHER INFORMATION: Synthesized

<400> SEQUENCE: 82

```
Asp Ile Gln Met Thr Gln Ser Pro Ser Ser Leu Ser Ala Ser Val Gly
1               5                   10                  15

Asp Arg Val Thr Ile Thr Cys Arg Ser Ser Gln Asn Ile Val His Ser
            20                  25                  30

Asn Gly Asn Thr Tyr Leu Asp Trp Tyr Gln Gln Thr Pro Gly Lys Ala
        35                  40                  45

Pro Lys Leu Leu Ile Tyr Lys Val Ser Asn Arg Phe Ser Gly Val Pro
    50                  55                  60

Ser Arg Phe Ser Gly Ser Gly Ser Gly Thr Asp Phe Thr Phe Thr Ile
65                  70                  75                  80

Ser Ser Leu Gln Pro Glu Asp Ile Ala Thr Tyr Tyr Cys Phe Gln Tyr
                85                  90                  95

Ser His Val Pro Trp Thr Phe Gly Gln Gly Thr Lys Leu Gln Ile Thr
            100                 105                 110
```

<210> SEQ ID NO 83
<211> LENGTH: 2121
<212> TYPE: DNA
<213> ORGANISM: artificial sequence
<220> FEATURE:
<223> OTHER INFORMATION: Synthesized

<400> SEQUENCE: 83

```
caagttcaac ttcaacaatc tggtgctgaa gttaaaaaac ctggttcttc tgttaaagtt      60

tcttgtaaag cctctggtta tacttttact aattattata tttattgggt tcgtcaagct     120

cctggtcaag gtcttgaatg gattggtggt attaatccta cttctggtgg ttctaatttt     180

aatgaaaaat ttaaaactcg tgttactatt actgttgatg aatctacgaa cactgcttat     240

atggaacttt cttctcttcg ttctgaagat actgcttttt atttttgtgc gcgtcaaggt     300

ctttggtttg attctgatgg tcgtggtttt gatttttggg gtcaaggttc cactgttact     360

gtctcgagcg ctagcaccaa gggcccatcg gtcttccccc tggcaccctc ctccaagagc     420

acctctgggg gcacagcggc cctgggctgc ctggtcaagg actacttccc cgaaccggtg     480

acggtgtcgt ggaactcagg cgccctgacc agcggcgtgc acaccttccc ggctgtccta     540

cagtcctcag gactctactc cctcagcagc gtggtgaccg tgccctccag cagcttgggc     600

acccagacct acatctgcaa cgtgaatcac aagcccagca acaccaaggt ggacaagaga     660

gttgagccca aatcttgtga caaaactcac acatgcccac cgtgcccagc acctgaactc     720

ctggggggac cgtcagtctt cctcttcccc ccaaaaccca aggacaccct catgatctcc     780

cggacccctg aggtcacatg cgtggtggtg gacgtgagcc acgaagaccc tgaggtcaag     840
```

```
ttcaactggt acgtggacgg cgtggaggtg cataatgcca agacaaagcc gcgggaggag    900

cagtacaaca gcacgtaccg tgtggtcagc gtcctcaccg tcctgcacca ggactggctg    960

aatggcaagg agtacaagtg caaggtctcc aacaaagccc tcccagcccc catcgagaaa   1020

accatctcca aagccaaagg gcagccccga gaaccacagg tgtacaccct gcccccatcc   1080

cgggaggaga tgaccaagaa ccaggtcagc ctgacctgcc tggtcaaagg cttctatccc   1140

agcgacatcg ccgtggagtg ggagagcaat gggcagccgg agaacaacta caagaccacg   1200

cctcccgtgc tggactccga cggctccttc ttcctctata gcaagctcac cgtggacaag   1260

agcaggtggc agcaggggaa cgtcttctca tgctccgtga tgcatgaggc tctgcacaac   1320

cactacacgc agaagagcct ctccctgtct ccgggtaaag gcggtggagg atccggcggt   1380

ggtggatcac aggtgcagct gcaggagtcg gggggaggcc tggtcaagcc tggagggtcc   1440

ctgagactct cctgtgcagc ctctggattc acctttagta gttattggat gagctgggtc   1500

cgccaggctc cagggaaggg gctggagtgg gtggccaaca taaaccgcga tggaagtgcg   1560

agttactatg tggactctgt gaagggccga ttcaccatct ccagagacga cgccaagaac   1620

tcactgtatc tgcaaatgaa cagcctgaga gctgaggaca cggctgtgta ttactgtgcg   1680

agagatcgtg gggtgggcta cttcgatctc tggggccgtg gcaccctggt caccgtctcg   1740

agcggtggag gcggttcagg cggaggtggt tccggcggtg gcggctccca gtctgccctg   1800

actcagcctg cctccgtgtc tgggtctcct ggacagtcga tcaccatctc ctgcactgga   1860

accagcagtg acgttggtgg ttataacttt gtctcctggt accaacaaca cccaggcaaa   1920

gcccccaaac tcatgatcta tgatgtcagt gatcggccct caggggtgtc tgatcgcttc   1980

tccggctcca agtctggcaa cacggcctcc ctgatcatct ctggcctcca ggctgacgac   2040

gaggctgatt attactgcag ctcatatggg agcagcagca ctcatgtgat tttcggcgga   2100

gggaccaagg tgaccgtcct a                                             2121
```

<210> SEQ ID NO 84
<211> LENGTH: 369
<212> TYPE: DNA
<213> ORGANISM: artificial sequence
<220> FEATURE:
<223> OTHER INFORMATION: Synthesized

<400> SEQUENCE: 84

```
caagttcaac ttcaacaatc tggtgctgaa gttaaaaaac ctggttcttc tgttaaagtt     60

tcttgtaaag cctctggtta tacttttact aattattata tttattgggt tcgtcaagct    120

cctggtcaag gtcttgaatg gattggtggt attaatccta cttctggtgg ttctaatttt    180

aatgaaaaat ttaaaactcg tgttactatt actgttgatg aatctacgaa cactgcttat    240

atggaacttt cttctcttcg ttctgaagat actgcttttt atttttgtgc gcgtcaaggt    300

ctttggtttg attctgatgg tcgtggtttt gatttttggg gtcaaggttc cactgttact    360

gtctcgagc                                                            369
```

<210> SEQ ID NO 85
<211> LENGTH: 732
<212> TYPE: DNA
<213> ORGANISM: artificial sequence
<220> FEATURE:
<223> OTHER INFORMATION: Synthesized

<400> SEQUENCE: 85

-continued

```
caggtgcagc tgcaggagtc ggggggaggc ctggtcaagc ctggagggtc cctgagactc     60

tcctgtgcag cctctggatt cacctttagt agttattgga tgagctgggt ccgccaggct    120

ccagggaagg ggctggagtg ggtggccaac ataaaccgcg atggaagtgc gagttactat    180

gtggactctg tgaagggccg attcaccatc tccagagacg acgccaagaa ctcactgtat    240

ctgcaaatga acagcctgag agctgaggac acggctgtgt attactgtgc gagagatcgt    300

ggggtgggct acttcgatct ctggggccgt ggcaccctgg tcaccgtctc gagcggtgga    360

ggcggttcag gcggaggtgg ttccggcggt ggcggctccc agtctgccct gactcagcct    420

gcctccgtgt ctgggtctcc tggacagtcg atcaccatct cctgcactgg aaccagcagt    480

gacgttggtg gttataactt tgtctcctgg taccaacaac acccaggcaa agcccccaaa    540

ctcatgatct atgatgtcag tgatcggccc tcaggggtgt ctgatcgctt ctccggctcc    600

aagtctggca acacggcctc cctgatcatc tctggcctcc aggctgacga cgaggctgat    660

tattactgca gctcatatgg gagcagcagc actcatgtga ttttcggcgg agggaccaag    720

gtgaccgtcc ta                                                        732
```

<210> SEQ ID NO 86
<211> LENGTH: 707
<212> TYPE: PRT
<213> ORGANISM: artificial sequence
<220> FEATURE:
<223> OTHER INFORMATION: Synthesized

<400> SEQUENCE: 86

```
Gln Val Gln Leu Gln Gln Ser Gly Ala Glu Val Lys Lys Pro Gly Ser
1               5                   10                  15

Ser Val Lys Val Ser Cys Lys Ala Ser Gly Tyr Thr Phe Thr Asn Tyr
            20                  25                  30

Tyr Ile Tyr Trp Val Arg Gln Ala Pro Gly Gln Gly Leu Glu Trp Ile
        35                  40                  45

Gly Gly Ile Asn Pro Thr Ser Gly Gly Ser Asn Phe Asn Glu Lys Phe
    50                  55                  60

Lys Thr Arg Val Thr Ile Thr Val Asp Glu Ser Thr Asn Thr Ala Tyr
65                  70                  75                  80

Met Glu Leu Ser Ser Leu Arg Ser Glu Asp Thr Ala Phe Tyr Phe Cys
                85                  90                  95

Ala Arg Gln Gly Leu Trp Phe Asp Ser Asp Gly Arg Gly Phe Asp Phe
            100                 105                 110

Trp Gly Gln Gly Ser Thr Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Arg Val Glu Pro Lys
    210                 215                 220

Ser Cys Asp Lys Thr His Thr Cys Pro Pro Cys Pro Ala Pro Glu Leu
```

-continued

```
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Asn Ser
    290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
            340                 345                 350

Gln Val Tyr Thr Leu Pro Pro Ser Arg Glu Glu Met Thr Lys Asn Gln
        355                 360                 365

Val Ser Leu Thr Cys Leu Val Lys Gly Phe Tyr Pro Ser Asp Ile Ala
    370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
            420                 425                 430

Val Met His Glu Ala Leu His Asn His Tyr Thr Gln Lys Ser Leu Ser
        435                 440                 445

Leu Ser Pro Gly Lys Gly Gly Gly Gly Ser Gly Gly Gly Gly Ser Gln
    450                 455                 460

Val Gln Leu Gln Glu Ser Gly Gly Gly Leu Val Lys Pro Gly Gly Ser
465                 470                 475                 480

Leu Arg Leu Ser Cys Ala Ala Ser Gly Phe Thr Phe Ser Ser Tyr Trp
                485                 490                 495

Met Ser Trp Val Arg Gln Ala Pro Gly Lys Gly Leu Glu Trp Val Ala
            500                 505                 510

Asn Ile Asn Arg Asp Gly Ser Ala Ser Tyr Tyr Val Asp Ser Val Lys
        515                 520                 525

Gly Arg Phe Thr Ile Ser Arg Asp Asp Ala Lys Asn Ser Leu Tyr Leu
    530                 535                 540

Gln Met Asn Ser Leu Arg Ala Glu Asp Thr Ala Val Tyr Tyr Cys Ala
545                 550                 555                 560

Arg Asp Arg Gly Val Gly Tyr Phe Asp Leu Trp Gly Arg Gly Thr Leu
                565                 570                 575

Val Thr Val Ser Ser Gly Gly Gly Gly Ser Gly Gly Gly Gly Ser Gly
            580                 585                 590

Gly Gly Gly Ser Gln Ser Ala Leu Thr Gln Pro Ala Ser Val Ser Gly
        595                 600                 605

Ser Pro Gly Gln Ser Ile Thr Ile Ser Cys Thr Gly Thr Ser Ser Asp
    610                 615                 620

Val Gly Gly Tyr Asn Phe Val Ser Trp Tyr Gln Gln His Pro Gly Lys
625                 630                 635                 640

Ala Pro Lys Leu Met Ile Tyr Asp Val Ser Asp Arg Pro Ser Gly Val
                645                 650                 655
```

Ser Asp Arg Phe Ser Gly Ser Lys Ser Gly Asn Thr Ala Ser Leu Ile
660 665 670

Ile Ser Gly Leu Gln Ala Asp Asp Glu Ala Asp Tyr Tyr Cys Ser Ser
675 680 685

Tyr Gly Ser Ser Ser Thr His Val Ile Phe Gly Gly Gly Thr Lys Val
690 695 700

Thr Val Leu
705

<210> SEQ ID NO 87
<211> LENGTH: 123
<212> TYPE: PRT
<213> ORGANISM: artificial sequence
<220> FEATURE:
<223> OTHER INFORMATION: Synthesized

<400> SEQUENCE: 87

Gln Val Gln Leu Gln Gln Ser Gly Ala Glu Val Lys Lys Pro Gly Ser
1 5 10 15

Ser Val Lys Val Ser Cys Lys Ala Ser Gly Tyr Thr Phe Thr Asn Tyr
20 25 30

Tyr Ile Tyr Trp Val Arg Gln Ala Pro Gly Gln Gly Leu Glu Trp Ile
35 40 45

Gly Gly Ile Asn Pro Thr Ser Gly Gly Ser Asn Phe Asn Glu Lys Phe
50 55 60

Lys Thr Arg Val Thr Ile Thr Val Asp Glu Ser Thr Asn Thr Ala Tyr
65 70 75 80

Met Glu Leu Ser Ser Leu Arg Ser Glu Asp Thr Ala Phe Tyr Phe Cys
85 90 95

Ala Arg Gln Gly Leu Trp Phe Asp Ser Asp Gly Arg Gly Phe Asp Phe
100 105 110

Trp Gly Gln Gly Ser Thr Val Thr Val Ser Ser
115 120

<210> SEQ ID NO 88
<211> LENGTH: 244
<212> TYPE: PRT
<213> ORGANISM: artificial sequence
<220> FEATURE:
<223> OTHER INFORMATION: Synthesized

<400> SEQUENCE: 88

Gln Val Gln Leu Gln Glu Ser Gly Gly Gly Leu Val Lys Pro Gly Gly
1 5 10 15

Ser Leu Arg Leu Ser Cys Ala Ala Ser Gly Phe Thr Phe Ser Ser Tyr
20 25 30

Trp Met Ser Trp Val Arg Gln Ala Pro Gly Lys Gly Leu Glu Trp Val
35 40 45

Ala Asn Ile Asn Arg Asp Gly Ser Ala Ser Tyr Tyr Val Asp Ser Val
50 55 60

Lys Gly Arg Phe Thr Ile Ser Arg Asp Asp Ala Lys Asn Ser Leu Tyr
65 70 75 80

Leu Gln Met Asn Ser Leu Arg Ala Glu Asp Thr Ala Val Tyr Tyr Cys
85 90 95

Ala Arg Asp Arg Gly Val Gly Tyr Phe Asp Leu Trp Gly Arg Gly Thr
100 105 110

Leu Val Thr Val Ser Ser Gly Gly Gly Gly Ser Gly Gly Gly Gly Ser

```
        115                 120                 125

Gly Gly Gly Gly Ser Gln Ser Ala Leu Thr Gln Pro Ala Ser Val Ser
    130                 135                 140

Gly Ser Pro Gly Gln Ser Ile Thr Ile Ser Cys Thr Gly Thr Ser Ser
145                 150                 155                 160

Asp Val Gly Gly Tyr Asn Phe Val Ser Trp Tyr Gln Gln His Pro Gly
                165                 170                 175

Lys Ala Pro Lys Leu Met Ile Tyr Asp Val Ser Asp Arg Pro Ser Gly
            180                 185                 190

Val Ser Asp Arg Phe Ser Gly Ser Lys Ser Gly Asn Thr Ala Ser Leu
        195                 200                 205

Ile Ile Ser Gly Leu Gln Ala Asp Asp Glu Ala Asp Tyr Tyr Cys Ser
    210                 215                 220

Ser Tyr Gly Ser Ser Ser Thr His Val Ile Phe Gly Gly Gly Thr Lys
225                 230                 235                 240

Val Thr Val Leu
```

<210> SEQ ID NO 89
<211> LENGTH: 657
<212> TYPE: DNA
<213> ORGANISM: artificial sequence
<220> FEATURE:
<223> OTHER INFORMATION: Synthesized

<400> SEQUENCE: 89

```
gatattcaaa tgactcaatc tccttcttct ctttctgctt ctgttggtga tcgtgttact     60

attacttgtc gttcttctca aaatattgtt cattctaatg gtaatactta tcttgattgg    120

tatcaacaaa ctcctggtaa agctcctaaa cttcttattt ataaagtttc taatcgtttt    180

tctggtgttc cttctcgttt ttctggttct ggttctggta ctgattttac ttttactatt    240

tcttctcttc aacctgaaga tattgctact tattattgtt ttcaatattc tcatgttcct    300

tggacttttg gtcaaggtac taaacttcaa attactcgta cggtggctgc accatctgtc    360

ttcatcttcc cgccatctga tgagcagttg aaatctggaa ctgcctctgt tgtgtgcctg    420

ctgaataact tctatcccag agaggccaaa gtacagtgga aggtggataa cgccctccaa    480

tcgggtaact cccaggagag tgtcacagag caggacagca aggacagcac ctacagcctc    540

agcagcaccc tgacgctgag caaagcagac tacgagaaac acaaagtcta cgcctgcgaa    600

gtcacccatc agggcctgag ctcgcccgtc acaaagagct tcaacagggg agagtgt       657
```

<210> SEQ ID NO 90
<211> LENGTH: 336
<212> TYPE: DNA
<213> ORGANISM: artificial sequence
<220> FEATURE:
<223> OTHER INFORMATION: Synthesized

<400> SEQUENCE: 90

```
gatattcaaa tgactcaatc tccttcttct ctttctgctt ctgttggtga tcgtgttact     60

attacttgtc gttcttctca aaatattgtt cattctaatg gtaatactta tcttgattgg    120

tatcaacaaa ctcctggtaa agctcctaaa cttcttattt ataaagtttc taatcgtttt    180

tctggtgttc cttctcgttt ttctggttct ggttctggta ctgattttac ttttactatt    240

tcttctcttc aacctgaaga tattgctact tattattgtt ttcaatattc tcatgttcct    300

tggacttttg gtcaaggtac taaacttcaa attact                              336
```

-continued

<210> SEQ ID NO 91
<211> LENGTH: 336
<212> TYPE: DNA
<213> ORGANISM: artificial sequence
<220> FEATURE:
<223> OTHER INFORMATION: Synthesized

<400> SEQUENCE: 91

```
gacatccaga tgacccagtc cccttccagc ctgtccgctt ccgtgggcga cagggtgacc     60

atcacctgca ggtcctccca gaacatcgtg cactccaacg gcaataccta cctggactgg    120

taccagcaga cccccggcaa ggcccctaag ctgctgatct acaaggtgag caaccggttc    180

agcggcgtgc cttcccggtt ttccggatcc ggctccggca cagacttcac cttcaccatc    240

tcctccctgc aacccgagga catcgccacc tactactgct tccagtactc ccatgtgccc    300

tggaccttcg gccagggcac caagctgcag atcacc                              336
```

<210> SEQ ID NO 92
<211> LENGTH: 218
<212> TYPE: PRT
<213> ORGANISM: artificial sequence
<220> FEATURE:
<223> OTHER INFORMATION: Synthesized

<400> SEQUENCE: 92

```
Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
            20                  25                  30

Asn Phe Val Ser Trp Tyr Gln Gln His Pro Gly Lys Ala Pro Lys Leu
        35                  40                  45

Met Ile Tyr Asp Val Ser Asp Arg Pro Ser Gly Val Ser Asp Arg Phe
    50                  55                  60

Ser Gly Ser Lys Ser Gly Asn Thr Ala Ser Leu Ile Ile Ser Gly Leu
65                  70                  75                  80

Gln Ala Asp Asp Glu Ala Asp Tyr Tyr Cys Ser Ser Tyr Gly Ser Ser
                85                  90                  95

Ser Thr His Val Ile Phe Gly Gly Gly Thr Lys Leu Thr Val Leu Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215
```

<210> SEQ ID NO 93
<211> LENGTH: 111
<212> TYPE: PRT
<213> ORGANISM: artificial sequence
<220> FEATURE:
<223> OTHER INFORMATION: Synthesized

<400> SEQUENCE: 93

```
Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
            20                  25                  30

Asn Phe Val Ser Trp Tyr Gln Gln His Pro Gly Lys Ala Pro Lys Leu
        35                  40                  45

Met Ile Tyr Asp Val Ser Asp Arg Pro Ser Gly Val Ser Asp Arg Phe
    50                  55                  60

Ser Gly Ser Lys Ser Gly Asn Thr Ala Ser Leu Ile Ile Ser Gly Leu
65                  70                  75                  80

Gln Ala Asp Asp Glu Ala Asp Tyr Tyr Cys Ser Ser Tyr Gly Ser Ser
                85                  90                  95

Ser Thr His Val Ile Phe Gly Gly Gly Thr Lys Leu Thr Val Leu
            100                 105                 110
```

<210> SEQ ID NO 94
<211> LENGTH: 2118
<212> TYPE: DNA
<213> ORGANISM: artificial sequence
<220> FEATURE:
<223> OTHER INFORMATION: Synthesized

<400> SEQUENCE: 94

```
caggtgcagc tgcagcagag cggcgccgag gtgaagaagc ccggcagcag cgtgaaggtg      60

agctgcaagg ccagcggcta caccttcacc aactactaca tctactgggt gcggcaggcc     120

cccggccagg gcctggagtg gatcggcggc atcaacccca ccagcggcgg cagcaacttc     180

aacgagaagt tcaagacccg ggtgaccatc accgccgacg agagcagcac caccgcctac     240

atggagctga gcagcctgcg gagcgaggac accgccttct acttctgcac ccggcagggc     300

ctgtggttcg acagcgacgg ccggggcttc gacttctggg gccagggcac caccgtgacc     360

gtgagcagcg ctagcaccaa gggcccatcg gtcttccccc tggcaccctc ctccaagagc     420

acctctgggg gcacagcggc cctgggctgc ctggtcaagg actacttccc cgaaccggtg     480

acggtgtcgt ggaactcagg cgccctgacc agcggcgtgc acaccttccc ggctgtccta     540

cagtcctcag gactctactc cctcagcagc gtggtgaccg tgccctccag cagcttgggc     600

acccagacct acatctgcaa cgtgaatcac aagcccagca acaccaaggt ggacaagaga     660

gttgagccca aatcttgtga caaaactcac acatgcccac cgtgcccagc acctgaactc     720

ctggggggac cgtcagtctt cctcttcccc ccaaaaccca aggacaccct catgatctcc     780

cggacccctg aggtcacatg cgtggtggtg gacgtgagcc acgaagaccc tgaggtcaag     840

ttcaactggt acgtggacgg cgtggaggtg cataatgcca agacaaagcc gcgggaggag     900

cagtacaaca gcacgtaccg tgtggtcagc gtcctcaccg tcctgcacca ggactggctg     960

aatggcaagg agtacaagtg caaggtctcc aacaaagccc tcccagcccc catcgagaaa    1020

accatctcca aagccaaagg gcagccccga gaaccacagg tgtacaccct gcccccatcc    1080

cgggatgagc tgaccaagaa ccaggtcagc ctgacctgcc tggtcaaagg cttctatccc    1140

agcgacatcg ccgtggagtg ggagagcaat gggcagccgg agaacaacta caagaccacg    1200

cctcccgtgc tggactccga cggctccttc ttcctctata gcaagctcac cgtggacaag    1260

agcaggtggc agcaggggaa cgtcttctca tgctccgtga tgcatgaggc tctgcacaac    1320
```

cactacacgc agaagagcct ctccctgtct ccgggtggcg gtggagggtc cggcggtggt 1380
ggatcacagg tgcaattgca ggagtcgggg ggaggcctgg tcaagcctgg agggtccctg 1440
agactctcct gtgcagcctc tggattcacc tttagtagtt attggatgag ctgggtccgc 1500
caggctccag ggaaggggct ggagtgggtg gccaacataa accgcgatgg aagtgcgagt 1560
tactatgtgg actctgtgaa gggccgattc accatctcca gagacgacgc caagaactca 1620
ctgtatctgc aaatgaacag cctgagagct gaggacacgg ctgtgtatta ctgtgcgaga 1680
gatcgtgggg tgggctactt cgatctctgg ggccgtggca ccctggtcac cgtctcgagc 1740
ggtggaggcg gttcaggcgg aggtggttcc ggcggtggcg gctcccagtc tgccctgact 1800
cagcctgcct ccgtgtctgg gtctcctgga cagtcgatca ccatctcctg cactggaacc 1860
agcagtgacg ttggtggtta taactttgtc tcctggtacc aacaacaccc aggcaaagcc 1920
cccaaactca tgatctatga tgtcagtgat cggccctcag ggtgtctga tcgcttctcc 1980 ggctccaagt ctggcaacac ggcctccctg atcatctctg gcctccaggc tgacgacgag 2040
gctgattatt actgcagctc atatgggagc agcagcactc atgtgatttt cggcggaggg 2100
accaaggtga ccgtccta 2118

<210> SEQ ID NO 95
<211> LENGTH: 369
<212> TYPE: DNA
<213> ORGANISM: artificial sequence
<220> FEATURE:
<223> OTHER INFORMATION: Synthesized

<400> SEQUENCE: 95
caggtgcagc tgcagcagag cggcgccgag gtgaagaagc ccggcagcag cgtgaaggtg 60
agctgcaagg ccagcggcta caccttcacc aactactaca tctactgggt gcggcaggcc 120
cccggccagg gcctggagtg gatcggcggc atcaacccca ccagcggcgg cagcaacttc 180
aacgagaagt tcaagacccg ggtgaccatc accgccgacg agagcagcac caccgcctac 240
atggagctga gcagcctgcg gagcgaggac accgccttct acttctgcac ccggcagggc 300
ctgtggttcg acagcgacgg ccggggcttc gacttctggg gccagggcac caccgtgacc 360
gtgagcagc 369

<210> SEQ ID NO 96
<211> LENGTH: 369
<212> TYPE: DNA
<213> ORGANISM: artificial sequence
<220> FEATURE:
<223> OTHER INFORMATION: Synthesized

<400> SEQUENCE: 96
caggtgcagc tgcagcaatc cggcgccgag gtgaagaagc ctggctccag cgtgaaggtg 60
tcctgcaagg cctccggcta caccttcacc aactactaca tctactgggt gaggcaggct 120
cctggccagg gactggagtg gatcggcggc atcaacccta cctccggcgg ctccaacttc 180
aacgagaagt tcaagacccg ggtgaccatc accgccgatg agagctccac caccgcctac 240
atggagctgt cctccctgag gtccgaggac accgcctttt acttctgcac caggcaggga 300
ctgtggttcg actccgacgg ccggggcttc gatttttggg gccagggcac cacagtgacc 360
gtgtcctcc 369

<210> SEQ ID NO 97

<211> LENGTH: 732
<212> TYPE: DNA
<213> ORGANISM: artificial sequence
<220> FEATURE:
<223> OTHER INFORMATION: Synthesized

<400> SEQUENCE: 97
caggtgcaat tgcaggagtc ggggggaggc ctggtcaagc ctggagggtc cctgagactc 60
tcctgtgcag cctctggatt cacctttagt agttattgga tgagctgggt ccgccaggct 120
ccagggaagg ggctggagtg ggtggccaac ataaaccgcg atggaagtgc gagttactat 180
gtggactctg tgaagggccg attcaccatc tccagagacg acgccaagaa ctcactgtat 240
ctgcaaatga acagcctgag agctgaggac acggctgtgt attactgtgc gagagatcgt 300
ggggtgggct acttcgatct ctggggccgt ggcaccctgg tcaccgtctc gagcggtgga 360
ggcggttcag gcggaggtgg ttccggcggt ggcggctccc agtctgccct gactcagcct 420
gcctccgtgt ctgggtctcc tggacagtcg atcaccatct cctgcactgg aaccagcagt 480
gacgttggtg gttataactt tgtctcctgg taccaacaac acccaggcaa agcccccaaa 540
ctcatgatct atgatgtcag tgatcggccc tcaggggtgt ctgatcgctt ctccggctcc 600
aagtctggca acacggcctc cctgatcatc tctggcctcc aggctgacga cgaggctgat 660
tattactgca gctcatatgg gagcagcagc actcatgtga ttttcggcgg agggaccaag 720
gtgaccgtcc ta 732

<210> SEQ ID NO 98
<211> LENGTH: 706
<212> TYPE: PRT
<213> ORGANISM: artificial sequence
<220> FEATURE:
<223> OTHER INFORMATION: Synthesized

<400> SEQUENCE: 98

Gln Val Gln Leu Gln Gln Ser Gly Ala Glu Val Lys Lys Pro Gly Ser
1               5                   10                  15

Ser Val Lys Val Ser Cys Lys Ala Ser Gly Tyr Thr Phe Thr Asn Tyr
            20                  25                  30

Tyr Ile Tyr Trp Val Arg Gln Ala Pro Gly Gln Gly Leu Glu Trp Ile
        35                  40                  45

Gly Gly Ile Asn Pro Thr Ser Gly Gly Ser Asn Phe Asn Glu Lys Phe
    50                  55                  60

Lys Thr Arg Val Thr Ile Thr Ala Asp Glu Ser Ser Thr Thr Ala Tyr
65                  70                  75                  80

Met Glu Leu Ser Ser Leu Arg Ser Glu Asp Thr Ala Phe Tyr Phe Cys
                85                  90                  95

Thr Arg Gln Gly Leu Trp Phe Asp Ser Asp Gly Arg Gly Phe Asp Phe
            100                 105                 110

Trp Gly Gln Gly Thr Thr Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

-continued

```
Thr Val Pro Ser Ser Ser Leu Gly Thr Gln Thr Tyr Ile Cys Asn Val
        195                 200                 205

Asn His Lys Pro Ser Asn Thr Lys Val Asp Lys Arg Val Glu Pro Lys
    210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Asn Ser
    290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
            340                 345                 350

Gln Val Tyr Thr Leu Pro Pro Ser Arg Asp Glu Leu Thr Lys Asn Gln
        355                 360                 365

Val Ser Leu Thr Cys Leu Val Lys Gly Phe Tyr Pro Ser Asp Ile Ala
    370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
            420                 425                 430

Val Met His Glu Ala Leu His Asn His Tyr Thr Gln Lys Ser Leu Ser
        435                 440                 445

Leu Ser Pro Gly Gly Gly Gly Gly Ser Gly Gly Gly Gly Ser Gln Val
    450                 455                 460

Gln Leu Gln Glu Ser Gly Gly Gly Leu Val Lys Pro Gly Gly Ser Leu
465                 470                 475                 480

Arg Leu Ser Cys Ala Ala Ser Gly Phe Thr Phe Ser Ser Tyr Trp Met
                485                 490                 495

Ser Trp Val Arg Gln Ala Pro Gly Lys Gly Leu Glu Trp Val Ala Asn
            500                 505                 510

Ile Asn Arg Asp Gly Ser Ala Ser Tyr Tyr Val Asp Ser Val Lys Gly
        515                 520                 525

Arg Phe Thr Ile Ser Arg Asp Asp Ala Lys Asn Ser Leu Tyr Leu Gln
    530                 535                 540

Met Asn Ser Leu Arg Ala Glu Asp Thr Ala Val Tyr Tyr Cys Ala Arg
545                 550                 555                 560

Asp Arg Gly Val Gly Tyr Phe Asp Leu Trp Gly Arg Gly Thr Leu Val
                565                 570                 575

Thr Val Ser Ser Gly Gly Gly Gly Ser Gly Gly Gly Gly Ser Gly Gly
            580                 585                 590

Gly Gly Ser Gln Ser Ala Leu Thr Gln Pro Ala Ser Val Ser Gly Ser
        595                 600                 605
```

Pro Gly Gln Ser Ile Thr Ile Ser Cys Thr Gly Thr Ser Ser Asp Val
    610                 615                 620

Gly Gly Tyr Asn Phe Val Ser Trp Tyr Gln Gln His Pro Gly Lys Ala
625                 630                 635                 640

Pro Lys Leu Met Ile Tyr Asp Val Ser Asp Arg Pro Ser Gly Val Ser
                645                 650                 655

Asp Arg Phe Ser Gly Ser Lys Ser Gly Asn Thr Ala Ser Leu Ile Ile
            660                 665                 670

Ser Gly Leu Gln Ala Asp Asp Glu Ala Asp Tyr Tyr Cys Ser Ser Tyr
        675                 680                 685

Gly Ser Ser Ser Thr His Val Ile Phe Gly Gly Gly Thr Lys Val Thr
    690                 695                 700

Val Leu
705

<210> SEQ ID NO 99
<211> LENGTH: 123
<212> TYPE: PRT
<213> ORGANISM: artificial sequence
<220> FEATURE:
<223> OTHER INFORMATION: Synthesized

<400> SEQUENCE: 99

Gln Val Gln Leu Gln Gln Ser Gly Ala Glu Val Lys Lys Pro Gly Ser
1               5                   10                  15

Ser Val Lys Val Ser Cys Lys Ala Ser Gly Tyr Thr Phe Thr Asn Tyr
            20                  25                  30

Tyr Ile Tyr Trp Val Arg Gln Ala Pro Gly Gln Gly Leu Glu Trp Ile
        35                  40                  45

Gly Gly Ile Asn Pro Thr Ser Gly Gly Ser Asn Phe Asn Glu Lys Phe
    50                  55                  60

Lys Thr Arg Val Thr Ile Thr Ala Asp Glu Ser Ser Thr Thr Ala Tyr
65                  70                  75                  80

Met Glu Leu Ser Ser Leu Arg Ser Glu Asp Thr Ala Phe Tyr Phe Cys
                85                  90                  95

Thr Arg Gln Gly Leu Trp Phe Asp Ser Asp Gly Arg Gly Phe Asp Phe
            100                 105                 110

Trp Gly Gln Gly Thr Thr Val Thr Val Ser Ser
        115                 120

<210> SEQ ID NO 100
<211> LENGTH: 244
<212> TYPE: PRT
<213> ORGANISM: artificial sequence
<220> FEATURE:
<223> OTHER INFORMATION: Synthesized

<400> SEQUENCE: 100

Gln Val Gln Leu Gln Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Trp Met Ser Trp Val Arg Gln Ala Pro Gly Lys Gly Leu Glu Trp Val
        35                  40                  45

Ala Asn Ile Asn Arg Asp Gly Ser Ala Ser Tyr Tyr Val Asp Ser Val
    50                  55                  60

Lys Gly Arg Phe Thr Ile Ser Arg Asp Asp Ala Lys Asn Ser Leu Tyr
65                  70                  75                  80

```
Leu Gln Met Asn Ser Leu Arg Ala Glu Asp Thr Ala Val Tyr Tyr Cys
                85                  90                  95

Ala Arg Asp Arg Gly Val Gly Tyr Phe Asp Leu Trp Gly Arg Gly Thr
            100                 105                 110

Leu Val Thr Val Ser Ser Gly Gly Gly Gly Ser Gly Gly Gly Gly Ser
        115                 120                 125

Gly Gly Gly Gly Ser Gln Ser Ala Leu Thr Gln Pro Ala Ser Val Ser
    130                 135                 140

Gly Ser Pro Gly Gln Ser Ile Thr Ile Ser Cys Thr Gly Thr Ser Ser
145                 150                 155                 160

Asp Val Gly Gly Tyr Asn Phe Val Ser Trp Tyr Gln Gln His Pro Gly
                165                 170                 175

Lys Ala Pro Lys Leu Met Ile Tyr Asp Val Ser Asp Arg Pro Ser Gly
            180                 185                 190

Val Ser Asp Arg Phe Ser Gly Ser Lys Ser Gly Asn Thr Ala Ser Leu
        195                 200                 205

Ile Ile Ser Gly Leu Gln Ala Asp Asp Glu Ala Asp Tyr Tyr Cys Ser
    210                 215                 220

Ser Tyr Gly Ser Ser Ser Thr His Val Ile Phe Gly Gly Gly Thr Lys
225                 230                 235                 240

Val Thr Val Leu


<210> SEQ ID NO 101
<211> LENGTH: 654
<212> TYPE: DNA
<213> ORGANISM: artificial sequence
<220> FEATURE:
<223> OTHER INFORMATION: Synthesized

<400> SEQUENCE: 101

cagtctgccc tgactcagcc tgcctccgtg tctgggtctc ctggacagtc gatcaccatc      60

tcctgcactg gaaccagcag tgacgttggt ggttataact ttgtctcctg gtaccaacaa     120

cacccaggca aagcccccaa actcatgatc tatgatgtca gtgatcggcc ctcaggggtg     180

tctgatcgct tctccggctc caagtctggc aacacggcct ccctgatcat ctctggcctc     240

caggctgacg acgaggctga ttattactgc agctcatatg gaagcagcag cactcatgtg     300

attttcggcg gagggaccaa gctgaccgtc ctacgtacgg tggctgcacc atctgtcttc     360

atcttcccgc catctgatga gcagttgaaa tctggaactg cctctgttgt gtgcctgctg     420

aataacttct atcccagaga ggccaaagta cagtggaagg tggataacgc cctccaatcg     480

ggtaactccc aggagagtgt cacagagcag gacagcaagg acagcaccta cagcctcagc     540

agcaccctga cgctgagcaa agcagactac gagaaacaca aagtctacgc ctgcgaagtc     600

acccatcagg gcctgagctc gcccgtcaca aagagcttca acaggggaga gtgt           654


<210> SEQ ID NO 102
<211> LENGTH: 333
<212> TYPE: DNA
<213> ORGANISM: artificial sequence
<220> FEATURE:
<223> OTHER INFORMATION: Synthesized

<400> SEQUENCE: 102

cagtctgccc tgactcagcc tgcctccgtg tctgggtctc ctggacagtc gatcaccatc      60

tcctgcactg gaaccagcag tgacgttggt ggttataact ttgtctcctg gtaccaacaa     120
```

```
cacccaggca aagcccccaa actcatgatc tatgatgtca gtgatcggcc ctcaggggtg    180

tctgatcgct tctccggctc caagtctggc aacacggcct ccctgatcat ctctggcctc    240

caggctgacg acgaggctga ttattactgc agctcatatg ggagcagcag cactcatgtg    300

attttcggcg gagggaccaa gctgaccgtc cta                                 333


<210> SEQ ID NO 103
<211> LENGTH: 218
<212> TYPE: PRT
<213> ORGANISM: artificial sequence
<220> FEATURE:
<223> OTHER INFORMATION: Synthesized

<400> SEQUENCE: 103

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
            20                  25                  30

Asn Phe Val Ser Trp Tyr Gln Gln His Pro Gly Lys Ala Pro Lys Leu
        35                  40                  45

Met Ile Tyr Asp Val Ser Asp Arg Pro Ser Gly Val Ser Asp Arg Phe
    50                  55                  60

Ser Gly Ser Lys Ser Gly Asn Thr Ala Ser Leu Ile Ile Ser Gly Leu
65                  70                  75                  80

Gln Ala Asp Asp Glu Ala Asp Tyr Tyr Cys Ser Ser Tyr Gly Ser Ser
                85                  90                  95

Ser Thr His Val Ile Phe Gly Gly Gly Thr Lys Leu Thr Val Leu Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215


<210> SEQ ID NO 104
<211> LENGTH: 111
<212> TYPE: PRT
<213> ORGANISM: artificial sequence
<220> FEATURE:
<223> OTHER INFORMATION: Synthesized

<400> SEQUENCE: 104

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
            20                  25                  30

Asn Phe Val Ser Trp Tyr Gln Gln His Pro Gly Lys Ala Pro Lys Leu
        35                  40                  45
```

-continued

```
Met Ile Tyr Asp Val Ser Asp Arg Pro Ser Gly Val Ser Asp Arg Phe
    50                  55                  60

Ser Gly Ser Lys Ser Gly Asn Thr Ala Ser Leu Ile Ile Ser Gly Leu
65                  70                  75                  80

Gln Ala Asp Asp Glu Ala Asp Tyr Tyr Cys Ser Ser Tyr Gly Ser Ser
                85                  90                  95

Ser Thr His Val Ile Phe Gly Gly Gly Thr Lys Leu Thr Val Leu
            100                 105                 110
```

<210> SEQ ID NO 105
<211> LENGTH: 2100
<212> TYPE: DNA
<213> ORGANISM: artificial sequence
<220> FEATURE:
<223> OTHER INFORMATION: Synthesized

<400> SEQUENCE: 105

```
caggtgcagc tgcaggagtc gggggggaggc ctggtcaagc ctggagggtc cctgagactc     60

tcctgtgcag cctctggatt cacctttagt agttattgga tgagctgggt ccgccaggct    120

ccagggaagg ggctggagtg ggtggccaac ataaaccgcg atggaagtgc gagttactat    180

gtggactctg tgaagggccg attcaccatc tccagagacg acgccaagaa ctcactgtat    240

ctgcaaatga acagcctgag agctgaggac acggctgtgt attactgtgc gagagatcgt    300

ggggtgggct acttcgatct ctggggccgt ggcaccctgg tcaccgtctc gagcgctagc    360

accaagggcc catcggtctt ccccctggca ccctcctcca agagcacctc tgggggcaca    420

gcggccctgg gctgcctggt caaggactac ttccccgaac cggtgacggt gtcgtggaac    480

tcaggcgccc tgaccagcgg cgtgcacacc ttcccggctg tcctacagtc ctcaggactc    540

tactccctca gcagcgtggt gaccgtgccc tccagcagct tgggcaccca gacctacatc    600

tgcaacgtga atcacaagcc cagcaacacc aaggtggaca agagagttga gcccaaatct    660

tgtgacaaaa ctcacacatg cccaccgtgc ccagcacctg aactcctggg gggaccgtca    720

gtcttcctct tccccccaaa acccaaggac accctcatga tctcccggac ccctgaggtc    780

acatgcgtgg tggtggacgt gagccacgaa gaccctgagg tcaagttcaa ctggtacgtg    840

gacggcgtgg aggtgcataa tgccaagaca aagccgcggg aggagcagta caacagcacg    900

taccgtgtgg tcagcgtcct caccgtcctg caccaggact ggctgaatgg caaggagtac    960

aagtgcaagg tctccaacaa agccctccca gcccccatcg agaaaaccat ctccaaagcc   1020

aaagggcagc cccgagaacc acaggtgtac accctgcccc catcccggga ggagatgacc   1080

aagaaccagg tcagcctgac ctgcctggtc aaaggcttct atcccagcga catcgccgtg   1140

gagtgggaga gcaatgggca gccggagaac aactacaaga ccacgcctcc cgtgctggac   1200

tccgacggct ccttcttcct ctatagcaag ctcaccgtgg acaagagcag gtggcagcag   1260

gggaacgtct tctcatgctc cgtgatgcat gaggctctgc acaaccacta cacgcagaag   1320

agcctctccc tgtctccggg taaaggcggt ggaggatccg gcggtggtgg atcacaggtg   1380

cagctgaagc agtcaggacc tggcctagtg cagccctcac agagcctgtc catcacctgc   1440

acagtctctg gtttctcatt aactaactat ggtgtacact gggttcgcca gtctccagga   1500

aagggtctgg agtggctggg agtgatatgg agtggtggaa acacagacta taatacacct   1560

ttcacatcca gactgagcat caacaaggac aattccaaga gccaagtttt ctttaaaatg   1620

aacagtctgc aatctaatga cacagccata tattactgtg ccagagccct cacctactat   1680

gattacgagt ttgcttactg gggccaaggg actctggtca ctgtctctag cggtggaggc   1740
```

ggttcaggcg gaggtggttc cggcggtggc ggctccgaca tcttgctgac tcagtctcca 1800
gtcatcctgt ctgtgagtcc aggagaaaga gtcagtttct cctgcagggc cagtcagagt 1860
attggcacaa acatacactg gtatcagcaa agaacaaatg gttctccaag gcttctcata 1920
aagtatgctt ctgagtctat ctctgggatt ccttccaggt ttagtggcag tggatcaggg 1980
acagatttta ctcttagcat caacagtgtg gagtctgaag atattgcaga ttattactgt 2040
caacaaaata ataactggcc aaccacgttc ggtgctggga ccaagctgga gctgaaacgt 2100

<210> SEQ ID NO 106
<211> LENGTH: 354
<212> TYPE: DNA
<213> ORGANISM: artificial sequence
<220> FEATURE:
<223> OTHER INFORMATION: Synthesized

<400> SEQUENCE: 106
caggtgcagc tgcaggagtc ggggggaggc ctggtcaagc ctggagggtc cctgagactc 60
tcctgtgcag cctctggatt cacctttagt agttattgga tgagctgggt ccgccaggct 120
ccagggaagg ggctggagtg ggtggccaac ataaaccgcg atggaagtgc gagttactat 180
gtggactctg tgaagggccg attcaccatc tccagagacg acgccaagaa ctcactgtat 240
ctgcaaatga acagcctgag agctgaggac acggctgtgt attactgtgc gagagatcgt 300
ggggtgggct acttcgatct ctggggccgt ggcaccctgg tcaccgtctc gagc 354

<210> SEQ ID NO 107
<211> LENGTH: 726
<212> TYPE: DNA
<213> ORGANISM: artificial sequence
<220> FEATURE:
<223> OTHER INFORMATION: Synthesized

<400> SEQUENCE: 107
caggtgcagc tgaagcagtc aggacctggc ctagtgcagc cctcacagag cctgtccatc 60
acctgcacag tctctggttt ctcattaact aactatggtg tacactgggt tcgccagtct 120
ccaggaaagg gtctggagtg gctgggagtg atatggagtg gtggaaacac agactataat 180
acacctttca catccagact gagcatcaac aaggacaatt ccaagagcca agttttcttt 240
aaaatgaaca gtctgcaatc taatgacaca gccatatatt actgtgccag agccctcacc 300
tactatgatt acgagtttgc ttactggggc caagggactc tggtcactgt ctctagcggt 360
ggaggcggtt caggcggagg tggttccggc ggtggcggct ccgacatctt gctgactcag 420
tctccagtca tcctgtctgt gagtccagga gaaagagtca gtttctcctg cagggccagt 480
cagagtattg gcacaaacat acactggtat cagcaaagaa caaatggttc tccaaggctt 540
ctcataaagt atgcttctga gtctatctct gggattcctt ccaggtttag tggcagtgga 600
tcagggacag attttactct tagcatcaac agtgtggagt ctgaagatat tgcagattat 660
tactgtcaac aaaataataa ctggccaacc acgttcggtg ctgggaccaa gctggagctg 720
aaacgt 726

<210> SEQ ID NO 108
<211> LENGTH: 700
<212> TYPE: PRT
<213> ORGANISM: artificial sequence
<220> FEATURE:
<223> OTHER INFORMATION: Synthesized

<400> SEQUENCE: 108

```
Gln Val Gln Leu Gln Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Trp Met Ser Trp Val Arg Gln Ala Pro Gly Lys Gly Leu Glu Trp Val
        35                  40                  45

Ala Asn Ile Asn Arg Asp Gly Ser Ala Ser Tyr Tyr Val Asp Ser Val
    50                  55                  60

Lys Gly Arg Phe Thr Ile Ser Arg Asp Asp Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Arg Gly Val Gly Tyr Phe Asp Leu Trp Gly Arg Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Arg Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Glu Glu Met Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415
```

```
Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
        435                 440                 445

Gly Gly Gly Gly Ser Gly Gly Gly Gly Ser Gln Val Gln Leu Lys Gln
    450                 455                 460

Ser Gly Pro Gly Leu Val Gln Pro Ser Gln Ser Leu Ser Ile Thr Cys
465                 470                 475                 480

Thr Val Ser Gly Phe Ser Leu Thr Asn Tyr Gly Val His Trp Val Arg
                485                 490                 495

Gln Ser Pro Gly Lys Gly Leu Glu Trp Leu Gly Val Ile Trp Ser Gly
            500                 505                 510

Gly Asn Thr Asp Tyr Asn Thr Pro Phe Thr Ser Arg Leu Ser Ile Asn
        515                 520                 525

Lys Asp Asn Ser Lys Ser Gln Val Phe Phe Lys Met Asn Ser Leu Gln
    530                 535                 540

Ser Asn Asp Thr Ala Ile Tyr Tyr Cys Ala Arg Ala Leu Thr Tyr Tyr
545                 550                 555                 560

Asp Tyr Glu Phe Ala Tyr Trp Gly Gln Gly Thr Leu Val Thr Val Ser
                565                 570                 575

Ser Gly Gly Gly Gly Ser Gly Gly Gly Gly Ser Gly Gly Gly Gly Ser
            580                 585                 590

Asp Ile Leu Leu Thr Gln Ser Pro Val Ile Leu Ser Val Ser Pro Gly
        595                 600                 605

Glu Arg Val Ser Phe Ser Cys Arg Ala Ser Gln Ser Ile Gly Thr Asn
    610                 615                 620

Ile His Trp Tyr Gln Gln Arg Thr Asn Gly Ser Pro Arg Leu Leu Ile
625                 630                 635                 640

Lys Tyr Ala Ser Glu Ser Ile Ser Gly Ile Pro Ser Arg Phe Ser Gly
                645                 650                 655

Ser Gly Ser Gly Thr Asp Phe Thr Leu Ser Ile Asn Ser Val Glu Ser
            660                 665                 670

Glu Asp Ile Ala Asp Tyr Tyr Cys Gln Gln Asn Asn Asn Trp Pro Thr
        675                 680                 685

Thr Phe Gly Ala Gly Thr Lys Leu Glu Leu Lys Arg
    690                 695                 700


<210> SEQ ID NO 109
<211> LENGTH: 118
<212> TYPE: PRT
<213> ORGANISM: artificial sequence
<220> FEATURE:
<223> OTHER INFORMATION: Synthesized

<400> SEQUENCE: 109

Gln Val Gln Leu Gln Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Trp Met Ser Trp Val Arg Gln Ala Pro Gly Lys Gly Leu Glu Trp Val
        35                  40                  45

Ala Asn Ile Asn Arg Asp Gly Ser Ala Ser Tyr Tyr Val Asp Ser Val
    50                  55                  60

Lys Gly Arg Phe Thr Ile Ser Arg Asp Asp Ala Lys Asn Ser Leu Tyr
65                  70                  75                  80
```

```
Leu Gln Met Asn Ser Leu Arg Ala Glu Asp Thr Ala Val Tyr Tyr Cys
                85                  90                  95

Ala Arg Asp Arg Gly Val Gly Tyr Phe Asp Leu Trp Gly Arg Gly Thr
            100                 105                 110

Leu Val Thr Val Ser Ser
        115


<210> SEQ ID NO 110
<211> LENGTH: 242
<212> TYPE: PRT
<213> ORGANISM: artificial sequence
<220> FEATURE:
<223> OTHER INFORMATION: Synthesized

<400> SEQUENCE: 110

Gln Val Gln Leu Lys Gln Ser Gly Pro Gly Leu Val Gln Pro Ser Gln
1               5                   10                  15

Ser Leu Ser Ile Thr Cys Thr Val Ser Gly Phe Ser Leu Thr Asn Tyr
            20                  25                  30

Gly Val His Trp Val Arg Gln Ser Pro Gly Lys Gly Leu Glu Trp Leu
        35                  40                  45

Gly Val Ile Trp Ser Gly Gly Asn Thr Asp Tyr Asn Thr Pro Phe Thr
    50                  55                  60

Ser Arg Leu Ser Ile Asn Lys Asp Asn Ser Lys Ser Gln Val Phe Phe
65                  70                  75                  80

Lys Met Asn Ser Leu Gln Ser Asn Asp Thr Ala Ile Tyr Tyr Cys Ala
                85                  90                  95

Arg Ala Leu Thr Tyr Tyr Asp Tyr Glu Phe Ala Tyr Trp Gly Gln Gly
            100                 105                 110

Thr Leu Val Thr Val Ser Ser Gly Gly Gly Gly Ser Gly Gly Gly Gly
        115                 120                 125

Ser Gly Gly Gly Gly Ser Asp Ile Leu Leu Thr Gln Ser Pro Val Ile
    130                 135                 140

Leu Ser Val Ser Pro Gly Glu Arg Val Ser Phe Ser Cys Arg Ala Ser
145                 150                 155                 160

Gln Ser Ile Gly Thr Asn Ile His Trp Tyr Gln Gln Arg Thr Asn Gly
                165                 170                 175

Ser Pro Arg Leu Leu Ile Lys Tyr Ala Ser Glu Ser Ile Ser Gly Ile
            180                 185                 190

Pro Ser Arg Phe Ser Gly Ser Gly Ser Gly Thr Asp Phe Thr Leu Ser
        195                 200                 205

Ile Asn Ser Val Glu Ser Glu Asp Ile Ala Asp Tyr Tyr Cys Gln Gln
    210                 215                 220

Asn Asn Asn Trp Pro Thr Thr Phe Gly Ala Gly Thr Lys Leu Glu Leu
225                 230                 235                 240

Lys Arg


<210> SEQ ID NO 111
<211> LENGTH: 642
<212> TYPE: DNA
<213> ORGANISM: artificial sequence
<220> FEATURE:
<223> OTHER INFORMATION: Synthesized

<400> SEQUENCE: 111

gacatcttgc tgactcagtc tccagtcatc ctgtctgtga gtccaggaga aagagtcagt      60
```

-continued

```
ttctcctgca gggccagtca gagtattggc acaaacatac actggtatca gcaaagaaca    120

aatggttctc caaggcttct cataaagtat gcttctgagt ctatctctgg gattccttcc    180

aggtttagtg gcagtggatc agggacagat tttactctta gcatcaacag tgtggagtct    240

gaagatattg cagattatta ctgtcaacaa aataataact ggccaaccac gttcggtgct    300

gggaccaagc tggagctgaa acgtacggtg gctgcaccat ctgtcttcat cttcccgcca    360

tctgatgagc agttgaaatc tggaactgcc tctgttgtgt gcctgctgaa taacttctat    420

cccagagagg ccaaagtaca gtggaaggtg gataacgccc tccaatcggg taactcccag    480

gagagtgtca cagagcagga cagcaaggac agcacctaca gcctcagcag caccctgacg    540

ctgagcaaag cagactacga gaaacacaaa gtctacgcct gcgaagtcac ccatcagggc    600

ctgagctcgc ccgtcacaaa gagcttcaac aggggagagt gt                       642


<210> SEQ ID NO 112
<211> LENGTH: 321
<212> TYPE: DNA
<213> ORGANISM: artificial sequence
<220> FEATURE:
<223> OTHER INFORMATION: Synthesized

<400> SEQUENCE: 112

gacatcttgc tgactcagtc tccagtcatc ctgtctgtga gtccaggaga aagagtcagt     60

ttctcctgca gggccagtca gagtattggc acaaacatac actggtatca gcaaagaaca    120

aatggttctc caaggcttct cataaagtat gcttctgagt ctatctctgg gattccttcc    180

aggtttagtg gcagtggatc agggacagat tttactctta gcatcaacag tgtggagtct    240

gaagatattg cagattatta ctgtcaacaa aataataact ggccaaccac gttcggtgct    300

gggaccaagc tggagctgaa a                                              321


<210> SEQ ID NO 113
<211> LENGTH: 214
<212> TYPE: PRT
<213> ORGANISM: artificial sequence
<220> FEATURE:
<223> OTHER INFORMATION: Synthesized

<400> SEQUENCE: 113

Asp Ile Leu Leu Thr Gln Ser Pro Val Ile Leu Ser Val Ser Pro Gly
1               5                   10                  15

Glu Arg Val Ser Phe Ser Cys Arg Ala Ser Gln Ser Ile Gly Thr Asn
            20                  25                  30

Ile His Trp Tyr Gln Gln Arg Thr Asn Gly Ser Pro Arg Leu Leu Ile
        35                  40                  45

Lys Tyr Ala Ser Glu Ser Ile Ser Gly Ile Pro Ser Arg Phe Ser Gly
    50                  55                  60

Ser Gly Ser Gly Thr Asp Phe Thr Leu Ser Ile Asn Ser Val Glu Ser
65                  70                  75                  80

Glu Asp Ile Ala Asp Tyr Tyr Cys Gln Gln Asn Asn Asn Trp Pro Thr
                85                  90                  95

Thr Phe Gly Ala Gly Thr Lys Leu Glu Leu Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140
```

```
Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 114
<211> LENGTH: 107
<212> TYPE: PRT
<213> ORGANISM: artificial sequence
<220> FEATURE:
<223> OTHER INFORMATION: Synthesized

<400> SEQUENCE: 114

```
Asp Ile Leu Leu Thr Gln Ser Pro Val Ile Leu Ser Val Ser Pro Gly
1               5                   10                  15

Glu Arg Val Ser Phe Ser Cys Arg Ala Ser Gln Ser Ile Gly Thr Asn
            20                  25                  30

Ile His Trp Tyr Gln Gln Arg Thr Asn Gly Ser Pro Arg Leu Leu Ile
        35                  40                  45

Lys Tyr Ala Ser Glu Ser Ile Ser Gly Ile Pro Ser Arg Phe Ser Gly
    50                  55                  60

Ser Gly Ser Gly Thr Asp Phe Thr Leu Ser Ile Asn Ser Val Glu Ser
65                  70                  75                  80

Glu Asp Ile Ala Asp Tyr Tyr Cys Gln Gln Asn Asn Asn Trp Pro Thr
                85                  90                  95

Thr Phe Gly Ala Gly Thr Lys Leu Glu Leu Lys
            100                 105
```

<210> SEQ ID NO 115
<211> LENGTH: 2109
<212> TYPE: DNA
<213> ORGANISM: artificial sequence
<220> FEATURE:
<223> OTHER INFORMATION: Synthesized

<400> SEQUENCE: 115

```
caggtgcagc tgaagcagtc aggacctggc ctagtgcagc cctcacagag cctgtccatc      60

acctgcacag tctctggttt ctcattaact aactatggtg tacactgggt tcgccagtct     120

ccaggaaagg gtctggagtg gctgggagtg atatggagtg gtggaaacac agactataat     180

acacctttca catccagact gagcatcaac aaggacaatt ccaagagcca agttttcttt     240

aaaatgaaca gtctgcaatc taatgacaca gccatatatt actgtgccag agccctcacc     300

tactatgatt acgagtttgc ttactggggc caagggactc tggtcactgt ctctagcgct     360

agcaccaagg gcccatcggt cttccccctg gcaccctcct ccaagagcac ctctgggggc     420

acagcggccc tgggctgcct ggtcaaggac tacttccccg aaccggtgac ggtgtcgtgg     480

aactcaggcg ccctgaccag cggcgtgcac accttcccgg ctgtcctaca gtcctcagga     540

ctctactccc tcagcagcgt ggtgaccgtg ccctccagca gcttgggcac ccagacctac     600

atctgcaacg tgaatcacaa gcccagcaac accaaggtgg acaagagagt tgagcccaaa     660

tcttgtgaca aaactcacac atgcccaccg tgcccagcac ctgaactcct ggggggaccg     720
```

```
tcagtcttcc tcttcccccc aaaacccaag gacaccctca tgatctcccg gacccctgag    780
gtcacatgcg tggtggtgga cgtgagccac gaagaccctg aggtcaagtt caactggtac    840
gtggacggcg tggaggtgca taatgccaag acaaagccgc gggaggagca gtacaacagc    900
acgtaccgtg tggtcagcgt cctcaccgtc ctgcaccagg actggctgaa tggcaaggag    960
tacaagtgca aggtctccaa caaagccctc ccagccccca tcgagaaaac catctccaaa   1020
gccaaagggc agccccgaga accacaggtg tacaccctgc ccccatcccg ggaggagatg   1080
accaagaacc aggtcagcct gacctgcctg gtcaaaggct tctatcccag cgacatcgcc   1140
gtggagtggg agagcaatgg gcagccggag aacaactaca agaccacgcc tcccgtgctg   1200
gactccgacg gctccttctt cctctatagc aagctcaccg tggacaagag caggtggcag   1260
caggggaacg tcttctcatg ctccgtgatg catgaggctc tgcacaacca ctacacgcag   1320
aagagcctct ccctgtctcc gggtaaaggc ggtggaggat ccggcggtgg tggatcacag   1380
gtgcagctgc aggagtcggg gggaggcctg gtcaagcctg gagggtccct gagactctcc   1440
tgtgcagcct ctggattcac ctttagtagt tattggatga gctgggtccg ccaggctcca   1500
gggaaggggc tggagtgggt ggccaacata aaccgcgatg gaagtgcgag ttactatgtg   1560
gactctgtga agggccgatt caccatctcc agagacgacg ccaagaactc actgtatctg   1620
caaatgaaca gcctgagagc tgaggacacg gctgtgtatt actgtgcgag agatcgtggg   1680
gtgggctact tcgatctctg gggccgtggc accctggtca ccgtctcgag cggtggaggc   1740
ggttcaggcg gaggtggttc cggcggtggc ggctcccagt ctgccctgac tcagcctgcc   1800
tccgtgtctg ggtctcctgg acagtcgatc accatctcct gcactggaac cagcagtgac   1860
gttggtggtt ataactttgt ctcctggtac caacaacacc caggcaaagc ccccaaactc   1920
atgatctatg atgtcagtga tcggccctca ggggtgtctg atcgcttctc cggctccaag   1980
tctggcaaca cggcctccct gatcatctct ggcctccagg ctgacgacga ggctgattat   2040
tactgcagct catatgggag cagcagcact catgtgattt tcggcggagg gaccaaggtg   2100
accgtccta                                                           2109
```

<210> SEQ ID NO 116
<211> LENGTH: 357
<212> TYPE: DNA
<213> ORGANISM: artificial sequence
<220> FEATURE:
<223> OTHER INFORMATION: Synthesized

<400> SEQUENCE: 116

```
caggtgcagc tgaagcagtc aggacctggc ctagtgcagc cctcacagag cctgtccatc     60
acctgcacag tctctggttt ctcattaact aactatggtg tacactgggt tcgccagtct    120
ccaggaaagg gtctggagtg gctgggagtg atatggagtg gtggaaacac agactataat    180
acacctttca catccagact gagcatcaac aaggacaatt ccaagagcca agttttcttt    240
aaaatgaaca gtctgcaatc taatgacaca gccatatatt actgtgccag agccctcacc    300
tactatgatt acgagtttgc ttactggggc caagggactc tggtcactgt ctctagc       357
```

<210> SEQ ID NO 117
<211> LENGTH: 732
<212> TYPE: DNA
<213> ORGANISM: artificial sequence
<220> FEATURE:
<223> OTHER INFORMATION: Synthesized

<400> SEQUENCE: 117
caggtgcagc tgcaggagtc ggggggaggc ctggtcaagc ctggagggtc cctgagactc 60
tcctgtgcag cctctggatt cacctttagt agttattgga tgagctgggt ccgccaggct 120
ccagggaagg ggctggagtg ggtggccaac ataaaccgcg atggaagtgc gagttactat 180
gtggactctg tgaagggccg attcaccatc tccagagacg acgccaagaa ctcactgtat 240
ctgcaaatga acagcctgag agctgaggac acggctgtgt attactgtgc gagagatcgt 300
ggggtgggct acttcgatct ctggggccgt ggcaccctgg tcaccgtctc gagcggtgga 360
ggcggttcag gcggaggtgg ttccggcggt ggcggctccc agtctgccct gactcagcct 420
gcctccgtgt ctgggtctcc tggacagtcg atcaccatct cctgcactgg aaccagcagt 480
gacgttggtg gttataactt tgtctcctgg taccaacaac acccaggcaa agcccccaaa 540
ctcatgatct atgatgtcag tgatcggccc tcaggggtgt ctgatcgctt ctccggctcc 600
aagtctggca acacggcctc cctgatcatc tctggcctcc aggctgacga cgaggctgat 660
tattactgca gctcatatgg gagcagcagc actcatgtga ttttcggcgg agggaccaag 720
gtgaccgtcc ta 732

<210> SEQ ID NO 118
<211> LENGTH: 703
<212> TYPE: PRT
<213> ORGANISM: artificial sequence
<220> FEATURE:
<223> OTHER INFORMATION: Synthesized

<400> SEQUENCE: 118

Gln Val Gln Leu Lys Gln Ser Gly Pro Gly Leu Val Gln Pro Ser Gln
1 5 10 15

Ser Leu Ser Ile Thr Cys Thr Val Ser Gly Phe Ser Leu Thr Asn Tyr
20 25 30

Gly Val His Trp Val Arg Gln Ser Pro Gly Lys Gly Leu Glu Trp Leu
35 40 45

Gly Val Ile Trp Ser Gly Gly Asn Thr Asp Tyr Asn Thr Pro Phe Thr
50 55 60

Ser Arg Leu Ser Ile Asn Lys Asp Asn Ser Lys Ser Gln Val Phe Phe
65 70 75 80

Lys Met Asn Ser Leu Gln Ser Asn Asp Thr Ala Ile Tyr Tyr Cys Ala
85 90 95

Arg Ala Leu Thr Tyr Tyr Asp Tyr Glu Phe Ala Tyr Trp Gly Gln Gly
100 105 110

Thr Leu Val Thr Val Ser Ser Ala Ser Thr Lys Gly Pro Ser Val Phe
115 120 125

Pro Leu Ala Pro Ser Ser Lys Ser Thr Ser Gly Gly Thr Ala Ala Leu
130 135 140

Gly Cys Leu Val Lys Asp Tyr Phe Pro Glu Pro Val Thr Val Ser Trp
145 150 155 160

Asn Ser Gly Ala Leu Thr Ser Gly Val His Thr Phe Pro Ala Val Leu
165 170 175

Gln Ser Ser Gly Leu Tyr Ser Leu Ser Ser Val Val Thr Val Pro Ser
180 185 190

Ser Ser Leu Gly Thr Gln Thr Tyr Ile Cys Asn Val Asn His Lys Pro
195 200 205

Ser Asn Thr Lys Val Asp Lys Arg Val Glu Pro Lys Ser Cys Asp Lys
210 215 220

-continued

```
Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys Gly Gly Gly Gly Ser Gly Gly Gly Gly Ser Gln Val Gln Leu Gln
    450                 455                 460

Glu Ser Gly Gly Gly Leu Val Lys Pro Gly Gly Ser Leu Arg Leu Ser
465                 470                 475                 480

Cys Ala Ala Ser Gly Phe Thr Phe Ser Ser Tyr Trp Met Ser Trp Val
                485                 490                 495

Arg Gln Ala Pro Gly Lys Gly Leu Glu Trp Val Ala Asn Ile Asn Arg
            500                 505                 510

Asp Gly Ser Ala Ser Tyr Tyr Val Asp Ser Val Lys Gly Arg Phe Thr
        515                 520                 525

Ile Ser Arg Asp Asp Ala Lys Asn Ser Leu Tyr Leu Gln Met Asn Ser
    530                 535                 540

Leu Arg Ala Glu Asp Thr Ala Val Tyr Tyr Cys Ala Arg Asp Arg Gly
545                 550                 555                 560

Val Gly Tyr Phe Asp Leu Trp Gly Arg Gly Thr Leu Val Thr Val Ser
                565                 570                 575

Ser Gly Gly Gly Gly Ser Gly Gly Gly Gly Ser Gly Gly Gly Gly Ser
            580                 585                 590

Gln Ser Ala Leu Thr Gln Pro Ala Ser Val Ser Gly Ser Pro Gly Gln
        595                 600                 605

Ser Ile Thr Ile Ser Cys Thr Gly Thr Ser Ser Asp Val Gly Gly Tyr
    610                 615                 620

Asn Phe Val Ser Trp Tyr Gln Gln His Pro Gly Lys Ala Pro Lys Leu
625                 630                 635                 640
```

-continued

```
Met Ile Tyr Asp Val Ser Asp Arg Pro Ser Gly Val Ser Asp Arg Phe
                645                 650                 655

Ser Gly Ser Lys Ser Gly Asn Thr Ala Ser Leu Ile Ile Ser Gly Leu
            660                 665                 670

Gln Ala Asp Asp Glu Ala Asp Tyr Tyr Cys Ser Ser Tyr Gly Ser Ser
        675                 680                 685

Ser Thr His Val Ile Phe Gly Gly Gly Thr Lys Val Thr Val Leu
    690                 695                 700


<210> SEQ ID NO 119
<211> LENGTH: 119
<212> TYPE: PRT
<213> ORGANISM: artificial sequence
<220> FEATURE:
<223> OTHER INFORMATION: Synthesized

<400> SEQUENCE: 119

Gln Val Gln Leu Lys Gln Ser Gly Pro Gly Leu Val Gln Pro Ser Gln
1               5                   10                  15

Ser Leu Ser Ile Thr Cys Thr Val Ser Gly Phe Ser Leu Thr Asn Tyr
            20                  25                  30

Gly Val His Trp Val Arg Gln Ser Pro Gly Lys Gly Leu Glu Trp Leu
        35                  40                  45

Gly Val Ile Trp Ser Gly Gly Asn Thr Asp Tyr Asn Thr Pro Phe Thr
    50                  55                  60

Ser Arg Leu Ser Ile Asn Lys Asp Asn Ser Lys Ser Gln Val Phe Phe
65                  70                  75                  80

Lys Met Asn Ser Leu Gln Ser Asn Asp Thr Ala Ile Tyr Tyr Cys Ala
                85                  90                  95

Arg Ala Leu Thr Tyr Tyr Asp Tyr Glu Phe Ala Tyr Trp Gly Gln Gly
            100                 105                 110

Thr Leu Val Thr Val Ser Ser
        115


<210> SEQ ID NO 120
<211> LENGTH: 244
<212> TYPE: PRT
<213> ORGANISM: artificial sequence
<220> FEATURE:
<223> OTHER INFORMATION: Synthesized

<400> SEQUENCE: 120

Gln Val Gln Leu Gln Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Trp Met Ser Trp Val Arg Gln Ala Pro Gly Lys Gly Leu Glu Trp Val
        35                  40                  45

Ala Asn Ile Asn Arg Asp Gly Ser Ala Ser Tyr Tyr Val Asp Ser Val
    50                  55                  60

Lys Gly Arg Phe Thr Ile Ser Arg Asp Asp Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Arg Gly Val Gly Tyr Phe Asp Leu Trp Gly Arg Gly Thr
            100                 105                 110

Leu Val Thr Val Ser Ser Gly Gly Gly Gly Ser Gly Gly Gly Gly Ser
        115                 120                 125
```

-continued

```
Gly Gly Gly Gly Ser Gln Ser Ala Leu Thr Gln Pro Ala Ser Val Ser
    130                 135                 140

Gly Ser Pro Gly Gln Ser Ile Thr Ile Ser Cys Thr Gly Thr Ser Ser
145                 150                 155                 160

Asp Val Gly Gly Tyr Asn Phe Val Ser Trp Tyr Gln Gln His Pro Gly
                165                 170                 175

Lys Ala Pro Lys Leu Met Ile Tyr Asp Val Ser Asp Arg Pro Ser Gly
            180                 185                 190

Val Ser Asp Arg Phe Ser Gly Ser Lys Ser Gly Asn Thr Ala Ser Leu
        195                 200                 205

Ile Ile Ser Gly Leu Gln Ala Asp Asp Glu Ala Asp Tyr Tyr Cys Ser
    210                 215                 220

Ser Tyr Gly Ser Ser Ser Thr His Val Ile Phe Gly Gly Gly Thr Lys
225                 230                 235                 240

Val Thr Val Leu
```

<210> SEQ ID NO 121
<211> LENGTH: 642
<212> TYPE: DNA
<213> ORGANISM: artificial sequence
<220> FEATURE:
<223> OTHER INFORMATION: Synthesized

<400> SEQUENCE: 121

```
gacatcttgc tgactcagtc tccagtcatc ctgtctgtga gtccaggaga aagagtcagt     60

ttctcctgca gggccagtca gagtattggc acaaacatac actggtatca gcaaagaaca    120

aatggttctc caaggcttct cataaagtat gcttctgagt ctatctctgg gattccttcc    180

aggtttagtg gcagtggatc agggacagat tttactctta gcatcaacag tgtggagtct    240

gaagatattg cagattatta ctgtcaacaa aataataact ggccaaccac gttcggtgct    300

gggaccaagc tggagctgaa acgtacggtg gctgcaccat ctgtcttcat cttcccgcca    360

tctgatgagc agttgaaatc tggaactgcc tctgttgtgt gcctgctgaa taacttctat    420

cccagagagg ccaaagtaca gtggaaggtg gataacgccc tccaatcggg taactcccag    480

gagagtgtca cagagcagga cagcaaggac agcacctaca gcctcagcag caccctgacg    540

ctgagcaaag cagactacga gaaacacaaa gtctacgcct gcgaagtcac ccatcagggc    600

ctgagctcgc ccgtcacaaa gagcttcaac aggggagagt gt                       642
```

<210> SEQ ID NO 122
<211> LENGTH: 321
<212> TYPE: DNA
<213> ORGANISM: artificial sequence
<220> FEATURE:
<223> OTHER INFORMATION: Synthesized

<400> SEQUENCE: 122

```
gacatcttgc tgactcagtc tccagtcatc ctgtctgtga gtccaggaga aagagtcagt     60

ttctcctgca gggccagtca gagtattggc acaaacatac actggtatca gcaaagaaca    120

aatggttctc caaggcttct cataaagtat gcttctgagt ctatctctgg gattccttcc    180

aggtttagtg gcagtggatc agggacagat tttactctta gcatcaacag tgtggagtct    240

gaagatattg cagattatta ctgtcaacaa aataataact ggccaaccac gttcggtgct    300

gggaccaagc tggagctgaa a                                              321
```

-continued

<210> SEQ ID NO 123
<211> LENGTH: 214
<212> TYPE: PRT
<213> ORGANISM: artificial sequence
<220> FEATURE:
<223> OTHER INFORMATION: Synthesized

<400> SEQUENCE: 123

Asp Ile Leu Leu Thr Gln Ser Pro Val Ile Leu Ser Val Ser Pro Gly
1 5 10 15

Glu Arg Val Ser Phe Ser Cys Arg Ala Ser Gln Ser Ile Gly Thr Asn
20 25 30

Ile His Trp Tyr Gln Gln Arg Thr Asn Gly Ser Pro Arg Leu Leu Ile
35 40 45

Lys Tyr Ala Ser Glu Ser Ile Ser Gly Ile Pro Ser Arg Phe Ser Gly
50 55 60

Ser Gly Ser Gly Thr Asp Phe Thr Leu Ser Ile Asn Ser Val Glu Ser
65 70 75 80

Glu Asp Ile Ala Asp Tyr Tyr Cys Gln Gln Asn Asn Asn Trp Pro Thr
85 90 95

Thr Phe Gly Ala Gly Thr Lys Leu Glu Leu Lys Arg Thr Val Ala Ala
100 105 110

Pro Ser Val Phe Ile Phe Pro Pro Ser Asp Glu Gln Leu Lys Ser Gly
115 120 125

Thr Ala Ser Val Val Cys Leu Leu Asn Asn Phe Tyr Pro Arg Glu Ala
130 135 140

Lys Val Gln Trp Lys Val Asp Asn Ala Leu Gln Ser Gly Asn Ser Gln
145 150 155 160

Glu Ser Val Thr Glu Gln Asp Ser Lys Asp Ser Thr Tyr Ser Leu Ser
165 170 175

Ser Thr Leu Thr Leu Ser Lys Ala Asp Tyr Glu Lys His Lys Val Tyr
180 185 190

Ala Cys Glu Val Thr His Gln Gly Leu Ser Ser Pro Val Thr Lys Ser
195 200 205

Phe Asn Arg Gly Glu Cys
210

<210> SEQ ID NO 124
<211> LENGTH: 107
<212> TYPE: PRT
<213> ORGANISM: artificial sequence
<220> FEATURE:
<223> OTHER INFORMATION: Synthesized

<400> SEQUENCE: 124

Asp Ile Leu Leu Thr Gln Ser Pro Val Ile Leu Ser Val Ser Pro Gly
1 5 10 15

Glu Arg Val Ser Phe Ser Cys Arg Ala Ser Gln Ser Ile Gly Thr Asn
20 25 30

Ile His Trp Tyr Gln Gln Arg Thr Asn Gly Ser Pro Arg Leu Leu Ile
35 40 45

Lys Tyr Ala Ser Glu Ser Ile Ser Gly Ile Pro Ser Arg Phe Ser Gly
50 55 60

Ser Gly Ser Gly Thr Asp Phe Thr Leu Ser Ile Asn Ser Val Glu Ser
65 70 75 80

Glu Asp Ile Ala Asp Tyr Tyr Cys Gln Gln Asn Asn Asn Trp Pro Thr
85 90 95

Thr Phe Gly Ala Gly Thr Lys Leu Glu Leu Lys
100 105

<210> SEQ ID NO 125
<211> LENGTH: 1344
<212> TYPE: DNA
<213> ORGANISM: artificial sequence
<220> FEATURE:
<223> OTHER INFORMATION: Synthesized

<400> SEQUENCE: 125
caggtgcagc tgaagcagtc aggacctggc ctagtgcagc cctcacagag cctgtccatc 60
acctgcacag tctctggttt ctcattaact aactatggtg tacactgggt tcgccagtct 120
ccaggaaagg gtctggagtg gctgggagtg atatggagtg gtggaaacac agactataat 180
acacctttca catccagact gagcatcaac aaggacaatt ccaagagcca agttttcttt 240
aaaatgaaca gtctgcaatc taatgacaca gccatatatt actgtgccag agccctcacc 300
tactatgatt acgagtttgc ttactggggc caagggactc tggtcactgt ctctagcgct 360
agcaccaagg gcccatcggt cttccccctg gcaccctcct ccaagagcac ctctgggggc 420
acagcggccc tgggctgcct ggtcaaggac tacttccccg aaccggtgac ggtgtcgtgg 480
aactcaggcg ccctgaccag cggcgtgcac accttcccgg ctgtcctaca gtcctcagga 540
ctctactccc tcagcagcgt ggtgaccgtg ccctccagca gcttgggcac ccagacctac 600
atctgcaacg tgaatcacaa gcccagcaac accaaggtgg acaagagagt tgagcccaaa 660
tcttgtgaca aaactcacac atgcccaccg tgcccagcac ctgaactcct ggggggaccg 720
tcagtcttcc tcttcccccc aaaacccaag gacaccctca tgatctcccg gacccctgag 780
gtcacatgcg tggtggtgga cgtgagccac gaagaccctg aggtcaagtt caactggtac 840
gtggacggcg tggaggtgca taatgccaag acaaagccgc gggaggagca gtacaacagc 900
acgtaccgtg tggtcagcgt cctcaccgtc ctgcaccagg actggctgaa tggcaaggag 960
tacaagtgca aggtctccaa caaagccctc ccagccccca tcgagaaaac catctccaaa 1020
gccaaagggc agccccgaga accacaggtg tacaccctgc ccccatcccg ggatgagctg 1080
accaagaacc aggtcagcct gacctgcctg gtcaaaggct tctatcccag cgacatcgcc 1140
gtggagtggg agagcaatgg gcagccggag aacaactaca agaccacgcc tcccgtgctg 1200
gactccgacg gctccttctt cctctatagc aagctcaccg tggacaagag caggtggcag 1260
caggggaacg tcttctcatg ctccgtgatg catgaggctc tgcacaacca ctacacgcag 1320
aagagcctct ccctgtctcc gggt 1344

<210> SEQ ID NO 126
<211> LENGTH: 357
<212> TYPE: DNA
<213> ORGANISM: artificial sequence
<220> FEATURE:
<223> OTHER INFORMATION: Synthesized

<400> SEQUENCE: 126
caggtgcagc tgaagcagtc aggacctggc ctagtgcagc cctcacagag cctgtccatc 60
acctgcacag tctctggttt ctcattaact aactatggtg tacactgggt tcgccagtct 120
ccaggaaagg gtctggagtg gctgggagtg atatggagtg gtggaaacac agactataat 180
acacctttca catccagact gagcatcaac aaggacaatt ccaagagcca agttttcttt 240
aaaatgaaca gtctgcaatc taatgacaca gccatatatt actgtgccag agccctcacc 300

-continued tactatgatt acgagtttgc ttactggggc caagggactc tggtcactgt ctctagc 357

<210> SEQ ID NO 127
<211> LENGTH: 448
<212> TYPE: PRT
<213> ORGANISM: artificial sequence
<220> FEATURE:
<223> OTHER INFORMATION: Synthesized

<400> SEQUENCE: 127

Gln Val Gln Leu Lys Gln Ser Gly Pro Gly Leu Val Gln Pro Ser Gln
1 5 10 15

Ser Leu Ser Ile Thr Cys Thr Val Ser Gly Phe Ser Leu Thr Asn Tyr
20 25 30

Gly Val His Trp Val Arg Gln Ser Pro Gly Lys Gly Leu Glu Trp Leu
35 40 45

Gly Val Ile Trp Ser Gly Gly Asn Thr Asp Tyr Asn Thr Pro Phe Thr
50 55 60

Ser Arg Leu Ser Ile Asn Lys Asp Asn Ser Lys Ser Gln Val Phe Phe
65 70 75 80

Lys Met Asn Ser Leu Gln Ser Asn Asp Thr Ala Ile Tyr Tyr Cys Ala
85 90 95

Arg Ala Leu Thr Tyr Tyr Asp Tyr Glu Phe Ala Tyr Trp Gly Gln Gly
100 105 110

Thr Leu Val Thr Val Ser Ser Ala Ser Thr Lys Gly Pro Ser Val Phe
115 120 125

Pro Leu Ala Pro Ser Ser Lys Ser Thr Ser Gly Gly Thr Ala Ala Leu
130 135 140

Gly Cys Leu Val Lys Asp Tyr Phe Pro Glu Pro Val Thr Val Ser Trp
145 150 155 160

Asn Ser Gly Ala Leu Thr Ser Gly Val His Thr Phe Pro Ala Val Leu
165 170 175

Gln Ser Ser Gly Leu Tyr Ser Leu Ser Ser Val Val Thr Val Pro Ser
180 185 190

Ser Ser Leu Gly Thr Gln Thr Tyr Ile Cys Asn Val Asn His Lys Pro
195 200 205

Ser Asn Thr Lys Val Asp Lys Arg Val Glu Pro Lys Ser Cys Asp Lys
210 215 220

Thr His Thr Cys Pro Pro Cys Pro Ala Pro Glu Leu Leu Gly Gly Pro
225 230 235 240

Ser Val Phe Leu Phe Pro Pro Lys Pro Lys Asp Thr Leu Met Ile Ser
245 250 255

Arg Thr Pro Glu Val Thr Cys Val Val Val Asp Val Ser His Glu Asp
260 265 270

Pro Glu Val Lys Phe Asn Trp Tyr Val Asp Gly Val Glu Val His Asn
275 280 285

Ala Lys Thr Lys Pro Arg Glu Glu Gln Tyr Asn Ser Thr Tyr Arg Val
290 295 300

Val Ser Val Leu Thr Val Leu His Gln Asp Trp Leu Asn Gly Lys Glu
305 310 315 320

Tyr Lys Cys Lys Val Ser Asn Lys Ala Leu Pro Ala Pro Ile Glu Lys
325 330 335

Thr Ile Ser Lys Ala Lys Gly Gln Pro Arg Glu Pro Gln Val Tyr Thr
340 345 350

Leu Pro Pro Ser Arg Asp Glu Leu Thr Lys Asn Gln Val Ser Leu Thr

```
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445


<210> SEQ ID NO 128
<211> LENGTH: 119
<212> TYPE: PRT
<213> ORGANISM: artificial sequence
<220> FEATURE:
<223> OTHER INFORMATION: Synthesized

<400> SEQUENCE: 128

Gln Val Gln Leu Lys Gln Ser Gly Pro Gly Leu Val Gln Pro Ser Gln
1               5                   10                  15

Ser Leu Ser Ile Thr Cys Thr Val Ser Gly Phe Ser Leu Thr Asn Tyr
            20                  25                  30

Gly Val His Trp Val Arg Gln Ser Pro Gly Lys Gly Leu Glu Trp Leu
        35                  40                  45

Gly Val Ile Trp Ser Gly Gly Asn Thr Asp Tyr Asn Thr Pro Phe Thr
    50                  55                  60

Ser Arg Leu Ser Ile Asn Lys Asp Asn Ser Lys Ser Gln Val Phe Phe
65                  70                  75                  80

Lys Met Asn Ser Leu Gln Ser Asn Asp Thr Ala Ile Tyr Tyr Cys Ala
                85                  90                  95

Arg Ala Leu Thr Tyr Tyr Asp Tyr Glu Phe Ala Tyr Trp Gly Gln Gly
            100                 105                 110

Thr Leu Val Thr Val Ser Ser
        115


<210> SEQ ID NO 129
<211> LENGTH: 642
<212> TYPE: DNA
<213> ORGANISM: artificial sequence
<220> FEATURE:
<223> OTHER INFORMATION: Synthesized

<400> SEQUENCE: 129

gacatcttgc tgactcagtc tccagtcatc ctgtctgtga gtccaggaga aagagtcagt      60

ttctcctgca gggccagtca gagtattggc acaaacatac actggtatca gcaaagaaca     120

aatggttctc caaggcttct cataaagtat gcttctgagt ctatctctgg gattccttcc     180

aggtttagtg gcagtggatc agggacagat tttactctta gcatcaacag tgtggagtct     240

gaagatattg cagattatta ctgtcaacaa aataataact ggccaaccac gttcggtgct     300

gggaccaagc tggagctgaa acgtacggtg gctgcaccat ctgtcttcat cttcccgcca     360

tctgatgagc agttgaaatc tggaactgcc tctgttgtgt gcctgctgaa taacttctat     420

cccagagagg ccaaagtaca gtggaaggtg gataacgccc tccaatcggg taactcccag     480

gagagtgtca cagagcagga cagcaaggac agcacctaca gcctcagcag caccctgacg     540
```

-continued

```
ctgagcaaag cagactacga gaaacacaaa gtctacgcct gcgaagtcac ccatcagggc    600

ctgagctcgc ccgtcacaaa gagcttcaac aggggagagt gt                       642


<210> SEQ ID NO 130
<211> LENGTH: 321
<212> TYPE: DNA
<213> ORGANISM: artificial sequence
<220> FEATURE:
<223> OTHER INFORMATION: Synthesized

<400> SEQUENCE: 130

gacatcttgc tgactcagtc tccagtcatc ctgtctgtga gtccaggaga aagagtcagt     60

ttctcctgca gggccagtca gagtattggc acaaacatac actggtatca gcaaagaaca    120

aatggttctc caaggcttct cataaagtat gcttctgagt ctatctctgg gattccttcc    180

aggtttagtg gcagtggatc agggacagat tttactctta gcatcaacag tgtggagtct    240

gaagatattg cagattatta ctgtcaacaa aataataact ggccaaccac gttcggtgct    300

gggaccaagc tggagctgaa a                                              321


<210> SEQ ID NO 131
<211> LENGTH: 214
<212> TYPE: PRT
<213> ORGANISM: artificial sequence
<220> FEATURE:
<223> OTHER INFORMATION: Synthesized

<400> SEQUENCE: 131

Asp Ile Leu Leu Thr Gln Ser Pro Val Ile Leu Ser Val Ser Pro Gly
1               5                   10                  15

Glu Arg Val Ser Phe Ser Cys Arg Ala Ser Gln Ser Ile Gly Thr Asn
            20                  25                  30

Ile His Trp Tyr Gln Gln Arg Thr Asn Gly Ser Pro Arg Leu Leu Ile
        35                  40                  45

Lys Tyr Ala Ser Glu Ser Ile Ser Gly Ile Pro Ser Arg Phe Ser Gly
    50                  55                  60

Ser Gly Ser Gly Thr Asp Phe Thr Leu Ser Ile Asn Ser Val Glu Ser
65                  70                  75                  80

Glu Asp Ile Ala Asp Tyr Tyr Cys Gln Gln Asn Asn Asn Trp Pro Thr
                85                  90                  95

Thr Phe Gly Ala Gly Thr Lys Leu Glu Leu Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 132
<211> LENGTH: 107
<212> TYPE: PRT
<213> ORGANISM: artificial sequence
<220> FEATURE:
<223> OTHER INFORMATION: Synthesized

<400> SEQUENCE: 132

```
Asp Ile Leu Leu Thr Gln Ser Pro Val Ile Leu Ser Val Ser Pro Gly
1               5                   10                  15

Glu Arg Val Ser Phe Ser Cys Arg Ala Ser Gln Ser Ile Gly Thr Asn
            20                  25                  30

Ile His Trp Tyr Gln Gln Arg Thr Asn Gly Ser Pro Arg Leu Leu Ile
        35                  40                  45

Lys Tyr Ala Ser Glu Ser Ile Ser Gly Ile Pro Ser Arg Phe Ser Gly
    50                  55                  60

Ser Gly Ser Gly Thr Asp Phe Thr Leu Ser Ile Asn Ser Val Glu Ser
65                  70                  75                  80

Glu Asp Ile Ala Asp Tyr Tyr Cys Gln Gln Asn Asn Asn Trp Pro Thr
                85                  90                  95

Thr Phe Gly Ala Gly Thr Lys Leu Glu Leu Lys
            100                 105
```

<210> SEQ ID NO 133
<211> LENGTH: 2106
<212> TYPE: DNA
<213> ORGANISM: artificial sequence
<220> FEATURE:
<223> OTHER INFORMATION: Synthesized

<400> SEQUENCE: 133

```
caggtgcagc tgaagcagtc aggacctggc ctagtgcagc cctcacagag cctgtccatc     60

acctgcacag tctctggttt ctcattaact aactatggtg tacactgggt tcgccagtct    120

ccaggaaagg gtctggagtg gctgggagtg atatggagtg gtggaaacac agactataat    180

acacctttca catccagact gagcatcaac aaggacaatt ccaagagcca agttttcttt    240

aaaatgaaca gtctgcaatc taatgacaca gccatatatt actgtgccag agccctcacc    300

tactatgatt acgagtttgc ttactggggc caagggactc tggtcactgt ctctagcgct    360

agcaccaagg gcccatcggt cttccccctg gcaccctcct ccaagagcac ctctgggggc    420

acagcggccc tgggctgcct ggtcaaggac tacttccccg aaccggtgac ggtgtcgtgg    480

aactcaggcg ccctgaccag cggcgtgcac accttcccgg ctgtcctaca gtcctcagga    540

ctctactccc tcagcagcgt ggtgaccgtg ccctccagca gcttgggcac ccagacctac    600

atctgcaacg tgaatcacaa gcccagcaac accaaggtgg acaagagagt tgagcccaaa    660

tcttgtgaca aaactcacac atgcccaccg tgcccagcac ctgaactcct ggggggaccg    720

tcagtcttcc tcttcccccc aaaacccaag gacaccctca tgatctcccg gacccctgag    780

gtcacatgcg tggtggtgga cgtgagccac gaagaccctg aggtcaagtt caactggtac    840

gtggacggcg tggaggtgca taatgccaag acaaagccgc gggaggagca gtacaacagc    900

acgtaccgtg tggtcagcgt cctcaccgtc ctgcaccagg actggctgaa tggcaaggag    960

tacaagtgca aggtctccaa caaagccctc ccagccccca tcgagaaaac catctccaaa   1020

gccaaagggc agccccgaga accacaggtg tacaccctgc ccccatcccg ggatgagctg   1080

accaagaacc aggtcagcct gacctgcctg gtcaaaggct tctatcccag cgacatcgcc   1140

gtggagtggg agagcaatgg gcagccggag aacaactaca agaccacgcc tcccgtgctg   1200
```

gactccgacg gctccttctt cctctatagc aagctcaccg tggacaagag caggtggcag 1260
caggggaacg tcttctcatg ctccgtgatg catgaggctc tgcacaacca ctacacgcag 1320
aagagcctct ccctgtctcc gggtggcggt ggagggtccg gcggtggtgg atcacaggtg 1380
caattgcagg agtcgggggg aggcctggtc aagcctggag ggtccctgag actctcctgt 1440
gcagcctctg gattcacctt tagtagttat tggatgagct gggtccgcca ggctccaggg 1500
aaggggctgg agtgggtggc caacataaac cgcgatggaa gtgcgagtta ctatgtggac 1560
tctgtgaagg gccgattcac catctccaga gacgacgcca agaactcact gtatctgcaa 1620
atgaacagcc tgagagctga ggacacggct gtgtattact gtgcgagaga tcgtggggtg 1680
ggctacttcg atctctgggg ccgtggcacc ctggtcaccg tctcgagcgg tggaggcggt 1740
tcaggcggag gtggttccgg cggtggcggc tcccagtctg ccctgactca gcctgcctcc 1800
gtgtctgggt ctcctggaca gtcgatcacc atctcctgca ctggaaccag cagtgacgtt 1860
ggtggttata actttgtctc ctggtaccaa caacacccag gcaaagcccc caaactcatg 1920
atctatgatg tcagtgatcg gccctcaggg gtgtctgatc gcttctccgg ctccaagtct 1980
ggcaacacgg cctccctgat catctctggc ctccaggctg acgacgaggc tgattattac 2040
tgcagctcat atgggagcag cagcactcat gtgattttcg gcggagggac caaggtgacc 2100
gtccta 2106

<210> SEQ ID NO 134
<211> LENGTH: 357
<212> TYPE: DNA
<213> ORGANISM: artificial sequence
<220> FEATURE:
<223> OTHER INFORMATION: Synthesized

<400> SEQUENCE: 134
caggtgcagc tgaagcagtc aggacctggc ctagtgcagc cctcacagag cctgtccatc 60
acctgcacag tctctggttt ctcattaact aactatggtg tacactgggt tcgccagtct 120
ccaggaaagg gtctggagtg gctgggagtg atatggagtg gtggaaacac agactataat 180
acacctttca catccagact gagcatcaac aaggacaatt ccaagagcca agttttcttt 240
aaaatgaaca gtctgcaatc taatgacaca gccatatatt actgtgccag agccctcacc 300
tactatgatt acgagtttgc ttactggggc caagggactc tggtcactgt ctctagc 357

<210> SEQ ID NO 135
<211> LENGTH: 732
<212> TYPE: DNA
<213> ORGANISM: artificial sequence
<220> FEATURE:
<223> OTHER INFORMATION: Synthesized

<400> SEQUENCE: 135
caggtgcagc tgcaggagtc ggggggaggc ctggtcaagc ctggagggtc cctgagactc 60
tcctgtgcag cctctggatt cacctttagt agttattgga tgagctgggt ccgccaggct 120
ccagggaagg ggctggagtg ggtggccaac ataaaccgcg atggaagtgc gagttactat 180
gtggactctg tgaagggccg attcaccatc tccagagacg acgccaagaa ctcactgtat 240
ctgcaaatga acagcctgag agctgaggac acggctgtgt attactgtgc gagagatcgt 300
ggggtgggct acttcgatct ctggggccgt ggcaccctgg tcaccgtctc gagcggtgga 360
ggcggttcag gcggaggtgg ttccggcggt ggcggctccc agtctgccct gactcagcct 420

```
gcctccgtgt ctgggtctcc tggacagtcg atcaccatct cctgcactgg aaccagcagt    480

gacgttggtg gttataactt tgtctcctgg taccaacaac acccaggcaa agcccccaaa    540

ctcatgatct atgatgtcag tgatcggccc tcaggggtgt ctgatcgctt ctccggctcc    600

aagtctggca acacggcctc cctgatcatc tctggcctcc aggctgacga cgaggctgat    660

tattactgca gctcatatgg gagcagcagc actcatgtga ttttcggcgg agggaccaag    720

gtgaccgtcc ta                                                        732
```

```
<210> SEQ ID NO 136
<211> LENGTH: 702
<212> TYPE: PRT
<213> ORGANISM: artificial sequence
<220> FEATURE:
<223> OTHER INFORMATION: Synthesized

<400> SEQUENCE: 136

Gln Val Gln Leu Lys Gln Ser Gly Pro Gly Leu Val Gln Pro Ser Gln
1               5                   10                  15

Ser Leu Ser Ile Thr Cys Thr Val Ser Gly Phe Ser Leu Thr Asn Tyr
            20                  25                  30

Gly Val His Trp Val Arg Gln Ser Pro Gly Lys Gly Leu Glu Trp Leu
        35                  40                  45

Gly Val Ile Trp Ser Gly Gly Asn Thr Asp Tyr Asn Thr Pro Phe Thr
    50                  55                  60

Ser Arg Leu Ser Ile Asn Lys Asp Asn Ser Lys Ser Gln Val Phe Phe
65                  70                  75                  80

Lys Met Asn Ser Leu Gln Ser Asn Asp Thr Ala Ile Tyr Tyr Cys Ala
                85                  90                  95

Arg Ala Leu Thr Tyr Tyr Asp Tyr Glu Phe Ala Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Arg Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300
```

```
Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Gly Gly Gly Gly Ser Gly Gly Gly Gly Ser Gln Val Gln Leu Gln Glu
    450                 455                 460

Ser Gly Gly Gly Leu Val Lys Pro Gly Gly Ser Leu Arg Leu Ser Cys
465                 470                 475                 480

Ala Ala Ser Gly Phe Thr Phe Ser Ser Tyr Trp Met Ser Trp Val Arg
                485                 490                 495

Gln Ala Pro Gly Lys Gly Leu Glu Trp Val Ala Asn Ile Asn Arg Asp
            500                 505                 510

Gly Ser Ala Ser Tyr Tyr Val Asp Ser Val Lys Gly Arg Phe Thr Ile
        515                 520                 525

Ser Arg Asp Asp Ala Lys Asn Ser Leu Tyr Leu Gln Met Asn Ser Leu
    530                 535                 540

Arg Ala Glu Asp Thr Ala Val Tyr Tyr Cys Ala Arg Asp Arg Gly Val
545                 550                 555                 560

Gly Tyr Phe Asp Leu Trp Gly Arg Gly Thr Leu Val Thr Val Ser Ser
                565                 570                 575

Gly Gly Gly Gly Ser Gly Gly Gly Gly Ser Gly Gly Gly Gly Ser Gln
            580                 585                 590

Ser Ala Leu Thr Gln Pro Ala Ser Val Ser Gly Ser Pro Gly Gln Ser
        595                 600                 605

Ile Thr Ile Ser Cys Thr Gly Thr Ser Ser Asp Val Gly Gly Tyr Asn
    610                 615                 620

Phe Val Ser Trp Tyr Gln Gln His Pro Gly Lys Ala Pro Lys Leu Met
625                 630                 635                 640

Ile Tyr Asp Val Ser Asp Arg Pro Ser Gly Val Ser Asp Arg Phe Ser
                645                 650                 655

Gly Ser Lys Ser Gly Asn Thr Ala Ser Leu Ile Ile Ser Gly Leu Gln
            660                 665                 670

Ala Asp Asp Glu Ala Asp Tyr Tyr Cys Ser Ser Tyr Gly Ser Ser Ser
        675                 680                 685

Thr His Val Ile Phe Gly Gly Gly Thr Lys Val Thr Val Leu
    690                 695                 700
```

<210> SEQ ID NO 137
<211> LENGTH: 119
<212> TYPE: PRT

```
<213> ORGANISM: artificial sequence
<220> FEATURE:
<223> OTHER INFORMATION: Synthesized

<400> SEQUENCE: 137

Gln Val Gln Leu Lys Gln Ser Gly Pro Gly Leu Val Gln Pro Ser Gln
1               5                   10                  15

Ser Leu Ser Ile Thr Cys Thr Val Ser Gly Phe Ser Leu Thr Asn Tyr
            20                  25                  30

Gly Val His Trp Val Arg Gln Ser Pro Gly Lys Gly Leu Glu Trp Leu
        35                  40                  45

Gly Val Ile Trp Ser Gly Gly Asn Thr Asp Tyr Asn Thr Pro Phe Thr
    50                  55                  60

Ser Arg Leu Ser Ile Asn Lys Asp Asn Ser Lys Ser Gln Val Phe Phe
65                  70                  75                  80

Lys Met Asn Ser Leu Gln Ser Asn Asp Thr Ala Ile Tyr Tyr Cys Ala
                85                  90                  95

Arg Ala Leu Thr Tyr Tyr Asp Tyr Glu Phe Ala Tyr Trp Gly Gln Gly
            100                 105                 110

Thr Leu Val Thr Val Ser Ser
        115


<210> SEQ ID NO 138
<211> LENGTH: 244
<212> TYPE: PRT
<213> ORGANISM: artificial sequence
<220> FEATURE:
<223> OTHER INFORMATION: Synthesized

<400> SEQUENCE: 138

Gln Val Gln Leu Gln Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Trp Met Ser Trp Val Arg Gln Ala Pro Gly Lys Gly Leu Glu Trp Val
        35                  40                  45

Ala Asn Ile Asn Arg Asp Gly Ser Ala Ser Tyr Tyr Val Asp Ser Val
    50                  55                  60

Lys Gly Arg Phe Thr Ile Ser Arg Asp Asp Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Arg Gly Val Gly Tyr Phe Asp Leu Trp Gly Arg Gly Thr
            100                 105                 110

Leu Val Thr Val Ser Ser Gly Gly Gly Gly Ser Gly Gly Gly Gly Ser
        115                 120                 125

Gly Gly Gly Gly Ser Gln Ser Ala Leu Thr Gln Pro Ala Ser Val Ser
    130                 135                 140

Gly Ser Pro Gly Gln Ser Ile Thr Ile Ser Cys Thr Gly Thr Ser Ser
145                 150                 155                 160

Asp Val Gly Gly Tyr Asn Phe Val Ser Trp Tyr Gln Gln His Pro Gly
                165                 170                 175

Lys Ala Pro Lys Leu Met Ile Tyr Asp Val Ser Asp Arg Pro Ser Gly
            180                 185                 190

Val Ser Asp Arg Phe Ser Gly Ser Lys Ser Gly Asn Thr Ala Ser Leu
        195                 200                 205
```

```
Ile Ile Ser Gly Leu Gln Ala Asp Asp Glu Ala Asp Tyr Tyr Cys Ser
    210                 215                 220

Ser Tyr Gly Ser Ser Ser Thr His Val Ile Phe Gly Gly Gly Thr Lys
225                 230                 235                 240

Val Thr Val Leu
```

```
<210> SEQ ID NO 139
<211> LENGTH: 654
<212> TYPE: DNA
<213> ORGANISM: Artificial Sequence
<220> FEATURE:
<223> OTHER INFORMATION: Synthesized

<400> SEQUENCE: 139

cagtctgccc tgactcagcc tgcctccgtg tctgggtctc ctggacagtc gatcaccatc     60

tcctgcactg gaaccagcag tgacgttggt ggttataact ttgtctcctg gtaccaacaa    120

cacccaggca aagcccccaa actcatgatc tatgatgtca gtgatcggcc ctcaggggtg    180

tctgatcgct tctccggctc caagtctggc aacacggcct ccctgatcat ctctggcctc    240

caggctgacg acgaggctga ttattactgc agctcatatg ggagcagcag cactcatgtg    300

attttcggcg gagggaccaa gctgaccgtc ctacgtacgg tggctgcacc atctgtcttc    360

atcttcccgc catctgatga gcagttgaaa tctggaactg cctctgttgt gtgcctgctg    420

aataacttct atcccagaga ggccaaagta cagtggaagg tggataacgc cctccaatcg    480

ggtaactccc aggagagtgt cacagagcag gacagcaagg acagcaccta cagcctcagc    540

agcaccctga cgctgagcaa agcagactac gagaaacaca aagtctacgc ctgcgaagtc    600

acccatcagg gcctgagctc gcccgtcaca aagagcttca acaggggaga gtgt          654
```

```
<210> SEQ ID NO 140
<211> LENGTH: 333
<212> TYPE: DNA
<213> ORGANISM: Artificial Sequence
<220> FEATURE:
<223> OTHER INFORMATION: Synthesized

<400> SEQUENCE: 140

cagtctgccc tgactcagcc tgcctccgtg tctgggtctc ctggacagtc gatcaccatc     60

tcctgcactg gaaccagcag tgacgttggt ggttataact ttgtctcctg gtaccaacaa    120

cacccaggca aagcccccaa actcatgatc tatgatgtca gtgatcggcc ctcaggggtg    180

tctgatcgct tctccggctc caagtctggc aacacggcct ccctgatcat ctctggcctc    240

caggctgacg acgaggctga ttattactgc agctcatatg ggagcagcag cactcatgtg    300

attttcggcg gagggaccaa gctgaccgtc cta                                 333
```

```
<210> SEQ ID NO 141
<211> LENGTH: 218
<212> TYPE: PRT
<213> ORGANISM: Artificial Sequence
<220> FEATURE:
<223> OTHER INFORMATION: Synthesized

<400> SEQUENCE: 141

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
            20                  25                  30

Asn Phe Val Ser Trp Tyr Gln Gln His Pro Gly Lys Ala Pro Lys Leu
```

```
        35                  40                  45

Met Ile Tyr Asp Val Ser Asp Arg Pro Ser Gly Val Ser Asp Arg Phe
    50                  55                  60

Ser Gly Ser Lys Ser Gly Asn Thr Ala Ser Leu Ile Ile Ser Gly Leu
65                  70                  75                  80

Gln Ala Asp Asp Glu Ala Asp Tyr Tyr Cys Ser Ser Tyr Gly Ser Ser
                85                  90                  95

Ser Thr His Val Ile Phe Gly Gly Gly Thr Lys Leu Thr Val Leu Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215
```

<210> SEQ ID NO 142
<211> LENGTH: 111
<212> TYPE: PRT
<213> ORGANISM: Artificial Sequence
<220> FEATURE:
<223> OTHER INFORMATION: Synthesized

<400> SEQUENCE: 142

```
Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
            20                  25                  30

Asn Phe Val Ser Trp Tyr Gln Gln His Pro Gly Lys Ala Pro Lys Leu
        35                  40                  45

Met Ile Tyr Asp Val Ser Asp Arg Pro Ser Gly Val Ser Asp Arg Phe
    50                  55                  60

Ser Gly Ser Lys Ser Gly Asn Thr Ala Ser Leu Ile Ile Ser Gly Leu
65                  70                  75                  80

Gln Ala Asp Asp Glu Ala Asp Tyr Tyr Cys Ser Ser Tyr Gly Ser Ser
                85                  90                  95

Ser Thr His Val Ile Phe Gly Gly Gly Thr Lys Leu Thr Val Leu
            100                 105                 110
```

<210> SEQ ID NO 143
<211> LENGTH: 1344
<212> TYPE: DNA
<213> ORGANISM: Artificial Sequence
<220> FEATURE:
<223> OTHER INFORMATION: Synthesized

<400> SEQUENCE: 143

```
caggtgcagc tgcaggagtc gggggaggc ctggtcaagc ctggagggtc cctgagactc      60

tcctgtgcag cctctggatt cacctttagt agttattgga tgagctgggt ccgccaggct    120
```

```
ccagggaagg ggctggagtg ggtggccaac ataaaccgcg atggaagtgc gagttactat    180

gtggactctg tgaagggccg attcaccatc tccagagacg acgccaagaa ctcactgtat    240

ctgcaaatga acagcctgag agctgaggac acggctgtgt attactgtgc gagagatcgt    300

ggggtgggct acttcgatct ctggggccgt ggcaccctgg tcaccgtctc gagcgctagc    360

accaagggcc catcggtctt ccccctggca ccctcctcca agagcacctc tgggggcaca    420

gcggccctgg gctgcctggt caaggactac ttccccgaac cggtgacggt gtcgtggaac    480

tcaggcgccc tgaccagcgg cgtgcacacc ttcccggctg tcctacagtc ctcaggactc    540

tactccctca gcagcgtggt gaccgtgccc tccagcagct tgggcaccca gacctacatc    600

tgcaacgtga atcacaagcc cagcaacacc aaggtggaca agagagttga gcccaaatct    660

tgtgacaaaa ctcacacatg cccaccgtgc ccagcacctg aactcctggg gggaccgtca    720

gtcttcctct tccccccaaa acccaaggac accctcatga tctcccggac ccctgaggtc    780

acatgcgtgg tggtggacgt gagccacgaa gaccctgagg tcaagttcaa ctggtacgtg    840

gacggcgtgg aggtgcataa tgccaagaca aagccgcggg aggagcagta caacagcacg    900

taccgtgtgg tcagcgtcct caccgtcctg caccaggact ggctgaatgg caaggagtac    960

aagtgcaagg tctccaacaa agccctccca gcccccatcg agaaaaccat ctccaaagcc   1020

aaagggcagc cccgagaacc acaggtgtac accctgcccc catcccggga ggagatgacc   1080

aagaaccagg tcagcctgac ctgcctggtc aaaggcttct atcccagcga catcgccgtg   1140

gagtgggaga gcaatgggca gccggagaac aactacaaga ccacgcctcc cgtgctggac   1200

tccgacggct ccttcttcct ctatagcaag ctcaccgtgg acaagagcag gtggcagcag   1260

gggaacgtct tctcatgctc cgtgatgcat gaggctctgc acaaccacta cacgcagaag   1320

agcctctccc tgtctccggg taaa                                          1344


<210> SEQ ID NO 144
<211> LENGTH: 354
<212> TYPE: DNA
<213> ORGANISM: Artificial Sequence
<220> FEATURE:
<223> OTHER INFORMATION: Synthesized

<400> SEQUENCE: 144

caggtgcagc tgcaggagtc gggggaggc ctggtcaagc ctggagggtc cctgagactc      60

tcctgtgcag cctctggatt cacctttagt agttattgga tgagctgggt ccgccaggct    120

ccagggaagg ggctggagtg ggtggccaac ataaaccgcg atggaagtgc gagttactat    180

gtggactctg tgaagggccg attcaccatc tccagagacg acgccaagaa ctcactgtat    240

ctgcaaatga acagcctgag agctgaggac acggctgtgt attactgtgc gagagatcgt    300

ggggtgggct acttcgatct ctggggccgt ggcaccctgg tcaccgtctc gagc          354


<210> SEQ ID NO 145
<211> LENGTH: 448
<212> TYPE: PRT
<213> ORGANISM: Artificial Sequence
<220> FEATURE:
<223> OTHER INFORMATION: Synthesized

<400> SEQUENCE: 145

Gln Val Gln Leu Gln Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
```

-continued

```
            20                  25                  30

Trp Met Ser Trp Val Arg Gln Ala Pro Gly Lys Gly Leu Glu Trp Val
        35                  40                  45

Ala Asn Ile Asn Arg Asp Gly Ser Ala Ser Tyr Tyr Val Asp Ser Val
    50                  55                  60

Lys Gly Arg Phe Thr Ile Ser Arg Asp Asp Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Arg Gly Val Gly Tyr Phe Asp Leu Trp Gly Arg Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Arg Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Glu Glu Met Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
        435                 440                 445
```

<210> SEQ ID NO 146
<211> LENGTH: 118
<212> TYPE: PRT
<213> ORGANISM: Artificial Sequence
<220> FEATURE:
<223> OTHER INFORMATION: Synthesized

<400> SEQUENCE: 146

```
Gln Val Gln Leu Gln Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Trp Met Ser Trp Val Arg Gln Ala Pro Gly Lys Gly Leu Glu Trp Val
        35                  40                  45

Ala Asn Ile Asn Arg Asp Gly Ser Ala Ser Tyr Tyr Val Asp Ser Val
    50                  55                  60

Lys Gly Arg Phe Thr Ile Ser Arg Asp Asp Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Arg Gly Val Gly Tyr Phe Asp Leu Trp Gly Arg Gly Thr
            100                 105                 110

Leu Val Thr Val Ser Ser
        115
```

<210> SEQ ID NO 147
<211> LENGTH: 654
<212> TYPE: DNA
<213> ORGANISM: Artificial Sequence
<220> FEATURE:
<223> OTHER INFORMATION: Synthesized

<400> SEQUENCE: 147

```
cagtctgccc tgactcagcc tgcctccgtg tctgggtctc ctggacagtc gatcaccatc     60

tcctgcactg gaaccagcag tgacgttggt ggttataact ttgtctcctg gtaccaacaa    120

cacccaggca aagcccccaa actcatgatc tatgatgtca gtgatcggcc ctcaggggtg    180

tctgatcgct tctccggctc caagtctggc aacacggcct ccctgatcat ctctggcctc    240

caggctgacg acgaggctga ttattactgc agctcatatg ggagcagcag cactcatgtg    300

attttcggcg gagggaccaa gctgaccgtc ctacgtacgg tggctgcacc atctgtcttc    360

atcttcccgc catctgatga gcagttgaaa tctggaactg cctctgttgt gtgcctgctg    420

aataacttct atcccagaga ggccaaagta cagtggaagg tggataacgc cctccaatcg    480

ggtaactccc aggagagtgt cacagagcag gacagcaagg acagcaccta cagcctcagc    540

agcaccctga cgctgagcaa agcagactac gagaaacaca aagtctacgc ctgcgaagtc    600

acccatcagg gcctgagctc gcccgtcaca aagagcttca acaggggaga gtgt          654
```

<210> SEQ ID NO 148
<211> LENGTH: 333
<212> TYPE: DNA
<213> ORGANISM: Artificial Sequence
<220> FEATURE:
<223> OTHER INFORMATION: Synthesized

<400> SEQUENCE: 148

```
cagtctgccc tgactcagcc tgcctccgtg tctgggtctc ctggacagtc gatcaccatc     60
```

-continued

```
tcctgcactg gaaccagcag tgacgttggt ggttataact ttgtctcctg gtaccaacaa    120

cacccaggca aagcccccaa actcatgatc tatgatgtca gtgatcggcc ctcaggggtg    180

tctgatcgct tctccggctc caagtctggc aacacggcct ccctgatcat ctctggcctc    240

caggctgacg acgaggctga ttattactgc agctcatatg ggagcagcag cactcatgtg    300

attttcggcg gagggaccaa gctgaccgtc cta                                 333


<210> SEQ ID NO 149
<211> LENGTH: 218
<212> TYPE: PRT
<213> ORGANISM: Artificial Sequence
<220> FEATURE:
<223> OTHER INFORMATION: Synthesized

<400> SEQUENCE: 149

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
            20                  25                  30

Asn Phe Val Ser Trp Tyr Gln Gln His Pro Gly Lys Ala Pro Lys Leu
        35                  40                  45

Met Ile Tyr Asp Val Ser Asp Arg Pro Ser Gly Val Ser Asp Arg Phe
    50                  55                  60

Ser Gly Ser Lys Ser Gly Asn Thr Ala Ser Leu Ile Ile Ser Gly Leu
65                  70                  75                  80

Gln Ala Asp Asp Glu Ala Asp Tyr Tyr Cys Ser Ser Tyr Gly Ser Ser
                85                  90                  95

Ser Thr His Val Ile Phe Gly Gly Gly Thr Lys Leu Thr Val Leu Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215


<210> SEQ ID NO 150
<211> LENGTH: 111
<212> TYPE: PRT
<213> ORGANISM: Artificial Sequence
<220> FEATURE:
<223> OTHER INFORMATION: Synthesized

<400> SEQUENCE: 150

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
            20                  25                  30

Asn Phe Val Ser Trp Tyr Gln Gln His Pro Gly Lys Ala Pro Lys Leu
```

```
        35                  40                  45

Met Ile Tyr Asp Val Ser Asp Arg Pro Ser Gly Val Ser Asp Arg Phe
    50                  55                  60

Ser Gly Ser Lys Ser Gly Asn Thr Ala Ser Leu Ile Ile Ser Gly Leu
65                  70                  75                  80

Gln Ala Asp Asp Glu Ala Asp Tyr Tyr Cys Ser Ser Tyr Gly Ser Ser
                85                  90                  95

Ser Thr His Val Ile Phe Gly Gly Gly Thr Lys Leu Thr Val Leu
            100                 105                 110


<210> SEQ ID NO 151
<211> LENGTH: 2100
<212> TYPE: DNA
<213> ORGANISM: Artificial Sequence
<220> FEATURE:
<223> OTHER INFORMATION: Synthesized

<400> SEQUENCE: 151

caggtgcagc tgcaggagtc gggggaggc ctggtcaagc ctggagggtc cctgagactc      60

tcctgtgcag cctctggatt cacctttagt agttattgga tgagctgggt ccgccaggct     120

ccagggaagg ggctggagtg ggtggccaac ataaaccgcg atggaagtgc gagttactat     180

gtggactctg tgaagggccg attcaccatc tccagagacg acgccaagaa ctcactgtat     240

ctgcaaatga acagcctgag agctgaggac acggctgtgt attactgtgc gagagatcgt     300

ggggtgggct acttcgatct ctggggccgt ggcaccctgg tcaccgtctc gagcgctagc     360

accaagggcc catcggtctt ccccctggca ccctcctcca agagcacctc tgggggcaca     420

gcggccctgg gctgcctggt caaggactac ttccccgaac cggtgacggt gtcgtggaac     480

tcaggcgccc tgaccagcgg cgtgcacacc ttcccggctg tcctacagtc ctcaggactc     540

tactccctca gcagcgtggt gaccgtgccc tccagcagct tgggcaccca gacctacatc     600

tgcaacgtga atcacaagcc cagcaacacc aaggtggaca agagagttga gcccaaatct     660

tgtgacaaaa ctcacacatg cccaccgtgc ccagcacctg aactcctggg gggaccgtca     720

gtcttcctct tccccccaaa acccaaggac accctcatga tctcccggac ccctgaggtc     780

acatgcgtgg tggtggacgt gagccacgaa gaccctgagg tcaagttcaa ctggtacgtg     840

gacggcgtgg aggtgcataa tgccaagaca aagccgcggg aggagcagta caacagcacg     900

taccgtgtgg tcagcgtcct caccgtcctg caccaggact ggctgaatgg caaggagtac     960

aagtgcaagg tctccaacaa agccctccca gcccccatcg agaaaaccat ctccaaagcc    1020

aaagggcagc cccgagaacc acaggtgtac accctgcccc catcccggga ggagatgacc    1080

aagaaccagg tcagcctgac ctgcctggtc aaaggcttct atcccagcga catcgccgtg    1140

gagtgggaga gcaatgggca gccggagaac aactacaaga ccacgcctcc cgtgctggac    1200

tccgacggct ccttcttcct ctatagcaag ctcaccgtgg acaagagcag gtggcagcag    1260

gggaacgtct tctcatgctc cgtgatgcat gaggctctgc acaaccacta cacgcagaag    1320

agcctctccc tgtctccggg taaaggcggt ggaggatccg gcggtggtgg atcacaggtg    1380

cagctgcagg agtcgggccc aggactggtg aagccttcgg agaccctgtc cctcacctgc    1440

actgtctctg gtggctccgt cagcagtggt gattactact ggacctggat acggcagtcc    1500

ccagggaagg gactggagtg gattggacac atctattaca gtgggaacac caattataac    1560

ccctccctca agagccgact caccatatca attgacacgt ccaagactca gttctccctg    1620

aagctgagtt ctgtgaccgc tgcggacacg gccatttatt actgtgtgcg agatcgagtg    1680
```

```
actggtgctt ttgatatctg gggccaaggg acaatggtca ccgtctcgag cggtggaggc   1740

ggttcaggcg gaggtggttc cggcggtggc ggctccgaca tccagatgac ccagtctcca   1800

tcctccctgt ctgcatctgt aggagacaga gtcaccatca cttgccaggc gagtcaggac   1860

atcagcaact atttaaattg gtatcagcag aaaccaggga aagcccctaa actcctgatc   1920

tacgatgcat ccaatttgga aacaggggtc ccatcaaggt tcagtggaag tggatctggg   1980

acagatttta ctttcaccat cagcagcctg cagcctgaag atattgcaac atatttctgt   2040

caacactttg atcatctccc gctcgctttc ggcggaggga ccaaggtgga aattaaacgt   2100
```

<210> SEQ ID NO 152
<211> LENGTH: 354
<212> TYPE: DNA
<213> ORGANISM: Artificial Sequence
<220> FEATURE:
<223> OTHER INFORMATION: Synthesized

<400> SEQUENCE: 152

```
caggtgcagc tgcaggagtc gggggaggc ctggtcaagc ctggagggtc cctgagactc     60

tcctgtgcag cctctggatt cacctttagt agttattgga tgagctgggt ccgccaggct    120

ccagggaagg ggctggagtg ggtggccaac ataaaccgcg atggaagtgc gagttactat    180

gtggactctg tgaagggccg attcaccatc tccagagacg acgccaagaa ctcactgtat    240

ctgcaaatga acagcctgag agctgaggac acggctgtgt attactgtgc gagagatcgt    300

ggggtgggct acttcgatct ctggggccgt ggcaccctgg tcaccgtctc gagc          354
```

<210> SEQ ID NO 153
<211> LENGTH: 726
<212> TYPE: DNA
<213> ORGANISM: Artificial Sequence
<220> FEATURE:
<223> OTHER INFORMATION: Synthesized

<400> SEQUENCE: 153

```
caggtgcagc tgcaggagtc gggcccagga ctggtgaagc cttcggagac cctgtccctc     60

acctgcactg tctctggtgg ctccgtcagc agtggtgatt actactggac ctggatacgg    120

cagtccccag ggaagggact ggagtggatt ggacacatct attacagtgg gaacaccaat    180

tataacccct ccctcaagag ccgactcacc atatcaattg acacgtccaa gactcagttc    240

tccctgaagc tgagttctgt gaccgctgcg gacacggcca tttattactg tgtgcgagat    300

cgagtgactg gtgcttttga tatctggggc caagggacaa tggtcaccgt ctcgagcggt    360

ggaggcggtt caggcggagg tggttccggc ggtggcggct ccgacatcca gatgacccag    420

tctccatcct ccctgtctgc atctgtagga gacagagtca ccatcacttg ccaggcgagt    480

caggacatca gcaactattt aaattggtat cagcagaaac cagggaaagc ccctaaactc    540

ctgatctacg atgcatccaa tttggaaaca ggggtcccat caaggttcag tggaagtgga    600

tctgggacag attttacttt caccatcagc agcctgcagc ctgaagatat tgcaacatat    660

ttctgtcaac actttgatca tctcccgctc gctttcggcg gagggaccaa ggtggaaatt    720

aaacgt                                                               726
```

<210> SEQ ID NO 154
<211> LENGTH: 700
<212> TYPE: PRT
<213> ORGANISM: Artificial Sequence
<220> FEATURE:

<223> OTHER INFORMATION: Synthesized

<400> SEQUENCE: 154

```
Gln Val Gln Leu Gln Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Trp Met Ser Trp Val Arg Gln Ala Pro Gly Lys Gly Leu Glu Trp Val
        35                  40                  45

Ala Asn Ile Asn Arg Asp Gly Ser Ala Ser Tyr Tyr Val Asp Ser Val
    50                  55                  60

Lys Gly Arg Phe Thr Ile Ser Arg Asp Asp Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Arg Gly Val Gly Tyr Phe Asp Leu Trp Gly Arg Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Arg Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Glu Glu Met Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400
```

```
Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
        435                 440                 445

Gly Gly Gly Gly Ser Gly Gly Gly Gly Ser Gln Val Gln Leu Gln Glu
    450                 455                 460

Ser Gly Pro Gly Leu Val Lys Pro Ser Glu Thr Leu Ser Leu Thr Cys
465                 470                 475                 480

Thr Val Ser Gly Gly Ser Val Ser Ser Gly Asp Tyr Tyr Trp Thr Trp
                485                 490                 495

Ile Arg Gln Ser Pro Gly Lys Gly Leu Glu Trp Ile Gly His Ile Tyr
            500                 505                 510

Tyr Ser Gly Asn Thr Asn Tyr Asn Pro Ser Leu Lys Ser Arg Leu Thr
        515                 520                 525

Ile Ser Ile Asp Thr Ser Lys Thr Gln Phe Ser Leu Lys Leu Ser Ser
    530                 535                 540

Val Thr Ala Ala Asp Thr Ala Ile Tyr Tyr Cys Val Arg Asp Arg Val
545                 550                 555                 560

Thr Gly Ala Phe Asp Ile Trp Gly Gln Gly Thr Met Val Thr Val Ser
                565                 570                 575

Ser Gly Gly Gly Gly Ser Gly Gly Gly Gly Ser Gly Gly Gly Gly Ser
            580                 585                 590

Asp Ile Gln Met Thr Gln Ser Pro Ser Ser Leu Ser Ala Ser Val Gly
        595                 600                 605

Asp Arg Val Thr Ile Thr Cys Gln Ala Ser Gln Asp Ile Ser Asn Tyr
    610                 615                 620

Leu Asn Trp Tyr Gln Gln Lys Pro Gly Lys Ala Pro Lys Leu Leu Ile
625                 630                 635                 640

Tyr Asp Ala Ser Asn Leu Glu Thr Gly Val Pro Ser Arg Phe Ser Gly
                645                 650                 655

Ser Gly Ser Gly Thr Asp Phe Thr Phe Thr Ile Ser Ser Leu Gln Pro
            660                 665                 670

Glu Asp Ile Ala Thr Tyr Phe Cys Gln His Phe Asp His Leu Pro Leu
        675                 680                 685

Ala Phe Gly Gly Gly Thr Lys Val Glu Ile Lys Arg
    690                 695                 700


<210> SEQ ID NO 155
<211> LENGTH: 118
<212> TYPE: PRT
<213> ORGANISM: Artificial Sequence
<220> FEATURE:
<223> OTHER INFORMATION: Synthesized

<400> SEQUENCE: 155

Gln Val Gln Leu Gln Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Trp Met Ser Trp Val Arg Gln Ala Pro Gly Lys Gly Leu Glu Trp Val
        35                  40                  45

Ala Asn Ile Asn Arg Asp Gly Ser Ala Ser Tyr Tyr Val Asp Ser Val
    50                  55                  60
```

-continued

```
Lys Gly Arg Phe Thr Ile Ser Arg Asp Asp Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Arg Gly Val Gly Tyr Phe Asp Leu Trp Gly Arg Gly Thr
            100                 105                 110

Leu Val Thr Val Ser Ser
        115
```

<210> SEQ ID NO 156
<211> LENGTH: 242
<212> TYPE: PRT
<213> ORGANISM: Artificial Sequence
<220> FEATURE:
<223> OTHER INFORMATION: Synthesized

<400> SEQUENCE: 156

```
Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Val Ser Ser Gly
            20                  25                  30

Asp Tyr Tyr Trp Thr Trp Ile Arg Gln Ser Pro Gly Lys Gly Leu Glu
        35                  40                  45

Trp Ile Gly His Ile Tyr Tyr Ser Gly Asn Thr Asn Tyr Asn Pro Ser
    50                  55                  60

Leu Lys Ser Arg Leu Thr Ile Ser Ile Asp Thr Ser Lys Thr Gln Phe
65                  70                  75                  80

Ser Leu Lys Leu Ser Ser Val Thr Ala Ala Asp Thr Ala Ile Tyr Tyr
                85                  90                  95

Cys Val Arg Asp Arg Val Thr Gly Ala Phe Asp Ile Trp Gly Gln Gly
            100                 105                 110

Thr Met Val Thr Val Ser Ser Gly Gly Gly Gly Ser Gly Gly Gly Gly
        115                 120                 125

Ser Gly Gly Gly Gly Ser Asp Ile Gln Met Thr Gln Ser Pro Ser Ser
    130                 135                 140

Leu Ser Ala Ser Val Gly Asp Arg Val Thr Ile Thr Cys Gln Ala Ser
145                 150                 155                 160

Gln Asp Ile Ser Asn Tyr Leu Asn Trp Tyr Gln Gln Lys Pro Gly Lys
                165                 170                 175

Ala Pro Lys Leu Leu Ile Tyr Asp Ala Ser Asn Leu Glu Thr Gly Val
            180                 185                 190

Pro Ser Arg Phe Ser Gly Ser Gly Ser Gly Thr Asp Phe Thr Phe Thr
        195                 200                 205

Ile Ser Ser Leu Gln Pro Glu Asp Ile Ala Thr Tyr Phe Cys Gln His
    210                 215                 220

Phe Asp His Leu Pro Leu Ala Phe Gly Gly Gly Thr Lys Val Glu Ile
225                 230                 235                 240

Lys Arg
```

<210> SEQ ID NO 157
<211> LENGTH: 642
<212> TYPE: DNA
<213> ORGANISM: Artificial Sequence
<220> FEATURE:
<223> OTHER INFORMATION: Synthesized

<400> SEQUENCE: 157

```
gacatccaga tgacccagtc tccatcctcc ctgtctgcat ctgtaggaga cagagtcacc     60

atcacttgcc aggcgagtca ggacatcagc aactatttaa attggtatca gcagaaacca    120

gggaaagccc ctaaactcct gatctacgat gcatccaatt tggaaacagg ggtcccatca    180

aggttcagtg gaagtggatc tgggacagat tttactttca ccatcagcag cctgcagcct    240

gaagatattg caacatattt ctgtcaacac tttgatcatc tcccgctcgc tttcggcgga    300

gggaccaagg tggaaattaa acgtacggtg gctgcaccat ctgtcttcat cttcccgcca    360

tctgatgagc agttgaaatc tggaactgcc tctgttgtgt gcctgctgaa taacttctat    420

cccagagagg ccaaagtaca gtggaaggtg gataacgccc tccaatcggg taactcccag    480

gagagtgtca cagagcagga cagcaaggac agcacctaca gcctcagcag caccctgacg    540

ctgagcaaag cagactacga gaaacacaaa gtctacgcct gcgaagtcac ccatcagggc    600

ctgagctcgc ccgtcacaaa gagcttcaac aggggagagt gt                       642
```

```
<210> SEQ ID NO 158
<211> LENGTH: 321
<212> TYPE: DNA
<213> ORGANISM: Artificial Sequence
<220> FEATURE:
<223> OTHER INFORMATION: Synthesized

<400> SEQUENCE: 158

gacatccaga tgacccagtc tccatcctcc ctgtctgcat ctgtaggaga cagagtcacc     60

atcacttgcc aggcgagtca ggacatcagc aactatttaa attggtatca gcagaaacca    120

gggaaagccc ctaaactcct gatctacgat gcatccaatt tggaaacagg ggtcccatca    180

aggttcagtg gaagtggatc tgggacagat tttactttca ccatcagcag cctgcagcct    240

gaagatattg caacatattt ctgtcaacac tttgatcatc tcccgctcgc tttcggcgga    300

gggaccaagg tggaaattaa a                                              321
```

```
<210> SEQ ID NO 159
<211> LENGTH: 214
<212> TYPE: PRT
<213> ORGANISM: Artificial Sequence
<220> FEATURE:
<223> OTHER INFORMATION: Synthesized

<400> SEQUENCE: 159

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Asp Ala Ser Asn Leu Glu Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Phe Cys Gln His Phe Asp His Leu Pro Leu
                85                  90                  95

Ala Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
```

-continued

```
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210


<210> SEQ ID NO 160
<211> LENGTH: 107
<212> TYPE: PRT
<213> ORGANISM: Artificial Sequence
<220> FEATURE:
<223> OTHER INFORMATION: Synthesized

<400> SEQUENCE: 160

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Asp Ala Ser Asn Leu Glu Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Phe Cys Gln His Phe Asp His Leu Pro Leu
                85                  90                  95

Ala Phe Gly Gly Gly Thr Lys Val Glu Ile Lys
            100                 105


<210> SEQ ID NO 161
<211> LENGTH: 2109
<212> TYPE: DNA
<213> ORGANISM: Artificial Sequence
<220> FEATURE:
<223> OTHER INFORMATION: Synthesized

<400> SEQUENCE: 161

caggtgcagc tgcaggagtc gggcccagga ctggtgaagc cttcggagac cctgtccctc      60

acctgcactg tctctggtgg ctccgtcagc agtggtgatt actactggac ctggatccgg     120

cagtccccag ggaagggact ggagtggatt ggacacatct attacagtgg gaacaccaat     180

tataacccct ccctcaagag ccgactcacc atatcaattg acacgtccaa gactcagttc     240

tccctgaagc tgagttctgt gaccgctgcg gacacggcca tttattactg tgtgcgagat     300

cgagtgactg gtgcttttga tatctggggc caagggacaa tggtcaccgt ctcgagcgct     360

agcaccaagg gcccatcggt cttccccctg gcaccctcct ccaagagcac ctctgggggc     420

acagcggccc tgggctgcct ggtcaaggac tacttccccg aaccggtgac ggtgtcgtgg     480

aactcaggcg ccctgaccag cggcgtgcac accttcccgg ctgtcctaca gtcctcagga     540

ctctactccc tcagcagcgt ggtgaccgtg ccctccagca gcttgggcac ccagacctac     600

atctgcaacg tgaatcacaa gcccagcaac accaaggtgg acaagagagt tgagcccaaa     660
```

tcttgtgaca aaactcacac atgcccaccg tgcccagcac ctgaactcct gggggggaccg 720
tcagtcttcc tcttcccccc aaaacccaag gacaccctca tgatctcccg gacccctgag 780
gtcacatgcg tggtggtgga cgtgagccac gaagaccctg aggtcaagtt caactggtac 840
gtggacggcg tggaggtgca taatgccaag acaaagccgc gggaggagca gtacaacagc 900
acgtaccgtg tggtcagcgt cctcaccgtc ctgcaccagg actggctgaa tggcaaggag 960
tacaagtgca aggtctccaa caaagccctc ccagccccca tcgagaaaac catctccaaa 1020
gccaaagggc agccccgaga accacaggtg tacaccctgc ccccatcccg ggaggagatg 1080
accaagaacc aggtcagcct gacctgcctg gtcaaaggct tctatcccag cgacatcgcc 1140
gtggagtggg agagcaatgg gcagccggag aacaactaca agaccacgcc tcccgtgctg 1200
gactccgacg gctccttctt cctctatagc aagctcaccg tggacaagag caggtggcag 1260
caggggaacg tcttctcatg ctccgtgatg catgaggctc tgcacaacca ctacacgcag 1320
aagagcctct ccctgtctcc gggtaaaggc ggtggaggat ccggcggtgg tggatcacag 1380
gtgcagctgc aggagtcggg gggaggcctg gtcaagcctg gagggtccct gagactctcc 1440
tgtgcagcct ctggattcac ctttagtagt tattggatga gctgggtccg ccaggctcca 1500
gggaaggggc tggagtgggt ggccaacata aaccgcgatg gaagtgcgag ttactatgtg 1560
gactctgtga agggccgatt caccatctcc agagacgacg ccaagaactc actgtatctg 1620
caaatgaaca gcctgagagc tgaggacacg gctgtgtatt actgtgcgag agatcgtggg 1680
gtgggctact tcgatctctg gggccgtggc accctggtca ccgtctcgag cggtggaggc 1740
ggttcaggcg gaggtggttc cggcggtggc ggctcccagt ctgccctgac tcagcctgcc 1800
tccgtgtctg ggtctcctgg acagtcgatc accatctcct gcactggaac cagcagtgac 1860
gttggtggtt ataactttgt ctcctggtac caacaacacc caggcaaagc ccccaaactc 1920
atgatctatg atgtcagtga tcggccctca ggggtgtctg atcgcttctc cggctccaag 1980
tctggcaaca cggcctccct gatcatctct ggcctccagg ctgacgacga ggctgattat 2040
tactgcagct catatgggag cagcagcact catgtgattt tcggcggagg gaccaaggtg 2100
accgtccta 2109

<210> SEQ ID NO 162
<211> LENGTH: 357
<212> TYPE: DNA
<213> ORGANISM: Artificial Sequence
<220> FEATURE:
<223> OTHER INFORMATION: Synthesized

<400> SEQUENCE: 162
caggtgcagc tgcaggagtc gggcccagga ctggtgaagc cttcggagac cctgtccctc 60
acctgcactg tctctggtgg ctccgtcagc agtggtgatt actactggac ctggatccgg 120
cagtccccag ggaagggact ggagtggatt ggacacatct attacagtgg gaacaccaat 180
tataacccct ccctcaagag ccgactcacc atatcaattg acacgtccaa gactcagttc 240
tccctgaagc tgagttctgt gaccgctgcg gacacggcca tttattactg tgtgcgagat 300
cgagtgactg gtgcttttga tatctggggc caagggacaa tggtcaccgt ctcgagc 357

<210> SEQ ID NO 163
<211> LENGTH: 732
<212> TYPE: DNA
<213> ORGANISM: Artificial Sequence
<220> FEATURE:

<223> OTHER INFORMATION: Synthesized

<400> SEQUENCE: 163
caggtgcagc tgcaggagtc gggggaggc ctggtcaagc ctggagggtc cctgagactc 60
tcctgtgcag cctctggatt cacctttagt agttattgga tgagctgggt ccgccaggct 120
ccagggaagg ggctggagtg ggtggccaac ataaaccgcg atggaagtgc gagttactat 180
gtggactctg tgaagggccg attcaccatc tccagagacg acgccaagaa ctcactgtat 240
ctgcaaatga acagcctgag agctgaggac acggctgtgt attactgtgc gagagatcgt 300
ggggtgggct acttcgatct ctggggccgt ggcaccctgg tcaccgtctc gagcggtgga 360
ggcggttcag gcggaggtgg ttccggcggt ggcggctccc agtctgccct gactcagcct 420
gcctccgtgt ctgggtctcc tggacagtcg atcaccatct cctgcactgg aaccagcagt 480
gacgttggtg gttataactt tgtctcctgg taccaacaac acccaggcaa agcccccaaa 540
ctcatgatct atgatgtcag tgatcggccc tcaggggtgt ctgatcgctt ctccggctcc 600
aagtctggca acacggcctc cctgatcatc tctggcctcc aggctgacga cgaggctgat 660
tattactgca gctcatatgg gagcagcagc actcatgtga ttttcggcgg agggaccaag 720
gtgaccgtcc ta 732

<210> SEQ ID NO 164
<211> LENGTH: 703
<212> TYPE: PRT
<213> ORGANISM: Artificial Sequence
<220> FEATURE:
<223> OTHER INFORMATION: Synthesized

<400> SEQUENCE: 164

Gln Val Gln Leu Gln Glu Ser Gly Pro Gly Leu Val Lys Pro Ser Glu
1 5 10 15

Thr Leu Ser Leu Thr Cys Thr Val Ser Gly Gly Ser Val Ser Ser Gly
20 25 30

Asp Tyr Tyr Trp Thr Trp Ile Arg Gln Ser Pro Gly Lys Gly Leu Glu
35 40 45

Trp Ile Gly His Ile Tyr Tyr Ser Gly Asn Thr Asn Tyr Asn Pro Ser
50 55 60

Leu Lys Ser Arg Leu Thr Ile Ser Ile Asp Thr Ser Lys Thr Gln Phe
65 70 75 80

Ser Leu Lys Leu Ser Ser Val Thr Ala Ala Asp Thr Ala Ile Tyr Tyr
85 90 95

Cys Val Arg Asp Arg Val Thr Gly Ala Phe Asp Ile Trp Gly Gln Gly
100 105 110

Thr Met Val Thr Val Ser Ser Ala Ser Thr Lys Gly Pro Ser Val Phe
115 120 125

Pro Leu Ala Pro Ser Ser Lys Ser Thr Ser Gly Gly Thr Ala Ala Leu
130 135 140

Gly Cys Leu Val Lys Asp Tyr Phe Pro Glu Pro Val Thr Val Ser Trp
145 150 155 160

Asn Ser Gly Ala Leu Thr Ser Gly Val His Thr Phe Pro Ala Val Leu
165 170 175

Gln Ser Ser Gly Leu Tyr Ser Leu Ser Ser Val Val Thr Val Pro Ser
180 185 190

Ser Ser Leu Gly Thr Gln Thr Tyr Ile Cys Asn Val Asn His Lys Pro
195 200 205

-continued

```
Ser Asn Thr Lys Val Asp Lys Arg Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys Gly Gly Gly Gly Ser Gly Gly Gly Gly Ser Gln Val Gln Leu Gln
    450                 455                 460

Glu Ser Gly Gly Gly Leu Val Lys Pro Gly Gly Ser Leu Arg Leu Ser
465                 470                 475                 480

Cys Ala Ala Ser Gly Phe Thr Phe Ser Ser Tyr Trp Met Ser Trp Val
                485                 490                 495

Arg Gln Ala Pro Gly Lys Gly Leu Glu Trp Val Ala Asn Ile Asn Arg
            500                 505                 510

Asp Gly Ser Ala Ser Tyr Tyr Val Asp Ser Val Lys Gly Arg Phe Thr
        515                 520                 525

Ile Ser Arg Asp Asp Ala Lys Asn Ser Leu Tyr Leu Gln Met Asn Ser
    530                 535                 540

Leu Arg Ala Glu Asp Thr Ala Val Tyr Tyr Cys Ala Arg Asp Arg Gly
545                 550                 555                 560

Val Gly Tyr Phe Asp Leu Trp Gly Arg Gly Thr Leu Val Thr Val Ser
                565                 570                 575

Ser Gly Gly Gly Gly Ser Gly Gly Gly Gly Ser Gly Gly Gly Gly Ser
            580                 585                 590

Gln Ser Ala Leu Thr Gln Pro Ala Ser Val Ser Gly Ser Pro Gly Gln
        595                 600                 605

Ser Ile Thr Ile Ser Cys Thr Gly Thr Ser Ser Asp Val Gly Gly Tyr
    610                 615                 620

Asn Phe Val Ser Trp Tyr Gln Gln His Pro Gly Lys Ala Pro Lys Leu
```

-continued 625 630 635 640

Met Ile Tyr Asp Val Ser Asp Arg Pro Ser Gly Val Ser Asp Arg Phe
645 650 655

Ser Gly Ser Lys Ser Gly Asn Thr Ala Ser Leu Ile Ile Ser Gly Leu
660 665 670

Gln Ala Asp Asp Glu Ala Asp Tyr Tyr Cys Ser Ser Tyr Gly Ser Ser
675 680 685

Ser Thr His Val Ile Phe Gly Gly Gly Thr Lys Val Thr Val Leu
690 695 700

<210> SEQ ID NO 165
<211> LENGTH: 119
<212> TYPE: PRT
<213> ORGANISM: Artificial Sequence
<220> FEATURE:
<223> OTHER INFORMATION: Synthesized

<400> SEQUENCE: 165

Gln Val Gln Leu Gln Glu Ser Gly Pro Gly Leu Val Lys Pro Ser Glu
1 5 10 15

Thr Leu Ser Leu Thr Cys Thr Val Ser Gly Gly Ser Val Ser Ser Gly
20 25 30

Asp Tyr Tyr Trp Thr Trp Ile Arg Gln Ser Pro Gly Lys Gly Leu Glu
35 40 45

Trp Ile Gly His Ile Tyr Tyr Ser Gly Asn Thr Asn Tyr Asn Pro Ser
50 55 60

Leu Lys Ser Arg Leu Thr Ile Ser Ile Asp Thr Ser Lys Thr Gln Phe
65 70 75 80

Ser Leu Lys Leu Ser Ser Val Thr Ala Ala Asp Thr Ala Ile Tyr Tyr
85 90 95

Cys Val Arg Asp Arg Val Thr Gly Ala Phe Asp Ile Trp Gly Gln Gly
100 105 110

Thr Met Val Thr Val Ser Ser
115

<210> SEQ ID NO 166
<211> LENGTH: 244
<212> TYPE: PRT
<213> ORGANISM: Artificial Sequence
<220> FEATURE:
<223> OTHER INFORMATION: Synthesized

<400> SEQUENCE: 166

Gln Val Gln Leu Gln Glu Ser Gly Gly Gly Leu Val Lys Pro Gly Gly
1 5 10 15

Ser Leu Arg Leu Ser Cys Ala Ala Ser Gly Phe Thr Phe Ser Ser Tyr
20 25 30

Trp Met Ser Trp Val Arg Gln Ala Pro Gly Lys Gly Leu Glu Trp Val
35 40 45

Ala Asn Ile Asn Arg Asp Gly Ser Ala Ser Tyr Tyr Val Asp Ser Val
50 55 60

Lys Gly Arg Phe Thr Ile Ser Arg Asp Asp Ala Lys Asn Ser Leu Tyr
65 70 75 80

Leu Gln Met Asn Ser Leu Arg Ala Glu Asp Thr Ala Val Tyr Tyr Cys
85 90 95

Ala Arg Asp Arg Gly Val Gly Tyr Phe Asp Leu Trp Gly Arg Gly Thr
100 105 110

-continued

```
Leu Val Thr Val Ser Ser Gly Gly Gly Gly Ser Gly Gly Gly Gly Ser
        115                 120                 125

Gly Gly Gly Gly Ser Gln Ser Ala Leu Thr Gln Pro Ala Ser Val Ser
    130                 135                 140

Gly Ser Pro Gly Gln Ser Ile Thr Ile Ser Cys Thr Gly Thr Ser Ser
145                 150                 155                 160

Asp Val Gly Gly Tyr Asn Phe Val Ser Trp Tyr Gln Gln His Pro Gly
                165                 170                 175

Lys Ala Pro Lys Leu Met Ile Tyr Asp Val Ser Asp Arg Pro Ser Gly
            180                 185                 190

Val Ser Asp Arg Phe Ser Gly Ser Lys Ser Gly Asn Thr Ala Ser Leu
        195                 200                 205

Ile Ile Ser Gly Leu Gln Ala Asp Asp Glu Ala Asp Tyr Tyr Cys Ser
    210                 215                 220

Ser Tyr Gly Ser Ser Ser Thr His Val Ile Phe Gly Gly Gly Thr Lys
225                 230                 235                 240

Val Thr Val Leu


<210> SEQ ID NO 167
<211> LENGTH: 654
<212> TYPE: DNA
<213> ORGANISM: Artificial Sequence
<220> FEATURE:
<223> OTHER INFORMATION: Synthesized

<400> SEQUENCE: 167

cagtctgccc tgactcagcc tgcctccgtg tctgggtctc ctggacagtc gatcaccatc      60

tcctgcactg gaaccagcag tgacgttggt ggttataact ttgtctcctg gtaccaacaa     120

cacccaggca aagcccccaa actcatgatc tatgatgtca gtgatcggcc ctcaggggtg     180

tctgatcgct tctccggctc caagtctggc aacacggcct ccctgatcat ctctggcctc     240

caggctgacg acgaggctga ttattactgc agctcatatg ggagcagcag cactcatgtg     300

attttcggcg gagggaccaa gctgaccgtc ctacgtacgg tggctgcacc atctgtcttc     360

atcttcccgc catctgatga gcagttgaaa tctggaactg cctctgttgt gtgcctgctg     420

aataacttct atcccagaga ggccaaagta cagtggaagg tggataacgc cctccaatcg     480

ggtaactccc aggagagtgt cacagagcag gacagcaagg acagcaccta cagcctcagc     540

agcaccctga cgctgagcaa agcagactac gagaaacaca aagtctacgc ctgcgaagtc     600

acccatcagg gcctgagctc gcccgtcaca aagagcttca acaggggaga gtgt           654


<210> SEQ ID NO 168
<211> LENGTH: 333
<212> TYPE: DNA
<213> ORGANISM: Artificial Sequence
<220> FEATURE:
<223> OTHER INFORMATION: Synthesized

<400> SEQUENCE: 168

cagtctgccc tgactcagcc tgcctccgtg tctgggtctc ctggacagtc gatcaccatc      60

tcctgcactg gaaccagcag tgacgttggt ggttataact ttgtctcctg gtaccaacaa     120

cacccaggca aagcccccaa actcatgatc tatgatgtca gtgatcggcc ctcaggggtg     180

tctgatcgct tctccggctc caagtctggc aacacggcct ccctgatcat ctctggcctc     240

caggctgacg acgaggctga ttattactgc agctcatatg ggagcagcag cactcatgtg     300

attttcggcg gagggaccaa gctgaccgtc cta                                  333
```

<210> SEQ ID NO 169
<211> LENGTH: 218
<212> TYPE: PRT
<213> ORGANISM: Artificial Sequence
<220> FEATURE:
<223> OTHER INFORMATION: Synthesized

<400> SEQUENCE: 169

```
Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
            20                  25                  30

Asn Phe Val Ser Trp Tyr Gln Gln His Pro Gly Lys Ala Pro Lys Leu
        35                  40                  45

Met Ile Tyr Asp Val Ser Asp Arg Pro Ser Gly Val Ser Asp Arg Phe
    50                  55                  60

Ser Gly Ser Lys Ser Gly Asn Thr Ala Ser Leu Ile Ile Ser Gly Leu
65                  70                  75                  80

Gln Ala Asp Asp Glu Ala Asp Tyr Tyr Cys Ser Ser Tyr Gly Ser Ser
                85                  90                  95

Ser Thr His Val Ile Phe Gly Gly Gly Thr Lys Leu Thr Val Leu Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215
```

<210> SEQ ID NO 170
<211> LENGTH: 111
<212> TYPE: PRT
<213> ORGANISM: Artificial Sequence
<220> FEATURE:
<223> OTHER INFORMATION: Synthesized

<400> SEQUENCE: 170

```
Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
            20                  25                  30

Asn Phe Val Ser Trp Tyr Gln Gln His Pro Gly Lys Ala Pro Lys Leu
        35                  40                  45

Met Ile Tyr Asp Val Ser Asp Arg Pro Ser Gly Val Ser Asp Arg Phe
    50                  55                  60

Ser Gly Ser Lys Ser Gly Asn Thr Ala Ser Leu Ile Ile Ser Gly Leu
65                  70                  75                  80

Gln Ala Asp Asp Glu Ala Asp Tyr Tyr Cys Ser Ser Tyr Gly Ser Ser
```

-continued

```
              85                  90                  95

Ser Thr His Val Ile Phe Gly Gly Gly Thr Lys Leu Thr Val Leu
            100                 105                 110


<210> SEQ ID NO 171
<211> LENGTH: 2127
<212> TYPE: DNA
<213> ORGANISM: Artificial Sequence
<220> FEATURE:
<223> OTHER INFORMATION: Synthesized

<400> SEQUENCE: 171

caggtgcagc tgcaggagtc gggggggaggc ctggtcaagc ctggagggtc cctgagactc     60

tcctgtgcag cctctggatt caccttttagt agttattgga tgagctgggt ccgccaggct    120

ccagggaagg ggctggagtg ggtggccaac ataaaccgcg atggaagtgc gagttactat    180

gtggactctg tgaagggccg attcaccatc tccagagacg acgccaagaa ctcactgtat    240

ctgcaaatga acagcctgag agctgaggac acggctgtgt attactgtgc gagagatcgt    300

ggggtgggct acttcgatct ctggggccgt ggcaccctgg tcaccgtctc gagcgctagc    360

accaagggcc catcggtctt ccccctggca ccctcctcca agagcacctc tgggggcaca    420

gcggccctgg gctgcctggt caaggactac ttccccgaac cggtgacggt gtcgtggaac    480

tcaggcgccc tgaccagcgg cgtgcacacc ttcccggctg tcctacagtc ctcaggactc    540

tactccctca gcagcgtggt gaccgtgccc tccagcagct tgggcaccca gacctacatc    600

tgcaacgtga atcacaagcc cagcaacacc aaggtggaca agagagttga gcccaaatct    660

tgtgacaaaa ctcacacatg cccaccgtgc ccagcacctg aactcctggg gggaccgtca    720

gtcttcctct tcccccccaaa acccaaggac accctcatga tctcccggac ccctgaggtc    780

acatgcgtgg tggtggacgt gagccacgaa gaccctgagg tcaagttcaa ctggtacgtg    840

gacggcgtgg aggtgcataa tgccaagaca aagccgcggg aggagcagta caacagcacg    900

taccgtgtgg tcagcgtcct caccgtcctg caccaggact ggctgaatgg caaggagtac    960

aagtgcaagg tctccaacaa agccctccca gcccccatcg agaaaaccat ctccaaagcc   1020

aaagggcagc cccgagaacc acaggtgtac accctgcccc catcccggga ggagatgacc   1080

aagaaccagg tcagcctgac ctgcctggtc aaaggcttct atcccagcga catcgccgtg   1140

gagtgggaga gcaatgggca gccggagaac aactacaaga ccacgcctcc cgtgctggac   1200

tccgacggct ccttcttcct ctatagcaag ctcaccgtgg acaagagcag gtggcagcag   1260

gggaacgtct tctcatgctc cgtgatgcat gaggctctgc acaaccacta cacgcagaag   1320

agcctctccc tgtctccggg taaaggcggt ggaggatccg gcggtggtgg atcacaagtt   1380

caacttcaac aatctggtgc tgaagttaaa aaacctggtt cttctgttaa agtttcttgt   1440

aaagcctctg gttatacttt tactaattat tatatttatt gggttcgtca agctcctggt   1500

caaggtcttg aatggattgg tggtattaat cctacttctg gtggttctaa ttttaatgaa   1560

aaatttaaaa ctcgtgttac tattactgtt gatgaatcta cgaacactgc ttatatggaa   1620

ctttcttctc ttcgttctga agatactgct tttttatttt gtgcgcgtca aggtctttgg   1680

tttgattctg atggtcgtgg ttttgatttt tggggtcaag gttccactgt tactgtctcg   1740

agcggtggag gcggttcagg cggaggtggt tccggcggtg gcggctccga tattcaaatg   1800

actcaatctc cttcttctct ttctgcttct gttggtgatc gtgttactat tacttgtcgt   1860

tcttctcaaa atattgttca ttctaatggt aatacttatc ttgattggta tcaacaaact   1920
```

-continued cctggtaaag ctcctaaact tcttatttat aaagtttcta atcgtttttc tggtgttcct 1980
tctcgttttt ctggttctgg ttctggtact gattttactt ttactatttc ttctcttcaa 2040
cctgaagata ttgctactta ttattgtttt caatattctc atgttccttg gacttttggt 2100
caaggtacta aacttcaaat tactcgt 2127

<210> SEQ ID NO 172
<211> LENGTH: 354
<212> TYPE: DNA
<213> ORGANISM: Artificial Sequence
<220> FEATURE:
<223> OTHER INFORMATION: Synthesized

<400> SEQUENCE: 172
caggtgcagc tgcaggagtc gggggaggc ctggtcaagc ctggagggtc cctgagactc 60
tcctgtgcag cctctggatt cacctttagt agttattgga tgagctgggt ccgccaggct 120
ccagggaagg ggctggagtg ggtggccaac ataaaccgcg atggaagtgc gagttactat 180
gtggactctg tgaagggccg attcaccatc tccagagacg acgccaagaa ctcactgtat 240
ctgcaaatga acagcctgag agctgaggac acggctgtgt attactgtgc gagagatcgt 300
ggggtgggct acttcgatct ctggggccgt ggcaccctgg tcaccgtctc gagc 354

<210> SEQ ID NO 173
<211> LENGTH: 753
<212> TYPE: DNA
<213> ORGANISM: Artificial Sequence
<220> FEATURE:
<223> OTHER INFORMATION: Synthesized

<400> SEQUENCE: 173
caagttcaac ttcaacaatc tggtgctgaa gttaaaaaac ctggttcttc tgttaaagtt 60
tcttgtaaag cctctggtta tacttttact aattattata tttattgggt tcgtcaagct 120
cctggtcaag gtcttgaatg gattggtggt attaatccta cttctggtgg ttctaatttt 180
aatgaaaaat ttaaaactcg tgttactatt actgttgatg aatctacgaa cactgcttat 240
atggaacttt cttctcttcg ttctgaagat actgcttttt atttttgtgc gcgtcaaggt 300
ctttggtttg attctgatgg tcgtggtttt gatttttggg gtcaaggttc cactgttact 360
gtctcgagcg gtggaggcgg ttcaggcgga ggtggttccg gcggtggcgg ctccgatatt 420
caaatgactc aatctccttc ttctctttct gcttctgttg gtgatcgtgt tactattact 480
tgtcgttctt ctcaaaatat tgttcattct aatggtaata cttatcttga ttggtatcaa 540
caaactcctg gtaaagctcc taaacttctt atttataaag tttctaatcg tttttctggt 600
gttccttctc gtttttctgg ttctggttct ggtactgatt ttacttttac tatttcttct 660
cttcaacctg aagatattgc tacttattat tgttttcaat attctcatgt tccttggact 720
tttggtcaag gtactaaact tcaaattact cgt 753

<210> SEQ ID NO 174
<211> LENGTH: 709
<212> TYPE: PRT
<213> ORGANISM: Artificial Sequence
<220> FEATURE:
<223> OTHER INFORMATION: Synthesized

<400> SEQUENCE: 174

Gln Val Gln Leu Gln Glu Ser Gly Gly Gly Leu Val Lys Pro Gly Gly
1               5                   10                  15

-continued

```
Ser Leu Arg Leu Ser Cys Ala Ala Ser Gly Phe Thr Phe Ser Ser Tyr
            20                  25                  30

Trp Met Ser Trp Val Arg Gln Ala Pro Gly Lys Gly Leu Glu Trp Val
        35                  40                  45

Ala Asn Ile Asn Arg Asp Gly Ser Ala Ser Tyr Tyr Val Asp Ser Val
    50                  55                  60

Lys Gly Arg Phe Thr Ile Ser Arg Asp Asp Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Arg Gly Val Gly Tyr Phe Asp Leu Trp Gly Arg Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Arg Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Glu Glu Met Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
```

```
        435                 440                 445

Gly Gly Gly Gly Ser Gly Gly Gly Gly Ser Gln Val Gln Leu Gln Gln
    450                 455                 460

Ser Gly Ala Glu Val Lys Lys Pro Gly Ser Ser Val Lys Val Ser Cys
465                 470                 475                 480

Lys Ala Ser Gly Tyr Thr Phe Thr Asn Tyr Tyr Ile Tyr Trp Val Arg
                485                 490                 495

Gln Ala Pro Gly Gln Gly Leu Glu Trp Ile Gly Gly Ile Asn Pro Thr
            500                 505                 510

Ser Gly Gly Ser Asn Phe Asn Glu Lys Phe Lys Thr Arg Val Thr Ile
        515                 520                 525

Thr Val Asp Glu Ser Thr Asn Thr Ala Tyr Met Glu Leu Ser Ser Leu
    530                 535                 540

Arg Ser Glu Asp Thr Ala Phe Tyr Phe Cys Ala Arg Gln Gly Leu Trp
545                 550                 555                 560

Phe Asp Ser Asp Gly Arg Gly Phe Asp Phe Trp Gly Gln Gly Ser Thr
                565                 570                 575

Val Thr Val Ser Ser Gly Gly Gly Gly Ser Gly Gly Gly Gly Ser Gly
            580                 585                 590

Gly Gly Gly Ser Asp Ile Gln Met Thr Gln Ser Pro Ser Ser Leu Ser
        595                 600                 605

Ala Ser Val Gly Asp Arg Val Thr Ile Thr Cys Arg Ser Ser Gln Asn
    610                 615                 620

Ile Val His Ser Asn Gly Asn Thr Tyr Leu Asp Trp Tyr Gln Gln Thr
625                 630                 635                 640

Pro Gly Lys Ala Pro Lys Leu Leu Ile Tyr Lys Val Ser Asn Arg Phe
                645                 650                 655

Ser Gly Val Pro Ser Arg Phe Ser Gly Ser Gly Ser Gly Thr Asp Phe
            660                 665                 670

Thr Phe Thr Ile Ser Ser Leu Gln Pro Glu Asp Ile Ala Thr Tyr Tyr
        675                 680                 685

Cys Phe Gln Tyr Ser His Val Pro Trp Thr Phe Gly Gln Gly Thr Lys
    690                 695                 700

Leu Gln Ile Thr Arg
705
```

<210> SEQ ID NO 175
<211> LENGTH: 118
<212> TYPE: PRT
<213> ORGANISM: Artificial Sequence
<220> FEATURE:
<223> OTHER INFORMATION: Synthesized

<400> SEQUENCE: 175

```
Gln Val Gln Leu Gln Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Trp Met Ser Trp Val Arg Gln Ala Pro Gly Lys Gly Leu Glu Trp Val
        35                  40                  45

Ala Asn Ile Asn Arg Asp Gly Ser Ala Ser Tyr Tyr Val Asp Ser Val
    50                  55                  60

Lys Gly Arg Phe Thr Ile Ser Arg Asp Asp Ala Lys Asn Ser Leu Tyr
65                  70                  75                  80

Leu Gln Met Asn Ser Leu Arg Ala Glu Asp Thr Ala Val Tyr Tyr Cys
```

```
                85                  90                  95

Ala Arg Asp Arg Gly Val Gly Tyr Phe Asp Leu Trp Gly Arg Gly Thr
            100                 105                 110

Leu Val Thr Val Ser Ser
        115


<210> SEQ ID NO 176
<211> LENGTH: 251
<212> TYPE: PRT
<213> ORGANISM: Artificial Sequence
<220> FEATURE:
<223> OTHER INFORMATION: Synthesized

<400> SEQUENCE: 176

Gln Val Gln Leu Gln Gln Ser Gly Ala Glu Val Lys Lys Pro Gly Ser
1               5                   10                  15

Ser Val Lys Val Ser Cys Lys Ala Ser Gly Tyr Thr Phe Thr Asn Tyr
            20                  25                  30

Tyr Ile Tyr Trp Val Arg Gln Ala Pro Gly Gln Gly Leu Glu Trp Ile
        35                  40                  45

Gly Gly Ile Asn Pro Thr Ser Gly Gly Ser Asn Phe Asn Glu Lys Phe
    50                  55                  60

Lys Thr Arg Val Thr Ile Thr Val Asp Glu Ser Thr Asn Thr Ala Tyr
65                  70                  75                  80

Met Glu Leu Ser Ser Leu Arg Ser Glu Asp Thr Ala Phe Tyr Phe Cys
                85                  90                  95

Ala Arg Gln Gly Leu Trp Phe Asp Ser Asp Gly Arg Gly Phe Asp Phe
            100                 105                 110

Trp Gly Gln Gly Ser Thr Val Thr Val Ser Ser Gly Gly Gly Gly Ser
        115                 120                 125

Gly Gly Gly Gly Ser Gly Gly Gly Gly Ser Asp Ile Gln Met Thr Gln
    130                 135                 140

Ser Pro Ser Ser Leu Ser Ala Ser Val Gly Asp Arg Val Thr Ile Thr
145                 150                 155                 160

Cys Arg Ser Ser Gln Asn Ile Val His Ser Asn Gly Asn Thr Tyr Leu
                165                 170                 175

Asp Trp Tyr Gln Gln Thr Pro Gly Lys Ala Pro Lys Leu Leu Ile Tyr
            180                 185                 190

Lys Val Ser Asn Arg Phe Ser Gly Val Pro Ser Arg Phe Ser Gly Ser
        195                 200                 205

Gly Ser Gly Thr Asp Phe Thr Phe Thr Ile Ser Ser Leu Gln Pro Glu
    210                 215                 220

Asp Ile Ala Thr Tyr Tyr Cys Phe Gln Tyr Ser His Val Pro Trp Thr
225                 230                 235                 240

Phe Gly Gln Gly Thr Lys Leu Gln Ile Thr Arg
                245                 250


<210> SEQ ID NO 177
<211> LENGTH: 657
<212> TYPE: DNA
<213> ORGANISM: Artificial Sequence
<220> FEATURE:
<223> OTHER INFORMATION: Synthesized

<400> SEQUENCE: 177

gatattcaaa tgactcaatc tccttcttct ctttctgctt ctgttggtga tcgtgttact      60

attacttgtc gttcttctca aaatattgtt cattctaatg gtaatactta tcttgattgg     120
```

```
tatcaacaaa ctcctggtaa agctcctaaa cttcttattt ataaagtttc taatcgtttt    180

tctggtgttc cttctcgttt ttctggttct ggttctggta ctgattttac ttttactatt    240

tcttctcttc aacctgaaga tattgctact tattattgtt ttcaatattc tcatgttcct    300

tggacttttg gtcaaggtac taaacttcaa attactcgta cggtggctgc accatctgtc    360

ttcatcttcc cgccatctga tgagcagttg aaatctggaa ctgcctctgt tgtgtgcctg    420

ctgaataact tctatcccag agaggccaaa gtacagtgga aggtggataa cgccctccaa    480

tcgggtaact cccaggagag tgtcacagag caggacagca aggacagcac ctacagcctc    540

agcagcaccc tgacgctgag caaagcagac tacgagaaac acaaagtcta cgcctgcgaa    600

gtcacccatc agggcctgag ctcgcccgtc acaaagagct tcaacagggg agagtgt       657
```

<210> SEQ ID NO 178
<211> LENGTH: 336
<212> TYPE: DNA
<213> ORGANISM: Artificial Sequence
<220> FEATURE:
<223> OTHER INFORMATION: Synthesized

<400> SEQUENCE: 178

```
gatattcaaa tgactcaatc tccttcttct ctttctgctt ctgttggtga tcgtgttact     60

attacttgtc gttcttctca aaatattgtt cattctaatg gtaatactta tcttgattgg    120

tatcaacaaa ctcctggtaa agctcctaaa cttcttattt ataaagtttc taatcgtttt    180

tctggtgttc cttctcgttt ttctggttct ggttctggta ctgattttac ttttactatt    240

tcttctcttc aacctgaaga tattgctact tattattgtt ttcaatattc tcatgttcct    300

tggacttttg gtcaaggtac taaacttcaa attact                              336
```

<210> SEQ ID NO 179
<211> LENGTH: 219
<212> TYPE: PRT
<213> ORGANISM: Artificial Sequence
<220> FEATURE:
<223> OTHER INFORMATION: Synthesized

<400> SEQUENCE: 179

```
Asp Ile Gln Met Thr Gln Ser Pro Ser Ser Leu Ser Ala Ser Val Gly
1               5                   10                  15

Asp Arg Val Thr Ile Thr Cys Arg Ser Ser Gln Asn Ile Val His Ser
            20                  25                  30

Asn Gly Asn Thr Tyr Leu Asp Trp Tyr Gln Gln Thr Pro Gly Lys Ala
        35                  40                  45

Pro Lys Leu Leu Ile Tyr Lys Val Ser Asn Arg Phe Ser Gly Val Pro
    50                  55                  60

Ser Arg Phe Ser Gly Ser Gly Ser Gly Thr Asp Phe Thr Phe Thr Ile
65                  70                  75                  80

Ser Ser Leu Gln Pro Glu Asp Ile Ala Thr Tyr Tyr Cys Phe Gln Tyr
                85                  90                  95

Ser His Val Pro Trp Thr Phe Gly Gln Gly Thr Lys Leu Gln Ile Thr
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
```

145 150 155 160

Ser Gly Asn Ser Gln Glu Ser Val Thr Glu Gln Asp Ser Lys Asp Ser
165 170 175

Thr Tyr Ser Leu Ser Ser Thr Leu Thr Leu Ser Lys Ala Asp Tyr Glu
180 185 190

Lys His Lys Val Tyr Ala Cys Glu Val Thr His Gln Gly Leu Ser Ser
195 200 205

Pro Val Thr Lys Ser Phe Asn Arg Gly Glu Cys
210 215

<210> SEQ ID NO 180
<211> LENGTH: 112
<212> TYPE: PRT
<213> ORGANISM: Artificial Sequence
<220> FEATURE:
<223> OTHER INFORMATION: Synthesized

<400> SEQUENCE: 180

Asp Ile Gln Met Thr Gln Ser Pro Ser Ser Leu Ser Ala Ser Val Gly
1 5 10 15

Asp Arg Val Thr Ile Thr Cys Arg Ser Ser Gln Asn Ile Val His Ser
20 25 30

Asn Gly Asn Thr Tyr Leu Asp Trp Tyr Gln Gln Thr Pro Gly Lys Ala
35 40 45

Pro Lys Leu Leu Ile Tyr Lys Val Ser Asn Arg Phe Ser Gly Val Pro
50 55 60

Ser Arg Phe Ser Gly Ser Gly Ser Gly Thr Asp Phe Thr Phe Thr Ile
65 70 75 80

Ser Ser Leu Gln Pro Glu Asp Ile Ala Thr Tyr Tyr Cys Phe Gln Tyr
85 90 95

Ser His Val Pro Trp Thr Phe Gly Gln Gly Thr Lys Leu Gln Ile Thr
100 105 110

<210> SEQ ID NO 181
<211> LENGTH: 2121
<212> TYPE: DNA
<213> ORGANISM: Artificial Sequence
<220> FEATURE:
<223> OTHER INFORMATION: Synthesized

<400> SEQUENCE: 181
caagttcaac ttcaacaatc tggtgctgaa gttaaaaaac ctggttcttc tgttaaagtt 60
tcttgtaaag cctctggtta tacttttact aattattata tttattgggt tcgtcaagct 120
cctggtcaag gtcttgaatg gattggtggt attaatccta cttctggtgg ttctaatttt 180
aatgaaaaat ttaaaactcg tgttactatt actgttgatg aatctacgaa cactgcttat 240
atggaacttt cttctcttcg ttctgaagat actgcttttt atttttgtgc gcgtcaaggt 300
ctttggtttg attctgatgg tcgtggtttt gatttttggg gtcaaggttc cactgttact 360
gtctcgagcg ctagcaccaa gggcccatcg gtcttccccc tggcaccctc ctccaagagc 420
acctctgggg gcacagcggc cctgggctgc ctggtcaagg actacttccc cgaaccggtg 480
acggtgtcgt ggaactcagg cgccctgacc agcggcgtgc acaccttccc ggctgtccta 540
cagtcctcag gactctactc cctcagcagc gtggtgaccg tgccctccag cagcttgggc 600
acccagacct acatctgcaa cgtgaatcac aagcccagca acaccaaggt ggacaagaga 660
gttgagccca aatcttgtga caaaactcac acatgcccac cgtgcccagc acctgaactc 720

-continued

```
ctggggggac cgtcagtctt cctcttcccc ccaaaaccca aggacaccct catgatctcc    780

cggacccctg aggtcacatg cgtggtggtg gacgtgagcc acgaagaccc tgaggtcaag    840

ttcaactggt acgtggacgg cgtggaggtg cataatgcca agacaaagcc gcgggaggag    900

cagtacaaca gcacgtaccg tgtggtcagc gtcctcaccg tcctgcacca ggactggctg    960

aatggcaagg agtacaagtg caaggtctcc aacaaagccc tcccagcccc catcgagaaa   1020

accatctcca aagccaaagg gcagccccga gaaccacagg tgtacaccct gcccccatcc   1080

cgggaggaga tgaccaagaa ccaggtcagc ctgacctgcc tggtcaaagg cttctatccc   1140

agcgacatcg ccgtggagtg ggagagcaat gggcagccgg agaacaacta caagaccacg   1200

cctcccgtgc tggactccga cggctccttc ttcctctata gcaagctcac cgtggacaag   1260

agcaggtggc agcaggggaa cgtcttctca tgctccgtga tgcatgaggc tctgcacaac   1320

cactacacgc agaagagcct ctccctgtct ccgggtaaag gcggtggagg atccggcggt   1380

ggtggatcac aggtgcagct gcaggagtcg gggggaggcc tggtcaagcc tggagggtcc   1440

ctgagactct cctgtgcagc ctctggattc acctttagta gttattggat gagctgggtc   1500

cgccaggctc cagggaaggg gctggagtgg gtggccaaca taaaccgcga tggaagtgcg   1560

agttactatg tggactctgt gaagggccga ttcaccatct ccagagacga cgccaagaac   1620

tcactgtatc tgcaaatgaa cagcctgaga gctgaggaca cggctgtgta ttactgtgcg   1680

agagatcgtg gggtgggcta cttcgatctc tggggccgtg gcaccctggt caccgtctcg   1740

agcggtggag gcggttcagg cggaggtggt tccggcggtg gcggctccca gtctgccctg   1800

actcagcctg cctccgtgtc tgggtctcct ggacagtcga tcaccatctc ctgcactgga   1860

accagcagtg acgttggtgg ttataacttt gtctcctggt accaacaaca cccaggcaaa   1920

gcccccaaac tcatgatcta tgatgtcagt gatcggccct caggggtgtc tgatcgcttc   1980

tccggctcca agtctggcaa cacggcctcc ctgatcatct ctggcctcca ggctgacgac   2040

gaggctgatt attactgcag ctcatatggg agcagcagca ctcatgtgat tttcggcgga   2100

gggaccaagg tgaccgtcct a                                              2121
```

<210> SEQ ID NO 182
<211> LENGTH: 369
<212> TYPE: DNA
<213> ORGANISM: Artificial Sequence
<220> FEATURE:
<223> OTHER INFORMATION: Synthesized

<400> SEQUENCE: 182

```
caagttcaac ttcaacaatc tggtgctgaa gttaaaaaac ctggttcttc tgttaaagtt     60

tcttgtaaag cctctggtta tacttttact aattattata tttattgggt tcgtcaagct    120

cctggtcaag gtcttgaatg gattggtggt attaatccta cttctggtgg ttctaatttt    180

aatgaaaaat ttaaaactcg tgttactatt actgttgatg aatctacgaa cactgcttat    240

atggaacttt cttctcttcg ttctgaagat actgcttttt atttttgtgc gcgtcaaggt    300

ctttggtttg attctgatgg tcgtggtttt gatttttggg gtcaaggttc cactgttact    360

gtctcgagc                                                            369
```

<210> SEQ ID NO 183
<211> LENGTH: 732
<212> TYPE: DNA
<213> ORGANISM: Artificial Sequence
<220> FEATURE:
<223> OTHER INFORMATION: Synthesized

<400> SEQUENCE: 183
caggtgcagc tgcaggagtc ggggggaggc ctggtcaagc ctggagggtc cctgagactc 60
tcctgtgcag cctctggatt cacctttagt agttattgga tgagctgggt ccgccaggct 120
ccagggaagg ggctggagtg ggtggccaac ataaaccgcg atggaagtgc gagttactat 180
gtggactctg tgaagggccg attcaccatc tccagagacg acgccaagaa ctcactgtat 240
ctgcaaatga acagcctgag agctgaggac acggctgtgt attactgtgc gagagatcgt 300
ggggtgggct acttcgatct ctggggccgt ggcaccctgg tcaccgtctc gagcggtgga 360
ggcggttcag gcggaggtgg ttccggcggt ggcggctccc agtctgccct gactcagcct 420
gcctccgtgt ctgggtctcc tggacagtcg atcaccatct cctgcactgg aaccagcagt 480
gacgttggtg gttataactt tgtctcctgg taccaacaac acccaggcaa agcccccaaa 540
ctcatgatct atgatgtcag tgatcggccc tcaggggtgt ctgatcgctt ctccggctcc 600
aagtctggca acacggcctc cctgatcatc tctggcctcc aggctgacga cgaggctgat 660
tattactgca gctcatatgg gagcagcagc actcatgtga ttttcggcgg agggaccaag 720
gtgaccgtcc ta 732

<210> SEQ ID NO 184
<211> LENGTH: 707
<212> TYPE: PRT
<213> ORGANISM: Artificial Sequence
<220> FEATURE:
<223> OTHER INFORMATION: Synthesized

<400> SEQUENCE: 184

Gln Val Gln Leu Gln Gln Ser Gly Ala Glu Val Lys Lys Pro Gly Ser
1 5 10 15

Ser Val Lys Val Ser Cys Lys Ala Ser Gly Tyr Thr Phe Thr Asn Tyr
20 25 30

Tyr Ile Tyr Trp Val Arg Gln Ala Pro Gly Gln Gly Leu Glu Trp Ile
35 40 45

Gly Gly Ile Asn Pro Thr Ser Gly Gly Ser Asn Phe Asn Glu Lys Phe
50 55 60

Lys Thr Arg Val Thr Ile Thr Val Asp Glu Ser Thr Asn Thr Ala Tyr
65 70 75 80

Met Glu Leu Ser Ser Leu Arg Ser Glu Asp Thr Ala Phe Tyr Phe Cys
85 90 95

Ala Arg Gln Gly Leu Trp Phe Asp Ser Asp Gly Arg Gly Phe Asp Phe
100 105 110

Trp Gly Gln Gly Ser Thr Val Thr Val Ser Ser Ala Ser Thr Lys Gly
115 120 125

Pro Ser Val Phe Pro Leu Ala Pro Ser Ser Lys Ser Thr Ser Gly Gly
130 135 140

Thr Ala Ala Leu Gly Cys Leu Val Lys Asp Tyr Phe Pro Glu Pro Val
145 150 155 160

Thr Val Ser Trp Asn Ser Gly Ala Leu Thr Ser Gly Val His Thr Phe
165 170 175

Pro Ala Val Leu Gln Ser Ser Gly Leu Tyr Ser Leu Ser Ser Val Val
180 185 190

Thr Val Pro Ser Ser Ser Leu Gly Thr Gln Thr Tyr Ile Cys Asn Val
195 200 205

Asn His Lys Pro Ser Asn Thr Lys Val Asp Lys Arg Val Glu Pro Lys

```
    210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Asn Ser
    290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
            340                 345                 350

Gln Val Tyr Thr Leu Pro Pro Ser Arg Glu Glu Met Thr Lys Asn Gln
        355                 360                 365

Val Ser Leu Thr Cys Leu Val Lys Gly Phe Tyr Pro Ser Asp Ile Ala
    370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
            420                 425                 430

Val Met His Glu Ala Leu His Asn His Tyr Thr Gln Lys Ser Leu Ser
        435                 440                 445

Leu Ser Pro Gly Lys Gly Gly Gly Gly Ser Gly Gly Gly Gly Ser Gln
    450                 455                 460

Val Gln Leu Gln Glu Ser Gly Gly Gly Leu Val Lys Pro Gly Gly Ser
465                 470                 475                 480

Leu Arg Leu Ser Cys Ala Ala Ser Gly Phe Thr Phe Ser Ser Tyr Trp
                485                 490                 495

Met Ser Trp Val Arg Gln Ala Pro Gly Lys Gly Leu Glu Trp Val Ala
            500                 505                 510

Asn Ile Asn Arg Asp Gly Ser Ala Ser Tyr Tyr Val Asp Ser Val Lys
        515                 520                 525

Gly Arg Phe Thr Ile Ser Arg Asp Asp Ala Lys Asn Ser Leu Tyr Leu
    530                 535                 540

Gln Met Asn Ser Leu Arg Ala Glu Asp Thr Ala Val Tyr Tyr Cys Ala
545                 550                 555                 560

Arg Asp Arg Gly Val Gly Tyr Phe Asp Leu Trp Gly Arg Gly Thr Leu
                565                 570                 575

Val Thr Val Ser Ser Gly Gly Gly Gly Ser Gly Gly Gly Gly Ser Gly
            580                 585                 590

Gly Gly Gly Ser Gln Ser Ala Leu Thr Gln Pro Ala Ser Val Ser Gly
        595                 600                 605

Ser Pro Gly Gln Ser Ile Thr Ile Ser Cys Thr Gly Thr Ser Ser Asp
    610                 615                 620

Val Gly Gly Tyr Asn Phe Val Ser Trp Tyr Gln Gln His Pro Gly Lys
625                 630                 635                 640
```

-continued

Ala Pro Lys Leu Met Ile Tyr Asp Val Ser Asp Arg Pro Ser Gly Val
645 650 655

Ser Asp Arg Phe Ser Gly Ser Lys Ser Gly Asn Thr Ala Ser Leu Ile
660 665 670

Ile Ser Gly Leu Gln Ala Asp Asp Glu Ala Asp Tyr Tyr Cys Ser Ser
675 680 685

Tyr Gly Ser Ser Ser Thr His Val Ile Phe Gly Gly Gly Thr Lys Val
690 695 700

Thr Val Leu
705

<210> SEQ ID NO 185
<211> LENGTH: 123
<212> TYPE: PRT
<213> ORGANISM: Artificial Sequence
<220> FEATURE:
<223> OTHER INFORMATION: Synthesized

<400> SEQUENCE: 185

Gln Val Gln Leu Gln Gln Ser Gly Ala Glu Val Lys Lys Pro Gly Ser
1 5 10 15

Ser Val Lys Val Ser Cys Lys Ala Ser Gly Tyr Thr Phe Thr Asn Tyr
20 25 30

Tyr Ile Tyr Trp Val Arg Gln Ala Pro Gly Gln Gly Leu Glu Trp Ile
35 40 45

Gly Gly Ile Asn Pro Thr Ser Gly Gly Ser Asn Phe Asn Glu Lys Phe
50 55 60

Lys Thr Arg Val Thr Ile Thr Val Asp Glu Ser Thr Asn Thr Ala Tyr
65 70 75 80

Met Glu Leu Ser Ser Leu Arg Ser Glu Asp Thr Ala Phe Tyr Phe Cys
85 90 95

Ala Arg Gln Gly Leu Trp Phe Asp Ser Asp Gly Arg Gly Phe Asp Phe
100 105 110

Trp Gly Gln Gly Ser Thr Val Thr Val Ser Ser
115 120

<210> SEQ ID NO 186
<211> LENGTH: 244
<212> TYPE: PRT
<213> ORGANISM: Artificial Sequence
<220> FEATURE:
<223> OTHER INFORMATION: Synthesized

<400> SEQUENCE: 186

Gln Val Gln Leu Gln Glu Ser Gly Gly Gly Leu Val Lys Pro Gly Gly
1 5 10 15

Ser Leu Arg Leu Ser Cys Ala Ala Ser Gly Phe Thr Phe Ser Ser Tyr
20 25 30

Trp Met Ser Trp Val Arg Gln Ala Pro Gly Lys Gly Leu Glu Trp Val
35 40 45

Ala Asn Ile Asn Arg Asp Gly Ser Ala Ser Tyr Tyr Val Asp Ser Val
50 55 60

Lys Gly Arg Phe Thr Ile Ser Arg Asp Asp Ala Lys Asn Ser Leu Tyr
65 70 75 80

Leu Gln Met Asn Ser Leu Arg Ala Glu Asp Thr Ala Val Tyr Tyr Cys
85 90 95

Ala Arg Asp Arg Gly Val Gly Tyr Phe Asp Leu Trp Gly Arg Gly Thr

```
            100                 105                 110

Leu Val Thr Val Ser Ser Gly Gly Gly Gly Ser Gly Gly Gly Gly Ser
        115                 120                 125

Gly Gly Gly Gly Ser Gln Ser Ala Leu Thr Gln Pro Ala Ser Val Ser
    130                 135                 140

Gly Ser Pro Gly Gln Ser Ile Thr Ile Ser Cys Thr Gly Thr Ser Ser
145                 150                 155                 160

Asp Val Gly Gly Tyr Asn Phe Val Ser Trp Tyr Gln Gln His Pro Gly
                165                 170                 175

Lys Ala Pro Lys Leu Met Ile Tyr Asp Val Ser Asp Arg Pro Ser Gly
            180                 185                 190

Val Ser Asp Arg Phe Ser Gly Ser Lys Ser Gly Asn Thr Ala Ser Leu
        195                 200                 205

Ile Ile Ser Gly Leu Gln Ala Asp Asp Glu Ala Asp Tyr Tyr Cys Ser
    210                 215                 220

Ser Tyr Gly Ser Ser Ser Thr His Val Ile Phe Gly Gly Gly Thr Lys
225                 230                 235                 240

Val Thr Val Leu


<210> SEQ ID NO 187
<211> LENGTH: 654
<212> TYPE: DNA
<213> ORGANISM: Artificial Sequence
<220> FEATURE:
<223> OTHER INFORMATION: Synthesized

<400> SEQUENCE: 187

cagtctgccc tgactcagcc tgcctccgtg tctgggtctc ctggacagtc gatcaccatc      60

tcctgcactg gaaccagcag tgacgttggt ggttataact ttgtctcctg gtaccaacaa     120

cacccaggca aagcccccaa actcatgatc tatgatgtca gtgatcggcc ctcaggggtg     180

tctgatcgct tctccggctc caagtctggc aacacggcct ccctgatcat ctctggcctc     240

caggctgacg acgaggctga ttattactgc agctcatatg ggagcagcag cactcatgtg     300

attttcggcg gagggaccaa gctgaccgtc ctacgtacgg tggctgcacc atctgtcttc     360

atcttcccgc catctgatga gcagttgaaa tctggaactg cctctgttgt gtgcctgctg     420

aataacttct atcccagaga ggccaaagta cagtggaagg tggataacgc cctccaatcg     480

ggtaactccc aggagagtgt cacagagcag gacagcaagg acagcaccta cagcctcagc     540

agcaccctga cgctgagcaa agcagactac gagaaacaca aagtctacgc ctgcgaagtc     600

acccatcagg gcctgagctc gcccgtcaca aagagcttca acaggggaga gtgt           654


<210> SEQ ID NO 188
<211> LENGTH: 333
<212> TYPE: DNA
<213> ORGANISM: Artificial Sequence
<220> FEATURE:
<223> OTHER INFORMATION: Synthesized

<400> SEQUENCE: 188

cagtctgccc tgactcagcc tgcctccgtg tctgggtctc ctggacagtc gatcaccatc      60

tcctgcactg gaaccagcag tgacgttggt ggttataact ttgtctcctg gtaccaacaa     120

cacccaggca aagcccccaa actcatgatc tatgatgtca gtgatcggcc ctcaggggtg     180

tctgatcgct tctccggctc caagtctggc aacacggcct ccctgatcat ctctggcctc     240

caggctgacg acgaggctga ttattactgc agctcatatg ggagcagcag cactcatgtg     300
```

atttcggcg gagggaccaa gctgaccgtc cta 333

<210> SEQ ID NO 189
<211> LENGTH: 218
<212> TYPE: PRT
<213> ORGANISM: Artificial Sequence
<220> FEATURE:
<223> OTHER INFORMATION: Synthesized

<400> SEQUENCE: 189

Gln Ser Ala Leu Thr Gln Pro Ala Ser Val Ser Gly Ser Pro Gly Gln
1 5 10 15

Ser Ile Thr Ile Ser Cys Thr Gly Thr Ser Ser Asp Val Gly Gly Tyr
20 25 30

Asn Phe Val Ser Trp Tyr Gln Gln His Pro Gly Lys Ala Pro Lys Leu
35 40 45

Met Ile Tyr Asp Val Ser Asp Arg Pro Ser Gly Val Ser Asp Arg Phe
50 55 60

Ser Gly Ser Lys Ser Gly Asn Thr Ala Ser Leu Ile Ile Ser Gly Leu
65 70 75 80

Gln Ala Asp Asp Glu Ala Asp Tyr Tyr Cys Ser Ser Tyr Gly Ser Ser
85 90 95

Ser Thr His Val Ile Phe Gly Gly Gly Thr Lys Leu Thr Val Leu Arg
100 105 110

Thr Val Ala Ala Pro Ser Val Phe Ile Phe Pro Pro Ser Asp Glu Gln
115 120 125

Leu Lys Ser Gly Thr Ala Ser Val Val Cys Leu Leu Asn Asn Phe Tyr
130 135 140

Pro Arg Glu Ala Lys Val Gln Trp Lys Val Asp Asn Ala Leu Gln Ser
145 150 155 160

Gly Asn Ser Gln Glu Ser Val Thr Glu Gln Asp Ser Lys Asp Ser Thr
165 170 175

Tyr Ser Leu Ser Ser Thr Leu Thr Leu Ser Lys Ala Asp Tyr Glu Lys
180 185 190

His Lys Val Tyr Ala Cys Glu Val Thr His Gln Gly Leu Ser Ser Pro
195 200 205

Val Thr Lys Ser Phe Asn Arg Gly Glu Cys
210 215

<210> SEQ ID NO 190
<211> LENGTH: 111
<212> TYPE: PRT
<213> ORGANISM: Artificial Sequence
<220> FEATURE:
<223> OTHER INFORMATION: Synthesized

<400> SEQUENCE: 190

Gln Ser Ala Leu Thr Gln Pro Ala Ser Val Ser Gly Ser Pro Gly Gln
1 5 10 15

Ser Ile Thr Ile Ser Cys Thr Gly Thr Ser Ser Asp Val Gly Gly Tyr
20 25 30

Asn Phe Val Ser Trp Tyr Gln Gln His Pro Gly Lys Ala Pro Lys Leu
35 40 45

Met Ile Tyr Asp Val Ser Asp Arg Pro Ser Gly Val Ser Asp Arg Phe
50 55 60

Ser Gly Ser Lys Ser Gly Asn Thr Ala Ser Leu Ile Ile Ser Gly Leu
65 70 75 80

```
Gln Ala Asp Asp Glu Ala Asp Tyr Tyr Cys Ser Ser Tyr Gly Ser Ser
                85                  90                  95

Ser Thr His Val Ile Phe Gly Gly Gly Thr Lys Leu Thr Val Leu
            100                 105                 110


<210> SEQ ID NO 191
<211> LENGTH: 2100
<212> TYPE: DNA
<213> ORGANISM: Artificial Sequence
<220> FEATURE:
<223> OTHER INFORMATION: Synthesized

<400> SEQUENCE: 191

caggtgcagc tgcaggagtc gggggaggc ctggtcaagc ctggagggtc cctgagactc      60

tcctgtgcag cctctggatt cacctttagt agttattgga tgagctgggt ccgccaggct     120

ccagggaagg ggctggagtg ggtggccaac ataaaccgcg atggaagtgc gagttactat     180

gtggactctg tgaagggccg attcaccatc tccagagacg acgccaagaa ctcactgtat     240

ctgcaaatga acagcctgag agctgaggac acggctgtgt attactgtgc gagagatcgt     300

ggggtgggct acttcgatct ctggggccgt ggcaccctgg tcaccgtctc gagcgctagc     360

accaagggcc catcggtctt ccccctggca ccctcctcca agagcacctc tgggggcaca     420

gcggccctgg gctgcctggt caaggactac ttccccgaac cggtgacggt gtcgtggaac     480

tcaggcgccc tgaccagcgg cgtgcacacc ttcccggctg tcctacagtc ctcaggactc     540

tactccctca gcagcgtggt gaccgtgccc tccagcagct tgggcaccca gacctacatc     600

tgcaacgtga atcacaagcc cagcaacacc aaggtggaca agagagttga gcccaaatct     660

tgtgacaaaa ctcacacatg cccaccgtgc ccagcacctg aactcctggg gggaccgtca     720

gtcttcctct tccccccaaa acccaaggac accctcatga tctcccggac ccctgaggtc     780

acatgcgtgg tggtggacgt gagccacgaa gaccctgagg tcaagttcaa ctggtacgtg     840

gacggcgtgg aggtgcataa tgccaagaca aagccgcggg aggagcagta caacagcacg     900

taccgtgtgg tcagcgtcct caccgtcctg caccaggact ggctgaatgg caaggagtac     960

aagtgcaagg tctccaacaa agccctccca gcccccatcg agaaaaccat ctccaaagcc    1020

aaagggcagc cccgagaacc acaggtgtac accctgcccc catcccggga ggagatgacc    1080

aagaaccagg tcagcctgac ctgcctggtc aaaggcttct atcccagcga catcgccgtg    1140

gagtgggaga gcaatgggca gccggagaac aactacaaga ccacgcctcc cgtgctggac    1200

tccgacggct ccttcttcct ctatagcaag ctcaccgtgg acaagagcag gtggcagcag    1260

gggaacgtct tctcatgctc cgtgatgcat gaggctctgc acaaccacta cacgcagaag    1320

agcctctccc tgtctccggg taaaggcggt ggaggatccg gcggtggtgg atcacaggtg    1380

cagctgaagc agtcaggacc tggcctagtg cagccctcac agagcctgtc catcacctgc    1440

acagtctctg gtttctcatt aactaactat ggtgtacact gggttcgcca gtctccagga    1500

aagggtctgg agtggctggg agtgatatgg agtggtggaa acacagacta taatacacct    1560

ttcacatcca gactgagcat caacaaggac aattccaaga gccaagtttt ctttaaaatg    1620

aacagtctgc aatctaatga cacagccata tattactgtg ccagagccct cacctactat    1680

gattacgagt ttgcttactg gggccaaggg actctggtca ctgtctctag cggtggaggc    1740

ggttcaggcg gaggtggttc cggcggtggc ggctccgaca tcttgctgac tcagtctcca    1800

gtcatcctgt ctgtgagtcc aggagaaaga gtcagtttct cctgcagggc cagtcagagt    1860
```

attggcacaa acatacactg gtatcagcaa agaacaaatg gttctccaag gcttctcata 1920
aagtatgctt ctgagtctat ctctgggatt ccttccaggt ttagtggcag tggatcaggg 1980
acagatttta ctcttagcat caacagtgtg gagtctgaag atattgcaga ttattactgt 2040
caacaaaata ataactggcc aaccacgttc ggtgctggga ccaagctgga gctgaaacgt 2100

<210> SEQ ID NO 192
<211> LENGTH: 354
<212> TYPE: DNA
<213> ORGANISM: Artificial Sequence
<220> FEATURE:
<223> OTHER INFORMATION: Synthesized

<400> SEQUENCE: 192
caggtgcagc tgcaggagtc gggggaggc ctggtcaagc ctggagggtc cctgagactc 60
tcctgtgcag cctctggatt cacctttagt agttattgga tgagctgggt ccgccaggct 120
ccagggaagg ggctggagtg ggtggccaac ataaaccgcg atggaagtgc gagttactat 180
gtggactctg tgaagggccg attcaccatc tccagagacg acgccaagaa ctcactgtat 240
ctgcaaatga acagcctgag agctgaggac acggctgtgt attactgtgc gagagatcgt 300
ggggtgggct acttcgatct ctggggccgt ggcaccctgg tcaccgtctc gagc 354

<210> SEQ ID NO 193
<211> LENGTH: 726
<212> TYPE: DNA
<213> ORGANISM: Artificial Sequence
<220> FEATURE:
<223> OTHER INFORMATION: Synthesized

<400> SEQUENCE: 193
caggtgcagc tgaagcagtc aggacctggc ctagtgcagc cctcacagag cctgtccatc 60
acctgcacag tctctggttt ctcattaact aactatggtg tacactgggt tcgccagtct 120
ccaggaaagg gtctggagtg gctgggagtg atatggagtg gtggaaacac agactataat 180
acacctttca catccagact gagcatcaac aaggacaatt ccaagagcca agttttcttt 240
aaaatgaaca gtctgcaatc taatgacaca gccatatatt actgtgccag agccctcacc 300
tactatgatt acgagtttgc ttactggggc caagggactc tggtcactgt ctctagcggt 360
ggaggcggtt caggcggagg tggttccggc ggtggcggct ccgacatctt gctgactcag 420
tctccagtca tcctgtctgt gagtccagga gaaagagtca gtttctcctg cagggccagt 480
cagagtattg gcacaaacat acactggtat cagcaaagaa caaatggttc tccaaggctt 540
ctcataaagt atgcttctga gtctatctct gggattcctt ccaggtttag tggcagtgga 600
tcagggacag attttactct tagcatcaac agtgtggagt ctgaagatat tgcagattat 660
tactgtcaac aaaataataa ctggccaacc acgttcggtg ctgggaccaa gctggagctg 720
aaacgt 726

<210> SEQ ID NO 194
<211> LENGTH: 700
<212> TYPE: PRT
<213> ORGANISM: Artificial Sequence
<220> FEATURE:
<223> OTHER INFORMATION: Synthesized

<400> SEQUENCE: 194

Gln Val Gln Leu Gln Glu Ser Gly Gly Gly Leu Val Lys Pro Gly Gly
1 5 10 15

-continued

```
Ser Leu Arg Leu Ser Cys Ala Ala Ser Gly Phe Thr Phe Ser Ser Tyr
            20                  25                  30

Trp Met Ser Trp Val Arg Gln Ala Pro Gly Lys Gly Leu Glu Trp Val
        35                  40                  45

Ala Asn Ile Asn Arg Asp Gly Ser Ala Ser Tyr Tyr Val Asp Ser Val
    50                  55                  60

Lys Gly Arg Phe Thr Ile Ser Arg Asp Asp Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Arg Gly Val Gly Tyr Phe Asp Leu Trp Gly Arg Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Arg Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Glu Glu Met Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
```

```
        435                 440                 445

Gly Gly Gly Gly Ser Gly Gly Gly Gly Ser Gln Val Gln Leu Lys Gln
    450                 455                 460

Ser Gly Pro Gly Leu Val Gln Pro Ser Gln Ser Leu Ser Ile Thr Cys
465                 470                 475                 480

Thr Val Ser Gly Phe Ser Leu Thr Asn Tyr Gly Val His Trp Val Arg
                485                 490                 495

Gln Ser Pro Gly Lys Gly Leu Glu Trp Leu Gly Val Ile Trp Ser Gly
            500                 505                 510

Gly Asn Thr Asp Tyr Asn Thr Pro Phe Thr Ser Arg Leu Ser Ile Asn
        515                 520                 525

Lys Asp Asn Ser Lys Ser Gln Val Phe Phe Lys Met Asn Ser Leu Gln
    530                 535                 540

Ser Asn Asp Thr Ala Ile Tyr Tyr Cys Ala Arg Ala Leu Thr Tyr Tyr
545                 550                 555                 560

Asp Tyr Glu Phe Ala Tyr Trp Gly Gln Gly Thr Leu Val Thr Val Ser
                565                 570                 575

Ser Gly Gly Gly Gly Ser Gly Gly Gly Gly Ser Gly Gly Gly Gly Ser
            580                 585                 590

Asp Ile Leu Leu Thr Gln Ser Pro Val Ile Leu Ser Val Ser Pro Gly
        595                 600                 605

Glu Arg Val Ser Phe Ser Cys Arg Ala Ser Gln Ser Ile Gly Thr Asn
    610                 615                 620

Ile His Trp Tyr Gln Gln Arg Thr Asn Gly Ser Pro Arg Leu Leu Ile
625                 630                 635                 640

Lys Tyr Ala Ser Glu Ser Ile Ser Gly Ile Pro Ser Arg Phe Ser Gly
                645                 650                 655

Ser Gly Ser Gly Thr Asp Phe Thr Leu Ser Ile Asn Ser Val Glu Ser
            660                 665                 670

Glu Asp Ile Ala Asp Tyr Tyr Cys Gln Gln Asn Asn Asn Trp Pro Thr
        675                 680                 685

Thr Phe Gly Ala Gly Thr Lys Leu Glu Leu Lys Arg
    690                 695                 700


<210> SEQ ID NO 195
<211> LENGTH: 118
<212> TYPE: PRT
<213> ORGANISM: Artificial Sequence
<220> FEATURE:
<223> OTHER INFORMATION: Synthesized

<400> SEQUENCE: 195

Gln Val Gln Leu Gln Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Trp Met Ser Trp Val Arg Gln Ala Pro Gly Lys Gly Leu Glu Trp Val
        35                  40                  45

Ala Asn Ile Asn Arg Asp Gly Ser Ala Ser Tyr Tyr Val Asp Ser Val
    50                  55                  60

Lys Gly Arg Phe Thr Ile Ser Arg Asp Asp Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Arg Gly Val Gly Tyr Phe Asp Leu Trp Gly Arg Gly Thr
```

```
            100                 105                 110

Leu Val Thr Val Ser Ser
        115


<210> SEQ ID NO 196
<211> LENGTH: 242
<212> TYPE: PRT
<213> ORGANISM: Artificial Sequence
<220> FEATURE:
<223> OTHER INFORMATION: Synthesized

<400> SEQUENCE: 196

Gln Val Gln Leu Lys Gln Ser Gly Pro Gly Leu Val Gln Pro Ser Gln
1               5                   10                  15

Ser Leu Ser Ile Thr Cys Thr Val Ser Gly Phe Ser Leu Thr Asn Tyr
            20                  25                  30

Gly Val His Trp Val Arg Gln Ser Pro Gly Lys Gly Leu Glu Trp Leu
        35                  40                  45

Gly Val Ile Trp Ser Gly Gly Asn Thr Asp Tyr Asn Thr Pro Phe Thr
    50                  55                  60

Ser Arg Leu Ser Ile Asn Lys Asp Asn Ser Lys Ser Gln Val Phe Phe
65                  70                  75                  80

Lys Met Asn Ser Leu Gln Ser Asn Asp Thr Ala Ile Tyr Tyr Cys Ala
                85                  90                  95

Arg Ala Leu Thr Tyr Tyr Asp Tyr Glu Phe Ala Tyr Trp Gly Gln Gly
            100                 105                 110

Thr Leu Val Thr Val Ser Ser Gly Gly Gly Gly Ser Gly Gly Gly Gly
        115                 120                 125

Ser Gly Gly Gly Gly Ser Asp Ile Leu Leu Thr Gln Ser Pro Val Ile
    130                 135                 140

Leu Ser Val Ser Pro Gly Glu Arg Val Ser Phe Ser Cys Arg Ala Ser
145                 150                 155                 160

Gln Ser Ile Gly Thr Asn Ile His Trp Tyr Gln Gln Arg Thr Asn Gly
                165                 170                 175

Ser Pro Arg Leu Leu Ile Lys Tyr Ala Ser Glu Ser Ile Ser Gly Ile
            180                 185                 190

Pro Ser Arg Phe Ser Gly Ser Gly Ser Gly Thr Asp Phe Thr Leu Ser
        195                 200                 205

Ile Asn Ser Val Glu Ser Glu Asp Ile Ala Asp Tyr Tyr Cys Gln Gln
    210                 215                 220

Asn Asn Asn Trp Pro Thr Thr Phe Gly Ala Gly Thr Lys Leu Glu Leu
225                 230                 235                 240

Lys Arg


<210> SEQ ID NO 197
<211> LENGTH: 642
<212> TYPE: DNA
<213> ORGANISM: Artificial Sequence
<220> FEATURE:
<223> OTHER INFORMATION: Synthesized

<400> SEQUENCE: 197

gacatcttgc tgactcagtc tccagtcatc ctgtctgtga gtccaggaga aagagtcagt      60

ttctcctgca gggccagtca gagtattggc acaaacatac actggtatca gcaaagaaca     120

aatggttctc caaggcttct cataaagtat gcttctgagt ctatctctgg gattccttcc     180

aggtttagtg gcagtggatc agggacagat tttactctta gcatcaacag tgtggagtct     240
```

```
gaagatattg cagattatta ctgtcaacaa aataataact ggccaaccac gttcggtgct    300

gggaccaagc tggagctgaa acgtacggtg gctgcaccat ctgtcttcat cttcccgcca    360

tctgatgagc agttgaaatc tggaactgcc tctgttgtgt gcctgctgaa taacttctat    420

cccagagagg ccaaagtaca gtggaaggtg gataacgccc tccaatcggg taactcccag    480

gagagtgtca cagagcagga cagcaaggac agcacctaca gcctcagcag caccctgacg    540

ctgagcaaag cagactacga gaaacacaaa gtctacgcct gcgaagtcac ccatcagggc    600

ctgagctcgc ccgtcacaaa gagcttcaac aggggagagt gt                       642


<210> SEQ ID NO 198
<211> LENGTH: 321
<212> TYPE: DNA
<213> ORGANISM: Artificial Sequence
<220> FEATURE:
<223> OTHER INFORMATION: Synthesized

<400> SEQUENCE: 198

gacatcttgc tgactcagtc tccagtcatc ctgtctgtga gtccaggaga aagagtcagt     60

ttctcctgca gggccagtca gagtattggc acaaacatac actggtatca gcaaagaaca    120

aatggttctc caaggcttct cataaagtat gcttctgagt ctatctctgg gattccttcc    180

aggtttagtg gcagtggatc agggacagat tttactctta gcatcaacag tgtggagtct    240

gaagatattg cagattatta ctgtcaacaa aataataact ggccaaccac gttcggtgct    300

gggaccaagc tggagctgaa a                                              321


<210> SEQ ID NO 199
<211> LENGTH: 214
<212> TYPE: PRT
<213> ORGANISM: Artificial Sequence
<220> FEATURE:
<223> OTHER INFORMATION: Synthesized

<400> SEQUENCE: 199

Asp Ile Leu Leu Thr Gln Ser Pro Val Ile Leu Ser Val Ser Pro Gly
1               5                   10                  15

Glu Arg Val Ser Phe Ser Cys Arg Ala Ser Gln Ser Ile Gly Thr Asn
            20                  25                  30

Ile His Trp Tyr Gln Gln Arg Thr Asn Gly Ser Pro Arg Leu Leu Ile
        35                  40                  45

Lys Tyr Ala Ser Glu Ser Ile Ser Gly Ile Pro Ser Arg Phe Ser Gly
    50                  55                  60

Ser Gly Ser Gly Thr Asp Phe Thr Leu Ser Ile Asn Ser Val Glu Ser
65                  70                  75                  80

Glu Asp Ile Ala Asp Tyr Tyr Cys Gln Gln Asn Asn Asn Trp Pro Thr
                85                  90                  95

Thr Phe Gly Ala Gly Thr Lys Leu Glu Leu Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175
```

```
Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 200
<211> LENGTH: 107
<212> TYPE: PRT
<213> ORGANISM: Artificial Sequence
<220> FEATURE:
<223> OTHER INFORMATION: Synthesized

<400> SEQUENCE: 200

```
Asp Ile Leu Leu Thr Gln Ser Pro Val Ile Leu Ser Val Ser Pro Gly
1               5                   10                  15

Glu Arg Val Ser Phe Ser Cys Arg Ala Ser Gln Ser Ile Gly Thr Asn
            20                  25                  30

Ile His Trp Tyr Gln Gln Arg Thr Asn Gly Ser Pro Arg Leu Leu Ile
        35                  40                  45

Lys Tyr Ala Ser Glu Ser Ile Ser Gly Ile Pro Ser Arg Phe Ser Gly
    50                  55                  60

Ser Gly Ser Gly Thr Asp Phe Thr Leu Ser Ile Asn Ser Val Glu Ser
65                  70                  75                  80

Glu Asp Ile Ala Asp Tyr Tyr Cys Gln Gln Asn Asn Asn Trp Pro Thr
                85                  90                  95

Thr Phe Gly Ala Gly Thr Lys Leu Glu Leu Lys
            100                 105
```

<210> SEQ ID NO 201
<211> LENGTH: 2109
<212> TYPE: DNA
<213> ORGANISM: Artificial Sequence
<220> FEATURE:
<223> OTHER INFORMATION: Synthesized

<400> SEQUENCE: 201

```
caggtgcagc tgaagcagtc aggacctggc ctagtgcagc cctcacagag cctgtccatc      60

acctgcacag tctctggttt ctcattaact aactatggtg tacactgggt tcgccagtct     120

ccaggaaagg gtctggagtg gctgggagtg atatggagtg gtggaaacac agactataat     180

acacctttca catccagact gagcatcaac aaggacaatt ccaagagcca agttttcttt     240

aaaatgaaca gtctgcaatc taatgacaca gccatatatt actgtgccag agccctcacc     300

tactatgatt acgagtttgc ttactggggc caagggactc tggtcactgt ctctagcgct     360

agcaccaagg gcccatcggt cttccccctg gcaccctcct ccaagagcac ctctgggggc     420

acagcggccc tgggctgcct ggtcaaggac tacttccccg aaccggtgac ggtgtcgtgg     480

aactcaggcg ccctgaccag cggcgtgcac accttcccgg ctgtcctaca gtcctcagga     540

ctctactccc tcagcagcgt ggtgaccgtg ccctccagca gcttgggcac ccagacctac     600

atctgcaacg tgaatcacaa gcccagcaac accaaggtgg acaagagagt tgagcccaaa     660

tcttgtgaca aaactcacac atgcccaccg tgcccagcac ctgaactcct ggggggaccg     720

tcagtcttcc tcttcccccc aaaacccaag gacaccctca tgatctcccg gacccctgag     780

gtcacatgcg tggtggtgga cgtgagccac gaagaccctg aggtcaagtt caactggtac     840
```

```
gtggacggcg tggaggtgca taatgccaag acaaagccgc gggaggagca gtacaacagc    900

acgtaccgtg tggtcagcgt cctcaccgtc ctgcaccagg actggctgaa tggcaaggag    960

tacaagtgca aggtctccaa caaagccctc ccagccccca tcgagaaaac catctccaaa   1020

gccaaagggc agccccgaga accacaggtg tacaccctgc ccccatcccg ggaggagatg   1080

accaagaacc aggtcagcct gacctgcctg gtcaaaggct tctatcccag cgacatcgcc   1140

gtggagtggg agagcaatgg gcagccggag aacaactaca agaccacgcc tcccgtgctg   1200

gactccgacg gctccttctt cctctatagc aagctcaccg tggacaagag caggtggcag   1260

caggggaacg tcttctcatg ctccgtgatg catgaggctc tgcacaacca ctacacgcag   1320

aagagcctct ccctgtctcc gggtaaaggc ggtggaggat ccggcggtgg tggatcacag   1380

gtgcagctgc aggagtcggg gggaggcctg gtcaagcctg gagggtccct gagactctcc   1440

tgtgcagcct ctggattcac ctttagtagt tattggatga gctgggtccg ccaggctcca   1500

gggaaggggc tggagtgggt ggccaacata aaccgcgatg gaagtgcgag ttactatgtg   1560

gactctgtga agggccgatt caccatctcc agagacgacg ccaagaactc actgtatctg   1620

caaatgaaca gcctgagagc tgaggacacg gctgtgtatt actgtgcgag agatcgtggg   1680

gtgggctact tcgatctctg ggccgtggc accctggtca ccgtctcgag cggtggaggc   1740

ggttcaggcg gaggtggttc cggcggtggc ggctcccagt ctgccctgac tcagcctgcc   1800

tccgtgtctg ggtctcctgg acagtcgatc accatctcct gcactggaac cagcagtgac   1860

gttggtggtt ataactttgt ctcctggtac caacaacacc caggcaaagc ccccaaactc   1920

atgatctatg atgtcagtga tcggccctca ggggtgtctg atcgcttctc cggctccaag   1980

tctggcaaca cggcctccct gatcatctct ggcctccagg ctgacgacga ggctgattat   2040

tactgcagct catatgggag cagcagcact catgtgattt tcggcggagg gaccaaggtg   2100

accgtccta                                                           2109
```

<210> SEQ ID NO 202
<211> LENGTH: 357
<212> TYPE: DNA
<213> ORGANISM: Artificial Sequence
<220> FEATURE:
<223> OTHER INFORMATION: Synthesized

<400> SEQUENCE: 202

```
caggtgcagc tgaagcagtc aggacctggc ctagtgcagc cctcacagag cctgtccatc     60

acctgcacag tctctggttt ctcattaact aactatggtg tacactgggt tcgccagtct    120

ccaggaaagg gtctggagtg gctgggagtg atatggagtg gtggaaacac agactataat    180

acacctttca catccagact gagcatcaac aaggacaatt ccaagagcca agttttcttt    240

aaaatgaaca gtctgcaatc taatgacaca gccatatatt actgtgccag agccctcacc    300

tactatgatt acgagtttgc ttactggggc caagggactc tggtcactgt ctctagc      357
```

<210> SEQ ID NO 203
<211> LENGTH: 732
<212> TYPE: DNA
<213> ORGANISM: Artificial Sequence
<220> FEATURE:
<223> OTHER INFORMATION: Synthesized

<400> SEQUENCE: 203

```
caggtgcagc tgcaggagtc gggggaggc ctggtcaagc ctggagggtc cctgagactc     60

tcctgtgcag cctctggatt cacctttagt agttattgga tgagctgggt ccgccaggct    120
```

```
ccagggaagg ggctggagtg ggtggccaac ataaaccgcg atggaagtgc gagttactat    180

gtggactctg tgaagggccg attcaccatc tccagagacg acgccaagaa ctcactgtat    240

ctgcaaatga acagcctgag agctgaggac acggctgtgt attactgtgc gagagatcgt    300

ggggtgggct acttcgatct ctggggccgt ggcaccctgg tcaccgtctc gagcggtgga    360

ggcggttcag gcggaggtgg ttccggcggt ggcggctccc agtctgccct gactcagcct    420

gcctccgtgt ctgggtctcc tggacagtcg atcaccatct cctgcactgg aaccagcagt    480

gacgttggtg gttataactt tgtctcctgg taccaacaac acccaggcaa agcccccaaa    540

ctcatgatct atgatgtcag tgatcggccc tcaggggtgt ctgatcgctt ctccggctcc    600

aagtctggca acacggcctc cctgatcatc tctggcctcc aggctgacga cgaggctgat    660

tattactgca gctcatatgg gagcagcagc actcatgtga ttttcggcgg agggaccaag    720

gtgaccgtcc ta                                                        732


<210> SEQ ID NO 204
<211> LENGTH: 703
<212> TYPE: PRT
<213> ORGANISM: Artificial Sequence
<220> FEATURE:
<223> OTHER INFORMATION: Synthesized

<400> SEQUENCE: 204

Gln Val Gln Leu Lys Gln Ser Gly Pro Gly Leu Val Gln Pro Ser Gln
1               5                   10                  15

Ser Leu Ser Ile Thr Cys Thr Val Ser Gly Phe Ser Leu Thr Asn Tyr
            20                  25                  30

Gly Val His Trp Val Arg Gln Ser Pro Gly Lys Gly Leu Glu Trp Leu
        35                  40                  45

Gly Val Ile Trp Ser Gly Gly Asn Thr Asp Tyr Asn Thr Pro Phe Thr
    50                  55                  60

Ser Arg Leu Ser Ile Asn Lys Asp Asn Ser Lys Ser Gln Val Phe Phe
65                  70                  75                  80

Lys Met Asn Ser Leu Gln Ser Asn Asp Thr Ala Ile Tyr Tyr Cys Ala
                85                  90                  95

Arg Ala Leu Thr Tyr Tyr Asp Tyr Glu Phe Ala Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Arg Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
```

-continued

```
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys Gly Gly Gly Gly Ser Gly Gly Gly Gly Ser Gln Val Gln Leu Gln
    450                 455                 460

Glu Ser Gly Gly Gly Leu Val Lys Pro Gly Gly Ser Leu Arg Leu Ser
465                 470                 475                 480

Cys Ala Ala Ser Gly Phe Thr Phe Ser Ser Tyr Trp Met Ser Trp Val
                485                 490                 495

Arg Gln Ala Pro Gly Lys Gly Leu Glu Trp Val Ala Asn Ile Asn Arg
            500                 505                 510

Asp Gly Ser Ala Ser Tyr Tyr Val Asp Ser Val Lys Gly Arg Phe Thr
        515                 520                 525

Ile Ser Arg Asp Asp Ala Lys Asn Ser Leu Tyr Leu Gln Met Asn Ser
    530                 535                 540

Leu Arg Ala Glu Asp Thr Ala Val Tyr Tyr Cys Ala Arg Asp Arg Gly
545                 550                 555                 560

Val Gly Tyr Phe Asp Leu Trp Gly Arg Gly Thr Leu Val Thr Val Ser
                565                 570                 575

Ser Gly Gly Gly Gly Ser Gly Gly Gly Gly Ser Gly Gly Gly Gly Ser
            580                 585                 590

Gln Ser Ala Leu Thr Gln Pro Ala Ser Val Ser Gly Ser Pro Gly Gln
        595                 600                 605

Ser Ile Thr Ile Ser Cys Thr Gly Thr Ser Ser Asp Val Gly Gly Tyr
    610                 615                 620

Asn Phe Val Ser Trp Tyr Gln Gln His Pro Gly Lys Ala Pro Lys Leu
625                 630                 635                 640

Met Ile Tyr Asp Val Ser Asp Arg Pro Ser Gly Val Ser Asp Arg Phe
                645                 650                 655

Ser Gly Ser Lys Ser Gly Asn Thr Ala Ser Leu Ile Ile Ser Gly Leu
            660                 665                 670
```

```
Gln Ala Asp Asp Glu Ala Asp Tyr Tyr Cys Ser Ser Tyr Gly Ser Ser
        675                 680                 685

Ser Thr His Val Ile Phe Gly Gly Gly Thr Lys Val Thr Val Leu
    690                 695                 700


<210> SEQ ID NO 205
<211> LENGTH: 119
<212> TYPE: PRT
<213> ORGANISM: Artificial Sequence
<220> FEATURE:
<223> OTHER INFORMATION: Synthesized

<400> SEQUENCE: 205

Gln Val Gln Leu Lys Gln Ser Gly Pro Gly Leu Val Gln Pro Ser Gln
1               5                   10                  15

Ser Leu Ser Ile Thr Cys Thr Val Ser Gly Phe Ser Leu Thr Asn Tyr
            20                  25                  30

Gly Val His Trp Val Arg Gln Ser Pro Gly Lys Gly Leu Glu Trp Leu
        35                  40                  45

Gly Val Ile Trp Ser Gly Gly Asn Thr Asp Tyr Asn Thr Pro Phe Thr
    50                  55                  60

Ser Arg Leu Ser Ile Asn Lys Asp Asn Ser Lys Ser Gln Val Phe Phe
65                  70                  75                  80

Lys Met Asn Ser Leu Gln Ser Asn Asp Thr Ala Ile Tyr Tyr Cys Ala
                85                  90                  95

Arg Ala Leu Thr Tyr Tyr Asp Tyr Glu Phe Ala Tyr Trp Gly Gln Gly
            100                 105                 110

Thr Leu Val Thr Val Ser Ser
        115


<210> SEQ ID NO 206
<211> LENGTH: 244
<212> TYPE: PRT
<213> ORGANISM: Artificial Sequence
<220> FEATURE:
<223> OTHER INFORMATION: Synthesized

<400> SEQUENCE: 206

Gln Val Gln Leu Gln Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Trp Met Ser Trp Val Arg Gln Ala Pro Gly Lys Gly Leu Glu Trp Val
        35                  40                  45

Ala Asn Ile Asn Arg Asp Gly Ser Ala Ser Tyr Tyr Val Asp Ser Val
    50                  55                  60

Lys Gly Arg Phe Thr Ile Ser Arg Asp Asp Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Arg Gly Val Gly Tyr Phe Asp Leu Trp Gly Arg Gly Thr
            100                 105                 110

Leu Val Thr Val Ser Ser Gly Gly Gly Gly Ser Gly Gly Gly Gly Ser
        115                 120                 125

Gly Gly Gly Gly Ser Gln Ser Ala Leu Thr Gln Pro Ala Ser Val Ser
    130                 135                 140

Gly Ser Pro Gly Gln Ser Ile Thr Ile Ser Cys Thr Gly Thr Ser Ser
```

```
145                 150                 155                 160

Asp Val Gly Gly Tyr Asn Phe Val Ser Trp Tyr Gln Gln His Pro Gly
                165                 170                 175

Lys Ala Pro Lys Leu Met Ile Tyr Asp Val Ser Asp Arg Pro Ser Gly
            180                 185                 190

Val Ser Asp Arg Phe Ser Gly Ser Lys Ser Gly Asn Thr Ala Ser Leu
        195                 200                 205

Ile Ile Ser Gly Leu Gln Ala Asp Asp Glu Ala Asp Tyr Tyr Cys Ser
    210                 215                 220

Ser Tyr Gly Ser Ser Ser Thr His Val Ile Phe Gly Gly Gly Thr Lys
225                 230                 235                 240

Val Thr Val Leu


<210> SEQ ID NO 207
<211> LENGTH: 107
<212> TYPE: PRT
<213> ORGANISM: Artificial Sequence
<220> FEATURE:
<223> OTHER INFORMATION: Synthesized

<400> SEQUENCE: 207

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105


<210> SEQ ID NO 208
<211> LENGTH: 14
<212> TYPE: PRT
<213> ORGANISM: Artificial Sequence
<220> FEATURE:
<223> OTHER INFORMATION: Synthesized

<400> SEQUENCE: 208

Thr Gly Thr Ser Ser Asp Val Gly Gly Tyr Asn Phe Val Ser
1               5                   10


<210> SEQ ID NO 209
<211> LENGTH: 7
<212> TYPE: PRT
<213> ORGANISM: Artificial Sequence
<220> FEATURE:
<223> OTHER INFORMATION: Synthesized

<400> SEQUENCE: 209

Asp Val Ser Asp Arg Pro Ser
1               5


<210> SEQ ID NO 210
<211> LENGTH: 11
```

```
<212> TYPE: PRT
<213> ORGANISM: Artificial Sequence
<220> FEATURE:
<223> OTHER INFORMATION: Synthesized

<400> SEQUENCE: 210

Ser Ser Tyr Gly Ser Ser Ser Thr His Val Ile
1               5                   10


<210> SEQ ID NO 211
<211> LENGTH: 330
<212> TYPE: PRT
<213> ORGANISM: Artificial Sequence
<220> FEATURE:
<223> OTHER INFORMATION: Synthesized

<400> SEQUENCE: 211

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320
```

-continued

Gln Lys Ser Leu Ser Leu Ser Pro Gly Lys
325 330

<210> SEQ ID NO 212
<211> LENGTH: 7
<212> TYPE: PRT
<213> ORGANISM: Artificial Sequence
<220> FEATURE:
<223> OTHER INFORMATION: Synthesized

<400> SEQUENCE: 212

Gly Phe Thr Phe Ser Ser Tyr
1 5

<210> SEQ ID NO 213
<211> LENGTH: 17
<212> TYPE: PRT
<213> ORGANISM: Artificial Sequence
<220> FEATURE:
<223> OTHER INFORMATION: Synthesized

<400> SEQUENCE: 213

Asn Ile Asn Arg Asp Gly Ser Ala Ser Tyr Tyr Val Asp Ser Val Lys
1 5 10 15

Gly

<210> SEQ ID NO 214
<211> LENGTH: 9
<212> TYPE: PRT
<213> ORGANISM: Artificial Sequence
<220> FEATURE:
<223> OTHER INFORMATION: Synthesized

<400> SEQUENCE: 214

Asp Arg Gly Val Gly Tyr Phe Asp Leu
1 5

<210> SEQ ID NO 215
<211> LENGTH: 107
<212> TYPE: PRT
<213> ORGANISM: Artificial Sequence
<220> FEATURE:
<223> OTHER INFORMATION: Synthesized

<400> SEQUENCE: 215

Arg Thr Val Ala Ala Pro Ser Val Phe Ile Phe Pro Pro Ser Asp Glu
1 5 10 15

Gln Leu Lys Ser Gly Thr Ala Ser Val Val Cys Leu Leu Asn Asn Phe
20 25 30

Tyr Pro Arg Glu Ala Lys Val Gln Trp Lys Val Asp Asn Ala Leu Gln
35 40 45

Ser Gly Asn Ser Gln Glu Ser Val Thr Glu Gln Asp Ser Lys Asp Ser
50 55 60

Thr Tyr Ser Leu Ser Ser Thr Leu Thr Leu Ser Lys Ala Asp Tyr Glu
65 70 75 80

Lys His Lys Val Tyr Ala Cys Glu Val Thr His Gln Gly Leu Ser Ser
85 90 95

Pro Val Thr Lys Ser Phe Asn Arg Gly Glu Cys
100 105

<210> SEQ ID NO 216
<211> LENGTH: 14

<212> TYPE: PRT
<213> ORGANISM: Artificial Sequence
<220> FEATURE:
<223> OTHER INFORMATION: Synthesized

<400> SEQUENCE: 216

Thr Gly Thr Ser Ser Asp Val Gly Gly Tyr Asn Phe Val Ser
1 5 10

<210> SEQ ID NO 217
<211> LENGTH: 7
<212> TYPE: PRT
<213> ORGANISM: Artificial Sequence
<220> FEATURE:
<223> OTHER INFORMATION: Synthesized

<400> SEQUENCE: 217

Asp Val Ser Asp Arg Pro Ser
1 5

<210> SEQ ID NO 218
<211> LENGTH: 11
<212> TYPE: PRT
<213> ORGANISM: Artificial Sequence
<220> FEATURE:
<223> OTHER INFORMATION: Synthesized

<400> SEQUENCE: 218

Ser Ser Tyr Gly Ser Ser Ser Thr His Val Ile
1 5 10

<210> SEQ ID NO 219
<211> LENGTH: 330
<212> TYPE: PRT
<213> ORGANISM: Artificial Sequence
<220> FEATURE:
<223> OTHER INFORMATION: Synthesized

<400> SEQUENCE: 219

Ala Ser Thr Lys Gly Pro Ser Val Phe Pro Leu Ala Pro Ser Ser Lys
1 5 10 15

Ser Thr Ser Gly Gly Thr Ala Ala Leu Gly Cys Leu Val Lys Asp Tyr
20 25 30

Phe Pro Glu Pro Val Thr Val Ser Trp Asn Ser Gly Ala Leu Thr Ser
35 40 45

Gly Val His Thr Phe Pro Ala Val Leu Gln Ser Ser Gly Leu Tyr Ser
50 55 60

Leu Ser Ser Val Val Thr Val Pro Ser Ser Ser Leu Gly Thr Gln Thr
65 70 75 80

Tyr Ile Cys Asn Val Asn His Lys Pro Ser Asn Thr Lys Val Asp Lys
85 90 95

Arg Val Glu Pro Lys Ser Cys Asp Lys Thr His Thr Cys Pro Pro Cys
100 105 110

Pro Ala Pro Glu Leu Leu Gly Gly Pro Ser Val Phe Leu Phe Pro Pro
115 120 125

Lys Pro Lys Asp Thr Leu Met Ile Ser Arg Thr Pro Glu Val Thr Cys
130 135 140

Val Val Val Asp Val Ser His Glu Asp Pro Glu Val Lys Phe Asn Trp
145 150 155 160

Tyr Val Asp Gly Val Glu Val His Asn Ala Lys Thr Lys Pro Arg Glu
165 170 175

```
Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330


<210> SEQ ID NO 220
<211> LENGTH: 10
<212> TYPE: PRT
<213> ORGANISM: Artificial Sequence
<220> FEATURE:
<223> OTHER INFORMATION: Synthesized

<400> SEQUENCE: 220

Gly Gly Gly Gly Ser Gly Gly Gly Gly Ser
1               5                   10


<210> SEQ ID NO 221
<211> LENGTH: 242
<212> TYPE: PRT
<213> ORGANISM: Artificial Sequence
<220> FEATURE:
<223> OTHER INFORMATION: Synthesized

<400> SEQUENCE: 221

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Val Ser Ser Gly
            20                  25                  30

Asp Tyr Tyr Trp Thr Trp Ile Arg Gln Ser Pro Gly Lys Gly Leu Glu
        35                  40                  45

Trp Ile Gly His Ile Tyr Tyr Ser Gly Asn Thr Asn Tyr Asn Pro Ser
    50                  55                  60

Leu Lys Ser Arg Leu Thr Ile Ser Ile Asp Thr Ser Lys Thr Gln Phe
65                  70                  75                  80

Ser Leu Lys Leu Ser Ser Val Thr Ala Ala Asp Thr Ala Ile Tyr Tyr
                85                  90                  95

Cys Val Arg Asp Arg Val Thr Gly Ala Phe Asp Ile Trp Gly Gln Gly
            100                 105                 110

Thr Met Val Thr Val Ser Ser Gly Gly Gly Gly Ser Gly Gly Gly Gly
        115                 120                 125

Ser Gly Gly Gly Gly Ser Asp Ile Gln Met Thr Gln Ser Pro Ser Ser
    130                 135                 140
```

```
Leu Ser Ala Ser Val Gly Asp Arg Val Thr Ile Thr Cys Gln Ala Ser
145                 150                 155                 160

Gln Asp Ile Ser Asn Tyr Leu Asn Trp Tyr Gln Gln Lys Pro Gly Lys
                165                 170                 175

Ala Pro Lys Leu Leu Ile Tyr Asp Ala Ser Asn Leu Glu Thr Gly Val
            180                 185                 190

Pro Ser Arg Phe Ser Gly Ser Gly Ser Gly Thr Asp Phe Thr Phe Thr
        195                 200                 205

Ile Ser Ser Leu Gln Pro Glu Asp Ile Ala Thr Tyr Phe Cys Gln His
    210                 215                 220

Phe Asp His Leu Pro Leu Ala Phe Gly Gly Gly Thr Lys Val Glu Ile
225                 230                 235                 240

Lys Arg


<210> SEQ ID NO 222
<211> LENGTH: 7
<212> TYPE: PRT
<213> ORGANISM: Artificial Sequence
<220> FEATURE:
<223> OTHER INFORMATION: Synthesized

<400> SEQUENCE: 222

Gly Phe Thr Phe Ser Ser Tyr
1               5


<210> SEQ ID NO 223
<211> LENGTH: 17
<212> TYPE: PRT
<213> ORGANISM: Artificial Sequence
<220> FEATURE:
<223> OTHER INFORMATION: Synthesized

<400> SEQUENCE: 223

Asn Ile Asn Arg Asp Gly Ser Ala Ser Tyr Tyr Val Asp Ser Val Lys
1               5                   10                  15

Gly


<210> SEQ ID NO 224
<211> LENGTH: 9
<212> TYPE: PRT
<213> ORGANISM: Artificial Sequence
<220> FEATURE:
<223> OTHER INFORMATION: Synthesized

<400> SEQUENCE: 224

Asp Arg Gly Val Gly Tyr Phe Asp Leu
1               5


<210> SEQ ID NO 225
<211> LENGTH: 119
<212> TYPE: PRT
<213> ORGANISM: Artificial Sequence
<220> FEATURE:
<223> OTHER INFORMATION: Synthesized

<400> SEQUENCE: 225

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Val Ser Ser Gly
            20                  25                  30

Asp Tyr Tyr Trp Thr Trp Ile Arg Gln Ser Pro Gly Lys Gly Leu Glu
```

```
        35                  40                  45

Trp Ile Gly His Ile Tyr Tyr Ser Gly Asn Thr Asn Tyr Asn Pro Ser
    50                  55                  60

Leu Lys Ser Arg Leu Thr Ile Ser Ile Asp Thr Ser Lys Thr Gln Phe
65                  70                  75                  80

Ser Leu Lys Leu Ser Ser Val Thr Ala Ala Asp Thr Ala Ile Tyr Tyr
                85                  90                  95

Cys Val Arg Asp Arg Val Thr Gly Ala Phe Asp Ile Trp Gly Gln Gly
            100                 105                 110

Thr Met Val Thr Val Ser Ser
        115


<210> SEQ ID NO 226
<211> LENGTH: 15
<212> TYPE: PRT
<213> ORGANISM: Artificial Sequence
<220> FEATURE:
<223> OTHER INFORMATION: Synthesized

<400> SEQUENCE: 226

Gly Gly Gly Gly Ser Gly Gly Gly Gly Ser Gly Gly Gly Gly Ser
1               5                   10                  15


<210> SEQ ID NO 227
<211> LENGTH: 108
<212> TYPE: PRT
<213> ORGANISM: Artificial Sequence
<220> FEATURE:
<223> OTHER INFORMATION: Synthesized

<400> SEQUENCE: 227

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Asp Ala Ser Asn Leu Glu Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Phe Cys Gln His Phe Asp His Leu Pro Leu
                85                  90                  95

Ala Phe Gly Gly Gly Thr Lys Val Glu Ile Lys Arg
            100                 105


<210> SEQ ID NO 228
<211> LENGTH: 7
<212> TYPE: PRT
<213> ORGANISM: Artificial Sequence
<220> FEATURE:
<223> OTHER INFORMATION: Synthesized

<400> SEQUENCE: 228

Ser Gly Asp Tyr Tyr Trp Thr
1               5


<210> SEQ ID NO 229
<211> LENGTH: 19
<212> TYPE: PRT
<213> ORGANISM: Artificial Sequence
```

<220> FEATURE:
<223> OTHER INFORMATION: Synthesized

<400> SEQUENCE: 229

Trp Ile Gly His Ile Tyr Tyr Ser Gly Asn Thr Asn Tyr Asn Pro Ser
1               5                   10                  15

Leu Lys Ser

<210> SEQ ID NO 230
<211> LENGTH: 9
<212> TYPE: PRT
<213> ORGANISM: Artificial Sequence
<220> FEATURE:
<223> OTHER INFORMATION: Synthesized

<400> SEQUENCE: 230

Asp Arg Val Thr Gly Ala Phe Asp Ile
1               5

<210> SEQ ID NO 231
<211> LENGTH: 11
<212> TYPE: PRT
<213> ORGANISM: Artificial Sequence
<220> FEATURE:
<223> OTHER INFORMATION: Synthesized

<400> SEQUENCE: 231

Gln Ala Ser Gln Asp Ile Ser Asn Tyr Leu Asn
1               5                   10

<210> SEQ ID NO 232
<211> LENGTH: 7
<212> TYPE: PRT
<213> ORGANISM: Artificial Sequence
<220> FEATURE:
<223> OTHER INFORMATION: Synthesized

<400> SEQUENCE: 232

Asp Ala Ser Asn Leu Glu Thr
1               5

<210> SEQ ID NO 233
<211> LENGTH: 9
<212> TYPE: PRT
<213> ORGANISM: Artificial Sequence
<220> FEATURE:
<223> OTHER INFORMATION: Synthesized

<400> SEQUENCE: 233

Gln His Phe Asp His Leu Pro Leu Ala
1               5

<210> SEQ ID NO 234
<211> LENGTH: 107
<212> TYPE: PRT
<213> ORGANISM: Artificial Sequence
<220> FEATURE:
<223> OTHER INFORMATION: Synthesized

<400> SEQUENCE: 234

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln

```
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105


<210> SEQ ID NO 235
<211> LENGTH: 11
<212> TYPE: PRT
<213> ORGANISM: Artificial Sequence
<220> FEATURE:
<223> OTHER INFORMATION: Synthesized

<400> SEQUENCE: 235

Gln Ala Ser Gln Asp Ile Ser Asn Tyr Leu Asn
1               5                   10


<210> SEQ ID NO 236
<211> LENGTH: 7
<212> TYPE: PRT
<213> ORGANISM: Artificial Sequence
<220> FEATURE:
<223> OTHER INFORMATION: Synthesized

<400> SEQUENCE: 236

Asp Ala Ser Asn Leu Glu Thr
1               5


<210> SEQ ID NO 237
<211> LENGTH: 9
<212> TYPE: PRT
<213> ORGANISM: Artificial Sequence
<220> FEATURE:
<223> OTHER INFORMATION: Synthesized

<400> SEQUENCE: 237

Gln His Phe Asp His Leu Pro Leu Ala
1               5


<210> SEQ ID NO 238
<211> LENGTH: 330
<212> TYPE: PRT
<213> ORGANISM: Artificial Sequence
<220> FEATURE:
<223> OTHER INFORMATION: Synthesized

<400> SEQUENCE: 238

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
```

```
                85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330


<210> SEQ ID NO 239
<211> LENGTH: 10
<212> TYPE: PRT
<213> ORGANISM: Artificial Sequence
<220> FEATURE:
<223> OTHER INFORMATION: Synthesized

<400> SEQUENCE: 239

Gly Gly Gly Gly Ser Gly Gly Gly Gly Ser
1               5                   10


<210> SEQ ID NO 240
<211> LENGTH: 244
<212> TYPE: PRT
<213> ORGANISM: Artificial Sequence
<220> FEATURE:
<223> OTHER INFORMATION: Synthesized

<400> SEQUENCE: 240

Gln Val Gln Leu Gln Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Trp Met Ser Trp Val Arg Gln Ala Pro Gly Lys Gly Leu Glu Trp Val
        35                  40                  45
```

-continued

```
Ala Asn Ile Asn Arg Asp Gly Ser Ala Ser Tyr Tyr Val Asp Ser Val
    50                  55                  60

Lys Gly Arg Phe Thr Ile Ser Arg Asp Asp Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Arg Gly Val Gly Tyr Phe Asp Leu Trp Gly Arg Gly Thr
            100                 105                 110

Leu Val Thr Val Ser Ser Gly Gly Gly Gly Ser Gly Gly Gly Gly Ser
        115                 120                 125

Gly Gly Gly Gly Ser Gln Ser Ala Leu Thr Gln Pro Ala Ser Val Ser
    130                 135                 140

Gly Ser Pro Gly Gln Ser Ile Thr Ile Ser Cys Thr Gly Thr Ser Ser
145                 150                 155                 160

Asp Val Gly Gly Tyr Asn Phe Val Ser Trp Tyr Gln Gln His Pro Gly
                165                 170                 175

Lys Ala Pro Lys Leu Met Ile Tyr Asp Val Ser Asp Arg Pro Ser Gly
            180                 185                 190

Val Ser Asp Arg Phe Ser Gly Ser Lys Ser Gly Asn Thr Ala Ser Leu
        195                 200                 205

Ile Ile Ser Gly Leu Gln Ala Asp Asp Glu Ala Asp Tyr Tyr Cys Ser
    210                 215                 220

Ser Tyr Gly Ser Ser Ser Thr His Val Ile Phe Gly Gly Gly Thr Lys
225                 230                 235                 240

Val Thr Val Leu


<210> SEQ ID NO 241
<211> LENGTH: 7
<212> TYPE: PRT
<213> ORGANISM: Artificial Sequence
<220> FEATURE:
<223> OTHER INFORMATION: Synthesized

<400> SEQUENCE: 241

Ser Gly Asp Tyr Tyr Trp Thr
1               5


<210> SEQ ID NO 242
<211> LENGTH: 16
<212> TYPE: PRT
<213> ORGANISM: Artificial Sequence
<220> FEATURE:
<223> OTHER INFORMATION: Synthesized

<400> SEQUENCE: 242

His Ile Tyr Tyr Ser Gly Asn Thr Asn Tyr Asn Pro Ser Leu Lys Ser
1               5                   10                  15


<210> SEQ ID NO 243
<211> LENGTH: 9
<212> TYPE: PRT
<213> ORGANISM: Artificial Sequence
<220> FEATURE:
<223> OTHER INFORMATION: Synthesized

<400> SEQUENCE: 243

Asp Arg Val Thr Gly Ala Phe Asp Ile
1               5


<210> SEQ ID NO 244
```

<211> LENGTH: 118
<212> TYPE: PRT
<213> ORGANISM: Artificial Sequence
<220> FEATURE:
<223> OTHER INFORMATION: Synthesized

<400> SEQUENCE: 244

Gln Val Gln Leu Gln Glu Ser Gly Gly Gly Leu Val Lys Pro Gly Gly
1 5 10 15

Ser Leu Arg Leu Ser Cys Ala Ala Ser Gly Phe Thr Phe Ser Ser Tyr
20 25 30

Trp Met Ser Trp Val Arg Gln Ala Pro Gly Lys Gly Leu Glu Trp Val
35 40 45

Ala Asn Ile Asn Arg Asp Gly Ser Ala Ser Tyr Tyr Val Asp Ser Val
50 55 60

Lys Gly Arg Phe Thr Ile Ser Arg Asp Asp Ala Lys Asn Ser Leu Tyr
65 70 75 80

Leu Gln Met Asn Ser Leu Arg Ala Glu Asp Thr Ala Val Tyr Tyr Cys
85 90 95

Ala Arg Asp Arg Gly Val Gly Tyr Phe Asp Leu Trp Gly Arg Gly Thr
100 105 110

Leu Val Thr Val Ser Ser
115

<210> SEQ ID NO 245
<211> LENGTH: 15
<212> TYPE: PRT
<213> ORGANISM: Artificial Sequence
<220> FEATURE:
<223> OTHER INFORMATION: Synthesized

<400> SEQUENCE: 245

Gly Gly Gly Gly Ser Gly Gly Gly Gly Ser Gly Gly Gly Gly Ser
1 5 10 15

<210> SEQ ID NO 246
<211> LENGTH: 111
<212> TYPE: PRT
<213> ORGANISM: Artificial Sequence
<220> FEATURE:
<223> OTHER INFORMATION: Synthesized

<400> SEQUENCE: 246

Gln Ser Ala Leu Thr Gln Pro Ala Ser Val Ser Gly Ser Pro Gly Gln
1 5 10 15

Ser Ile Thr Ile Ser Cys Thr Gly Thr Ser Ser Asp Val Gly Gly Tyr
20 25 30

Asn Phe Val Ser Trp Tyr Gln Gln His Pro Gly Lys Ala Pro Lys Leu
35 40 45

Met Ile Tyr Asp Val Ser Asp Arg Pro Ser Gly Val Ser Asp Arg Phe
50 55 60

Ser Gly Ser Lys Ser Gly Asn Thr Ala Ser Leu Ile Ile Ser Gly Leu
65 70 75 80

Gln Ala Asp Asp Glu Ala Asp Tyr Tyr Cys Ser Ser Tyr Gly Ser Ser
85 90 95

Ser Thr His Val Ile Phe Gly Gly Gly Thr Lys Val Thr Val Leu
100 105 110

<210> SEQ ID NO 247
<211> LENGTH: 5

<212> TYPE: PRT
<213> ORGANISM: Artificial Sequence
<220> FEATURE:
<223> OTHER INFORMATION: Synthesized

<400> SEQUENCE: 247

Ser Tyr Trp Met Ser
1               5

<210> SEQ ID NO 248
<211> LENGTH: 17
<212> TYPE: PRT
<213> ORGANISM: Artificial Sequence
<220> FEATURE:
<223> OTHER INFORMATION: Synthesized

<400> SEQUENCE: 248

Asn Ile Asn Arg Asp Gly Ser Ala Ser Tyr Tyr Val Asp Ser Val Lys
1               5                   10                  15

Gly

<210> SEQ ID NO 249
<211> LENGTH: 9
<212> TYPE: PRT
<213> ORGANISM: Artificial Sequence
<220> FEATURE:
<223> OTHER INFORMATION: Synthesized

<400> SEQUENCE: 249

Asp Arg Gly Val Gly Tyr Phe Asp Leu
1               5

<210> SEQ ID NO 250
<211> LENGTH: 14
<212> TYPE: PRT
<213> ORGANISM: Artificial Sequence
<220> FEATURE:
<223> OTHER INFORMATION: Synthesized

<400> SEQUENCE: 250

Thr Gly Thr Ser Ser Asp Val Gly Gly Tyr Asn Phe Val Ser
1               5                   10

<210> SEQ ID NO 251
<211> LENGTH: 7
<212> TYPE: PRT
<213> ORGANISM: Artificial Sequence
<220> FEATURE:
<223> OTHER INFORMATION: Synthesized

<400> SEQUENCE: 251

Asp Val Ser Asp Arg Pro Ser
1               5

<210> SEQ ID NO 252
<211> LENGTH: 11
<212> TYPE: PRT
<213> ORGANISM: Artificial Sequence
<220> FEATURE:
<223> OTHER INFORMATION: Synthesized

<400> SEQUENCE: 252

Ser Ser Tyr Gly Ser Ser Ser Thr His Val Ile
1               5                   10

<210> SEQ ID NO 253

<211> LENGTH: 107
<212> TYPE: PRT
<213> ORGANISM: Artificial Sequence
<220> FEATURE:
<223> OTHER INFORMATION: Synthesized

<400> SEQUENCE: 253

Arg Thr Val Ala Ala Pro Ser Val Phe Ile Phe Pro Pro Ser Asp Glu
1 5 10 15

Gln Leu Lys Ser Gly Thr Ala Ser Val Val Cys Leu Leu Asn Asn Phe
20 25 30

Tyr Pro Arg Glu Ala Lys Val Gln Trp Lys Val Asp Asn Ala Leu Gln
35 40 45

Ser Gly Asn Ser Gln Glu Ser Val Thr Glu Gln Asp Ser Lys Asp Ser
50 55 60

Thr Tyr Ser Leu Ser Ser Thr Leu Thr Leu Ser Lys Ala Asp Tyr Glu
65 70 75 80

Lys His Lys Val Tyr Ala Cys Glu Val Thr His Gln Gly Leu Ser Ser
85 90 95

Pro Val Thr Lys Ser Phe Asn Arg Gly Glu Cys
100 105

<210> SEQ ID NO 254
<211> LENGTH: 14
<212> TYPE: PRT
<213> ORGANISM: Artificial Sequence
<220> FEATURE:
<223> OTHER INFORMATION: Synthesized

<400> SEQUENCE: 254

Thr Gly Thr Ser Ser Asp Val Gly Gly Tyr Asn Phe Val Ser
1 5 10

<210> SEQ ID NO 255
<211> LENGTH: 7
<212> TYPE: PRT
<213> ORGANISM: Artificial Sequence
<220> FEATURE:
<223> OTHER INFORMATION: Synthesized

<400> SEQUENCE: 255

Asp Val Ser Asp Arg Pro Ser
1 5

<210> SEQ ID NO 256
<211> LENGTH: 11
<212> TYPE: PRT
<213> ORGANISM: Artificial Sequence
<220> FEATURE:
<223> OTHER INFORMATION: Synthesized

<400> SEQUENCE: 256

Ser Ser Tyr Gly Ser Ser Ser Thr His Val Ile
1 5 10

<210> SEQ ID NO 257
<211> LENGTH: 330
<212> TYPE: PRT
<213> ORGANISM: Artificial Sequence
<220> FEATURE:
<223> OTHER INFORMATION: Synthesized

<400> SEQUENCE: 257

Ala Ser Thr Lys Gly Pro Ser Val Phe Pro Leu Ala Pro Ser Ser Lys

-continued

```
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330
```

<210> SEQ ID NO 258
<211> LENGTH: 10
<212> TYPE: PRT
<213> ORGANISM: Artificial Sequence
<220> FEATURE:
<223> OTHER INFORMATION: Synthesized

<400> SEQUENCE: 258

```
Gly Gly Gly Gly Ser Gly Gly Gly Gly Ser
1               5                   10
```

<210> SEQ ID NO 259
<211> LENGTH: 251
<212> TYPE: PRT

<213> ORGANISM: Artificial Sequence
<220> FEATURE:
<223> OTHER INFORMATION: Synthesized

<400> SEQUENCE: 259

```
Gln Val Gln Leu Gln Gln Ser Gly Ala Glu Val Lys Lys Pro Gly Ser
1               5                   10                  15

Ser Val Lys Val Ser Cys Lys Ala Ser Gly Tyr Thr Phe Thr Asn Tyr
            20                  25                  30

Tyr Ile Tyr Trp Val Arg Gln Ala Pro Gly Gln Gly Leu Glu Trp Ile
        35                  40                  45

Gly Gly Ile Asn Pro Thr Ser Gly Gly Ser Asn Phe Asn Glu Lys Phe
    50                  55                  60

Lys Thr Arg Val Thr Ile Thr Val Asp Glu Ser Thr Asn Thr Ala Tyr
65                  70                  75                  80

Met Glu Leu Ser Ser Leu Arg Ser Glu Asp Thr Ala Phe Tyr Phe Cys
                85                  90                  95

Ala Arg Gln Gly Leu Trp Phe Asp Ser Asp Gly Arg Gly Phe Asp Phe
            100                 105                 110

Trp Gly Gln Gly Ser Thr Val Thr Val Ser Ser Gly Gly Gly Gly Ser
        115                 120                 125

Gly Gly Gly Gly Ser Gly Gly Gly Gly Ser Asp Ile Gln Met Thr Gln
    130                 135                 140

Ser Pro Ser Ser Leu Ser Ala Ser Val Gly Asp Arg Val Thr Ile Thr
145                 150                 155                 160

Cys Arg Ser Ser Gln Asn Ile Val His Ser Asn Gly Asn Thr Tyr Leu
                165                 170                 175

Asp Trp Tyr Gln Gln Thr Pro Gly Lys Ala Pro Lys Leu Leu Ile Tyr
            180                 185                 190

Lys Val Ser Asn Arg Phe Ser Gly Val Pro Ser Arg Phe Ser Gly Ser
        195                 200                 205

Gly Ser Gly Thr Asp Phe Thr Phe Thr Ile Ser Ser Leu Gln Pro Glu
    210                 215                 220

Asp Ile Ala Thr Tyr Tyr Cys Phe Gln Tyr Ser His Val Pro Trp Thr
225                 230                 235                 240

Phe Gly Gln Gly Thr Lys Leu Gln Ile Thr Arg
                245                 250
```

<210> SEQ ID NO 260
<211> LENGTH: 7
<212> TYPE: PRT
<213> ORGANISM: Artificial Sequence
<220> FEATURE:
<223> OTHER INFORMATION: Synthesized

<400> SEQUENCE: 260

```
Gly Phe Thr Phe Ser Ser Tyr
1               5
```

<210> SEQ ID NO 261
<211> LENGTH: 17
<212> TYPE: PRT
<213> ORGANISM: Artificial Sequence
<220> FEATURE:
<223> OTHER INFORMATION: Synthesized

<400> SEQUENCE: 261

```
Asn Ile Asn Arg Asp Gly Ser Ala Ser Tyr Tyr Val Asp Ser Val Lys
1               5                   10                  15
```

Gly

<210> SEQ ID NO 262
<211> LENGTH: 9
<212> TYPE: PRT
<213> ORGANISM: Artificial Sequence
<220> FEATURE:
<223> OTHER INFORMATION: Synthesized

<400> SEQUENCE: 262

Asp Arg Gly Val Gly Tyr Phe Asp Leu
1 5

<210> SEQ ID NO 263
<211> LENGTH: 123
<212> TYPE: PRT
<213> ORGANISM: Artificial Sequence
<220> FEATURE:
<223> OTHER INFORMATION: Synthesized

<400> SEQUENCE: 263

Gln Val Gln Leu Gln Gln Ser Gly Ala Glu Val Lys Lys Pro Gly Ser
1 5 10 15

Ser Val Lys Val Ser Cys Lys Ala Ser Gly Tyr Thr Phe Thr Asn Tyr
20 25 30

Tyr Ile Tyr Trp Val Arg Gln Ala Pro Gly Gln Gly Leu Glu Trp Ile
35 40 45

Gly Gly Ile Asn Pro Thr Ser Gly Gly Ser Asn Phe Asn Glu Lys Phe
50 55 60

Lys Thr Arg Val Thr Ile Thr Val Asp Glu Ser Thr Asn Thr Ala Tyr
65 70 75 80

Met Glu Leu Ser Ser Leu Arg Ser Glu Asp Thr Ala Phe Tyr Phe Cys
85 90 95

Ala Arg Gln Gly Leu Trp Phe Asp Ser Asp Gly Arg Gly Phe Asp Phe
100 105 110

Trp Gly Gln Gly Ser Thr Val Thr Val Ser Ser
115 120

<210> SEQ ID NO 264
<211> LENGTH: 15
<212> TYPE: PRT
<213> ORGANISM: Artificial Sequence
<220> FEATURE:
<223> OTHER INFORMATION: Synthesized

<400> SEQUENCE: 264

Gly Gly Gly Gly Ser Gly Gly Gly Gly Ser Gly Gly Gly Gly Ser
1 5 10 15

<210> SEQ ID NO 265
<211> LENGTH: 113
<212> TYPE: PRT
<213> ORGANISM: Artificial Sequence
<220> FEATURE:
<223> OTHER INFORMATION: Synthesized

<400> SEQUENCE: 265

Asp Ile Gln Met Thr Gln Ser Pro Ser Ser Leu Ser Ala Ser Val Gly
1 5 10 15

Asp Arg Val Thr Ile Thr Cys Arg Ser Ser Gln Asn Ile Val His Ser
20 25 30

```
Asn Gly Asn Thr Tyr Leu Asp Trp Tyr Gln Gln Thr Pro Gly Lys Ala
        35                  40                  45

Pro Lys Leu Leu Ile Tyr Lys Val Ser Asn Arg Phe Ser Gly Val Pro
    50                  55                  60

Ser Arg Phe Ser Gly Ser Gly Ser Gly Thr Asp Phe Thr Phe Thr Ile
65                  70                  75                  80

Ser Ser Leu Gln Pro Glu Asp Ile Ala Thr Tyr Tyr Cys Phe Gln Tyr
                85                  90                  95

Ser His Val Pro Trp Thr Phe Gly Gln Gly Thr Lys Leu Gln Ile Thr
            100                 105                 110

Arg


<210> SEQ ID NO 266
<211> LENGTH: 10
<212> TYPE: PRT
<213> ORGANISM: Artificial Sequence
<220> FEATURE:
<223> OTHER INFORMATION: Synthesized

<400> SEQUENCE: 266

Gly Tyr Thr Phe Thr Asn Tyr Tyr Ile Tyr
1               5                   10


<210> SEQ ID NO 267
<211> LENGTH: 17
<212> TYPE: PRT
<213> ORGANISM: Artificial Sequence
<220> FEATURE:
<223> OTHER INFORMATION: Synthesized

<400> SEQUENCE: 267

Gly Ile Asn Pro Thr Ser Gly Gly Ser Asn Phe Asn Glu Lys Phe Lys
1               5                   10                  15

Thr


<210> SEQ ID NO 268
<211> LENGTH: 14
<212> TYPE: PRT
<213> ORGANISM: Artificial Sequence
<220> FEATURE:
<223> OTHER INFORMATION: Synthesized

<400> SEQUENCE: 268

Gln Gly Leu Trp Phe Asp Ser Asp Gly Arg Gly Phe Asp Phe
1               5                   10


<210> SEQ ID NO 269
<211> LENGTH: 16
<212> TYPE: PRT
<213> ORGANISM: Artificial Sequence
<220> FEATURE:
<223> OTHER INFORMATION: Synthesized

<400> SEQUENCE: 269

Arg Ser Ser Gln Asn Ile Val His Ser Asn Gly Asn Thr Tyr Leu Asp
1               5                   10                  15


<210> SEQ ID NO 270
<211> LENGTH: 7
<212> TYPE: PRT
<213> ORGANISM: Artificial Sequence
<220> FEATURE:
<223> OTHER INFORMATION: Synthesized
```

<400> SEQUENCE: 270

Lys Val Ser Asn Arg Phe Ser
1 5

<210> SEQ ID NO 271
<211> LENGTH: 9
<212> TYPE: PRT
<213> ORGANISM: Artificial Sequence
<220> FEATURE:
<223> OTHER INFORMATION: Synthesized

<400> SEQUENCE: 271

Phe Gln Tyr Ser His Val Pro Trp Thr
1 5

<210> SEQ ID NO 272
<211> LENGTH: 107
<212> TYPE: PRT
<213> ORGANISM: Artificial Sequence
<220> FEATURE:
<223> OTHER INFORMATION: Synthesized

<400> SEQUENCE: 272

Arg Thr Val Ala Ala Pro Ser Val Phe Ile Phe Pro Pro Ser Asp Glu
1 5 10 15

Gln Leu Lys Ser Gly Thr Ala Ser Val Val Cys Leu Leu Asn Asn Phe
20 25 30

Tyr Pro Arg Glu Ala Lys Val Gln Trp Lys Val Asp Asn Ala Leu Gln
35 40 45

Ser Gly Asn Ser Gln Glu Ser Val Thr Glu Gln Asp Ser Lys Asp Ser
50 55 60

Thr Tyr Ser Leu Ser Ser Thr Leu Thr Leu Ser Lys Ala Asp Tyr Glu
65 70 75 80

Lys His Lys Val Tyr Ala Cys Glu Val Thr His Gln Gly Leu Ser Ser
85 90 95

Pro Val Thr Lys Ser Phe Asn Arg Gly Glu Cys
100 105

<210> SEQ ID NO 273
<211> LENGTH: 16
<212> TYPE: PRT
<213> ORGANISM: Artificial Sequence
<220> FEATURE:
<223> OTHER INFORMATION: Synthesized

<400> SEQUENCE: 273

Arg Ser Ser Gln Asn Ile Val His Ser Asn Gly Asn Thr Tyr Leu Asp
1 5 10 15

<210> SEQ ID NO 274
<211> LENGTH: 7
<212> TYPE: PRT
<213> ORGANISM: Artificial Sequence
<220> FEATURE:
<223> OTHER INFORMATION: Synthesized

<400> SEQUENCE: 274

Lys Val Ser Asn Arg Phe Ser
1 5

<210> SEQ ID NO 275
<211> LENGTH: 9
<212> TYPE: PRT

<213> ORGANISM: Artificial Sequence
<220> FEATURE:
<223> OTHER INFORMATION: Synthesized

<400> SEQUENCE: 275

Phe Gln Tyr Ser His Val Pro Trp Thr
1               5

<210> SEQ ID NO 276
<211> LENGTH: 330
<212> TYPE: PRT
<213> ORGANISM: Artificial Sequence
<220> FEATURE:
<223> OTHER INFORMATION: Synthesized

<400> SEQUENCE: 276

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320
```

```
Gln Lys Ser Leu Ser Leu Ser Pro Gly Lys
                325                 330


<210> SEQ ID NO 277
<211> LENGTH: 10
<212> TYPE: PRT
<213> ORGANISM: Artificial Sequence
<220> FEATURE:
<223> OTHER INFORMATION: Synthesized

<400> SEQUENCE: 277

Gly Gly Gly Gly Ser Gly Gly Gly Gly Ser
1               5                   10


<210> SEQ ID NO 278
<211> LENGTH: 244
<212> TYPE: PRT
<213> ORGANISM: Artificial Sequence
<220> FEATURE:
<223> OTHER INFORMATION: Synthesized

<400> SEQUENCE: 278

Gln Val Gln Leu Gln Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Trp Met Ser Trp Val Arg Gln Ala Pro Gly Lys Gly Leu Glu Trp Val
        35                  40                  45

Ala Asn Ile Asn Arg Asp Gly Ser Ala Ser Tyr Tyr Val Asp Ser Val
    50                  55                  60

Lys Gly Arg Phe Thr Ile Ser Arg Asp Asp Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Arg Gly Val Gly Tyr Phe Asp Leu Trp Gly Arg Gly Thr
            100                 105                 110

Leu Val Thr Val Ser Ser Gly Gly Gly Gly Ser Gly Gly Gly Gly Ser
        115                 120                 125

Gly Gly Gly Gly Ser Gln Ser Ala Leu Thr Gln Pro Ala Ser Val Ser
    130                 135                 140

Gly Ser Pro Gly Gln Ser Ile Thr Ile Ser Cys Thr Gly Thr Ser Ser
145                 150                 155                 160

Asp Val Gly Gly Tyr Asn Phe Val Ser Trp Tyr Gln Gln His Pro Gly
                165                 170                 175

Lys Ala Pro Lys Leu Met Ile Tyr Asp Val Ser Asp Arg Pro Ser Gly
            180                 185                 190

Val Ser Asp Arg Phe Ser Gly Ser Lys Ser Gly Asn Thr Ala Ser Leu
        195                 200                 205

Ile Ile Ser Gly Leu Gln Ala Asp Asp Glu Ala Asp Tyr Tyr Cys Ser
    210                 215                 220

Ser Tyr Gly Ser Ser Ser Thr His Val Ile Phe Gly Gly Gly Thr Lys
225                 230                 235                 240

Val Thr Val Leu


<210> SEQ ID NO 279
<211> LENGTH: 10
<212> TYPE: PRT
<213> ORGANISM: Artificial Sequence
<220> FEATURE:
```

<223> OTHER INFORMATION: Synthesized

<400> SEQUENCE: 279

Gly Tyr Thr Phe Thr Asn Tyr Tyr Ile Tyr
1 5 10

<210> SEQ ID NO 280
<211> LENGTH: 17
<212> TYPE: PRT
<213> ORGANISM: Artificial Sequence
<220> FEATURE:
<223> OTHER INFORMATION: Synthesized

<400> SEQUENCE: 280

Gly Ile Asn Pro Thr Ser Gly Gly Ser Asn Phe Asn Glu Lys Phe Lys
1 5 10 15

Thr

<210> SEQ ID NO 281
<211> LENGTH: 14
<212> TYPE: PRT
<213> ORGANISM: Artificial Sequence
<220> FEATURE:
<223> OTHER INFORMATION: Synthesized

<400> SEQUENCE: 281

Gln Gly Leu Trp Phe Asp Ser Asp Gly Arg Gly Phe Asp Phe
1 5 10

<210> SEQ ID NO 282
<211> LENGTH: 118
<212> TYPE: PRT
<213> ORGANISM: Artificial Sequence
<220> FEATURE:
<223> OTHER INFORMATION: Synthesized

<400> SEQUENCE: 282

Gln Val Gln Leu Gln Glu Ser Gly Gly Gly Leu Val Lys Pro Gly Gly
1 5 10 15

Ser Leu Arg Leu Ser Cys Ala Ala Ser Gly Phe Thr Phe Ser Ser Tyr
20 25 30

Trp Met Ser Trp Val Arg Gln Ala Pro Gly Lys Gly Leu Glu Trp Val
35 40 45

Ala Asn Ile Asn Arg Asp Gly Ser Ala Ser Tyr Tyr Val Asp Ser Val
50 55 60

Lys Gly Arg Phe Thr Ile Ser Arg Asp Asp Ala Lys Asn Ser Leu Tyr
65 70 75 80

Leu Gln Met Asn Ser Leu Arg Ala Glu Asp Thr Ala Val Tyr Tyr Cys
85 90 95

Ala Arg Asp Arg Gly Val Gly Tyr Phe Asp Leu Trp Gly Arg Gly Thr
100 105 110

Leu Val Thr Val Ser Ser
115

<210> SEQ ID NO 283
<211> LENGTH: 15
<212> TYPE: PRT
<213> ORGANISM: Artificial Sequence
<220> FEATURE:
<223> OTHER INFORMATION: Synthesized

<400> SEQUENCE: 283

-continued

Gly Gly Gly Gly Ser Gly Gly Gly Gly Ser Gly Gly Gly Gly Ser
1 5 10 15

<210> SEQ ID NO 284
<211> LENGTH: 111
<212> TYPE: PRT
<213> ORGANISM: Artificial Sequence
<220> FEATURE:
<223> OTHER INFORMATION: Synthesized

<400> SEQUENCE: 284

Gln Ser Ala Leu Thr Gln Pro Ala Ser Val Ser Gly Ser Pro Gly Gln
1 5 10 15

Ser Ile Thr Ile Ser Cys Thr Gly Thr Ser Ser Asp Val Gly Gly Tyr
20 25 30

Asn Phe Val Ser Trp Tyr Gln Gln His Pro Gly Lys Ala Pro Lys Leu
35 40 45

Met Ile Tyr Asp Val Ser Asp Arg Pro Ser Gly Val Ser Asp Arg Phe
50 55 60

Ser Gly Ser Lys Ser Gly Asn Thr Ala Ser Leu Ile Ile Ser Gly Leu
65 70 75 80

Gln Ala Asp Asp Glu Ala Asp Tyr Tyr Cys Ser Ser Tyr Gly Ser Ser
85 90 95

Ser Thr His Val Ile Phe Gly Gly Gly Thr Lys Val Thr Val Leu
100 105 110

<210> SEQ ID NO 285
<211> LENGTH: 5
<212> TYPE: PRT
<213> ORGANISM: Artificial Sequence
<220> FEATURE:
<223> OTHER INFORMATION: Synthesized

<400> SEQUENCE: 285

Ser Tyr Trp Met Ser
1 5

<210> SEQ ID NO 286
<211> LENGTH: 17
<212> TYPE: PRT
<213> ORGANISM: Artificial Sequence
<220> FEATURE:
<223> OTHER INFORMATION: Synthesized

<400> SEQUENCE: 286

Asn Ile Asn Arg Asp Gly Ser Ala Ser Tyr Tyr Val Asp Ser Val Lys
1 5 10 15

Gly

<210> SEQ ID NO 287
<211> LENGTH: 9
<212> TYPE: PRT
<213> ORGANISM: Artificial Sequence
<220> FEATURE:
<223> OTHER INFORMATION: Synthesized

<400> SEQUENCE: 287

Asp Arg Gly Val Gly Tyr Phe Asp Leu
1 5

<210> SEQ ID NO 288
<211> LENGTH: 14
<212> TYPE: PRT

<213> ORGANISM: Artificial Sequence
<220> FEATURE:
<223> OTHER INFORMATION: Synthesized

<400> SEQUENCE: 288

Thr Gly Thr Ser Ser Asp Val Gly Gly Tyr Asn Phe Val Ser
1               5                   10

<210> SEQ ID NO 289
<211> LENGTH: 7
<212> TYPE: PRT
<213> ORGANISM: Artificial Sequence
<220> FEATURE:
<223> OTHER INFORMATION: Synthesized

<400> SEQUENCE: 289

Asp Val Ser Asp Arg Pro Ser
1               5

<210> SEQ ID NO 290
<211> LENGTH: 11
<212> TYPE: PRT
<213> ORGANISM: Artificial Sequence
<220> FEATURE:
<223> OTHER INFORMATION: Synthesized

<400> SEQUENCE: 290

Ser Ser Tyr Gly Ser Ser Ser Thr His Val Ile
1               5                   10

<210> SEQ ID NO 291
<211> LENGTH: 107
<212> TYPE: PRT
<213> ORGANISM: Artificial Sequence
<220> FEATURE:
<223> OTHER INFORMATION: Synthesized

<400> SEQUENCE: 291

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 292
<211> LENGTH: 14
<212> TYPE: PRT
<213> ORGANISM: Artificial Sequence
<220> FEATURE:
<223> OTHER INFORMATION: Synthesized

<400> SEQUENCE: 292

Thr Gly Thr Ser Ser Asp Val Gly Gly Tyr Asn Phe Val Ser
1               5                   10

<210> SEQ ID NO 293
<211> LENGTH: 7
<212> TYPE: PRT
<213> ORGANISM: Artificial Sequence
<220> FEATURE:
<223> OTHER INFORMATION: Synthesized

<400> SEQUENCE: 293

Asp Val Ser Asp Arg Pro Ser
1               5

<210> SEQ ID NO 294
<211> LENGTH: 11
<212> TYPE: PRT
<213> ORGANISM: Artificial Sequence
<220> FEATURE:
<223> OTHER INFORMATION: Synthesized

<400> SEQUENCE: 294

Ser Ser Tyr Gly Ser Ser Ser Thr His Val Ile
1               5                   10

<210> SEQ ID NO 295
<211> LENGTH: 330
<212> TYPE: PRT
<213> ORGANISM: Artificial Sequence
<220> FEATURE:
<223> OTHER INFORMATION: Synthesized

<400> SEQUENCE: 295

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu

-continued

```
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330


<210> SEQ ID NO 296
<211> LENGTH: 10
<212> TYPE: PRT
<213> ORGANISM: Artificial Sequence
<220> FEATURE:
<223> OTHER INFORMATION: Synthesized

<400> SEQUENCE: 296

Gly Gly Gly Gly Ser Gly Gly Gly Gly Ser
1               5                   10


<210> SEQ ID NO 297
<211> LENGTH: 242
<212> TYPE: PRT
<213> ORGANISM: Artificial Sequence
<220> FEATURE:
<223> OTHER INFORMATION: Synthesized

<400> SEQUENCE: 297

Gln Val Gln Leu Lys Gln Ser Gly Pro Gly Leu Val Gln Pro Ser Gln
1               5                   10                  15

Ser Leu Ser Ile Thr Cys Thr Val Ser Gly Phe Ser Leu Thr Asn Tyr
            20                  25                  30

Gly Val His Trp Val Arg Gln Ser Pro Gly Lys Gly Leu Glu Trp Leu
        35                  40                  45

Gly Val Ile Trp Ser Gly Gly Asn Thr Asp Tyr Asn Thr Pro Phe Thr
    50                  55                  60

Ser Arg Leu Ser Ile Asn Lys Asp Asn Ser Lys Ser Gln Val Phe Phe
65                  70                  75                  80

Lys Met Asn Ser Leu Gln Ser Asn Asp Thr Ala Ile Tyr Tyr Cys Ala
                85                  90                  95

Arg Ala Leu Thr Tyr Tyr Asp Tyr Glu Phe Ala Tyr Trp Gly Gln Gly
            100                 105                 110

Thr Leu Val Thr Val Ser Ser Gly Gly Gly Gly Ser Gly Gly Gly Gly
        115                 120                 125

Ser Gly Gly Gly Gly Ser Asp Ile Leu Leu Thr Gln Ser Pro Val Ile
    130                 135                 140

Leu Ser Val Ser Pro Gly Glu Arg Val Ser Phe Ser Cys Arg Ala Ser
145                 150                 155                 160

Gln Ser Ile Gly Thr Asn Ile His Trp Tyr Gln Gln Arg Thr Asn Gly
                165                 170                 175

Ser Pro Arg Leu Leu Ile Lys Tyr Ala Ser Glu Ser Ile Ser Gly Ile
            180                 185                 190
```

```
Pro Ser Arg Phe Ser Gly Ser Gly Ser Gly Thr Asp Phe Thr Leu Ser
        195                 200                 205

Ile Asn Ser Val Glu Ser Glu Asp Ile Ala Asp Tyr Tyr Cys Gln Gln
    210                 215                 220

Asn Asn Asn Trp Pro Thr Thr Phe Gly Ala Gly Thr Lys Leu Glu Leu
225                 230                 235                 240

Lys Arg


<210> SEQ ID NO 298
<211> LENGTH: 7
<212> TYPE: PRT
<213> ORGANISM: Artificial Sequence
<220> FEATURE:
<223> OTHER INFORMATION: Synthesized

<400> SEQUENCE: 298

Gly Phe Thr Phe Ser Ser Tyr
1               5


<210> SEQ ID NO 299
<211> LENGTH: 17
<212> TYPE: PRT
<213> ORGANISM: Artificial Sequence
<220> FEATURE:
<223> OTHER INFORMATION: Synthesized

<400> SEQUENCE: 299

Asn Ile Asn Arg Asp Gly Ser Ala Ser Tyr Tyr Val Asp Ser Val Lys
1               5                   10                  15

Gly


<210> SEQ ID NO 300
<211> LENGTH: 9
<212> TYPE: PRT
<213> ORGANISM: Artificial Sequence
<220> FEATURE:
<223> OTHER INFORMATION: Synthesized

<400> SEQUENCE: 300

Asp Arg Gly Val Gly Tyr Phe Asp Leu
1               5


<210> SEQ ID NO 301
<211> LENGTH: 119
<212> TYPE: PRT
<213> ORGANISM: Artificial Sequence
<220> FEATURE:
<223> OTHER INFORMATION: Synthesized

<400> SEQUENCE: 301

Gln Val Gln Leu Lys Gln Ser Gly Pro Gly Leu Val Gln Pro Ser Gln
1               5                   10                  15

Ser Leu Ser Ile Thr Cys Thr Val Ser Gly Phe Ser Leu Thr Asn Tyr
            20                  25                  30

Gly Val His Trp Val Arg Gln Ser Pro Gly Lys Gly Leu Glu Trp Leu
        35                  40                  45

Gly Val Ile Trp Ser Gly Gly Asn Thr Asp Tyr Asn Thr Pro Phe Thr
    50                  55                  60

Ser Arg Leu Ser Ile Asn Lys Asp Asn Ser Lys Ser Gln Val Phe Phe
65                  70                  75                  80

Lys Met Asn Ser Leu Gln Ser Asn Asp Thr Ala Ile Tyr Tyr Cys Ala
                85                  90                  95
```

```
Arg Ala Leu Thr Tyr Tyr Asp Tyr Glu Phe Ala Tyr Trp Gly Gln Gly
            100                 105                 110

Thr Leu Val Thr Val Ser Ser
        115


<210> SEQ ID NO 302
<211> LENGTH: 15
<212> TYPE: PRT
<213> ORGANISM: Artificial Sequence
<220> FEATURE:
<223> OTHER INFORMATION: Synthesized

<400> SEQUENCE: 302

Gly Gly Gly Gly Ser Gly Gly Gly Gly Ser Gly Gly Gly Gly Ser
1               5                   10                  15


<210> SEQ ID NO 303
<211> LENGTH: 108
<212> TYPE: PRT
<213> ORGANISM: Artificial Sequence
<220> FEATURE:
<223> OTHER INFORMATION: Synthesized

<400> SEQUENCE: 303

Asp Ile Leu Leu Thr Gln Ser Pro Val Ile Leu Ser Val Ser Pro Gly
1               5                   10                  15

Glu Arg Val Ser Phe Ser Cys Arg Ala Ser Gln Ser Ile Gly Thr Asn
            20                  25                  30

Ile His Trp Tyr Gln Gln Arg Thr Asn Gly Ser Pro Arg Leu Leu Ile
        35                  40                  45

Lys Tyr Ala Ser Glu Ser Ile Ser Gly Ile Pro Ser Arg Phe Ser Gly
    50                  55                  60

Ser Gly Ser Gly Thr Asp Phe Thr Leu Ser Ile Asn Ser Val Glu Ser
65                  70                  75                  80

Glu Asp Ile Ala Asp Tyr Tyr Cys Gln Gln Asn Asn Asn Trp Pro Thr
                85                  90                  95

Thr Phe Gly Ala Gly Thr Lys Leu Glu Leu Lys Arg
            100                 105


<210> SEQ ID NO 304
<211> LENGTH: 5
<212> TYPE: PRT
<213> ORGANISM: Artificial Sequence
<220> FEATURE:
<223> OTHER INFORMATION: Synthesized

<400> SEQUENCE: 304

Asn Tyr Gly Val His
1               5


<210> SEQ ID NO 305
<211> LENGTH: 16
<212> TYPE: PRT
<213> ORGANISM: Artificial Sequence
<220> FEATURE:
<223> OTHER INFORMATION: Synthesized

<400> SEQUENCE: 305

Val Ile Trp Ser Gly Gly Asn Thr Asp Tyr Asn Thr Pro Phe Thr Ser
1               5                   10                  15


<210> SEQ ID NO 306
```

<211> LENGTH: 11
<212> TYPE: PRT
<213> ORGANISM: Artificial Sequence
<220> FEATURE:
<223> OTHER INFORMATION: Synthesized

<400> SEQUENCE: 306

Ala Leu Thr Tyr Tyr Asp Tyr Glu Phe Ala Tyr
1 5 10

<210> SEQ ID NO 307
<211> LENGTH: 11
<212> TYPE: PRT
<213> ORGANISM: Artificial Sequence
<220> FEATURE:
<223> OTHER INFORMATION: Synthesized

<400> SEQUENCE: 307

Arg Ala Ser Gln Ser Ile Gly Thr Asn Ile His
1 5 10

<210> SEQ ID NO 308
<211> LENGTH: 7
<212> TYPE: PRT
<213> ORGANISM: Artificial Sequence
<220> FEATURE:
<223> OTHER INFORMATION: Synthesized

<400> SEQUENCE: 308

Tyr Ala Ser Glu Ser Ile Ser
1 5

<210> SEQ ID NO 309
<211> LENGTH: 9
<212> TYPE: PRT
<213> ORGANISM: Artificial Sequence
<220> FEATURE:
<223> OTHER INFORMATION: Synthesized

<400> SEQUENCE: 309

Gln Gln Asn Asn Asn Trp Pro Thr Thr
1 5

<210> SEQ ID NO 310
<211> LENGTH: 107
<212> TYPE: PRT
<213> ORGANISM: Artificial Sequence
<220> FEATURE:
<223> OTHER INFORMATION: Synthesized

<400> SEQUENCE: 310

Arg Thr Val Ala Ala Pro Ser Val Phe Ile Phe Pro Pro Ser Asp Glu
1 5 10 15

Gln Leu Lys Ser Gly Thr Ala Ser Val Val Cys Leu Leu Asn Asn Phe
20 25 30

Tyr Pro Arg Glu Ala Lys Val Gln Trp Lys Val Asp Asn Ala Leu Gln
35 40 45

Ser Gly Asn Ser Gln Glu Ser Val Thr Glu Gln Asp Ser Lys Asp Ser
50 55 60

Thr Tyr Ser Leu Ser Ser Thr Leu Thr Leu Ser Lys Ala Asp Tyr Glu
65 70 75 80

Lys His Lys Val Tyr Ala Cys Glu Val Thr His Gln Gly Leu Ser Ser
85 90 95

Pro Val Thr Lys Ser Phe Asn Arg Gly Glu Cys 100 105

<210> SEQ ID NO 311
<211> LENGTH: 11
<212> TYPE: PRT
<213> ORGANISM: Artificial Sequence
<220> FEATURE:
<223> OTHER INFORMATION: Synthesized

<400> SEQUENCE: 311

Arg Ala Ser Gln Ser Ile Gly Thr Asn Ile His
1 5 10

<210> SEQ ID NO 312
<211> LENGTH: 7
<212> TYPE: PRT
<213> ORGANISM: Artificial Sequence
<220> FEATURE:
<223> OTHER INFORMATION: Synthesized

<400> SEQUENCE: 312

Tyr Ala Ser Glu Ser Ile Ser
1 5

<210> SEQ ID NO 313
<211> LENGTH: 9
<212> TYPE: PRT
<213> ORGANISM: Artificial Sequence
<220> FEATURE:
<223> OTHER INFORMATION: Synthesized

<400> SEQUENCE: 313

Gln Gln Asn Asn Asn Trp Pro Thr Thr
1 5

<210> SEQ ID NO 314
<211> LENGTH: 330
<212> TYPE: PRT
<213> ORGANISM: Artificial Sequence
<220> FEATURE:
<223> OTHER INFORMATION: Synthesized

<400> SEQUENCE: 314

Ala Ser Thr Lys Gly Pro Ser Val Phe Pro Leu Ala Pro Ser Ser Lys
1 5 10 15

Ser Thr Ser Gly Gly Thr Ala Ala Leu Gly Cys Leu Val Lys Asp Tyr
20 25 30

Phe Pro Glu Pro Val Thr Val Ser Trp Asn Ser Gly Ala Leu Thr Ser
35 40 45

Gly Val His Thr Phe Pro Ala Val Leu Gln Ser Ser Gly Leu Tyr Ser
50 55 60

Leu Ser Ser Val Val Thr Val Pro Ser Ser Ser Leu Gly Thr Gln Thr
65 70 75 80

Tyr Ile Cys Asn Val Asn His Lys Pro Ser Asn Thr Lys Val Asp Lys
85 90 95

Arg Val Glu Pro Lys Ser Cys Asp Lys Thr His Thr Cys Pro Pro Cys
100 105 110

Pro Ala Pro Glu Leu Leu Gly Gly Pro Ser Val Phe Leu Phe Pro Pro
115 120 125

Lys Pro Lys Asp Thr Leu Met Ile Ser Arg Thr Pro Glu Val Thr Cys
130 135 140

Val Val Val Asp Val Ser His Glu Asp Pro Glu Val Lys Phe Asn Trp 145 150 155 160

Tyr Val Asp Gly Val Glu Val His Asn Ala Lys Thr Lys Pro Arg Glu
165 170 175

Glu Gln Tyr Asn Ser Thr Tyr Arg Val Val Ser Val Leu Thr Val Leu
180 185 190

His Gln Asp Trp Leu Asn Gly Lys Glu Tyr Lys Cys Lys Val Ser Asn
195 200 205

Lys Ala Leu Pro Ala Pro Ile Glu Lys Thr Ile Ser Lys Ala Lys Gly
210 215 220

Gln Pro Arg Glu Pro Gln Val Tyr Thr Leu Pro Pro Ser Arg Glu Glu
225 230 235 240

Met Thr Lys Asn Gln Val Ser Leu Thr Cys Leu Val Lys Gly Phe Tyr
245 250 255

Pro Ser Asp Ile Ala Val Glu Trp Glu Ser Asn Gly Gln Pro Glu Asn
260 265 270

Asn Tyr Lys Thr Thr Pro Pro Val Leu Asp Ser Asp Gly Ser Phe Phe
275 280 285

Leu Tyr Ser Lys Leu Thr Val Asp Lys Ser Arg Trp Gln Gln Gly Asn
290 295 300

Val Phe Ser Cys Ser Val Met His Glu Ala Leu His Asn His Tyr Thr
305 310 315 320

Gln Lys Ser Leu Ser Leu Ser Pro Gly Lys
325 330

<210> SEQ ID NO 315
<211> LENGTH: 10
<212> TYPE: PRT
<213> ORGANISM: Artificial Sequence
<220> FEATURE:
<223> OTHER INFORMATION: Synthesized

<400> SEQUENCE: 315

Gly Gly Gly Gly Ser Gly Gly Gly Gly Ser
1 5 10

<210> SEQ ID NO 316
<211> LENGTH: 244
<212> TYPE: PRT
<213> ORGANISM: Artificial Sequence
<220> FEATURE:
<223> OTHER INFORMATION: Synthesized

<400> SEQUENCE: 316

Gln Val Gln Leu Gln Glu Ser Gly Gly Gly Leu Val Lys Pro Gly Gly
1 5 10 15

Ser Leu Arg Leu Ser Cys Ala Ala Ser Gly Phe Thr Phe Ser Ser Tyr
20 25 30

Trp Met Ser Trp Val Arg Gln Ala Pro Gly Lys Gly Leu Glu Trp Val
35 40 45

Ala Asn Ile Asn Arg Asp Gly Ser Ala Ser Tyr Tyr Val Asp Ser Val
50 55 60

Lys Gly Arg Phe Thr Ile Ser Arg Asp Asp Ala Lys Asn Ser Leu Tyr
65 70 75 80

Leu Gln Met Asn Ser Leu Arg Ala Glu Asp Thr Ala Val Tyr Tyr Cys
85 90 95

Ala Arg Asp Arg Gly Val Gly Tyr Phe Asp Leu Trp Gly Arg Gly Thr
100 105 110

-continued

```
Leu Val Thr Val Ser Ser Gly Gly Gly Gly Ser Gly Gly Gly Gly Ser
        115                 120                 125

Gly Gly Gly Gly Ser Gln Ser Ala Leu Thr Gln Pro Ala Ser Val Ser
    130                 135                 140

Gly Ser Pro Gly Gln Ser Ile Thr Ile Ser Cys Thr Gly Thr Ser Ser
145                 150                 155                 160

Asp Val Gly Gly Tyr Asn Phe Val Ser Trp Tyr Gln Gln His Pro Gly
                165                 170                 175

Lys Ala Pro Lys Leu Met Ile Tyr Asp Val Ser Asp Arg Pro Ser Gly
            180                 185                 190

Val Ser Asp Arg Phe Ser Gly Ser Lys Ser Gly Asn Thr Ala Ser Leu
        195                 200                 205

Ile Ile Ser Gly Leu Gln Ala Asp Asp Glu Ala Asp Tyr Tyr Cys Ser
    210                 215                 220

Ser Tyr Gly Ser Ser Ser Thr His Val Ile Phe Gly Gly Gly Thr Lys
225                 230                 235                 240

Val Thr Val Leu


<210> SEQ ID NO 317
<211> LENGTH: 5
<212> TYPE: PRT
<213> ORGANISM: Artificial Sequence
<220> FEATURE:
<223> OTHER INFORMATION: Synthesized

<400> SEQUENCE: 317

Asn Tyr Gly Val His
1               5


<210> SEQ ID NO 318
<211> LENGTH: 16
<212> TYPE: PRT
<213> ORGANISM: Artificial Sequence
<220> FEATURE:
<223> OTHER INFORMATION: Synthesized

<400> SEQUENCE: 318

Val Ile Trp Ser Gly Gly Asn Thr Asp Tyr Asn Thr Pro Phe Thr Ser
1               5                   10                  15


<210> SEQ ID NO 319
<211> LENGTH: 11
<212> TYPE: PRT
<213> ORGANISM: Artificial Sequence
<220> FEATURE:
<223> OTHER INFORMATION: Synthesized

<400> SEQUENCE: 319

Ala Leu Thr Tyr Tyr Asp Tyr Glu Phe Ala Tyr
1               5                   10


<210> SEQ ID NO 320
<211> LENGTH: 118
<212> TYPE: PRT
<213> ORGANISM: Artificial Sequence
<220> FEATURE:
<223> OTHER INFORMATION: Synthesized

<400> SEQUENCE: 320

Gln Val Gln Leu Gln Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
```

```
            20                  25                  30

Trp Met Ser Trp Val Arg Gln Ala Pro Gly Lys Gly Leu Glu Trp Val
        35                  40                  45

Ala Asn Ile Asn Arg Asp Gly Ser Ala Ser Tyr Tyr Val Asp Ser Val
    50                  55                  60

Lys Gly Arg Phe Thr Ile Ser Arg Asp Asp Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Arg Gly Val Gly Tyr Phe Asp Leu Trp Gly Arg Gly Thr
            100                 105                 110

Leu Val Thr Val Ser Ser
        115


<210> SEQ ID NO 321
<211> LENGTH: 15
<212> TYPE: PRT
<213> ORGANISM: Artificial Sequence
<220> FEATURE:
<223> OTHER INFORMATION: Synthesized

<400> SEQUENCE: 321

Gly Gly Gly Gly Ser Gly Gly Gly Gly Ser Gly Gly Gly Gly Ser
1               5                   10                  15


<210> SEQ ID NO 322
<211> LENGTH: 111
<212> TYPE: PRT
<213> ORGANISM: Artificial Sequence
<220> FEATURE:
<223> OTHER INFORMATION: Synthesized

<400> SEQUENCE: 322

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
            20                  25                  30

Asn Phe Val Ser Trp Tyr Gln Gln His Pro Gly Lys Ala Pro Lys Leu
        35                  40                  45

Met Ile Tyr Asp Val Ser Asp Arg Pro Ser Gly Val Ser Asp Arg Phe
    50                  55                  60

Ser Gly Ser Lys Ser Gly Asn Thr Ala Ser Leu Ile Ile Ser Gly Leu
65                  70                  75                  80

Gln Ala Asp Asp Glu Ala Asp Tyr Tyr Cys Ser Ser Tyr Gly Ser Ser
                85                  90                  95

Ser Thr His Val Ile Phe Gly Gly Gly Thr Lys Val Thr Val Leu
            100                 105                 110


<210> SEQ ID NO 323
<211> LENGTH: 5
<212> TYPE: PRT
<213> ORGANISM: Artificial Sequence
<220> FEATURE:
<223> OTHER INFORMATION: Synthesized

<400> SEQUENCE: 323

Ser Tyr Trp Met Ser
1               5


<210> SEQ ID NO 324
```

<211> LENGTH: 17
<212> TYPE: PRT
<213> ORGANISM: Artificial Sequence
<220> FEATURE:
<223> OTHER INFORMATION: Synthesized

<400> SEQUENCE: 324

Asn Ile Asn Arg Asp Gly Ser Ala Ser Tyr Tyr Val Asp Ser Val Lys
1 5 10 15

Gly

<210> SEQ ID NO 325
<211> LENGTH: 9
<212> TYPE: PRT
<213> ORGANISM: Artificial Sequence
<220> FEATURE:
<223> OTHER INFORMATION: Synthesized

<400> SEQUENCE: 325

Asp Arg Gly Val Gly Tyr Phe Asp Leu
1 5

<210> SEQ ID NO 326
<211> LENGTH: 14
<212> TYPE: PRT
<213> ORGANISM: Artificial Sequence
<220> FEATURE:
<223> OTHER INFORMATION: Synthesized

<400> SEQUENCE: 326

Thr Gly Thr Ser Ser Asp Val Gly Gly Tyr Asn Phe Val Ser
1 5 10

<210> SEQ ID NO 327
<211> LENGTH: 7
<212> TYPE: PRT
<213> ORGANISM: Artificial Sequence
<220> FEATURE:
<223> OTHER INFORMATION: Synthesized

<400> SEQUENCE: 327

Asp Val Ser Asp Arg Pro Ser
1 5

<210> SEQ ID NO 328
<211> LENGTH: 11
<212> TYPE: PRT
<213> ORGANISM: Artificial Sequence
<220> FEATURE:
<223> OTHER INFORMATION: Synthesized

<400> SEQUENCE: 328

Ser Ser Tyr Gly Ser Ser Ser Thr His Val Ile
1 5 10

<210> SEQ ID NO 329
<211> LENGTH: 5
<212> TYPE: PRT
<213> ORGANISM: Artificial Sequence
<220> FEATURE:
<223> OTHER INFORMATION: Synthesized

<400> SEQUENCE: 329

Gly Gly Gly Gly Ser
1 5

What is claimed is:

1. A method of producing an antibody comprising culturing a host cell having one or more isolated nucleic acids encoding the antibody or an expression vector comprising said one or more isolated nucleic acids encoding the antibody so that the antibody is produced, wherein the antibody is a bispecific tetravalent antibody comprising:

two IgG1 heavy chains;

two kappa light chains; and two single chain Fv (scFv) domains;

wherein the two IgG1 heavy chains and kappa light chains form an IgG moiety with a binding specificity to EGFR;

wherein the two scFv domains have a binding specificity to HER3; and wherein the each scFv domain is connected to the C-terminus of either of the IgG1 heavy chains by a connector, wherein the IgG1 heavy chain comprises a heavy chain CDR1 comprising the amino acid sequence of NYGVH (SEQ ID NO:317), a heavy chain CDR2 comprising the amino acid sequence of VIWSGGNTDYNTPFTS (SEQ ID NO:318), and a heavy chain CDR3 comprising the amino acid sequence of ALTYYDYEFAY (SEQ ID NO:319), and wherein the kappa light chain comprises a light chain CDR1 comprising the amino acid sequence of RASQSIGTNIH (SEQ ID NO:311), a light chain CDR2 comprising the amino acid sequence of YASESIS (SEQ ID NO:312), a light chain CDR3 comprising the amino acid sequence of QQNNNWPTT (SEQ ID NO:313); and wherein the scFv comprises a heavy chain CDR1 comprising the amino acid sequence of SYWMS (SEQ ID NO:323), a heavy chain CDR2 comprising the amino acid sequence of NINRDGSASYYVDSVKG (SEQ ID NO:324), a heavy chain CDR3 comprising the amino acid sequence of DRGVGYFDL (SEQ ID NO:325), a light chain CDR1 comprising the amino acid sequence of TGTSSDVGGYNFVS (SEQ ID NO:326), a light chain CDR2 comprising the amino acid sequence of DVSDRPS (SEQ ID NO:327), and a light chain CDR3 comprising the amino acid sequence of SSYGSSSTHVI (SEQ ID NO:328).

2. The method of claim 1, wherein the IgG1 heavy chain comprises a heavy chain variable region comprising the amino acid sequence of SEQ ID NO:137 or 119; and wherein the kappa light chain comprises a light chain variable region comprising the amino acid sequence of SEQ ID NO:132 or 114.

3. The method of claim 1, wherein the scFv comprises a heavy chain variable region comprising the amino acid sequence of

```
                                          (SEQ ID NO: 320)
QVQLQESGGGLVKPGGSLRLSCAASGFTFSSYWMSWVRQAPGKGLEWVA

NINRDGSASYYVDSVKGRFTISRDDAKNSLYLQMNSLRAEDTAVYYCAR

DRGVGYFDLWGRGTLVTVSS;
```

and a light chain variable region comprising the amino acid sequence of

```
                                          (SEQ ID NO: 322)
QSALTQPASVSGSPGQSITISCTGTSSDVGGYNFVSWYQQHPGKAPKLM
```

-continued

```
IYDVSDRPSGVSDRFSGSKSGNTASLIISGLQADDEADYYCSSYGSSST

HVIFGGGTKVTVL.
```

4. The method of claim 1, wherein the IgG1 heavy chain comprises a heavy chain variable region comprising the amino acid sequence of SEQ ID NO:137 or 119; and wherein the kappa light chain comprises a light chain variable region comprising the amino acid sequence of SEQ ID NO:132 or 114, wherein the scFv comprises a heavy chain variable region comprising the amino acid sequence of

```
                                          (SEQ ID NO: 320)
QVQLQESGGGLVKPGGSLRLSCAASGFTFSSYWMSWVRQAPGKGLEWVA

NINRDGSASYYVDSVKGRFTISRDDAKNSLYLQMNSLRAEDTAVYYCAR

DRGVGYFDLWGRGTLVTVSS;
```

and a light chain variable region comprising the amino acid sequence of

```
                                          (SEQ ID NO: 322)
QSALTQPASVSGSPGQSITISCTGTSSDVGGYNFVSWYQQHPGKAPKLM

IYDVSDRPSGVSDRFSGSKSGNTASLIISGLQADDEADYYCSSYGSSST

HVIFGGGTKVTVL.
```

5. The method of claim 1, wherein the scFv domain has a structure order of N terminus—heavy chain variable region—linker—light chain variable region—C terminus, or N—terminus—light chain variable region—linker—heavy chain variable region—C-terminus.

6. The method of claim 5, wherein the linker comprises the amino acid sequence of $(\text{gly-gly-gly-gly-ser})_m$ (SEQ ID NO:321), wherein m is an integral of at least 3.

7. The method of claim 1, wherein the connector comprises the amino acid sequence of $(\text{gly-gly-gly-gly-ser})_n$ (SEQ ID NO:329), wherein n is an integral of at least 1.

8. The method of claim 1, wherein the IgG1 heavy chain is humanized or human IgG1 heavy chain.

9. The method of claim 1, wherein the kappa light chain is humanized or human kappa light chain.

10. The method of claim 1, wherein the IgG1 heavy chain, connector, and scFv domain comprises the amino acid sequence of SEQ ID NO: 136, and the kappa light chain comprises the amino acid sequence of SEQ ID NO: 131.

11. The method of claim 1, wherein the method comprises:

(1) transfecting the host cell with an expression vector comprising one or more nucleic acids encoding the antibody;

(2) culturing the transfected host cell to produce antibodies in the supernatant; and (3) purifying the antibodies from the supernatant using protein affinity chromatography and/or size exclusion chromatography.

12. The method of claim 11, wherein the host cell is transfected with the expression vector using linear polyethyleneimine (PEI).

13. The method of claim 1, wherein the host cell is a mammalian cell.

14. The method of claim 1, wherein the expression vector contains a strong CMV-derived promoter.

* * * * *